(12) United States Patent
Denis et al.

(10) Patent No.: US 7,569,600 B2
(45) Date of Patent: Aug. 4, 2009

(54) **COMPOUNDS AND METHODS FOR THE TREATMENT OF PREVENTION OF *FLAVIVIRUS* INFECTIONS**

(75) Inventors: Real Denis, Montréal (CA); Carl Poisson, Montréal (CA); Sanjoy Kumar Das, Pierrefonds (CA); Irina Motorina, Blainville (CA); Rabindra Rej, Montréal (CA); Constantin G. Yannopoulos, Ile Perrot (CA); Laval Chan Chun Kong, Kirkland (CA)

(73) Assignee: ViroChem Pharma Inc., Laval QC (CA)

( * ) Notice: Subject to any disclaimer, the term of this patent is extended or adjusted under 35 U.S.C. 154(b) by 261 days.

(21) Appl. No.: 11/433,749

(22) Filed: May 15, 2006

(65) Prior Publication Data

US 2006/0276533 A1 Dec. 7, 2006

Related U.S. Application Data

(60) Provisional application No. 60/680,482, filed on May 13, 2005.

(51) Int. Cl.
*A61K 31/38* (2006.01)
*C07D 333/42* (2006.01)

(52) U.S. Cl. ............... 514/447; 514/448; 514/444; 549/68; 549/70; 549/59

(58) Field of Classification Search ............... 549/68, 549/70, 59; 514/447, 448, 444
See application file for complete search history.

(56) References Cited

U.S. PATENT DOCUMENTS

| | | | |
|---|---|---|---|
| 3,076,817 A | 2/1963 | Fiesselmann et al. | |
| 3,470,151 A | 9/1969 | Doyel et al. | |
| 4,180,662 A | 12/1979 | Pfister et al. | |
| 4,877,793 A | 10/1989 | Davies | |
| 5,783,705 A | 7/1998 | Blok et al. | |
| 6,187,799 B1 | 2/2001 | Wood et al. | |
| 6,248,767 B1 | 6/2001 | Blok et al. | |
| 6,294,276 B1 | 9/2001 | Ogino | |
| 6,380,214 B1 | 4/2002 | Gant et al. | |
| 6,414,013 B1 | 7/2002 | Fancelli et al. | |
| 6,432,994 B1 | 8/2002 | Wu et al. | |
| 6,448,290 B1 | 9/2002 | Ohuchida et al. | |
| 6,458,805 B2 | 10/2002 | Blok et al. | |
| 6,620,767 B1 | 9/2003 | Ducray et al. | |
| 6,660,728 B2 | 12/2003 | Scheunemann et al. | |
| 6,660,732 B2 | 12/2003 | Betageri et al. | |
| 6,683,103 B2 | 1/2004 | Wu et al. | |
| 6,734,207 B2 | 5/2004 | Uckun et al. | |
| 6,747,057 B2 | 6/2004 | Ruzafa et al. | |
| 6,835,745 B2 | 12/2004 | Coghlan et al. | |
| 6,858,223 B2 | 2/2005 | Hafner | |
| 6,881,741 B2 | 4/2005 | Kong et al. | |
| 6,887,877 B2 | 5/2005 | Chan Chun Kong et al. | |
| 6,892,279 B2 | 5/2005 | Mekheil | |
| 6,960,594 B2 | 11/2005 | Labrecque et al. | |
| 6,982,279 B2 | 1/2006 | Peukert et al. | |
| 6,984,737 B2 | 1/2006 | Hartmann et al. | |
| 7,019,027 B2 | 3/2006 | Linden et al. | |
| 7,084,170 B2 | 8/2006 | Grossman et al. | |
| 7,084,171 B2 | 8/2006 | Grainger et al. | |
| 7,098,240 B2 | 8/2006 | Griffiths et al. | |
| 7,098,241 B2 | 8/2006 | Grossman et al. | |
| 7,138,530 B2 | 11/2006 | Subasinghe et al. | |
| 7,166,639 B2 | 1/2007 | Wan et al. | |
| 7,179,836 B2 | 2/2007 | Adams et al. | |
| 2005/0009804 A1 | 1/2005 | King et al. | |
| 2007/0099929 A1 | 5/2007 | Thede et al. | |

FOREIGN PATENT DOCUMENTS

| | | |
|---|---|---|
| CA | 2 496 680 A1 | 11/1998 |
| CA | 2 385 972 A1 | 4/2001 |
| DE | 1 055 007 | 4/1959 |
| DE | 199 03 398 A1 | 8/2000 |
| DE | 199 20 247 A1 | 11/2000 |
| JP | 63-141984 | 6/1988 |
| JP | 7-48360 | 2/1995 |
| JP | 2001-010957 | 1/2001 |
| JP | 2004-513163 | 4/2004 |
| WO | WO 98/49162 A1 | 11/1998 |
| WO | WO 98/52558 | 11/1998 |
| WO | WO 98/52559 | 11/1998 |
| WO | WO 00/20358 | 4/2000 |
| WO | WO 00/66094 | 11/2000 |
| WO | WO 02/28353 | 4/2002 |
| WO | WO 02/38542 A1 | 5/2002 |
| WO | WO 2004/052879 A1 | 6/2004 |
| WO | WO 2005/063734 | 7/2005 |

(Continued)

OTHER PUBLICATIONS

Written Opinion and International Search Report for International Application No. PCT/CA2006/000786.

(Continued)

*Primary Examiner*—Rei-tsang Shiao
(74) *Attorney, Agent, or Firm*—Millen, White, Zelano & Branigan, P.C.

(57) ABSTRACT

Compounds represented by formula I:

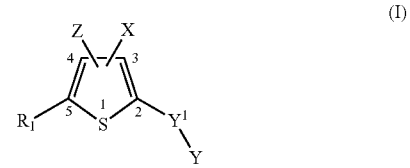

or pharmaceutically acceptable salts and solvates thereof, wherein $R_1$, X, Y, $Y_1$, and Z are as defined herein, are useful for treating flaviviridae viral infections.

90 Claims, No Drawings

FOREIGN PATENT DOCUMENTS

| | | |
|---|---|---|
| WO | WO 2006/072347 | 7/2006 |
| WO | WO 2006/072348 A2 | 7/2006 |

OTHER PUBLICATIONS

David McKinnon et al., "The Conversions of Izothiazolium Salts into Thiophenecarboxylic Ester Derivatives", Can. J. Chem., 1984, vol. 62, pp. 1580-1584.

Pilar Goya et al., Synthesis of 4-Oxo- 3,4-dihydro-1 H-thieno [3,4-c] and thieno [3,2-c][1,2,6]thiadiazine 2,2-Dioxides, Synthesis, Apr. 1989, pp. 280-282.

Bo Sung Kim et al., "Reactions of Thiaroylketene S,N-Acetals with 1,3-Dicarbonyl Compounds in the Presence of Mercury (II) Acetate: A General Route to 2-Acyl-and 2 Aroyl-3-(alkylamino)-5-arylthiopenes and 2-(Ethoxycarbonyl)-3-(methylamino)-5-arylthiopenes", J. Org. Chem., 1998, vol. 63, pp. 6086-6087.

Bo Sung Kim et al., "A Facile and Convenient Synthesis of 3-Alkylamino-5-arylthiopenes with a Variety of Substituents at C-2 and Studies of Reaction Mechanisms", J. Org. Chem, 2000, vol. 65, pp. 3690-3699.

Ya. L. Gol'dfarb et al., "Action of Alkali Metals in Liquid Ammonia on Substituted Thiophenes. Communication 9. Preparation of 5-Mercapto-4-Ketoalkanoic Acids by Reductive Cleavage of 4-Acetylamino- and 4-Nitrothiphene-2-Carboxylic Acids", Izv. Akad. Nauk SSSR, Ser. Khim., 1984, vol. 10, pp. 2136-2139.

J. R. Desai et al.; J. Ind. Chem. Soc., vol. 74, 1997, p. 160, "Thieno[3,2-d]pyrimidines— Part-I: Preparation and Antimicrobial Activity of 3-N-Substituted-tioureido-2-methyl-6-phenylthieno[3,2-d]pyrimidin-4(3H)-ones", ISR ref. XP002220249.

E. Marchand, G. Morel, Bull. Soc. Chim. FR. vol. 133, No. 9, 1996, p. 903-912, "Alpha-Thioxothioamides Reactions de cycloaddition [4+2] avec l'acetylenedicarboxylate de dimethyle et le propiolate de methyle", ISR ref. XP002220251.

W. Kantlehner et al., J. Prakt. Chem., vol. 338, 1996, p. 403-413; "Orthoamide, IL. Umsetzungen von Orthoamid-Derivaten mit Schwefel und Selen, Synthesen von 1,3-Thiazol- und 1,3-Selenazolderivaten" ISR ref. XP002220245.

S. Vega et al., Eur. J. Med. Chem. vol. 23, No. 4, 1988, p. 329-334; "Thiophene Isosteres: Synthesis and Pharmacological Study of 3-(azol-l-yl)thieno isothiazole-1, 1-dioxides" ISR ref. XP002220246.

R.A. Smith et al., Bioorg. Med. Chem. Lett. vol. 11, No. 20, 2001, p. 2775-2778; "Discovery of Heterocyclic Ureas as a New Class of Raf Kinase Inhibitors: Identification of a Second Generation Lead by a Combinatorial Chemistry Approach", ISR ref. XP001118699.

A.M. Redman et al., Bioorg. Med. Chem. Lett., vol. 11, 2001, p. 9-12; "P38 Kinase Inhibitors for the Treatment of Arthritis and Osteoporosis: Thienyl, Furyl, and Pyrrolyl Ureas", ISR ref. XP004225311.

D.J. Lee et al., Chemical Abstracts Service, Columbus, OH, U.S., "Novel Synthesis of 5,6-Dihydro-4H-thieno[3,2-b]pyrrol-5-ones via the Rhodium(II)-Mediated Wolff Rearrangement of 3-(2-Thienyl)-3-oxo-2-diazopropanoates"; Database accession No. 2002:151873, ISR ref. XP002220252.

M. Sugiyama et al., Chem. Pharm. Bull. vol. 37, No. 8, 1989, p. 2091-2102; "Condensed Thienopyrimidines. I. Synthesis and Gastric Antisecretory Activity of 2,3-Dihydro-5H-oxazolothienopyrimidin-5-one Derivatives", ISR ref. XP001118351.

J.C. Lancelot et al., J. Heterocycl. Chem. vol. 33, No. 2, 1996, p. 427-430; "A Facile Synthesis of New Beta-Lactams", ISR ref. XP002220247.

J.R. Desai et al., J. Inst. Chemists (INDIA) vol. 67, 1995, p. 136-137, "Thieno[3,2-d]pyrimidines—Part—II: Preparation and Antimicrobial Activity of 2-methyl-3-N-Arylsulphonamido-6-Phenylthieno[3,2-d]Pyrimidin-4(3H)-ones", ISR ref. XP002220249.

Goldfarb et al., Zhurnal Obshchei Khimi, vol. 29, 1959, pp. 3636-3644.

Patent Abstract for Japanese Patent Publication No. 2001-010957, Jan. 16, 2001.

International Search Report for Application No. PCT/CA02/00876 mailed Nov. 26, 2002.

International Search Report for International Application No. PCT/CA2007/002064, 2007.

CA 139:365176, Roberts et al., "Preparation of Nucleoside Derivatives for Treating Hepatitis C Virus Infection.", 2003.

CA 142:253391, Hadziyannis et al., "Emerging Treatments in Chronic Hepatitis B.", 2004.

CA 129: 285628, Sostegni et al., "Sequential Versus Concomitant Administration of Ribavirin and Interferon alpha-3 in Patients whit Chronic Hepatitis C not Responding to Interferon Alone." 1998.

CA 2007:977620, Vicari et al., "Safety, Pharmacokietics and Immune Effects in Normal Volunteers of CPG 10101(ACTILON).", 2007.

Office Action issued Mar. 29, 2006 in U.S. App. No. 10/730,272.
Office Action issued Aug. 24, 2006 in U.S. Appl. No. 10/730,272.
Office Action issued Mar. 14, 2007 in U.S. Appl. No. 10/730,272.
Notice of Allowance issued Sep. 28, 2007 in U.S. Appl. No. 10/730,272.
Office Action issued May 2, 2008 in U.S. Appl. No. 11/433,749.
Office Action issued Sep. 18, 2007 in U.S. Appl. No. 11/042,442.
Notice of Allowance issued Mar. 17, 2008 in U.S. Appl. No. 11/042,442.
U.S. Appl. No. 11/442,442.
U.S. Appl. No. 11/984,330.
U.S. Appl. No. 12/068,237.

Chan, L. et al., Scientific presentation: 16th ICAR—Savannah, Apr. 2003, Shire BioChem Inc.

Chan, Laval et al., Bioorganic & Medicinal Chemistry Letters, 14 (2004), 793-796.

Chan, Laval et al., Bioorganic & Medicinal Chemistry Letters, 14 (2004), 797-800.

Chan, Laval et al., J. Med. Chem 2003, 46, 1283-1285.

Liu et al., Liquid Crystals, 2001, vol. 28, No. 4, p. 581-589.

Nguyen-Ba et al., "Discovery and SAR Studies of a Novel Class of HCV NS5B RNA-dependent RNA Polymerase Inhibitors," The 16th International Conference on Antiviral Research (ICAR) convened on Apr. 27-May 1, 2003.

Poisson, Carl, "Discovery and Structure-Activity Relationship of Trisubstituted Thiophene Derivatives as Potent Inhibitors of Hepatitis C Virus Replication," 15th QOMSBOC, Ottawa, ON, Nov. 5-7, 2004.

Yannopoulos, Constantin G. et al., Bioorganic & Medicinal Chemistry Letters, 14 (2004), 5333-5337.

B.P. Fabrichnyi, et al., "Synthesis of Aliphatic Amino Acids from Thiophene Derivatives", pp. 1093-1102, May 1970.

Office Action issued Apr. 2, 2007 in U.S. Appl. No. 11/042,442.
Notice of Allowance issued Jun. 16, 2008 in U.S. Appl. No. 11/042,442.

Compound Registration Forms—Maybridge—31 pages, 2000-2002.

Translation of "Notice of Grounds for Rejection" for Japanese Patent Application No. 2003-503618 dated Oct. 7, 2008.

COMPOUNDS AND METHODS FOR THE TREATMENT OF PREVENTION OF *FLAVIVIRUS* INFECTIONS

This application claims the benefit of U.S. Provisional Application Ser. No. 60/680,482, filed May 13, 2005.

The present invention relates to novel compounds and a method for the treatment or prevention of Flavivirus infections using novel compounds.

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50-60 nm. The HCV genome is a single-stranded, positive-sense RNA of about 9,600 bp coding for a polyprotein of 3009-3030 amino-acids, which is cleaved co and post-translationally into mature viral proteins (core, E1, E2, p7, NS2, NS3, NS4A, NS4B, NS5A, NS5B). It is believed that the structural glycoproteins, E1 and E2, are embedded into a viral lipid envelope and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

The only treatment currently available for HCV infection is interferon-α (IFN-α). However, according to different clinical studies, only 70% of treated patients normalize alanine aminotransferase (ALT) levels in the serum and after discontinuation of IFN, 35% to 45% of these responders relapse. In general, only 20% to 25% of patients have long-term responses to IFN. Clinical studies have shown that combination treatment with IFN and ribavirin (RIBA) results in a superior clinical response to that of IFN alone.

There is therefore a great need for the development of anti-viral agents for use in treating or preventing Flavivirus infections.

In one aspect, the present invention provides a compound having the formula I:

(I)

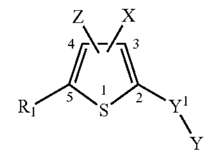

or pharmaceutically acceptable salts thereof;

wherein, $R_1$ is chosen from optionally substituted $C_{3-12}$ cycloalkyl, optionally substituted $C_{4-12}$ cycloalkenyl, optionally substituted —C(O)—$C_{3-12}$ cycloalkyl, optionally substituted —C(O)—$C_{4-12}$ cycloalkenyl, optionally substituted 5 to 12 member spiroheterocycloalkyl and optionally substituted 8 to 12 member spiroheterocycloalkenyl;

Z is chosen from H, halogen, optionally substituted $C_{1-6}$ alkyl, optionally substituted $C_{2-6}$ alkenyl and optionally substituted $C_{2-6}$ alkynyl;

X is chosen from:

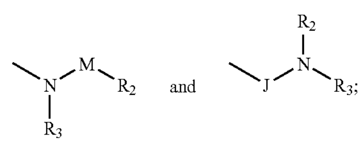

M is chosen from:

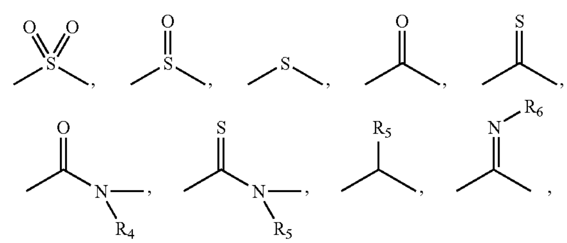

and a bond;

$R_2$, $R_3$ and $R_6$ are each indendently chosen from H, optionally substituted $C_{1-12}$ alkyl, optionally substituted $C_{2-12}$ alkenyl, optionally substituted $C_{2-12}$ alkynyl, optionally substituted $C_{6-14}$ aryl, optionally substituted $C_{7-16}$ aralkyl, optionally substituted 5-12 member heteroaryl, optionally substituted 6-18 member heteroaralkyl, optionally substituted 3-12 member heterocycle, and optionally substituted 4-18 member heterocycle-alkyl;

$R_4$ and $R_5$ are ach independently chosen from H, optionally substituted $C_{1-6}$ alkyl, optionally substituted $C_{2-6}$ alkenyl and optionally substituted $C_{2-6}$ alkynyl;

J is chosen from:

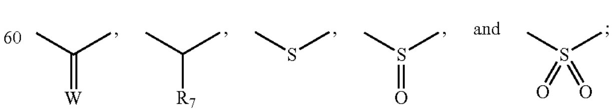

W is chosen from O, S and $NR_8$;

$R_7$ is chosen from H, optionally substituted $C_{1-12}$ alkyl, optionally substituted $C_{2-12}$ alkenyl optionally substituted, optionally substituted $C_{2-12}$ alkynyl, optionally substituted $C_{6-14}$ aryl and optionally substituted $C_{7-16}$ aralkyl;

$R_8$ is chosen from H, optionally substituted $C_{1-12}$ alkyl, optionally substituted $C_{2-12}$ alkenyl, optionally substituted $C_{2-12}$ alkynyl, optionally substituted $C_{6-14}$ aryl, optionally substituted $C_{7-16}$ aralkyl, optionally substituted 5-12 member heteroaryl, optionally substituted 6-18 member heteroaralkyl, optionally substituted 3-12 member heterocycle, and optionally substituted 4-18 member heterocycle-alkyl;

$Y^1$ is chosen from a bond, optionally substituted $C_{1-6}$ alkyl, optionally substituted $C_{2-6}$ alkenyl, and optionally substituted $C_{2-6}$ alkynyl;

Y is chosen from $COOR_9$, $COCOOR_9$, $P(O)OR_aOR_b$, $S(O)OR_9$, $S(O)_2OR_9$, tetrazole, $CON(R_9)CH(R_9)COOR_9$, $CONR_{10}R_{11}$, $CON(R_9)$—$SO_2$—$R_9$, $CONR_9OH$ and halogen;

$R_9$, $R_{10}$ and $R_{11}$, are each independently chosen from H, optionally substituted $C_{1-12}$ alkyl, optionally substituted $C_{2-12}$ alkenyl, optionally substituted $CZ_{2-12}$ alkynyl, optionally substituted $C_{6-14}$ aryl, optionally substituted $C_{7-16}$ aralkyl, optionally substituted 5-12 member heteroaryl, optionally substituted 6-18 member heteroaralkyl, optionally substituted 3-12 member heterocycle, and optionally substituted 4-18 member heterocycle-alkyl, or $R_{10}$ and $R_{11}$ are taken together with the nitrogen atom to form an optionally substituted 3 to 10 member heterocycle or an optionally substituted 5-12 member heteroaryl; and $R_a$ and $R_b$ are each independently chosen from H, optionally substituted $C_{1-12}$ alkyl, optionally substituted $C_{2-12}$ alkenyl, optionally substituted $C_{2-12}$ alkynyl, optionally substituted $C_{6-14}$ aryl, optionally substituted $C_{7-16}$ aralkyl, optionally substituted 5-12 member heteroaryl, optionally substituted 6-18 member heteroaralkyl, optionally substituted 3-12 member heterocycle, and optionally substituted 4-18 member heterocycle-alkyl, or $R_a$ and $R_b$ are taken together with the oxygen atoms to form an optionally substituted 5 to 10 member heterocycle or an optionally substituted 5-12 member heteroaryl.

In another aspect, there is provided a method for treating or preventing a Flaviviridae viral infection in a host comprising administering to the host a therapeutically effective amount of a compound, composition or combination of the invention.

In another aspect, there is provided a pharmaceutical composition comprising at least one compound of the invention and at least one pharmaceutically acceptable carrier or excipient.

In another aspect, there is provided a combination comprising a compound of the invention and one or more additional agents chosen from viral serine protease inhibitors, viral polymerase inhibitors, viral helicase inhibitors, immunomudulating agents, antioxidant agents, antibacterial agents, and antisense agents.

In a further aspect, there is provided the use of a compound, composition or combination of the invention for treating or preventing a Flaviviridae viral infection in a host.

In still another aspect, there is provided the use of a compound, composition or combination of the invention for inhibiting or reducing the activity of viral polymerase in a host.

In still another aspect, there is provided the use of a compound, composition or combination of the invention for the manufacture of a medicament for treating or preventing a viral Flaviridae infection in a host.

In one embodiment, compounds of the present invention comprise those wherein the following embodiments are present, either independently or in combination.

In accordance with a compound or method aspect, the compounds of the present invention are represented by formula IA:

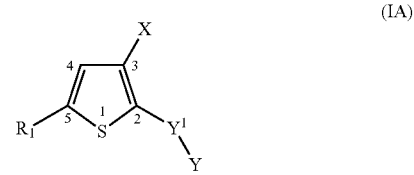

(IA)

or pharmaceutically acceptable salts thereof;

wherein, each of X, $Y^1$, Y and $R_1$ are as defined above and wherein each of the above-mentioned alkyl, alkenyl, alkynyl, aryl, aralkyl, heterocycle, heteroaryl, heteroaralkyl, heterocycle-alkyl, cycloalkyl and cycloalkenyl groups is optionally substituted.

In one embodiment, M is chosen from:

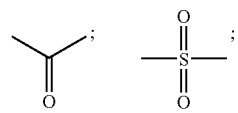

and a bond.

In a further embodiment, M is:

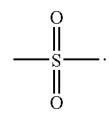

In an alternative embodiment, M is:

In one embodiment, J is chosen from:

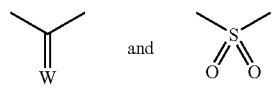

wherein, W is as defined above.

In an alternative embodiment, J is:

In a further embodiment, J is:

In a further embodiment, $Y^1$ is chosen from $CH_2$, $CH=CH$, $CH_2-CH_2$ and a bond.

In a further embodiment, $Y^1$ is a bond.

In a further embodiment, $Y^1-Y$ is COOH.

In accordance with a further compound or method aspect, the compounds of the present invention are represented by formula IB:

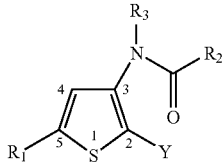

(IB)

or pharmaceutically acceptable salts thereof;

wherein each of X, $Y^1$, Y and $R_1$ are as defined above and wherein each of the above-mentioned alkyl, alkenyl, alkynyl, aryl, aralkyl, heterocycle, heteroaryl, heteroaralkyl, heterocycle-alkyl, cycloalkyl and cycloalkenyl groups is optionally substituted.

In accordance with a compound or method aspect, the compounds of the present invention are represented by formula IC:

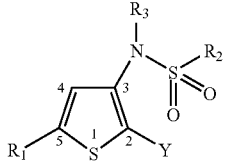

(IC)

or pharmaceutically acceptable salts thereof;

wherein, each of X, Y, $R_1$, $R_2$ and $R_3$ are as defined above and wherein each of the above-mentioned alkyl, alkenyl, alkynyl, aryl, aralkyl, heterocycle, heteroaryl, heteroaralkyl, heterocycle-alkyl, cycloalkyl and cycloalkenyl groups is optionally substituted.

According to a further aspect of the invention, $R_1$ is $C_{3-12}$ cycloalkyl (e.g., cyclopentyl, cyclohexyl, cycloheptyl) unsubstituted or substituted one or more times by $R_{17}$, $C_{4-12}$ cycloalkenyl (e.g., cyclopentenyl, cyclohexenyl, cycloheptenyl) unsubstituted or substituted one or more times by $R_{17}$, $-C(O)-C_{3-12}$ cycloalkyl unsubstituted or substituted one or more times by $R_{17}$, $-C(O)-C_{4-12}$ cycloalkenyl unsubstituted or substituted one or more times by $R_{17}$, 5 to 12 member spiroheterocycloalkyl (e.g., 2,4-dioxo-1,3-diaza-spiro[4.5]dec-8-yl) unsubstituted or substituted one or more times by $R_{17}$, or 8 to 12 member spiroheterocycloalkenyl (e.g., 1,4-dioxa-spiro[4.5]dec-7-en-8-yl) unsubstituted or substituted one or more times by $R_{17}$.

$R_{17}$ is halogen, oxo, $-NH_2$, $-NH(C_{1-4}$ alkyl), $-N(C_{1-4}$ alkyl$)_2$, $-CONH_2$, $-CONH(C_{1-4}$ alkyl), $-CON(C_{1-4}$ alkyl$)_2$, $-NHCOH$, $-N(C_{1-4}$ alkyl)COH, $-N(C_{1-4}$ alkyl)$COC_{1-4}$ alkyl, $-NHCOC_{1-4}$ alkyl, $-C(O)H$, $-C(O)C_{1-4}$ alkyl, carboxy, $-C(O)O$ $C_{1-4}$ alkyl, hydroxyl, $C_{1-4}$ alkoxy, nitro, nitroso, azido, cyano, $-S(O)_{0-2}H$, $-S(O)_{0-2}C_{1-4}$ alkyl, $-SO_2NH_2$, $-SO_2NH(C_{1-4}$ alkyl), $-SO_2N(C_{1-4}$ alkyl$)_2$, $-NHSO_2H$, $-N(C_{1-4}$ alkyl)$SO_2H$, $-N(C_{1-4}$ alkyl)$SO_2C_{1-4}$ alkyl, or $-NHSO_2C_{1-4}$ alkyl.

According to a further aspect of the invention, $R_2$ is H, $C_{1-12}$ alkyl (e.g., methyl or ethyl) unsubstituted or substituted one or more times by $R_{17}$, $C_{2-12}$ alkenyl (e.g., ethenyl or propenyl) unsubstituted or substituted one or more times by $R_{17}$, $C_{2-12}$ alkynyl (e.g., ethynyl or propynyl) unsubstituted or substituted one or more times by $R_{17}$, $C_{6-14}$ aryl (e.g., phenyl or naphthyl) which is unsubstituted or substituted one or more times by $R_{18}$, or $C_{7-16}$ aralkyl (e.g., benzyl, phenethyl, phenpropyl) unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{20}$, or 4-18 member heterocycle-alkyl unsubstituted or substituted one or more times by $R_{20}$.

$R_{18}$ is halogen, $C_{1-6}$ alkyl, $-NH_2$, $-NH(C_{1-4}$ alkyl), $-N(C_{1-4}$ alkyl$)_2$, $-CONH_2$, $-CONH(C_{1-4}$ alkyl), $-CON(C_{1-4}$ alkyl$)_2$, $-NHCOH$, $-N(C_{1-4}$ alkyl)COH, $-N(C_{1-4}$ alkyl)$COC_{1-4}$ alkyl, $-NHCOC_{1-4}$ alkyl, $-C(O)H$, $-C(O)C_{1-4}$ alkyl, carboxy, $-C(O)O$ $C_{1-4}$ alkyl, hydroxyl, $C_{1-6}$ alkoxy, nitro, nitroso, azido, cyano, $-S(O)_{0-2}H$, $-S(O)_{0-2}C_{1-4}$ alkyl, $-SO_2NH_2$, $-SO_2NH(C_{1-4}$ alkyl), $-SO_2N(C_{1-4}$ alkyl$)_2$, $-NHSO_2H$, $-N(C_{1-4}$ alkyl)$SO_2H$, $-N(C_{1-4}$ alkyl)$SO_2C_{1-4}$ alkyl, $-NHSO_2C_{1-4}$ alkyl, 5-12 member heteroaryl unsubstituted or substituted by $R_{21}$, 6-18 member heteroaralkyl unsubstituted or substituted by $R_{21}$, 3-12 member heterocycle unsubstituted or substituted by $R_{17}$, or 4-18 member heterocycle-alkyl unsubstituted or substituted by $R_{17}$.

$R_{19}$ is halogen, $C_{1-6}$ alkyl, $-NH_2$, $-NH(C_{1-4}$ alkyl), $-N(C_{1-4}$ alkyl$)_2$, $-CONH_2$, $-CONH(C_{1-4}$ alkyl), $-CON(C_{1-4}$ alkyl$)_2$, $-NHCOH$, $-N(C_{1-4}$ alkyl)COH, $-N(C_{1-4}$ alkyl)$COC_{1-4}$ alkyl, $-NHCOC_{1-4}$ alkyl, $-C(O)H$, $-C(O)C_{1-4}$ alkyl, carboxy, $-C(O)O$ $C_{1-4}$ alkyl, hydroxyl, $C_{1-6}$ alkoxy, nitro, nitroso, azido, cyano, $-S(O)_{0-2}H$, $-S(O)_{0-2}C_{1-4}$ alkyl, $-SO_2NH_2$, $-SO_2NH(C_{1-4}$ alkyl), $-SO_2N(C_{1-4}$ alkyl$)_2$, $-NHSO_2H$, $-N(C_{1-4}$ alkyl)$SO_2H$, $-N(C_{1-4}$ alkyl)$SO_2C_{1-4}$ alkyl, $-NHSO_2C_{1-4}$ alkyl, $C_{6-10}$ aryl unsubstituted or substituted by $R_{21}$, $C_{6-10}$ aryloxy unsubstituted or substituted by $R_{21}$, or $C_{7-10}$ arylalkyl unsubstituted or substituted by $R_{21}$.

$R_{20}$ is halogen, oxo, $C_{1-6}$ alkyl, $-NH_2$, $-NH(C_{1-4}$ alkyl), $-N(C_{1-4}$ alkyl$)_2$, $-CONH_2$, $-CONH(C_{1-4}$ alkyl), $-CON(C_{1-4}$ alkyl$)_2$, $-NHCOH$, $-N(C_{1-4}$ alkyl)COH, $-N(C_{1-4}$ alkyl)$COC_{1-4}$ alkyl, $-NHCOC_{1-4}$ alkyl, $-C(O)H$, $-C(O)C_{1-4}$ alkyl, carboxy, $-C(O)O$ $C_{1-4}$ alkyl, hydroxyl, $C_{1-6}$ alkoxy, nitro, nitroso, azido, cyano, $-S(O)_{0-2}H$, $-S(O)_{0-2}C_{1-4}$ alkyl, $-SO_2NH_2$, $-SO_2NH(C_{1-4}$ alkyl), $-SO_2N(C_{1-4}$ alkyl$)_2$, $-NHSO_2H$, $-N(C_{1-4}$ alkyl)$SO_2H$, $-N(C_{1-4}$ alkyl)$SO_2C_{1-4}$ alkyl, $-NHSO_2C_{1-4}$ alkyl, $C_{6-10}$ aryl unsubstituted or substituted by $R_{17}$, $C_{6-10}$ aryloxy unsubstituted or substituted by $R_{17}$, or $C_{7-10}$ arylalkyl unsubstituted or substituted by $R_{17}$.

$R_{21}$ is halogen, $-NH_2$, $-NH(C_{1-4}$ alkyl), $-N(C_{1-4}$ alkyl$)_2$, $-CONH_2$, $-CONH(C_{1-4}$ alkyl), $-CON(C_{1-4}$ alkyl$)_2$, $-NHCOH$, $-N(C_{1-4}$ alkyl)COH, $-N(C_{1-4}$ alkyl)$COC_{1-4}$ alkyl, $-NHCOC_{1-4}$ alkyl, $-C(O)H$, $-C(O)C_{1-4}$ alkyl, carboxy, $-C(O)O$ $C_{1-4}$ alkyl, hydroxyl, $C_{1-4}$ alkoxy, nitro, nitroso, azido, cyano, $-S(O)_{0-2}H$, $-S(O)_{0-2}C_{1-4}$ alkyl, $-SO_2NH_2$, $-SO_2NH(C_{1-4}$ alkyl), —$SO_2N(C_{1-4}$ alkyl$)_2$, —$NHSO_2H$, —$N(C_{1-4}$ alkyl$)SO_2H$, —$N(C_{1-4}$ alkyl$)SO_2C_{1-4}$ alkyl, or —$NHSO_2C_{1-4}$ alkyl.

According to a further aspect of the invention, $R_3$ is $C_{1-12}$ alkyl (e.g., methyl or ethyl) unsubstituted or substituted one or more times by $R_{17}$, $C_{2-12}$ alkenyl (e.g., ethenyl or propenyl) unsubstituted or substituted one or more times by $R_{17}$, $C_{2-12}$ alkynyl (e.g., ethynyl or propynyl) unsubstituted or substituted one or more times by $R_{17}$, $C_{6-14}$ aryl (e.g., phenyl or naphthyl) which is unsubstituted or substituted one or more times by $R_{18}$, or $C_{7-16}$ aralkyl (e.g., benzyl, phenethyl, phenpropyl) unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{19}$, or 4-18 member heterocycle-alkyl unsubstituted or substituted one or more times by $R_{19}$.

According to a further aspect of the invention, Z is H, halogen, is $C_{1-6}$ alkyl (e.g., methyl or ethyl) unsubstituted or substituted one or more times by $R_{17}$, $C_{2-6}$ alkenyl (e.g., ethenyl or propenyl) unsubstituted or substituted one or more times by $R_{17}$, or $C_{2-6}$ alkynyl (e.g., ethynyl or propynyl) unsubstituted or substituted one or more times by $R_{17}$.

According to a further aspect of the invention, $R_4$ is H, $C_{1-6}$ alkyl (e.g., methyl or ethyl) which is unsubstituted or substituted one or more times by $R_{17}$, $C_{2-6}$ alkenyl (e.g., ethenyl or propenyl) which is unsubstituted or substituted one or more times by $R_{17}$, or $C_{2-6}$ alkynyl (e.g., ethynyl or propynyl) which is unsubstituted or substituted one or more times by $R_{17}$.

According to a further aspect of the invention, $R_5$ is H, $C_{1-6}$ alkyl (e.g., methyl or ethyl) which is unsubstituted or substituted one or more times by $R_{17}$, $C_{2-6}$ alkenyl (e.g., ethenyl or propenyl) which is unsubstituted or substituted one or more times by $R_{17}$, or $C_{2-6}$ alkynyl (e.g., ethynyl or propynyl) which is unsubstituted or substituted one or more times by $R_{17}$.

According to a further aspect of the invention, $R_6$ is H, $C_{1-12}$ alkyl (e.g., methyl or ethyl) which is unsubstituted or substituted one or more times by $R_{17}$, $C_{2-12}$ alkenyl (e.g., ethenyl or propenyl) which is unsubstituted or substituted one or more times by $R_{17}$, or $C_{2-12}$ alkynyl (e.g., ethynyl or propynyl) which is unsubstituted or substituted one or more times by $R_{17}$, $C_{6-14}$ aryl (e.g., phenyl or naphthyl) which is unsubstituted or substituted one or more times by $R_{18}$, $C_{7-16}$ aralkyl (e.g., benzyl, phenethyl, phenpropyl) which is unsubstituted or substituted one or more times by $R_{18}$, 5-12 member heteroaryl which is unsubstituted or substituted one or more times by $R_{19}$, 6-18 member heteroaralkyl which is unsubstituted or substituted one or more times by $R_{19}$, 3-12 member heterocycle which is unsubstituted or substituted one or more times by $R_{19}$, or 4-18 member heterocycle-alkyl which is unsubstituted or substituted one or more times by $R_{19}$.

According to a further aspect of the invention, $R_7$ is H, $C_{1-12}$ alkyl (e.g., methyl or ethyl) unsubstituted or substituted one or more times by $R_{17}$, $C_{2-12}$ alkenyl (e.g., ethenyl or propenyl) unsubstituted or substituted one or more times by $R_{17}$, $C_{2-12}$ alkynyl (e.g., ethynyl or propynyl) unsubstituted or substituted one or more times by $R_{17}$, $C_{6-14}$ aryl (e.g., phenyl or naphthyl) which is unsubstituted or substituted one or more times by $R_{18}$, or $C_{7-16}$ aralkyl (e.g., benzyl, phenethyl, phenpropyl) unsubstituted or substituted one or more times by $R_{18}$.

According to a further aspect of the invention, $R_8$ is H, $C_{1-12}$ alkyl (e.g., methyl or ethyl) unsubstituted or substituted one or more times by $R_{17}$, $C_{2-12}$ alkenyl (e.g., ethenyl or propenyl) unsubstituted or substituted one or more times by $R_{17}$, $C_{2-12}$ alkynyl (e.g., ethynyl or propynyl) unsubstituted or substituted one or more times by $R_{17}$, $C_{6-14}$ aryl (e.g., phenyl or naphthyl) which is unsubstituted or substituted one or more times by $R_{18}$, $C_{7-16}$ aralkyl (e.g., benzyl, phenethyl, phenpropyl) unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{19}$, or 4-18 member heterocycle-alkyl unsubstituted or substituted one or more times by $R_{19}$.

In one embodiment, Y is chosen from $COOR_9$, $COCOOR_9$, $CON(R_9)SO_2R_9$, $P(O)OR_aOR_b$, $S(O)_2OR_9$, tetrazole, $CON(R_9)CH(R_9)COOR_9$, $CONR_{10}R_{11}$, and $CONR_9OH$.

In a further embodiment, any of $R_a$, $R_b$, $R_9$, $R_{10}$, and $R_{11}$ are each independently chosen from H, optionally substituted $C_{1-6}$ alkyl, optionally substituted $C_{2-6}$ alkenyl and optionally substituted $C_{2-6}$ alkynyl.

According to a further aspect of the invention, $R_9$, $R_{10}$ and $R_{11}$, are each independently H, $C_{1-12}$ alkyl (e.g., methyl or ethyl) unsubstituted or substituted one or more times by $R_{17}$, $C_{2-12}$ alkenyl (e.g., ethenyl or propenyl) unsubstituted or substituted one or more times by $R_{17}$, $C_{2-12}$ alkynyl (e.g., ethynyl or propynyl) unsubstituted or substituted one or more times by $R_{17}$, $C_{6-14}$ aryl (e.g., phenyl or naphthyl) which is unsubstituted or substituted one or more times by $R_{18}$, or $C_{7-16}$ aralkyl (e.g., benzyl, phenethyl, phenpropyl) unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{19}$, or 4-18 member heterocycle-alkyl unsubstituted or substituted one or more times by $R_{19}$;

alternatively, $R_{10}$ and $R_{11}$ are taken together with the nitrogen atom to form a 3 to 10 member heterocycle unsubstituted or substituted one or more times by $R_{19}$ or 5-12 member heteroaryl unsubstituted or substituted one or more times by $R_{19}$.

According to a further aspect of the invention, $R_a$ and $R_b$ are each independently $C_{1-12}$ alkyl (e.g., methyl or ethyl) unsubstituted or substituted one or more times by $R_{17}$, $C_{2-12}$ alkenyl (e.g., ethenyl or propenyl) unsubstituted or substituted one or more times by $R_{17}$, $C_{2-12}$ alkynyl (e.g., ethynyl or propynyl) unsubstituted or substituted one or more times by $R_{17}$, $C_{6-14}$ aryl (e.g., phenyl or naphthyl) which is unsubstituted or substituted one or more times by $R_{18}$, or $C_{7-16}$ aralkyl (e.g., benzyl, phenethyl, phenpropyl) unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{19}$, or 4-18 member heterocycle-alkyl unsubstituted or substituted one or more times by $R_{19}$;

or $R_a$ and $R_b$ are taken together with the oxygen atom to form a 5 to 10 member heterocycle unsubstituted or substituted one or more times by $R_{19}$ or a 5-12 member heteroaryl unsubstituted or substituted one or more times by $R_{19}$.

In a further embodiment, $R_a$, $R_b$, $R_9$, $R_{10}$, and $R_{11}$ are each independently chosen from H and optionally substituted $C_{1-6}$ alkyl.

In a further embodiment, $R_a$, $R_b$, $R_9$, $R_{10}$, and $R_{11}$ are each independently chosen from H and methyl.

In a further embodiment, $R_a$, $R_b$, $R_9$, $R_{10}$, and $R_{11}$ are each H.

In one embodiment, Y is chosen from $COOR_9$, $CONR_{10}R_{11}$ and $CON(R_9)CH(R_9)$—$COOR_9$.

In a further embodiment, Y is chosen from $COOR_9$, $CONR_{10}R_{11}$ and $CONR_9CH_2COOR_9$.

In a further embodiment, Y is COOH.

In a further embodiment, Y is $CONH_2$.

In a further embodiment, Y is $CONHCH_2COOH$.

In a further embodiment, Y is $COOCH_3$.

According to a further aspect of the invention, $Y^1$ is a bond, $C_{1-6}$ alkyl (e.g., methyl or ethyl) which is unsubstituted or substituted one or more times by $R_{17}$, $C_{2-6}$ alkenyl (e.g., ethenyl or propenyl) which is unsubstituted or substituted one or more times by $R_{17}$, or $C_{2-6}$ alkynyl (e.g., ethynyl or propynyl) which is unsubstituted or substituted one or more times by $R_{17}$.

In further embodiments:

$R_3$ is chosen from H, optionally substituted $C_{1-12}$ alkyl, optionally substituted $C_{2-12}$ alkenyl, optionally substituted $C_{2-12}$ alkynyl, optionally substituted $C_{7-16}$ aralkyl, optionally substituted 5-12 member heteroaryl, optionally substituted 6-18 member heteroaralkyl, optionally substituted 3-12 member heterocycle, and optionally substituted 5-18 member heterocycle-alkyl;

$R_3$ is $C_{1-12}$ alkyl;

$R_3$ is $C_{3-12}$ cycloalkyl;

$R_3$ is $C_{7-16}$ aralkyl;

$R_3$ is 3-12 member heterocycle;

$R_3$ is 5-12 member heteroaryl;

$R_3$ is 5-7 member heterocycle, 5-7 member heteroaryl or $C_{5-7}$cycloalkyl which are optionally substituted; or $R_3$ is 6-7 member heterocycle, 5-7 heteroaryl or $C_{6-7}$cycloalkyl which are optionally substituted.

In a further embodiment, $R_3$ is chosen from H, methyl, ethyl, i-propyl, cyclopropyl, cyclohexyl, piperidinyl, $N(C_{1-6}$ alkyl)-piperidinyl (e.g., N-methyl-piperidinyl), piperazinyl, pyrrolidinyl, azetidinyl, aziridinyl, piperidinylmethyl, dioxanyl, hexahydrothiopyrany, methylazepanyl, $N(C_{1-6}$ alkyl)-piperidinylmethyl dioxolanyl, tetrahydrothiopyranyl, dioxolanylmethyl, dioxanylmethyl, and azepanyl; any of which can be optionally substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;

wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl, or $R_c$ and $R_d$ are taken together with the oxygens to form an optionally substituted 3 to 10 member heterocycle or an optionally substituted 5-12 member heteroaryl, or $R_{13}$ and $R_{14}$ are taken together with the nitrogen to form an optionally substituted 3 to 10 member heterocycle or an optionally substituted 5-12 member heteroaryl.

In a further embodiment, $R_3$ is chosen from allyl, pyridinyl, pyridinylmethyl, phenyl and benzyl; any of which can be optionally substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, and optionally substituted 4-18 member heterocycle-alkyl, hydroxyl, $NR_{13}R_{14}$, $C(O)OR_{12}$, cyano, azido, amidino and guanido;

wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl, or $R_c$ and $R_d$ are taken together with the oxygens to form an optionally substituted 3 to 10 member heterocycle or an optionally substituted 5-12 member heteroaryl, or $R_{13}$ and $R_{14}$ are taken together with the nitrogen to form an optionally substituted 3 to 10 member heterocycle or an optionally substituted 5-12 member heteroaryl.

In one embodiment, $R_3$ is cyclohexyl unsubstituted or substituted by one or more substituents independently chosen from halogen, $SO_2R_f$, $CONR_gR_h$, $C_{1-6}$ alkyl, $C_{7-12}$ aralkyl, $C_{6-12}$ aryl, $C_{1-6}$ alkyloxy, $C_{2-6}$ alkenyloxy, $C_{2-6}$ alkynyloxy, $C(O)C_{1-6}$ alkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_gR_h$, $C(O)OR_f$ and cyano;

wherein $R_f$, $R_g$ and $R_h$ in each case are independently H, $C_{1-6}$ alkyl, $C_{2-6}$ alkenyl, or $C_{2-6}$ alkynyl.

In one embodiment, $R_3$ is piperidinyl unsubstituted or substituted by one or more substituents independently chosen from halogen, $SO_2R_f$, $CONR_gR_h$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C(O)C_{1-6}$ alkyl, $C(O)NHR_f$, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_gR_h$, $C(O)OR_f$ and cyano;

wherein $R_f$, $R_g$ and $R_h$ in each case are independently H, $C_{1-6}$ alkyl, $C_{2-6}$ alkenyl, or $C_{2-6}$ alkynyl.

In one embodiment, $R_3$ is $N(C_{1-6}$ alkyl)-piperidinyl unsubstituted or substituted by one or more substituents independently chosen from halogen, $SO_2R_f$, $CONR_gR_h$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C(O)C_{1-6}$ alkyl, $C(O)NHR_f$, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_gR_h$, $C(O)OR_f$ and cyano;

wherein $R_f$, $R_g$ and $R_h$ in each case are independently H or $C_{1-6}$ alkyl.

In accordance with a further aspect of the invention, $R_3$ is $C_{1-12}$ alkyl (e.g., methyl, ethyl, i-propyl, cyclopropyl, cyclobutyl, cyclopentyl, cyclohexyl, or cycloheptyl, especially cyclohexyl) unsubstituted or substituted one or more times by $R_{17}$, or $C_{6-14}$ aryl (e.g., phenyl or naphthyl, especially phenyl) which is unsubstituted or substituted one or more times by $R_{18}$.

In one embodiment, $R_3$ is cyclohexyl, N-methyl-piperidinyl, N-ethyl-piperidinyl, N-propyl-piperidinyl, hexahydrothiopyranyl, azepanyl, methylazepanyl, tetrahydropyranyl, piperidinylmethyl, pyridinyl, pyridinylmethyl, tetrahydrothiopyranyl, dioxolanylmethyl, dioxanylmethyl, N-isopropyl-piperidinyl, N-butyl-piperidinyl, N-pentyl-piperidinyl, N-hexylpiperidinyl, N-cyclohexyl-piperidinyl, N-acetyl-piperidinyl, N-benzyl-piperidinyl, hydroxycyclohexyl, oxocyclohexyl, hydroxyiminocyclohexyl, aminocyclohexyl or methoxycyclohexyl.

In further embodiments:

$R_3$ is chosen from H, methyl, isopropyl, piperidinyl, piperidinylmethyl, dioxolanyl and cyclohexyl;

$R_3$ is cyclohexyl;

$R_3$ is N-methyl-4-piperidinyl;

$R_3$ is hydroxycyclohexyl;

$R_3$ is 4-hydroxycyclohexyl;

$R_3$ is methoxycyclohexyl;

$R_3$ is 4-methoxycyclohexyl;

$R_3$ is dioxolanyl;

$R_3$ is isopropyl;

$R_3$ is cyclopentyl;

$R_3$ is phenyl;

$R_3$ is H or methyl;

$R_3$ is H;

$R_3$ is methyl; or $R_3$ is benzyl, thiophenylmethyl, or furanylmethyl.

In additional embodiments:

$R_2$ is optionally substituted 3-6 member heterocycle or optionally substituted 5-7 member heteroaryl.

In a further embodiment, $R_2$ is chosen from thienyl, furanyl, pyridinyl, oxazolyl, thiazolyl, pyrrolyl, benzofuranyl, indolyl, benzoxazolyl, benzothienyl, benzothiazolyl, and quinolinyl, any of which can be optionally substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, $NR_{13}R_{14}$, $C(O)OR_{12}$, cyano, azido, amidino and guanido;

wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl, or $R_c$ and $R_d$ are taken together with the oxygens to form an optionally substituted 5 to 10 member heterocycle or an optionally substituted 5-12 member heteroaryl, or $R_{13}$ and $R_{14}$ are taken together with the nitrogen to form an optionally substituted 3 to 10 member heterocycle or an optionally substituted 5-12 member heteroaryl.

In a further embodiment, $R_2$ is chosen from piperazinyl and pyrrolidinyl any of which can be optionally substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;

wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl, or $R_c$ and $R_d$ are taken together with the oxygens to form an optionally substituted 5 to 10 member heterocycle or an optionally substituted 5-12 member heteroaryl, or $R_{13}$ and $R_{14}$ are taken together with the nitrogen to form an optionally substituted 3 to 10 member heterocycle or an optionally substituted 5-12 member heteroaryl.

In a further embodiment, $R_2$ is chosen from thienyl, furanyl, pyridinyl, pyrrolyl, indolyl, piperazinyl and benzothienyl.

In a further embodiment, $R_2$ is $C_{1-12}$ alkyl optionally substituted.

In a further embodiment, $R_2$ is $C_{3-12}$ cycloalkyl optionally substituted.

In a further embodiment, $R_2$ is $C_{5-12}$ cycloalkyl optionally substituted.

In a further embodiment, $R_2$ is $C_{5-7}$ cycloalkyl optionally substituted.

In one embodiment, $R_2$ is optionally substituted $C_{6-7}$cycloalkyl.

In one embodiment, $R_2$ is optionally substituted $C_6$cycloalkyl.

In a further embodiment, $R_2$ is chosen from cyclopropyl, cyclobutyl, cyclopentyl, cyclopentenyl cyclohexyl, cycloheptyl, 2-(cyclopentyl)-ethyl, methyl, ethyl, vinyl, propyl, propenyl, isopropyl, butyl, butenyl isobutyl, pentyl, neopentyl or t-butyl any of which can be optionally substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;

wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 3-18 member heteroaralkyl, and $C_{7-18}$ aralkyl, or Rc and Rd are taken together with the oxygen atoms to form an optionally substituted 5 to 10 member heterocycle or an optionally substituted 5-12 member heteroaryl, or $R_{13}$ and $R_{14}$ are taken together with the nitrogen atom to form an optionally substituted 3 to 10 member heterocycle or an optionally substituted 5-12 member heteroaryl.

In a further embodiment, $R_2$ is cyclohexyl unsubstituted or substituted by one or more substituents independently chosen from halogen, nitro, nitroso, $SO_3R_f$, $SO_2R_f$, $PO_3R_cR_d$, $CONR_gR_h$, $C_{1-6}$ alkyl, $C_{7-12}$ aralkyl, $C_{6-12}$ aryl, $C_{1-6}$ alkyloxy $C_{6-12}$ aryloxy, $C(O)C_{1-6}$ alkyl, $C(O)C_{6-12}$ aryl, $C(O)C_{7-12}$ aralkyl, $C(O)NHR_f$ optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_gR_h$, $C(O)OR_f$ cyano, azido, amidino and guanido;

wherein $R_f$, $R_c$, $R_d$, $R_g$ and $R_h$ in each case are independently H, $C_{1-6}$ alkyl, $C_{2-6}$ alkenyl, $C_{2-6}$ alkynyl, $C_{6-10}$ aryl, optionally substituted 5-12 member heteroaryl, optionally substituted 6-18 member heteroaralkyl, optionally substituted 3-12 member heterocycle, optionally substituted 4-18 member heterocycle-alkyl or $C_{6-10}$ aralkyl.

In still a further embodiment, $R_2$ is cyclohexyl unsubstituted or substituted by one or more substituents independently chosen from halogen, $SO_2R_f$, $CONR_gR_h$, $C_{1-6}$ alkyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{6-12}$ aryl, $C(O)C_{7-12}$ aralkyl, $C(O)NHR_f$ optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_gR_h$, $C(O)OR_f$, cyano and azido;

wherein $R_f$, $R_g$ and $R_h$ in each case are independently H, $C_{1-6}$ alkyl, $C_{6-10}$ aryl, optionally substituted 5-12 member heteroaryl, optionally substituted 6-18 member heteroaralkyl, optionally substituted 3-12 member heterocycle, optionally substituted 4-18 member heterocycle-alkyl, $C_{7-12}$ aralkyl or $C_{6-10}$ aralkyl.

In one embodiment, $R_2$ is cyclohexyl substituted by one or more substituents independently chosen from $C_{1-6}$ alkyl, halogen, $C_{2-6}$ alkenyl, $C_{2-6}$ alkynyl or $C_{1-6}$ alkyloxy, $C_{2-6}$ alkenyloxy, and $C_{2-6}$ alkynyloxy.

In accordance with a further aspect of the invention, $R_2$ is $C_{3-12}$ cycloalkyl (e.g., cyclopropyl, cyclobutyl, cyclopentyl, cyclohexyl, or cycloheptyl, especially cyclohexyl) unsubstituted or substituted one or more times by $R_{17}$, or $C_{6-14}$ aryl (e.g., phenyl or naphthyl, especially phenyl) which is unsubstituted or substituted one or more times by $R_{18}$.

In further embodiments:
$R_2$ is cyclohexyl substituted by $C_{1-6}$ alkyl;
$R_2$ is cyclohexyl substituted by $C_{1-3}$ alkyl;
$R_2$ is 4-methyl-cyclohexyl or 2-hydroxy-4-methyl-cyclohexyl; or
$R_2$ is 4-methylcyclohexyl.

In one embodiment, $R_2$ is chosen from optionally substituted $C_{6-14}$ aryl, optionally substituted 5-12 member heteroaryl, optionally substituted 6-18 member heteroaralkyl, optionally substituted 3-12 member heterocycle, and optionally substituted 4-18 member heterocycle-alkyl, and $C_{7-12}$ aralkyl.

In a further embodiment, $R_2$ is chosen from a $C_{6-12}$ aryl, 3-10 member heterocycle and 5-10 member heteroaryl which in each case are optionally substituted.

In a further embodiment, $R_2$ is a $C_6$ aryl, a 3-6 member heterocycle or 5-7 member heteroaryl which in each case is optionally substituted.

In a further embodiment, $R_2$ is optionally substituted $C_{6-12}$ aryl.

In a further embodiment, $R_2$ is an aryl chosen from indenyl, naphthyl and biphenyl which is in each case optionally substituted.

In a further embodiment, $R_2$ is phenyl substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, $NR_{13}R_{14}$, $C(O)OR_{12}$, cyano, azido, amidino and guanido;

wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, optionally substituted 5-12 member heteroaryl, optionally substituted 6-18 member heteroaralkyl, optionally substituted 3-12 member heterocycle, optionally substituted 4-18 member heterocycle-alkyl, and $C_{7-18}$ aralkyl, or $R_c$ and $R_d$ are taken together with the oxygen atoms to form an optionally substituted 5 to 10 member heterocycle or an optionally substituted 5-12 member heteroaryl, or $R_{13}$ and $R_{14}$ are taken together with the nitrogen atom to form an optionally substituted 3 to 10 member heterocycle or an optionally substituted 5-12 member heteroaryl.

In a further embodiment, $R_2$ is phenyl substituted by one or more substituents chosen from halogen, nitro, $CONR_{13}R_{14}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, $NR_{13}R_{14}$, $C(O)OR_{12}$, cyano, and azido;

wherein $R_{12}$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl, or $R_{13}$ and $R_{14}$ are taken together with the nitrogen to form an optionally substituted 3 to 10 member heterocycle or an optionally substituted 5-12 member heteroaryl.

In a further embodiment, $R_2$ is phenyl substituted by one or two substituents chosen from halogen, $C_{1-6}$ alkyl, $NR_{13}R_{14}$, nitro, $CONR_{13}R_{14}$, $C(O)OC_{1-6}$ alkyl, COOH or $C_{1-6}$ alkyloxy, $C_{2-6}$ alkenyloxy, $C_{2-6}$ alkynyloxy $C(O)OR_{12}$, cyano, and azido;

wherein $R_{12}$, $R_{13}$ and $R_{14}$ are each independently chosen from H, $C_{1-12}$ alkyl, $C_{2-12}$ alkenyl, $C_{2-12}$ alkynyl, $C_{6-14}$ aryl optionally substituted 5-12 member heteroaryl, optionally substituted 6-18 member heteroaralkyl, optionally substituted 3-12 member heterocycle, optionally substituted 4-18 member heterocycle-alkyl, and $C_{7-18}$ aralkyl;

or $R_{13}$ and $R_{14}$ are taken together with the nitrogen to form an optionally substituted 3 to 10 member heterocycle or an optionally substituted 5-12 member heteroaryl.

In a further embodiment, $R_2$ is chosen from phenyl, pyridinyl, thiophenyl, benzofuran, thiazole, and pyrazole, which are unsubstituted or substituted with at least one substituent chosen from a halogen, $C_{1-6}$ alkyl, $C_{1-6}$ alkyloxy, $C_{2-6}$ alkenyloxy, $C_{2-6}$ alkynyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a $C_{3-8}$ heterocycle.

In a further embodiment, $R_2$ is chosen from thienyl, furanyl, pyridyl, oxazolyl, thiazolyl, pyrrolyl, benzofuranyl, indolyl, benzoxazolyl, benzothienyl, benzothiazolyl and quinolinyl, any of which can be substituted by at least one substituent chosen from $C_{1-6}$ alkyl, amino, halogen, nitro, amido, CN, $COOC_{1-6}$ alkyl, $C_{1-6}$ alkyloxy, $C_{2-6}$ alkenyloxy, and $C_{2-6}$ alkynyloxy.

In a further embodiment, $R_2$ is methylphenyl.

In a further embodiment, $R_2$ is dichlorophenyl.

In a further embodiment, $R_1$ is chosen from optionally substituted $C_{3-12}$ cycloalkyl, optionally substituted $C_{4-12}$ cycloalkenyl, optionally substituted —C(O)—$C_{3-12}$ cycloalkyl, optionally substituted —C(O)—$C_{4-12}$ cycloalkenyl, optionally substituted 5 to 12 member spiroheterocycloalkyl, and optionally substituted 8 to 12 member spiroheterocycloalkenyl; provided that the spiroheterocycloalkyl or spiroheterocycloalkenyl moiety comprises a cycloalkyl or cycloalkenyl moiety directly attached to position 5 of the compound of formula I.

In one embodiment $R_1$ is chosen from optionally substituted $C_{3-12}$ cycloalkyl, optionally substituted $C_{4-12}$ cycloalkenyl, and optionally substituted 5 to 12 member spiroheterocycloalkyl provided that the spiroheterocycloalkyl moiety comprises a cycloalkyl moiety directly attached to position 5 of the compound of formula I.

In one embodiment $R_1$ is chosen from optionally substituted $C_{3-12}$ cycloalkyl, optionally substituted $C_{4-12}$ cycloalkenyl, and optionally substituted 9 to 12 member spiroheterocycloalkyl provided that the spiroheterocycloalkyl moiety comprises a cycloalkyl moiety directly attached to position 5 of the compound of formula I.

In one embodiment $R_1$ is chosen from optionally substituted $C_{3-12}$ cycloalkyl, optionally substituted $C_{4-12}$ cycloalkenyl, and optionally substituted 9 to 11 member spiroheterocycloalkyl provided that the spiroheterocycloalkyl moiety comprises a cycloalkyl moiety directly attached to position 5 of the compound of formula I.

In one embodiment $R_1$ is chosen from optionally substituted $C_{3-12}$ cycloalkyl, and optionally substituted $C_{4-12}$ cycloalkenyl.

In accordance with a further aspect of the invention, $R_1$ is $C_{3-12}$ cycloalkyl (e.g., cyclopropyl, cyclobutyl, cyclopentyl, cyclohexyl, or cycloheptyl, especially cyclohexyl) unsubstituted or substituted one or more times by $R_{17}$, or $C_{4-12}$ cycloalkenyl (e.g., cyclopentenyl, cyclohexenyl, cycloheptenyl, cyclooctenyl, especially cyclohexenyl) which is unsubstituted or substituted one or more times by $R_{17}$.

In a further embodiment $R_1$ is chosen from optionally substituted $C_{3-10}$ cycloalkyl or optionally substituted $C_{4-10}$ cycloalkenyl.

In a further embodiment $R_1$ is chosen from optionally substituted $C_{3-7}$ cycloalkyl or optionally substituted $C_{4-7}$ cycloalkenyl.

In a further embodiment, $R_1$ is $C_{5-7}$ cycloalkyl or $C_{5-7}$ cycloalkenyl which are each unsubstituted or substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;
wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl,
or $R_c$ and $R_d$ are taken together with the oxygens to form an optionally substituted 5 to 10 member heterocycle or an optionally substituted 5-12 member heteroaryl,
or $R_{13}$ and $R_{14}$ are taken together with the nitrogen to form an optionally substituted 3 to 10 member heterocycle or an optionally substituted 5-12 member heteroaryl.

In a further embodiment, $R_1$ is $C_{5-7}$ cycloalkyl or $C_{5-7}$ cycloalkenyl which are each unsubstituted or substituted by one or more substituents chosen from halogen, nitro, nitroso, $CONR_{13}R_{14}$, $C_{1-6}$ alkyl, $C_{2-6}$ alkenyl, $C_{1-6}$ alkyloxy, $C_{2-6}$ alkenyloxy, $C(O)C_{1-6}$ alkyl, $C(O)C_{2-6}$ alkenyl, hydroxyl, oxo, oxime, $NR_{13}R_{14}$, $C(O)OR_{12}$, cyano, azido, amidino and guanido;
wherein $R_{12}$, $R_{13}$ and $R_{14}$ are each independently chosen from H, $C_{1-12}$ alkyl, $C_{2-12}$ alkenyl, and $C_{2-12}$ alkynyl.

In yet a further embodiment, $R_1$ is chosen from cyclopropyl, cyclobutyl, cyclopentyl, cyclohexyl cycloheptyl, cyclooctanyl, cyclocyclononanyl, cyclodecanyl, cycloundecanyl, cyclopentenyl, cyclohexenyl, cycloheptenyl, cyclooctenyl, cyclocyclononenyl, cyclodecenyl, cycloundecenyl, cyclopentadienyl, cyclohexadienyl, cycloheptadienyl, cyclooctadienyl, cyclodadienyl, cycloundecadienyl, bicyclohexyl, bicycloheplanyl, bicycloolanyl, bicyclocyclononanyl, bicyclodecanyl, bicycloundecanyl, bicyclohexenyl, bicycloheptenyl, bicyclooctenyl, bicyclocyclononenyl, bicyclodecenyl, and bicycloundecenyl;
each of which is unsubstituted or substituted by one or more substituent chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;
wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl,
or $R_c$ and $R_d$ are taken together with the oxygens to form an optionally substituted 5 to 10 member heterocycle or an optionally substituted 5-12 member heteroaryl,
or $R_{13}$ and $R_{14}$ are taken together with the nitrogen to form an optionally substituted 3 to 10 member heterocycle or an optionally substituted 5-12 member heteroaryl.

In yet a further embodiment, $R_1$ is chosen from cyclopropyl, cyclobutyl, cyclopentyl, cyclohexyl cycloheptyl, cyclooctanyl, cyclocyclononanyl, cyclodecanyl, cycloundecanyl, cyclopentenyl, cyclohexenyl, cycloheptenyl, cyclooctenyl, cyclocyclononenyl cyclodecenyl, cycloundecenyl, cyclopentadienyl, cyclohexadienyl, cycloheptadienyl, cyclooctadienyl, cyclodadienyl, cycloundecadienyl, bicyclohexyl, bicycloheplanyl, bicycloolanyl, bicyclocyclononanyl, bicyclodecanyl, bicycloundecanyl, bicyclohexenyl, bicycloheptenyl, bicyclooctenyl, bicyclocyclononenyl, bicyclodecenyl, and bicycloundecenyl; each optionally substituted.

In yet a further embodiment, $R_1$ is chosen from cyclopentyl, cyclohexyl cycloheptyl, cyclooctanyl, cyclopentenyl, cyclohexenyl, cycloheptenyl, cyclooctenyl, cyclopentadienyl, cyclohexadienyl, cycloheptadienyl, cyclooctadienyl, bicyclohexyl, bicycloheplanyl, bicycloolanyl, bicyclocyclononanyl, bicyclodecanyl, bicycloundecanyl, bicyclohexenyl, bicycloheptenyl, bicyclooctenyl, bicyclocyclononenyl, bicyclodecenyl, and bicycloundecenyl;
each of which is unsubstituted or substituted by one or more substituent chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;
wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl,
or $R_c$ and $R_d$ are taken together with the oxygens to form an optionally substituted 5 to 10 member heterocycle or an optionally substituted 5-12 member heteroaryl,
or $R_{13}$ and $R_{14}$ are taken together with the nitrogen to form an optionally substituted 3 to 10 member heterocycle or an optionally substituted 5-12 member heteroaryl.

In yet a further embodiment, $R_1$ is chosen from cyclopentyl, cyclohexyl, cycloheptyl, cyclooctanyl, cyclopentenyl, cyclohexenyl, cycloheptenyl, cyclooctenyl, cyclopentadienyl, cyclohexadienyl, cycloheptadienyl, cyclooctadienyl, bicyclohexyl, bicycloheplanyl, bicycloolanyl, bicyclocyclononanyl, bicyclodecanyl, bicycloundecanyl, bicyclohexenyl, bicycloheptenyl, bicyclooctenyl, bicyclocyclononenyl, bicyclodecenyl, and bicycloundecenyl; each optionally substituted.

In yet a further embodiment, $R_1$ is chosen from cyclopentyl, cyclohexyl, cycloheptyl, cyclooctanyl, cyclopentenyl, cyclohexenyl, cycloheptenyl, cyclooctenyl, bicyclohexyl, bicycloheplanyl, bicycloolanyl, bicyclocyclononanyl, bicyclodecanyl, and bicycloundecanyl;

each of which is unsubstituted or substituted by one or more substituent chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;

wherein $R_{12}$, $R_c$, $R_d$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl, or $R_c$ and $R_d$ are taken together with the oxygens to form an optionally substituted 5 to 10 member heterocycle or an optionally substituted 5-12 member heteroaryl, or $R_{13}$ and $R_{14}$ are taken together with the nitrogen to form an optionally A substituted 3 to 10 member heterocycle or an optionally substituted 5-12 member heteroaryl.

In yet a further embodiment, $R_1$ is chosen from cyclopentyl, cyclohexyl cycloheptyl, cyclooctanyl, cyclopentenyl, cyclohexenyl, cycloheptenyl, cyclooctenyl, bicyclohexyl, bicycloheplanyl, bicycloolanyl, bicyclocyclononanyl, bicyclodecanyl, bicycloundecanyl; each optionally substituted.

In yet a further embodiment, $R_1$ is chosen from optionally substituted cyclohexyl (e.g., substituted by $R_{17}$) and optionally substituted cyclohexenyl (e.g., substituted by $R_{17}$).

In accordance with a further aspect of the invention, when $R_1$ is cycloalkenyl, the cycloalkenyl ring preferably has one double bond. In addition, when $R_1$ is cycloalkenyl, the cycloalkenyl ring preferably has one double bond which is between the carbons in positions 1 and 2 of the ring.

In accordance with a further aspect of the invention,
X is

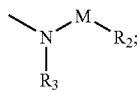

M is

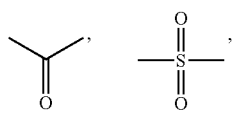

or a bond;

$R_3$ is $C_{1-12}$ alkyl (e.g., methyl, ethyl, i-propyl, cyclopropyl, cyclobutyl, cyclopentyl, cyclohexyl, or cycloheptyl, especially cyclohexyl) unsubstituted or substituted one or more times by $R_{17}$, or $C_{6-14}$ aryl (e.g., phenyl or naphthyl, especially phenyl) which is unsubstituted or substituted one or more times by $R_{18}$;

$R_2$ is $C_{3-12}$ cycloalkyl (e.g., cyclopropyl, cyclobutyl, cyclopentyl, cyclohexyl, or cycloheptyl, especially cyclohexyl) unsubstituted or substituted one or more times by $R_{17}$, or $C_{6-12}$ aryl (e.g., phenyl or naphthyl, especially phenyl) which is unsubstituted or substituted one or more times by $R_{18}$; and $R_1$ is $C_{3-12}$ cycloalkyl (e.g., cyclopropyl, cyclobutyl, cyclopentyl, cyclohexyl, or A cycloheptyl, especially cyclohexyl) unsubstituted or substituted one or more times by $R_{17}$, or $C_{4-12}$ cycloalkenyl (e.g., cyclopentenyl, cyclohexenyl, cycloheptenyl, cyclooctenyl, especially cyclohexenyl) which is unsubstituted or substituted one or more times by $R_{17}$.

According to an aspect of the invention, the compounds of the invention are selected from:

| Compound # | Name |
|---|---|
| 1 | 5-Cyclohex-1-enyl-3-[(trans-4-hydroxy-cyclohexyl)-(trans-4-methyl-cyclohexanecarbonyl)-amino]-thiophene-2-carboxylic acid; |
| 2 | 5-Cyclohexyl-3-[(trans-4-hydroxy-cyclohexyl)-(trans-4-methyl-cyclohexanecarbonyl)-amino]-thiophene-2-carboxylic acid; |
| 3 | 5-Cyclopent-1-enyl-3-[(trans-4-hydroxy-cyclohexyl)-(trans-4-methyl-cyclohexanecarbonyl)-amino]-thiophene-2-carboxylic acid; |
| 4 | 3-[(trans-4-Hydroxy-cyclohexyl)-(trans-4-methyl-cyclohexanecarbonyl)-amino]-5-(4-methyl-cyclohex-1-enyl)-thiophene-2-carboxylic acid; |
| 5 | 5-Cyclohept-1-enyl-3-[(trans-4-hydroxy-cyclohexyl)-(trans-4-methyl-cyclohexanecarbonyl)-amino]-thiophene-2-carboxylic acid; |
| 6 | 5-Cycloheptyl-3-[(trans-4-hydroxy-cyclohexyl)-(trans-4-methyl-cyclohexanecarbonyl)-amino]-thiophene-2-carboxylic acid; |
| 7 | 5-Cyclohex-1-enyl-3-[isopropyl-(trans-4-methyl-cyclohexanecarbonyl)-amino]-thiophene-2-carboxylic acid; |
| 8 | 5-Cyclohex-1-enyl-3-[(trans-4-methyl-cyclohexanecarbonyl)-(4-oxo-cyclohexyl)-amino]-thiophene-2-carboxylic acid; |
| 9 | 5-Cyclohex-1-enyl-3-[(cis-4-hydroxy-cyclohexyl)-(trans-4-methyl-cyclohexanecarbonyl)-amino]-thiophene-2-carboxylic acid; |
| 10 | 5-Cyclohex-1-enyl-3-[(trans-4-methyl-cyclohexanecarbonyl)-phenyl-amino]-thiophene-2-carboxylic acid; |
| 11 | 5-Cyclohex-1-enyl-3-[cyclohexyl-(4-methyl-cyclohexanecarbonyl)-amino]-thiophene-2-carboxylic acid; (e.g 5-Cyclohex-1-enyl-3-[cyclohexyl-(trans-4-methyl-cyclohexanecarbonyl)-amino]-thiophene-2-carboxylic acid) |
| 12 | 5-Cyclohex-1-enyl-3-[(trans-4-methoxy-cyclohexyl)-(4-methyl-cyclohexanecarbonyl)-amino]-thiophene-2-carboxylic acid; (e.g. 5-Cyclohex-1-enyl-3-[(trans-4-methoxy-cyclohexyl)-(trans-4-methyl-cyclohexanecarbonyl)-amino]-thiophene-2-carboxylic acid;)- |
| 13 | 5-(4-Tert-butyl-cyclohex-1-enyl)-3-[(4-hydroxy-cyclohexyl)-(4-methyl-cyclohexanecarbonyl)-amino]-thiophene-2-carboxylic acid; (e.g. 5-(4-Tert-butyl-cyclohex-1-enyl)-3-[(trans-4-hydroxy-cyclohexyl)-(trans-4-methyl-cyclohexanecarbonyl)-amino]-thiophene-2-carboxylic acid;)- |
| 14 | 5-(1,4,Dioxa-spiro[4.5.]dec-7-en-8-yl)-3-[(4-hydroxy-cyclohexyl)-(4-methyl-cyclohexanecarbonyl)-amino]-thiophene-2-carboxylic acid; (e.g. 5-(1,4,Dioxa-spiro[4.5.]dec-7-en-8-yl)-3-[(trans-4-hydroxy-cyclohexyl)-(trans-4-methyl-cyclohexanecarbonyl)-amino]-thiophene-2-carboxylic acid); |
| 15 | 5-Cyclopent-1-enyl-3-[(2,4-dichloro-benzoyl)-isopropyl-amino]-thiophene-2-carboxylic acid; |
| 16 | 5-Cyclopent-1-enyl-3-[(4-hydroxy-cyclohexyl)-(4-methyl-cyclohexanecarbonyl)-amino]-thiophene-2-carboxylic acid; (e.g. 5-Cyclopent-1-enyl-3-[(trans-4-hydroxy-cyclohexyl)-(trans-4-methyl-cyclohexanecarbonyl)-amino]-thiophene-2-carboxylic acid) |
| 17 | 5-(4,4-dimethyl-cyclohexyl)-3-[(cis-4-methoxy-cyclohexyl)-(trans-4-methyl-cyclohexanecarbonyl)-amino]-thiophene-2-carboxylic acid;- |

| Compound # | Name |
|---|---|
| 18 | Morpholine-4-carboxylic acid; 4-[(2-carboxy-5-cyclohex-1-enyl-thiophene-yl)-(4-methyl-cyclohexanecarbonyl)-amino]-cyclohexyl ester; (e.g 5-Cyclohex-1-enyl-3-[[trans-4-morpholinocarbamoyloxy)-cyclohexyl]-(trans-4-methyl-cyclohexanecarbonyl)-amino]-thiophene-2-carboxylic acid); |
| 19 | 5-Cyclohex-1-enyl-3-[[4-(1-methoxy2-methyl-propylcarbamoyloxy)-cyclohexyl]-(4-methyl-cyclohexanecarbonyl)-amino]-thiophene-2-carboxylic acid; (e.g. 5-Cyclohex-1-enyl-3-[[trans-4-(1-methoxycarbonyl-2-methyl-propylcarbamoyloxy)-cyclohexyl]-(trans-4-methyl-cyclohexanecarbonyl)-amino]-thiophene-2-carboxylic acid); |
| 20 | 5-(4,4-Dimethyl-cyclohex-1-enyl)-3-[(4-methoxy-cyclohexyl)-(4-methyl-cyclohexanecarbonyl)-amino]-thiophene-2-carboxylic acid; (e.g. 5-(4,4-Dimethyl-cyclohex-1-enyl)-3-[(trans-4-methoxy-cyclohexyl)-(trans-4-methyl-cyclohexanecarbonyl)-amino]-thiophene-2-carboxylic acid); |
| 21 | 5-(4,4-Dimethyl-cyclohexyl)-3-[(4-methoxy-cyclohexyl)-(4-methyl-cyclohexanecarbonyl)-amino]-thiophene-2-carboxylic acid; (e.g. 5-(4,4-Dimethyl-cyclohexyl)-3-[(trans-4-methoxy-cyclohexyl)-(trans-4-methyl-cyclohexanecarbonyl)-amino]-thiophene-2-carboxylic acid); |
| 22 | 5-Cyclohex-1-enyl-3-[(4-ethoxy-cyclohexyl)-(4-methyl-cyclohexanecarbonyl)-amino]-thiophene-2-carboxylic acid; (e.g 5-Cyclohex-1-enyl-3-[(trans-4-ethoxy-cyclohexyl)-(trans-4-methyl-cyclohexanecarbonyl)-amino]-thiophene-2-carboxylic acid); |
| 23 | 5-Cyclohex-1-enyl-3-[(cis-4-methoxy-cyclohexyl)-(4-methyl-cyclohexanecarbonyl)-amino]-thiophene-2-carboxylic acid (e.g., 5-Cyclohex-1-enyl-3-[(cis-4-methoxy-cyclohexyl)-(4-trans-methyl-cyclohexanecarbonyl)-amino]-thiophene-2-carboxylic acid); |
| 24 | 5-Cyclohex-1-enyl-3-[(4-methoxymethoxy-cyclohexyl)-(4-methyl-cyclohexanecarbonyl)-amino]-thiophene-2-carboxylic acid; (e.g. 5-Cyclohex-1-enyl-3-[(trans-4-methoxymethoxy-cyclohexyl)-(trans-4-methyl-cyclohexanecarbonyl)-amino]-thiophene-2-carboxylic acid); |
| 25 | 3-[(4-trans-hydroxy-cyclohexyl)-(4-trans-methyl-cyclohexanecarbonyl)-amino]-5-(4-oxo-cyclohex-1-enyl)-thiophene-2-carboxylic acid; |
| 26 | 5-{4-benzyloxyimino-cyclohex-1-enyl}-3-[(4-trans-hydroxy-cyclohexyl)-(4-trans-methyl-cyclohexanecarbonyl)-amino]-thiophene-2-carboxylic acid; |
| 27 | 5-{4-ethoxyimino-cyclohex-1-enyl}-3-[(4-trans-hydroxy-cyclohexyl)-(4-trans-methyl-cyclohexanecarbonyl)-amino]-thiophene-2-carboxylic acid; |
| 28 | 5-bicyclo[2.2.1]hept-2-en-2-yl-3-[(4-trans-hydroxy-cyclohexyl)-(4-trans-methyl-cyclohexanecarbonyl)-amino]-thiophene-2-carboxylic acid; |
| 29 | 5-cyclohex-1-enyl-3-[(trans-4-methyl-cyclohexanecarbonyl)-(tetrahydro-pyran-4-yl)-amino]-thiophene-2-carboxylic acid; |
| 30 | 5-cyclohex-1-enyl-3-[[1,3]dioxan-5-yl-(trans-4-methyl cyclohexanecarbonyl)-amino]-thiophene-2-carboxylic acid; |
| 31 | 5-cyclohex-1-enyl-3-[(2,4-dichloro-benzoyl)-isopropyl-amino]-thiophene-2-carboxylic acid; |
| 32 | 5-cyclohex-1-enyl-3-[(1,3-dimethyl-2,4-dioxo-1,3-diaza-spiro[4.5]dec-8-yl)-(trans-4-methyl-cyclohexanecarbonyl)-amino]-thiophene-2-carboxylic acid; |
| 33 | 3-[(trans-4-hydroxy-cyclohexyl)-(trans-4-methyl-cyclohexanecarbonyl)-amino]-5-(4-phenoxy-cyclohex-1-enyl)-thiophene-2-carboxylic acid; |
| 34 | RS-5-(4-hydroxy-cyclohex-1-enyl)-3-[(4-trans-hydroxy-cyclohexyl)-(4-trans-methyl-cyclohexanecarbonyl)-amino]-thiophene-2-carboxylic acid; |
| 35 | 5-(4,4-dimethyl-cyclohex-1-enyl)-3-[(trans-4-hydroxy-cyclohexyl)-(trans-4-methyl-cyclohexanecarbonyl)-amino]-thiophene-2-carboxylic acid; |
| 36 | 5-cyclohex-1-enyl-3-[(trans-4-methyl-cyclohexanecarbonyl)-(2-methyl-[1,3]dioxan-5-yl)-amino]-thiophene-2-carboxylic acid; |
| 37 | 5-cyclohex-1-enyl-3-[methyl-(trans-4-methyl-cyclohexanecarbonyl)-amino]-thiophene-2-carboxylic acid; |
| 38 | 5-cyclohex-1-enyl-3-[(4,4-dimethyl-cyclohexyl)-(trans-4-methyl-cyclohexanecarbonyl)-amino]-thiophene-2-carboxylic acid; |
| 39 | 5-cyclohex-1-enyl-3-[(trans-4-methyl-cyclohexanecarbonyl)-(3-methyl-cyclohexyl)-amino]-thiophene-2-carboxylic acid; |
| 40 | 3-[bicyclo[3.2.1]oct-3-yl-(trans-4-methylcyclohexanecarbonyl)-amino]-5-cyclohex-1-enyl-thiophene-2-carboxylic acid; |
| 41 | 5-cyclohex-1-enyl-3-[(trans-4-methyl-cyclohexanecarbonyl)-(cis 4-[1,2,4]triazol-1-yl-cyclohexyl)-amino]-thiophene-2-carboxylic acid; |
| 42 | 5-cyclohex-1-enyl-3-[(trans-4-methyl-cyclohexanecarbonyl)-(tetrahydrothiopyran-4-yl)-amino]-thiophene-2-carboxylic acid; |
| 43 | 3-[isopropyl-(trans-4-methyl-cyclohexanecarbonyl)-amino]-5-(4-methyl-cyclohex-1-enyl)-thiophene-2-carboxylic acid; |
| 44 | 3-[(4-trans-tert-butyl-cyclohexyl)-(4-trans-methyl-cyclohexanecarbonyl)-amino]-5-cyclohex-1-enyl-thiophene-2-carboxylic acid; |
| 45 | 3-[(4-cis-tert-butyl-cyclohexyl)-(4-trans-methyl-cyclohexanecarbonyl)-amino]-5-cyclohex-1-enyl-thiophene-2-carboxylic acid; |
| 46 | 5-cyclohept-1-enyl-3-[cyclohexyl-(4-trans-methyl-cyclohexanecarbonyl)-amino]-thiophene-2-carboxylic acid; |
| 47 | RS-3-[cyclohexyl-(4-trans-methyl-cyclohexanecarbonyl)-amino]-5-(4-methyl-cyclohex-1-enyl)-thiophene-2-carboxylic acid; |
| 48 | 5-cyclohex-1-enyl-3-[(trans-4-methylcyclohexanecarbonyl)-(trans-4-[1,2,4]triazol-1-yl-cyclohexyl)-amino]-thiophene-2-carboxylic acid; hydrochloride |
| 49 | 3-[(cis-4-cyanocyclohexyl)-(trans-4-methylcyclohexanecarbonyl)-amino]-5-cyclohex-1-enyl-thiophene-2-carboxylic acid; |
| 50 | 3-[(trans-4-cyanocyclohexyl)-(trans-4-methyl-cyclohexanecarbonyl)-amino]-5-cyclohex-1-enyl-thiophene-2-carboxylic acid; |
| 51 | 5-cyclohex-1-enyl-3-[cyclopropyl-(trans-4-methyl-cyclohexanecarbonyl)-amino]-thiophene-2-carboxylic acid; |
| 52 | 5-cyclohex-1-enyl-3-[(trans-4-methyl-cyclohexanecarbonyl)-(trans-4-methyl-cyclohexyl)-amino]-thiophene-2-carboxylic acid; |
| 53 | 5-cyclohex-1-enyl-3-[(trans-4-methyl-cyclohexanecarbonyl)-(cis-4-methyl-cyclohexyl)-amino]-thiophene-2-carboxylic acid; |
| 54 | 5-cyclohex-1-enyl-3-[(4-ethoxyimino-cyclohexyl)-(trans-4-methyl-cyclohexanecarbonyl)-amino]-thiophene-2-carboxylic acid; |
| 55 | 5-(3-hydroxy-cyclohex-1-enyl)-3-{(trans-4-methyl-cyclohexanecarbonyl)-[trans-4-(tetrahydro-pyran-2-yloxy)-cyclohexyl]-amino}-thiophene-2-carboxylic acid; |
| 56 | 4-[(2-carboxy-5-cyclohex-1-enyl-thiophen-3-yl)-(trans-4-methyl-cyclohexanecarbonyl)-amino]-1-methyl-piperidinium |
| 57 | 5-cyclohex-1-enyl-3-[(cis-4-fluoro-cyclohexyl)-(trans-4-methyl-cyclohexanecarbonyl)-amino]-thiophene-2-carboxylic acid; |
| 58 | RS-3-[(4-trans-methyl-cyclohexanecarbonyl)-(4-oxo-cyclohexyl)-amino]-5-(2-methyl-cyclohex-2-enyl)-thiophene-2-carboxylic acid; |
| 59 | RS-3-[(4-trans-methyl-cyclohexanecarbonyl)-(4-oxo-cyclohexyl)-amino]-5-(6-methyl-cyclohex-1-enyl)-thiophene-2-carboxylic acid; |
| 60 | RS-3-[(4-trans-hydroxy-cyclohexyl)-(4-trans-methyl-cyclohexanecarbonyl)-amino]-5-(6-methyl-cyclohex-1-enyl)-thiophene-2-carboxylic acid; |
| 61 | RS-3-[(4-trans-hydroxy-cyclohexyl)-(4-trans-methyl-cyclohexanecarbonyl)-amino]-5-(5-methyl-cyclohex-1-enyl)-thiophene-2-carboxylic acid; |
| 62 | 5-cyclohex-1-enyl-3-{(trans-4-methyl-cyclohexanecarbonyl)-[trans-4-(1h-tetrazol-5-yl)-cyclohexyl]-amino}-thiophene-2-carboxylic acid; |
| 63 | 5-cyclohex-1-enyl-3-[(trans-4-methyl-cyclohexanecarbonyl)-(1-oxo-hexahydro-1-thiopyran-4-yl)-amino]-thiophene-2-carboxylic acid; |
| 64 | 5-(4,4-dimethyl-cyclohexyl)-3-[(trans-4-hydroxy-cyclohexyl)-(trans-4-methyl-cyclohexanecarbonyl)-amino]-thiophene-2-carboxylic acid; |
| 65 | 5-cyclohex-1-enyl-3-[(cis/trans-decahydro-naphthalen-2-yl)-(4 trans-methyl-cyclohexanecarbonyl)-amino]-thiophene-2-carboxylic acid; |
| 66 | RS-5-cyclohex-1-enyl-3-[(4-trans-methyl-cyclohexanecarbonyl)-(1,2,3,4-tetrahydro-naphthalen-2-yl)-amino]-thiophene-2-carboxylic acid; |
| 67 | RS-5-cyclohex-1-enyl-3-[(7-methoxy-1,2,3,4-tetrahydro-naphthalen-2-yl)-(4-trans-methyl-cyclohexanecarbonyl)-amino]-thiophene-2-carboxylic acid; |

-continued

| Compound # | Name |
|---|---|
| 68 | 3-[(3-trans-carboxy-4-trans-methylcarbamoyl-cyclohexyl)-(4-trans-methyl-cyclohexanecarbonyl)-amino]-5-cyclohex-1-enyl-thiophene-2-carboxylic acid; |
| 69 | 5-cyclohex-1-enyl-3-[(trans-4-methyl-cyclohexanecarbonyl)-(1-oxo-hexahydro-1lambda*4*-thiopyran-4-yl)-amino]-thiophene-2-carboxylic acid; |
| 70 | 5-cyclohex-1-enyl-3-[(trans-4-fluoro-cyclohexyl)-(trans-4-methyl-cyclohexanecarbonyl)-amino]-thiophene-2-carboxylic acid; |
| 71 | 4-[(5-cyclohex-1-enyl-2-methoxycarbonyl-thiophen-3-yl)-(trans-4-methyl-cyclohexanecarbonyl)-amino]-1-methyl-piperidinium; chloride |
| 72 | RS-5-cyclohex-1-enyl-3-[(4-trans-methyl-cyclohexanecarbonyl)-(2-methyl-1,3-dioxo-octahydro-isoindol-5-yl)-amino]-thiophene-2-carboxylic acid; |
| 73 | 5-cyclohex-1-enyl-3-[cis-(1,3-dimethyl-2-oxo-1,3-diaza-spiro[4.5]dec-8-yl)-(trans-4-methyl-cyclohexanecarbonyl)-amino]-thiophene-2-carboxylic acid; |
| 74 | 5-cyclohex-1-enyl-3-[trans-(1,3-dimethyl-2-oxo-1,3-diaza-spiro[4.5]dec-8-yl)-(trans-4-methyl-cyclohexanecarbonyl)-amino]-thiophene-2-carboxylic acid; |
| 75 | 5-(4,4-dimethyl-cyclohex-1-enyl)-3-[(1,3-dimethyl-2,4-dioxo-1,3-diaza-spiro[4.5]dec-8-yl)-(trans-4-methyl-cyclohexanecarbonyl)-amino]-thiophene-2-carboxylic acid; |
| 76 | 5-Cyclohex-1-enyl-3-(2,4-dimethyl-benzenesulfonylamino)-thiophene-2-carboxylic acid |
| 77 | 3-[(trans-4-hydroxy-cyclohexyl)-(trans-4-methyl-cyclohexanecarbonyl)-amino]-5-(trans-4-methyl-cyclohexyl)-thiophene-2-carboxylic acid; |
| 78 | 3-[(trans-4-hydroxy-cyclohexyl)-(trans-4-methyl-cyclohexanecarbonyl)-amino]-5-(cis-4-methyl-cyclohexyl)-thiophene-2-carboxylic acid; |
| 79 | 5-(4,4-dimethyl-cyclohexyl)-3-[(1,3-dimethyl-2,4-dioxo-1,3-diaza-spiro[4.5]dec-8-yl)-(trans-4-methyl-cyclohexanecarbonyl)-amino]-thiophene-2-carboxylic acid; |
| 80 | 5-cyclohex-1-enyl-3-[(trans-4-methyl-cyclohexanecarbonyl)-cis-(3-oxo-2-aza-spiro[4.5]dec-8-yl)-amino]-thiophene-2-carboxylic acid; |
| 81 | 5-cyclohex-1-enyl-3-[(trans-4-methyl-cyclohexanecarbonyl)-trans-(3-oxo-2-aza-spiro[4.5]dec-8-yl)-amino]-thiophene-2-carboxylic acid; |
| 82 | 5-(3-hydroxy-cyclohex-1-enyl)-3-[(trans-4-hydroxy-cyclohexyl)-(trans-4-methyl-cyclohexanecarbonyl)-amino]-thiophene-2-carboxylic acid; |
| 83 | 5-(4,4-dimethyl-cyclohexyl)-3-[(trans-4-fluoro-cyclohexyl)-(trans-4-methyl-cyclohexanecarbonyl)-amino]-thiophene-2-carboxylic acid; |
| 84 | 5-cyclohex-1-enyl-3-[(trans-4-methyl-cyclohexanecarbonyl)-cis-(2-methyl-3-oxo-2-aza-spiro[4.5]dec-8-yl)-amino]-thiophene-2-carboxylic acid; |
| 85 | 5-(4-cis/trans-hydroxy-cyclohexyl)-3-[(4-trans-hydroxy-cyclohexyl)-(4-trans-methyl-cyclohexanecarbonyl)-amino]-thiophene-2-carboxylic acid; |
| 86 | 3-[(4-trans-hydroxy-cyclohexyl)-(4-trans-methyl-cyclohexanecarbonyl)-amino]-5-(4-oxo-cyclohexyl)-thiophene-2-carboxylic acid; |
| 87 | RS-5-cyclohex-1-enyl-3-[(4-trans-methyl-cyclohexanecarbonyl)-(3-oxo-octahydro-indolizin-7-yl)-amino]-thiophene-2-carboxylic acid; |
| 88 | 4-[(2-carboxy-5-cyclohex-1-enyl-thiophen-3-yl)-(trans-4-methyl-cyclohexanecarbonyl)-amino]-1,1-dimethyl-piperidinium |
| 89 | 4-[[5-cyclohex-1-enyl-2-(2,2-dimethyl-propionyloxymethoxycarbonyl)-thiophen-3-yl]-(trans-4-methyl-cyclohexanecarbonyl)-amino]-1-methyl-piperidinium; chloride |
| 90 | 4-[(5-cyclohex-1-enyl-2-isopropoxycarbonyl oxymethoxycarbonyl-thiophen-3-yl)-(trans-4-methyl-cyclohexanecarbonyl)-amino]-1-methyl-piperidinium chloride |
| 91 | 5-cyclohex-1-enyl-3-[(4,4-difluoro-cyclohexyl)-(trans-4-methyl-cyclohexanecarbonyl)-amino]-thiophene-2-carboxylic acid; |
| 92 | 5-cyclohex-1-enyl-3-[[1-(2,2-difluoro-ethyl)-piperidin-4-yl]-(trans-4-methyl-cyclohexanecarbonyl)-amino]-thiophene-2-carboxylic acid; |
| 93 | 5-(4,4-dimethyl-cyclohexyl)-3-[(trans-4-methyl-cyclohexanecarbonyl)-(1-methyl-piperidin-4-yl)-amino]-thiophene-2-carboxylic acid; |
| 94 | 5-(4,4-dimethyl-cyclohex-1-enyl)-3-[(trans-4-methyl-cyclohexanecarbonyl)-(cis-4-[1,2,4]triazol-1-yl-cyclohexyl)-amino]-thiophene-2-carboxylic acid; hydrochloride |
| 95 | 5-(4,4-dimethyl-cyclohex-1-enyl)-3-[(trans-4-methyl-cyclohexanecarbonyl)-(trans-4-[1,2,4]triazol-1-yl-cyclohexyl)-amino]-thiophene-2-carboxylic acid; hydrochloride |
| 96 | 5-cyclohex-1-enyl-3-[(trans, 4-methyl-cyclohexanecarbonyl)-(1-pyrimidin-5-yl-piperidin-4-yl)-amino]-thiophene-2-carboxylic acid; |
| 97 | 5-(4,4-dimethyl-cyclohexyl)-3-[[1,3]dioxan-5-yl-(trans-4-methyl-cyclohexanecarbonyl)-amino]-thiophene-2-carboxylic acid; |
| 98 | 5-cyclohex-1-enyl-3-[(1-formyl-piperidin-4-yl)-(trans-4-methyl-cyclohexanecarbonyl)-amino]-thiophene-2-carboxylic acid; |
| 99 | 3-[(cis-4-cyano-4-methyl-cyclohexyl)-(trans-4-methyl-cyclohexanecarbonyl)-amino]-5-cyclohex-1-enyl-thiophene-2-carboxylic acid; |
| 100 | 5-(4,4-dimethyl-cyclohexyl)-3-[(trans-4-methoxy-cyclohexyl)-(trans-4-methyl-cyclohexanecarbonyl)-amino]-thiophene-2-carboxylate(s)-5-amino-1-carboxy-pentyl-ammonium; |
| 101 | 5-cyclohex-1-enyl-3-[(1-methanesulfonyl-piperidin-4-yl)-(trans-4-methyl-cyclohexanecarbonyl)-amino]-thiophene-2-carboxylic acid; |
| 102 | 3-[(1-cyano-piperidin-4-yl)-(trans, 4-methyl-cyclohexanecarbonyl)-amino]-5-cyclohex-1-enyl-thiophene-2-carboxylic acid; |
| 103 | 5-cyclohex-1-enyl-3-[(trans, 4-methyl-cyclohexanecarbonyl)-(1-pyrimidin-2-yl-piperidin-4-yl)-amino]-thiophene-2-carboxylic acid; |
| 104 | 5-cyclohex-1-enyl-3-[(trans-4-methyl-cyclohexanecarbonyl)-(cis-4-[1,2,3]triazol-1-yl-cyclohexyl)-amino]-thiophene-2-carboxylic acid; |
| 105 | 5-cyclohex-1-enyl-3-[(trans-4-methyl-cyclohexanecarbonyl)-(trans-4-[1,2,3]triazol-1-yl-cyclohexyl)-amino]-thiophene-2-carboxylic acid; |
| 106 | 3-[(trans-4-cyano-4-methyl-cyclohexyl)-(trans-4-methylcyclohexanecarbonyl)-amino]-5-cyclohex-1-enyl-thiophene-2-carboxylic acid; |
| 107 | 5-cyclohex-1-enyl-3-[(trans, 4-methyl-cyclohexanecarbonyl)-piperidin-4-yl-amino]-thiophene-2-carboxylic acid; |
| 108 | 3-[(trans-4-methoxy-cyclohexyl)-(trans-4-methyl-cyclohexanecarbonyl)-amino]-5-(4-trifluoromethyl-cyclohexyl)-thiophene-2-carboxylic acid; |
| 109 | 5-(4,4-dimethyl-cyclohexyl)-3-[(trans-4-methoxy-cyclohexyl)-(trans-4-methyl-cyclohexanecarbonyl)-amino]-thiophene-2-carboxylatemethyl-((2s,3r,4r,5r)-2,3,4,5,6-pentahydroxy-hexyl)-ammonium; |
| 110 | 5-(4,4-dimethyl-cyclohexyl)-3-[(trans-4-methoxy-cyclohexyl)-(trans-4-methyl-cyclohexanecarbonyl)-amino]-thiophene-2-carboxylate(2-hydroxy-ethyl)-trimethyl-ammonium; |
| 111 | 5-cyclohex-1-enyl-3-[(2-methoxy-1-methoxymethyl-ethyl)-(trans-4-methyl-cyclohexanecarbonyl)-amino]-thiophene-2-carboxylic acid; |
| 112 | 5-cyclohexyl-3-[(4-trans-methoxy-cyclohexyl)-(4-trans-methyl-cyclohexanecarbonyl)-amino]-thiophene-2-carboxylic acid; |
| 113 | 3-[(4-trans-methoxy-cyclohexyl)-(4-trans-methyl-cyclohexanecarbonyl)-amino]-5-(4-oxo-cyclohexyl)-thiophene-2-carboxylic acid; |
| 114 | 5-(4,4-dimethyl-cyclohex-1-enyl)-3-[(4-trans-methoxymethoxy-cyclohexyl)-(4-trans-methyl-cyclohexanecarbonyl)-amino]-thiophene-2-carboxylic acid; |
| 115 | RS-5-cyclohex-1-enyl-3-[cyclohex-3-enyl-(4-trans-methyl-cyclohexanecarbonyl)-amino]-thiophene-2-carboxylic acid; |
| 116 | 5-(4,4-dimethyl-cyclohexyl)-3-[(4-trans-methoxymethoxy-cyclohexyl)-(4-trans-methyl-cyclohexanecarbonyl)-amino]-thiophene-2-carboxylic acid; |
| 117 | 5-(4,4-dimethyl-cyclohexyl)-3-[(trans-4-methyl-cyclohexanecarbonyl)-(cis-4-[1,2,4]triazol-1-yl-cyclohexyl)-amino]-thiophene-2-carboxylic acid; hydrochloride |
| 118 | 5-(4,4-dimethyl-cyclohexyl)-3-[(trans-4-methyl-cyclohexanecarbonyl)-(trans-4-[1,2,4]triazol-1-yl-cyclohexyl)-amino]-thiophene-2-carboxylic acid; hydrochloride |
| 119 | 5-(2,6-difluoro-cyclohex-1-enyl)-3-[(trans-4-methoxy-cyclohexyl)-(trans-4-methyl-cyclohexanecarbonyl)-amino]-thiophene-2-carboxylic acid; |

| Compound # | Name |
|---|---|
| 120 | 5-(2,3-difluoro-cyclohex-1-enyl)-3-[(trans-4-methoxy-cyclohexyl)-(trans-4-methyl-cyclohexanecarbonyl)-amino]-thiophene-2-carboxylic acid; |
| 121 | ammonium; 5-cyclohex-1-enyl-3-[(4-methyl-cyclohexanecarbonyl)-(1-pyridin-3-ylmethyl-piperidin-4-yl)-amino]-thiophene-2-carboxylate |
| 122 | 5-(4,4-difluoro-cyclohexyl)-3-[(4-trans-methoxy-cyclohexyl)-(4-trans-methyl-cyclohexanecarbonyl)-amino]-thiophene-2-carboxylic acid; |
| 123 | RS-5-(4-fluoro-cyclohex-3-enyl)-3-[(4-trans-methoxy-cyclohexyl)-(4-trans-methyl-cyclohexanecarbonyl)-amino]-thiophene-2-carboxylic acid; |
| 124 | 3-[(trans-4-methoxy-cyclohexyl)-(trans-4-methyl-cyclohexanecarbonyl)-amino]-5-(4-trifluoromethyl-cyclohex-1-enyl)-thiophene-2-carboxylic acid; |
| 125 | 5-cyclohex-1-enyl-3-[(trans-4-ethoxymethoxy-cyclohexyl)-(trans-4-methyl-cyclohexanecarbonyl)-amino]-thiophene-2-carboxylic acid; |
| 126 | 5-cyclohex-1-enyl-3-[(4-cis/trans-methoxymethyl-cyclohexyl)-(4-trans-methyl-cyclohexanecarbonyl)-amino]-thiophene-2-carboxylic acid; |
| 127 | 5-cyclohex-1-enyl-3-[(trans, 4-methyl-cyclohexanecarbonyl)-(1-phenyl-piperidin-4-yl)-amino]-thiophene-2-carboxylic acid; |
| 128 | 5-cyclohex-1-enyl-3-[(trans-4-methyl-cyclohexanecarbonyl)-trans(2-methyl-3-oxo-2-aza-spiro[4.5]dec-8-yl)-amino]-thiophene-2-carboxylic acid; |
| 129 | 5-cyclohex-1-enyl-3-[trans(2-ethyl-3-oxo-2-aza-spiro[4.5]dec-8-yl)-(trans-4-methylcyclohexanecarbonyl)-amino]-thiophene-2-carboxylic acid; |
| 130 | 5-cyclohex-1-enyl-3-[cis(2-ethyl-3-oxo-2-aza-spiro[4.5]dec-8-yl)-(trans-4-methylcyclohexanecarbonyl)-amino]-thiophene-2-carboxylic acid; |
| 131 | 5-cyclohex-1-enyl-3-[(4-cis-methoxymethyl-cyclohexyl)-(4-trans-methyl-cyclohexanecarbonyl)-amino]-thiophene-2-carboxylic acid; |
| 132 | 5-cyclohex-1-enyl-3-[(4-trans-methoxymethyl-cyclohexyl)-(4-trans-methyl-cyclohexanecarbonyl)-amino]-thiophene-2-carboxylic acid; |
| 133 | 5-cyclohex-1-enyl-3-[(cis-4-isobutyrylamino-cyclohexyl)-(trans-4-methyl-cyclohexanecarbonyl)-amino]-thiophene-2-carboxylic acid; |
| 134 | 5-cyclohex-1-enyl-3-[(trans-4-isobutyrylamino-cyclohexyl)-(trans-4-methyl-cyclohexanecarbonyl)-amino]-thiophene-2-carboxylic acid; |
| 135 | 5-(4,4-dimethyl-cyclohexyl)-3-[(trans-4-methyl-cyclohexanecarbonyl)-(trans-4-[1,2,3]triazol-1-yl-cyclohexyl)-amino]-thiophene-2-carboxylic acid; |
| 136 | 3-[benzo[1,3]dioxol-5-yl-(trans-4-methyl-cyclohexanecarbonyl)-amino]-5-cyclohex-1-enyl-thiophene-2-carboxylic acid; |
| 137 | 5-(4-cis/trans-fluoro-cyclohexyl)-3-[(4-trans-methoxy-cyclohexyl)-(4-trans-methyl-cyclohexanecarbonyl)-amino]-thiophene-2-carboxylic acid; |
| 138 | 5-(5,5-dimethyl-cyclohex-1-enyl)-3-[(4-trans-methoxy-cyclohexyl)-(4-trans-methyl-cyclohexanecarbonyl)-amino]-thiophene-2-carboxylic acid; |
| 139 | 5-cyclohex-1-enyl-3-[[1-(2-fluoro-ethyl)-piperidin-4-yl]-(trans-4-methyl-cyclohexanecarbonyl)-amino]-thiophene-2-carboxylic acid; |
| 140 | 5-cyclohex-1-enyl-3-{(trans-4-methyl-cyclohexanecarbonyl)-[4-(methyl-propionyl-amino)-cyclohexyl]-amino}-thiophene-2-carboxylic acid; |
| 141 | 5-cyclohex-1-enyl-3-[(1-isobutyryl-piperidin-4-yl)-(trans-4-methyl-cyclohexanecarbonyl)-amino]-thiophene-2-carboxylic acid; |
| 142 | 5-cyclohex-1-enyl-3-[(trans-4-methyl-cyclohexanecarbonyl)-(trans-4-methylsulfanylmethoxy-cyclohexyl)-amino]-thiophene-2-carboxylic acid; |
| 143 | 3-[(4-trans-hydroxy-cyclohexyl)-(4-trans-methyl-cyclohexanecarbonyl)-amino]-thiophene-2-carboxylic acid; |
| 144 | 5-bromo-3-[(trans-4-hydroxy-cyclohexyl)-(trans-4-methyl-cyclohexanecarbonyl)-amino]-thiophene-2-carboxylic acid; |
| 145 | 3-[(trans-4-methoxy-cyclohexyl)-(trans-4-methyl-cyclohexanecarbonyl)-amino]-thiophene-2-carboxylic acid; |
| 146 | 5-Cyclohex-2-enyl-3-[(trans-4-hydroxy-cyclohexyl)-(trans-4-methyl-cyclohexanecarbonyl)-amino]-thiophene-2-carboxylic acid; |
| 147 | 5-Cyclohex-3-enyl-3-[(trans-4-hydroxy-cyclohexyl)-(trans-4-methyl-cyclohexanecarbonyl)-amino]-thiophene-2-carboxylic acid; |
| 148 | 3-[(trans-4-Hydroxy-cyclohexyl)-(trans-4-methyl-cyclohexanecarbonyl)-amino]-5-(4-methyl-cyclohexyl)-thiophene-2-carboxylic acid; |
| 149 | 3-[(trans-4-Hydroxy-cyclohexyl)-(trans-4-methyl-cyclohexanecarbonyl)-amino]-5-(4-methyl-cyclohex-2-enyl)-thiophene-2-carboxylic acid; |
| 150 | 3-[(trans-4-Hydroxy-cyclohexyl)-(trans-4-methyl-cyclohexanecarbonyl)-amino]-5-(4-methyl-cyclohex-3-enyl)-thiophene-2-carboxylic acid; |
| 151 | 3-[(trans-4-Hydroxy-cyclohexyl)-(trans-4-methyl-cyclohexanecarbonyl)-amino]-5-(4-phenyl-cyclohex-1-enyl)-thiophene-2-carboxylic acid; |
| 152 | 3-[(trans-4-Hydroxy-cyclohexyl)-(trans-4-methyl-cyclohexanecarbonyl)-amino]-5-(4-phenoxy-cyclohex-1-enyl)-thiophene-2-carboxylic acid; |
| 153 | 3-[(trans-4-Hydroxy-cyclohexyl)-(trans-4-methyl-cyclohexanecarbonyl)-amino]-5-(4-phenoxy-cyclohexyl)-thiophene-2-carboxylic acid; |
| 154 | 3-[(trans-4-Hydroxy-cyclohexyl)-(trans-4-methyl-cyclohexanecarbonyl)-amino]-5-(3,4,4a,5,6,7,8,8a-octahydro-naphthalen-2-yl)-thiophene-2-carboxylic acid; |
| 155 | 5-Bicyclo[2.2.1]hept-2-yl-3-[(trans-4-hydroxy-cyclohexyl)-(trans-4-methyl-cyclohexanecarbonyl)-amino]-thiophene-2-carboxylic acid; |
| 156 | 5-Cyclohex-1-enyl-3-[(trans-4-methylcyclohexanecarbonyl)-(1-methyl-piperidin-4-yl)-amino]-thiophene-2-carboxylic acid; |
| 157 | 5-Cyclohex-1-enyl-3-[isopropyl-(4-methyl-benzoyl)-amino]-thiophene-2-carboxylic acid; and pharmaceutically acceptable salts and solvates thereof. |

A compound of formula (I) may be prepared by reacting a compound of formula (II):

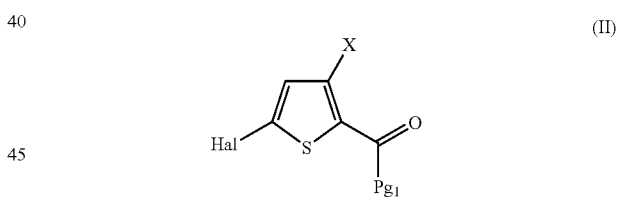

(II)

with a compound of the formula:
$R_1$—$B(OH)_2$ or $R_1$—$B_1$,
under conventional Suzuki coupling conditions;
wherein;
X is as defined above, for example, —$NR_3$—CO—$R_2$,
$R_1$, $R_2$ and $R_3$ are as defined herein, $Pg_1$ is OH or a carboxyl protecting group, Hal is Cl, Br, or I (e.g., Br), and $B_1$ is a boronate such as

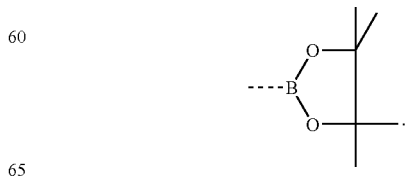

In a further embodiment, $Pg_1$ is methoxy.

The Suzuki Coupling, which is a palladium-catalyzed cross coupling between organoboronic acid and halides is well known in the art. Conditions for such coupling are described in the examples of the present application and in Suzuki et al. Chem. Rev. 1995, 95, 2457-2483.

The term "carboxyl protecting group" is well known in the field of organic chemistry. Such protecting groups may be found in "Protective Groups in Organic Synthesis" second edition, Wiley-Interscience publication, by T. W. Greene and P. G. M. Wuts. Example of carboxyl protecting groups include but are not limited to esters such as methyl ester, amides such as N,N-Dimethyl and hydrazides such as N-phenyl.

Alternatively, a compound of formula (I) may be prepared by reacting a compound of formula:

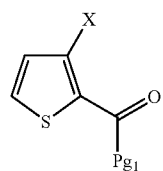

(IIa)

in the presence of a strong base such as Lithium diisopropylamide (LDA) in order to generate the carbanion followed by reacting the resulting mixture with a ketone intermediate of formula (IIIa):

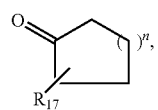

(IIIa)

or a ketone intermediate of formula (IIIb):

under conventional coupling conditions;
wherein;

X is as defined above, for example, $-NR_3-CO-R_2$, $R_a$, $R_2$ and $R_3$ are as defined herein, $Pg_1$ is OH or a carboxyl protecting group, n is an integer chosen between 0 and 2 and the compound of formula (IIIa) is optionally substituted by one or more $R_{17}$. In a further embodiment, $Pg_1$ is methoxy, n is 1 and $R_{17}$ is H.

In one embodiment, the present invention provides a pharmaceutical composition comprising at least one compound according to the invention described herein and at least one pharmaceutically acceptable carrier or excipient.

In one embodiment, the present invention provides a pharmaceutical composition comprising at least one compound according to the invention described herein and at least one compound according to the invention described herein, and further comprising administering at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

In another embodiment, there is provided a combination comprising a Least one compound according to the invention described herein and one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

In one combination embodiment, the compound and additional agent are administered sequentially.

In another combination embodiment, the compound and additional agent are administered simultaneously.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The additional agents for the compositions and combinations include, for example, ribavirin, amantadine, merimepodib, Levovirin, Viramidine, and maxamine.

"Immunomodulatory agent" as used herein means those agents that are effective to enhance or potentiate the immune system response in a mammal. Immunomodulatory agents include, for example, class I interferons (such as α-, β-, δ- and Ω-interferons, τ-interferons, consensus interferons and asialo-interferons), class II interferons (such as γ-interferons) and pegylated interferons.

The term "class I interferon" as used herein means an interferon selected from a group of interferons that all bind to receptor type 1. This includes both naturally and synthetically produced class I interferons. Examples of class I interferons include α-, β-, δ- and Ω-interferons, τ-interferons, consensus interferons and asialo-interferons. The term "class II interferon" as used herein means an interferon selected from a group of interferons that all bind to receptor type II. Examples of class II interferons include γ-interferons.

The term "viral serine protease inhibitor" as used herein means an agent that is effective to inhibit the function of the viral serine protease including HCV serine protease in a mammal. Inhibitors of HCV serine protease include, for example, those compounds described in WO 99/07733 (Boehringer Ingelheim), WO 99/07734 (Boehringer Ingelheim), WO 00/09558 (Boehringer Ingelheim), WO 00/09543 (Boehringer Ingelheim), WO 00/59929 (Boehringer Ingelheim), WO 02/060926 (BMS), WO 2006039488 (Vertex), WO 2005077969 (Vertex), WO 2005035525 (Vertex), WO 2005028502 (vertex) WO 2005007681 (Vertex), WO 2004092162 (Vertex), WO 2004092161 (Vertex), WO 2003035060 (Vertex), of WO 03/087092 (Vertex), WO 02/18369 (Vertex), or WO98/17679 (Vertex).

Specific examples of inhibitors of HCV NS3 protease, include BILN-2061 (Boehringer Ingelheim) SCH-6 and SCH-503034 (Schering-Plough), telaprevir (Vertex) and ITMN-B (InterMune) and GS9132 (Gilead).

The term "viral polymerase inhibitors" as used herein means an agent that is effective to inhibit the function of a viral polymerase including an HCV polymerase in a mammal. Inhibitors of HCV polymerase include non-nucleosides, for example, those compounds described in:

WO 03/010140 (Boehringer Ingelheim), WO 03/026587 (Bristol Myers Squibb); WO 02/100846 A1, WO 02/100851 A2, WO 01/85172 A1 (GSK), WO 02/098424 A1 (GSK), WO 00/06529 (Merck), WO 02/06246 A1 (Merck), WO 01/47883 (Japan Tobacco), WO 03/000254 (Japan Tobacco) and EP 1 256 628 A2 (Agouron).

Furthermore other inhibitors of HCV polymerase also include nucleoside analogs, for example, those compounds described in: WO 01/90121 A2 (Idenix), WO 02/069903 A2 (Biocryst Pharmaceuticals Inc.), and WO 02/057287 A2 (Merck/Isis) and WO 02/057425 A2 (Merck/Isis).

Specific examples of inhibitors of an HCV polymerase, include JTK-002/003 and JTK-109 (Japan Tobacco), HCV-796 (Viropharma) R1626/R1479 (Roche), R1656, (Roche-Pharmasset) and Valopicitabine (Idenix).

Inhibitor internal ribosome entry site (IRES) include ISIS-14803 (ISIS Pharmaceuticals) and those compounds described in WO 2006019831 (PTC therapeutics).

In one embodiment, the additional agent is interferon α, ribavirin, silybum marianum, interleukine-12, amantadine, ribozyme, thymosin, N-acetyl cysteine or cyclosporin.

In one embodiment, the additional agent is interferon α 1A, interferon α 1B, interferon α 2A, or interferon α 2B.

In one embodiment, viral serine protease inhibitor is a flaviviridae serine protease inhibitor.

In one embodiment, viral polymerase inhibitor is a flaviviridae polymerase inhibitor.

In one embodiment, viral helicase inhibitor is a flaviviridae helicase inhibitor.

In further embodiments:
viral serine protease inhibitor is HCV serine protease inhibitor;
viral polymerase inhibitor is HCV polymerase inhibitor;
viral helicase inhibitor is HCV helicase inhibitor.

In one embodiment, the present invention provides a method for treating or preventing a Flaviviridae viral infection in a host comprising administering to the host a therapeutically effective amount of at least one compound according to formula I.

In one embodiment, the viral infection is chosen from Flavivirus infections.

In one embodiment, the Flavivirus infection is Hepatitis C virus (HCV), bovine viral diarrhea virus (BVDV), hog cholera virus, dengue fever virus, Japanese encephalitis virus or yellow fever virus.

In one embodiment, the Flaviviridea viral infection is hepatitis C viral infection (HCV).

In one embodiment, the present invention provides a method for treating or preventing a Flaviviridae viral infection in a host comprising administering to the host a therapeutically effective amount of at least one compound according to the invention described herein, and further comprising administering at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

In one embodiment, there is provided a method for inhibiting or reducing the activity of viral polymerase in a host comprising administering a therapeutically effective amount of a compound according to the invention described herein.

In one embodiment, there is provided a method for inhibiting or reducing the activity of viral polymerase in a host comprising administering a therapeutically effective amount of a compound according to the invention described herein and further comprising administering one or more viral polymerase inhibitors.

In one embodiment, viral polymerase is a Flaviviridae viral polymerase.

In one embodiment, viral polymerase is a RNA-dependant RNA-polymerase.

In one embodiment, viral polymerase is HCV polymerase.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components for use in the method of the present invention or combinations of the present invention may be administered either sequentially or simultaneously in separate or combined pharmaceutical formulations.

In one embodiment, the present invention provides the use of a compound according to the invention described herein for treating or preventing Flaviviridae viral infection in a host.

In one embodiment, the present invention provides the use of a compound according to the invention described herein for the manufacture of a medicament for treating or preventing a viral Flaviridea infection in a host.

In one embodiment, the present invention provides the use of a compound according to the invention described herein for inhibiting or reducing the activity of viral polymerase in a host.

It will be appreciated by those skilled in the art that the compounds in accordance with the present invention can exists as stereoisomers (for example, optical (+ and −), geometrical (cis and trans) and conformational isomers (axial and equatorial). All such stereoisomers are included in the scope of the present invention.

It will be appreciated by those skilled in the art that the compounds in accordance with the present invention can contain a chiral center. The compounds of formula may thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

In one embodiment, the compounds of the present invention are provided in the form of a single enantiomer at least 95%, at least 97% and at least 99% free of the corresponding enantiomer.

In a further embodiment the compound of the present invention are in the form of the (+) enantiomer at least 95% free of the corresponding (−) enantiomer.

In a further embodiment the compound of the present invention are in the form of the (+) enantiomer at least 97% free of the corresponding (−) enantiomer.

In a further embodiment the compound of the present invention are in the form of the (+) enantiomer at least 99% free of the corresponding (−) enantiomer.

In a further embodiment, the compounds of the present invention are in the form of the (−) enantiomer at least 95% free of the corresponding (+) enantiomer.

In a further embodiment the compound of the present invention are in the form of the (−) enantiomer at least 97% free of the corresponding (+) enantiomer.

In a further embodiment the compound of the present invention are in the form of the (−) enantiomer at least 99% free of the corresponding (+) enantiomer.

There is also provided pharmaceutically acceptable salts of the compounds of the present invention. By the term pharmaceutically acceptable salts of compounds are meant those derived from pharmaceutically acceptable inorganic and organic acids and bases. Examples of suitable acids include hydrochloric, hydrobromic, sulphuric, nitric, perchloric, fumaric, mateic, phosphoric, glycollic, lactic, saticylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not themselves pharmaceutically acceptable, may be useful as intermediates in obtaining the compounds of the invention and their pharmaceutically acceptable acid addition salts.

Salts derived from amino acids are also included (e.g. L-arginine, L-Lysine).

Salts derived from appropriate bases include alkali metals (e.g. calcium, sodium, lithium, potassium), alkaline earth metals (e.g. magnesium), ammonium, $NR_{4^+}$ (where R is $C_{1-4}$ alkyl) salts, choline and tromethamine.

A reference hereinafter to a compound according to the invention includes that compound and its pharmaceutically acceptable salts.

In one embodiment of the invention, the pharmaceutically acceptable salt is a sodium salt.

In one embodiment of the invention, the pharmaceutically acceptable salt is a lithium salt.

In one embodiment of the invention, the pharmaceutically acceptable salt is a potassium salt.

It will be appreciated by those skilled in the art that the compounds in accordance with the present invention can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will further be appreciated by those skilled in the art that the compounds in accordance with the present invention can exist in different solvate forms, for example hydrates. Solvates of the compounds of the invention may also form when solvent molecules are incorporated into the crystalline lattice structure of the compound molecule during the crystallization process.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety. The terms "alkenyl" and "alkynyl" represent a linear, branched or cyclic hydrocarbon moiety which has one or more double bonds or triple bonds in the chain. Examples of alkyl, alkenyl, and alkynyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl, butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cyclohexenyl, cyclohexdienyl and cyclohexyl. Where indicated the "alkyl," "alkenyl," and "alkynyl" can be optionally substituted such as in the case of haloalkyls in which one or more hydrogen atom is replaced by a halogen, e.g., an alkylhalide. Examples of haloalkyls include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl. Aside from halogens, where indicated, the alkyl, alkenyl or alkynyl groups can also be optionally substituted by, for example, oxo, $-NR_dR_e$, $-CONR_dR_e$, $=NO-R_e$, $NR_dCOR_e$, carboxy, $-C(=NR_d)NR_eR_f$, azido, cyano, $C_{1-6}$ alkyloxy, $C_{2-6}$ alkenyloxy, $C_{2-6}$ alkynyloxy, $-N(R_d)C(=NR_e)-NR_fR_g$, hydroxyl, nitro, nitroso, $-N(R_h)CONR_iR_j$, $S(O)_{0-2}R_a$, $C(O)R_a$, $C(O)OR_a$, $NR_aC(O)R_b$, $SO_2NR_aR_b$, $NR_aSO_2R_b$, $NR_aSO_2NR_bR_c$, $CR_aN=OR_b$, and/or $NR_aCOOR_b$, wherein $R_a$-$R_j$ are each independently H, $C_{1-4}$ alkyl, $C_{2-4}$ alkenyl or $C_{2-4}$ alkynyl.

The terms "cycloalkyl", and "cycloalkenyl" represent a cyclic hydrocarbon alkyl or alkenyl, respectively, and are meant to include monocyclic (e.g., cyclohexyl), spiro (e.g., spiro[2.3]hexanyl), fused (e.g., bicyclo[4.4.0]decanyl), and bridged (e.g., bicyclo[2.2.1]heplanyl)hydrocarbon moieties.

The terms "alkoxy," "alkenyloxy," and "alkynyloxy" represent an alkyl, alkenyl or alkynyl moiety, respectively, which is covalently bonded to the adjacent atom through an oxygen atom. Like the alkyl, alkenyl and alkynyl groups, where indicated the alkoxy, alkenyloxy and alkynyloxy groups can also be optionally substituted. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy. The alkoxy, alkenyloxy, and alkynyloxy groups can be optionally substituted by, for example, halogens, oxo, $-NR_dR_e$, $-CONR_dR_e$, $-NR_dCOR_e$, carboxy, $-C(=NR_d)NR_eR_f$, azido, cyano, $-N(R_d)C(=NR_e)NR_fR_g$, hydroxyl, nitro, nitroso, $C_{1-6}$ alkyl, $C_{2-6}$ alkenyl, $C_{2-6}$ alkynyl, $-N(R_h)CONR_iR_j$, $S(O)_{0-2}R_a$, $C(O)R_a$, $C(O)OR_a$, $=NO-R_e$, $NR_aC(O)R_b$, $SO_2NR_aR_b$, $NR_aSO_2R_b$, $NR_aSO_2NR_bR_c$, $CR_aN=OR_b$, and/or $NR_aCOOR_b$, wherein $R_a$-$R_j$ are each independently H, $C_{1-4}$ alkyl, $C_{2-4}$ alkenyl or $C_{2-4}$ alkynyl.

The term "aryl" represents a carbocyclic moiety containing at least one benzenoid-type ring (i.e., may be monocyclic or polycyclic), and which where indicated may be optionally substituted with one or more substituents. Examples include but are not limited to phenyl, tolyl, dimethylphenyl, aminophenyl, anilinyl, naphthyl, anthryl, phenanthryl or biphenyl. The aryl groups can be optionally substituted by, for example, halogens, $-NR_dR_e$, $-CONR_dR_e$, $-NR_dCOR_e$, carboxy, $-C(=NR_d)NR_eR_f$, azido, cyano, $-N(R_d)C(=NR_e)NR_fR_g$, hydroxyl, nitro, nitroso, $-N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, $C(O)R_a$, $C(O)OR_a$, $NR_aC(O)R_b$, $SO_2NR_aR_b$, $NR_aSO_2R_b$, $NR_aSO_2NR_bR_c$, $CR_aN=OR_b$, and/or $NR_aCOOR_b$, wherein $R_a$-$R_j$ are each independently H, $C_{1-4}$ alkyl, $C_{2-4}$ alkenyl or $C_{2-4}$ alkynyl.

The term "aralkyl" represents an aryl group attached to the adjacent atom by an alkyl, alkenyl or alkynyl. Like the aryl groups, where indicated the aralkyl groups can also be optionally substituted. Examples include but are not limited to benzyl, benzhydryl, trityl, phenethyl, 3-phenylpropyl, 2-phenylpropyl, 4-phenylbutyl and naphthylmethyl. Where indicated, the aralkyl groups can be optionally substituted by, for example, halogens, $-NR_dR_e$, $-CONR_dR_e$, $-NR_dCOR_e$, carboxy, $-C(=NR_d)NR_eR_f$, azido, cyano, $-N(R_d)C(=NR_e)NR_fR_g$, hydroxyl, nitro, nitroso, $-N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, C$_{2-6}$ alkynyloxy, S(O)$_{0-2}$R$_a$, optionally substituted 5-12 member heteroaryl, optionally substituted 6-18 member heteroaralkyl, optionally substituted 3-12 member heterocycle, optionally substituted 4-18 member heterocycle-alkyl, C(O)R$_a$, C(O)OR$_a$, NR$_a$C(O)R$_b$, SO$_2$NR$_a$R$_b$, NR$_a$SO$_2$R$_b$, NR$_a$SO$_2$NR$_b$R$_c$, CR$_a$N=OR$_b$, and/or NR$_a$CO-OR$_b$, wherein R$_a$-R$_j$ are each independently H, C$_{1-4}$ alkyl, C$_{2-4}$ alkenyl or C$_{2-4}$ alkynyl.

The term "heterocycle" represents an optionally substituted, non aromatic, saturated or partially saturated wherein said cyclic moiety is interrupted by at least one heteroatom selected from oxygen (O), sulfur (S) or nitrogen (N). Heterocycles may be monocyclic or polycyclic rings. Examples include but are not limited to azetidinyl, dioxolanyl, morpholinyl, morpholino, oxetanyl, piperazinyl, piperidyl, piperidino, cyclopentapyrazolyl, cyclopentaoxazinyl, cyclopentafuranyl. Where indicated, the heterocyclic groups can be optionally substituted by, for example, halogens, oxo, —NR$_d$R$_e$, —CONR$_d$R$_e$, =NO—R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{7-12}$ aralkyl, C$_{6-12}$ aryl, C$_{1-6}$ alkyloxy, C$_{2-6}$ alkenyloxy, C$_{2-6}$ alkynyloxy, S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, C(O)R$_a$, C(O)OR$_a$, NR$_a$C(O)R$_b$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl.

The term "heterocycle-alkyl" represents an optionally substituted heterocycle group attached to the adjacent atom by an alkyl, alkenyl or alkynyl group. It is understood that in a 5-18 member heterocycle-alkyl moiety, the 5-18 member represent the atoms that are present in both the heterocycle moiety and the alkyl, alkenyl or alkynyl group. For example, the following groups are encompassed by a 7 member heterocycle-alkyl (* represents the attachment point):

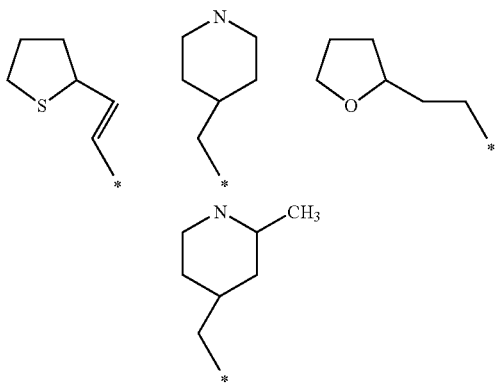

Where indicated the heterocycle-alkyl groups can be optionally substituted by, for example, halogens, oxo, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, C(O)R$_a$, C(O)OR$_a$, NR$_a$C(O)R$_b$, =NO—R$_e$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl.

The term "heteroaryl" represents an optionally substituted aromatic cyclic moiety wherein said cyclic moiety is interrupted by at least one heteroatom selected from oxygen (O), sulfur (S) or nitrogen (N). Heteroaryls may be monocyclic or polycyclic rings. Examples include but are not limited to azepinyl, aziridinyl, azetyl, diazepinyl, dithiadiazinyl, dioxazepinyl, dithiazolyl, furanyl, isooxazolyl, isothiazolyl, imidazolyl, oxadiazolyl, oxiranyl, oxazinyl, oxazolyl, pyrazinyl, pyridazinyl, pyrimidinyl, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, benzoxazinyl, benzothiazinyl, quinazolinyl, naphthyridinyl, quinolinyl, isoquinolinyl, benzopyranyl, pyridopyridazinyl and pyridopyrimidinyl. Where indicated the heteroaryl groups can be optionally substituted by, for example, halogens, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, C(O)R$_a$, C(O)OR$_a$, NR$_a$C(O)R$_b$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl.

The term "heteroaralkyl" represents an optionally substituted heteroaryl group attached to the adjacent atom by an alkyl, alkenyl or alkynyl group. Where indicated the heteroaralkyl groups can be optionally substituted by, for example, halogens, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, C(O)R$_a$, C(O)OR$_a$, NR$_a$C(O)R$_b$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl. It is understood that in a 6-18 member heteroaralkyl moiety, the 6-18 member represents the atoms that are present in both the heterocycle moiety and the alkyl, alkenyl or alkynyl groups. For example, the following groups are encompassed by a 7 member heteroaralkyl (* represents the attachment point):

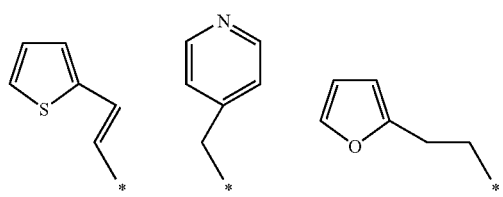

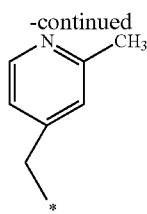

"Halogen atom" is specifically a fluorine atom, chlorine atom, bromine atom or iodine atom.

The term "amidino" represents —C(=NR$_d$)NR$_e$R$_f$ wherein R$_d$, R$_e$ and R$_f$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_e$ and R$_f$ are taken together with the nitrogen to which they are attached to form an optionally substituted 4 to 10 member heterocycle or an optionally substituted 5-12 member heteroaryl.

The term "guanidino" represents —N(R$_d$)C(=NR$_e$)NR$_f$R$_g$ wherein R$_d$, R$_e$, R$_f$ and R$_g$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_f$ and R$_g$ are taken together with the nitrogen to which they are attached to form an optionally substituted 4 to 10 member heterocycle or an optionally substituted 5-12 member heteroaryl.

The term "amido" represents —CONR$_d$R$_e$ and —NR$_d$COR$_e$, wherein R$_d$ and R$_e$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_d$ and R$_e$ are taken together with the nitrogen to which they are attached (or the nitrogen atom and CO group in the case of —NR$_d$COR$_e$) to form an optionally substituted 4 to 10 member heterocycle or an optionally substituted 5-12 member heteroaryl.

The term "amino" represents a derivative of ammonia obtained by substituting one or more hydrogen atom and includes —NR$_d$R$_e$, wherein R$_d$ and R$_e$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_d$ and R$_e$ are taken together with the nitrogen to which they are attached to form an optionally substituted 4 to 10 member heterocycle or an optionally substituted 5-12 member heteroaryl.

The term "sulfonamido" represents SO$_2$NR$_d$R$_e$, and —NR$_d$SO$_2$R$_e$, wherein R$_d$ and R$_e$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_d$ and R$_e$ are taken together with the nitrogen to which they are attached to form an optionally substituted 4 to 10 member heterocycle or an optionally substituted 5-12 member heteroaryl.

When there is a sulfur atom present, the sulfur atom can be at different oxidation levels, i.e., S, SO, or SO$_2$. All such oxidation levels are within the scope of the present invention.

The term "independently" means that a substituent can be the same or a different definition for each item.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, for example, in the range of 0.5 to 60 mg/kg/day, or, for example, in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 μM, about 2 to 50 μM, about 3 to about 30 μM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

When the compounds of the present invention or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

While it is possible that, for use in therapy, a compound of the invention may be administered as the raw chemical it is preferable to present the active ingredient as a pharmaceutical composition. The invention thus further provides a pharmaceutical composition comprising compounds of the present invention or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouth-washes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The following general schemes and examples are provided to illustrate various embodiments of the present invention and shall not be considered as limiting in scope. It will be appreciated by those of skill in the art that other compounds of the present invention can be obtained by substituting the generically or specifically described reactants and/or operating conditions used in the following examples. Synthesis methods to obtain thiophene compounds are also described in patent applications WO02/100851, U.S. Pat. No. 2004-0116509, WO2004/052885, U.S. Pat. No.2005-0009804, W02004/052879 and U.S. Pat No. 2004-0192707, the disclosures of which are hereby incorporated by reference.

In the foregoing and in the following examples, all temperatures are set forth uncorrected in degrees Celsius; and, unless otherwise indicated, all parts and percentages are by weight.

The following abbreviations may be used as follows:

| | |
|---|---|
| DCC | 1,3-dicyclohexylcarbodiimide |
| DCE | 1,2-dichloroethane |
| DCM | dichloromethane |
| DIPEA | N,N-diisopropylethylamine |
| DMF | N,N-dimethylformamide |
| Hal | halogen |
| LAH | lithium aluminium hydride |
| MeOH | Methanol |
| TFA | trifluoroacetic acid |
| THF | tetrahydrofuran |
| LDA | lithium diisopropylamide |

Purifications by HPLC were all performed using reverse phase C18 column packed with 5 μm particles. Column diameter was 19 mm and length was 100 mm. Eluent was an appropriate gradient of acetonitrile and water with a 3 mM HCl concentration.

EXAMPLE 1

Preparation of 5-cyclohex-1-enyl-3-[(trans-4-hydroxy-cyclohexyl)-(trans-4-methyl-cyclohexanecarbonyl)-amino]-thiophene-2-carboxylic acid (compound #1)

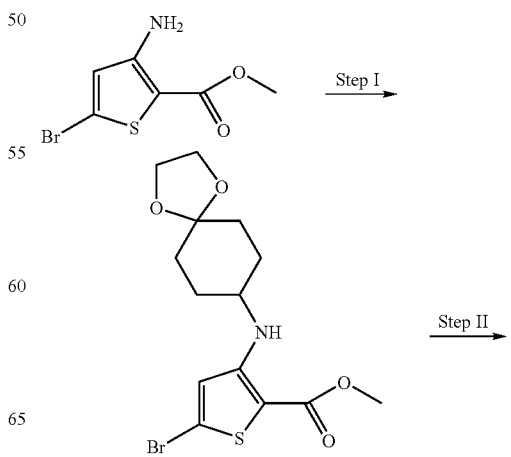

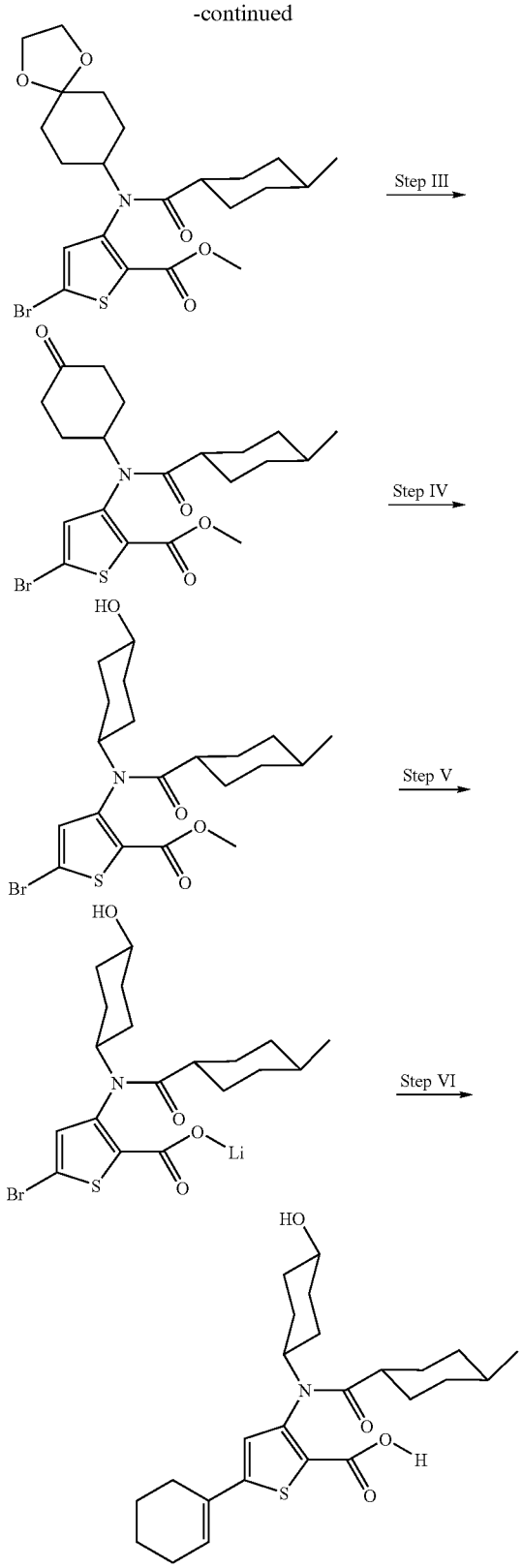

Step I

A suspension of 3-amino-5-bromo-thiophene-2-carboxylic acid methyl ester (17.0 g, 72.0 mmol) in dry THF (21 ml) was treated with 1,4-cyclohexanedione monoethylene ketal (11.3 mg, 72.0 mmol), followed by dibutyltin dichloride (1.098 gr, 3.6 mmol). After 5 min, phenyl silane (9.74 ml, 79.2 mmol) was added and the reaction mixture was stirred overnight at room temperature. After concentration, the residue was dissolved in EtOAc washed with $NaHCO_3$ then brine. The organic layer was separated, dried on $Na_2SO_4$, filtered and concentrated. The crude material was diluted in hexane (500 ml). After filtration, the mother liquor was evaporated to dryness to give 5-Bromo-3-(1,4-dioxa-spiro[4.5]dec-8-ylamino)-thiophene-2-carboxylic acid methyl ester (24.79 g, 92% yield). $^1$H NMR ($CDCl_3$, 400 MHz): 6.90 (br s, 1H), 6.65 (s, 1H), 3.95 (s, 4H), 3.78 (s, 3H), 3.35 (m, 1H), 2.00 (m, 2H), 1.80 (m, 2H), 1.65 (m, 4H).

Step II

A—Preparation of trans-4-methylcyclohexyl Carboxylic Acid Chloride

Oxalyl chloride (2M in DCM, 117 ml) was added drop wise to a suspension of trans-4-methylcyclohexyl carboxylic acid (16.6 g, 117 mmol) in DCM (33 ml) and DMF (0.1 ml) the reaction mixture was stirred 3 h at room temperature. DCM was removed under reduced pressure and the residue was co-evaporated with DCM. The residue was dissolved in toluene to make a 1M solution.

B—Preparation of the Target Compound

The 1M solution of trans-4-methylcyclohexyl carboxylic acid chloride was added to a solution of 5-bromo-3-(1,4-dioxa-spiro[4.5]dec-8-ylamino)-thiophene-2-carboxylic acid methyl ester (24.79 g, 65 mmol) in toluene (25 ml) followed by pyridine (5.78 ml, 71.5 mmol). The resulting mixture was then stirred for 16 h at reflux. The reaction mixture was diluted with toluene (60 ml) and cooled down to 5° C. After the addition of pyridine (12 ml) and MeOH (5.6 ml), the mixture was stirred 2 h at 5° C. The white suspension was filtered off and the toluene was added to the mother liquor. The organic phase was washed with 10% citric acid, aq. Sat $NaHCO_3$, dried ($Na_2SO_4$) and concentrated. The residue was triturated in boiling hexane (1500 ml). The reaction mixture was allowed to cool down to room temperature. The reaction flask was immersed into ice bath, and stirred for 30 min; white solid was filtered off, and washed with cold hexane (225 ml). The solid was purified by silica gel column chromatography using 20% EtOAc:hexanes as eluent to furnished the final compound 5-Bromo-3-[(1,4-dioxa-spiro[4.5] dec-8-yl)-(trans-4-methyl-cyclohexanecarbonyl)-amino]-thiophene-2-carboxylic acid methyl ester (10.5 g, 32%). $^1$H NMR ($CDCl_3$, 400 MHz): 6.84 (s, 1H), 4.62 (m, 1H), 3.90-3.82 (m, 4H), 3.80 (s, 3H), 1.92-1.81 (m, 2H), 1.77-1.11 (m, 14H), 1.79 (d, 3H), 0.77-0.59 (m, 2H).

Step III

The 5-bromo-3-[(1,4-dioxa-spiro[4.5]dec-8-yl)-(trans-4-methylcyclohexane-carbonyl)-amino]-thiophene-2-carboxylic acid methyl ester (8.6 g, 17 mmol) was dissolved in tetrahydrofuran (100 ml) and treated with 3N HCl solution (50 ml). The reaction was stirred at 40° C. for 3 hours. The reaction mixture was evaporated under reduced pressure. The residue was dissolved in EtOAc and wash with aq. sat. $NaHCO_3$ solution. The organic layer was separated, dried on $Na_2SO_4$, filtered and concentrated to give 5-Bromo-3-[(trans-4-methyl-cyclohexanecarbonyl)-(4-oxo-cyclohexyl)-amino]-thiophene-2-carboxylic acid methyl ester as a solid (7.4 g, 95%).

Step IV

To a cold (0° C.) solution of 5-Bromo-3-[(trans-4-methyl-cyclohexanecarbonyl)-(4-oxo-cyclohexyl)-amino]-thiophene-2-carboxylic acid methyl ester (5.9 g, 12.9 mmol) in 50 ml of MeOH under a positive $N_2$ add $NaBH_4$ (250 mg, 6.4 mmol, 0.5 eq.) portion wise (approx. 30 minutes). After the addition is completed, check for reaction completion by TLC Hexane:EtOAc 1:1). Add 10 ml of HCl 2% and stirred for 15 min. The reaction mixture was concentrated under vacuum to dryness. The reaction mixture was recuperated with water (25 ml) and extracted with EtOAC. The organic phases were combined and dried over $MgSO_4$ and concentrated to dryness. The residue was purified by silica gel column chromatography using EtOAc:hexanes as eluent to obtain 5-Bromo-3-[(trans-4-hydroxy-cyclohexyl)-(trans-4-methyl-cyclohexane-carbonyl)-amino]-thiophene-2-carboxylic acid methyl ester (4.5 g, 77% yield) as a solid.

Step V

5-Bromo-3-[(trans-4-hydroxy-cyclohexyl)-(trans-4-methyl-cyclohexane-carbonyl)-amino]-thiophene-2-carboxylic acid methyl ester (3.0 g, 6.68 mmol) was dissolved in a 3:2:1 mixture of THF: methanol: $H_2O$ (50.ml) and treated with a 1N solution of $LiOH.H_2O$ (8.0 ml, 8.0 mmol). After 2 hours of stirring at 60° C., the reaction mixture was evaporated to dryness and used as it is for the next step.

Step VI

A solution of 5-bromo-3-[(trans-4-hydroxy-cyclohexyl)-(trans-4-methyl-cyclohexanecarbonyl)-amino]-thiophene-2-carboxylate (2.8 g, 6.3 mmol) and cyclohen-1-ylboronic acid (1.18 g, 9.4 mmol) in a mixture of DME (40.0 mL) and 2M aqueous $Na_2CO_3$ (20.0 mL) was treated with $Pd(PPh_3)_4$ (145 mg, 0.126 mmol). The reaction was heated at reflux for 0.25 h. The reaction mixture was diluted with ethyl acetate and water. The water layer was separated, washed with EtOAc and filtered on Celite. This solution was acidified to pH 4 with aq. 1N HCl solution. The white solid was filtered. This residue was purified with silica gel column chromatography using $CH_2Cl_2$:MeOH as eluent to provide 5-cyclohex-1-enyl-3-[(trans-4-hydroxy-cyclohexyl)-(4-trans-methyl-cyclohexanecarbonyl)-amino]-thiophene-2-carboxylic acid (2.3 g, 82%) 1H NMR ($CD_3OD$, 400 MHz): δ [ppm] 6.8 (s, 1H), 6.4-6.3 (bs, 1H), 4.45-4.30 (m, 1H), 3.35 (m, 1H), 2.5-2.30 (m, 2H), 2.30-2.15 (m, 2H), 2.15-2.0 (m, 1H), 1.98-1.42 (m, 14H), 1.42-1.20 (m, 5H), 1.1-0.9 (m, 1H), 0.8 (d, J=6.5 Hz, 3H), 0.65-0.48 (m, 2H).

Using essentially the same procedure described above the following compounds can be prepared:

5-Cyclohex-1-enyl-3-[isopropyl-(trans-4-methyl-cyclohexanecarbonyl)-amino]-thiophene-2-carboxylic acid (compound#7)

5-Cyclohex-1-enyl-3-[(trans-4-methyl-cyclohexanecarbonyl)-(4-oxo-cyclohexyl)-amino]-thiophene-2-carboxylic acid (compound#8)

5-Cylopent-1-enyl-3-[(2,4-dichloro-benzoyl)-isopropyl-amino]-thiophene-2-carboxylic acid (compound #15)

5-Cyclohex-1-enyl-3-[(4-hydroxy-cyclohexyl)-(4-methyl-cyclohexanecarbonyl)-amino]-thiophene-2-carboxylic acid (compound #16)

5-Cyclohex-1-enyl-3-[(2,4-dichlorobenzoyl)-isopropyl-amino]-thiophene-2-carboxylic acid (compound#31)

5-Bromo-3-[(trans-4-hydroxy-cyclohexyl)-(trans-4-methyl-cyclohexane-carbonyl)-amino]-thiophene-2-carboxylic acid (compound #144)

5-Cyclohex-1-enyl-3-[methyl-(trans-4-methyl-cyclohexanecarbonyl)-amino]-thiophene-2-carboxylic acid (compound #37)

5-Cyclohex-1-enyl-3-[(4,4-dimethyl-cyclohexyl)-(trans-4-methyl-cyclohexanecarbonyl)-amino]-thiophene-2-carboxylic acid (compound #38)

5-Cyclohex-1-enyl-3-[(trans-4-methyl-cyclohexanecarbonyl)-(3-methyl-cyclohexyl)-amino]-thiophene-2-carboxylic acid (compound #39)

5-(4,4-Dimethyl-cyclohex-1-enyl)-3-[(trans-4-hydroxy-cyclohexyl)-(trans-4-methyl-cyclohexanecarbonyl)-amino]-thiophene-2-carboxylic acid (compound #35)

3-[Isopropyl-(trans-4-methyl-cyclohexanecarbonyl)-amino]-5-(4-methyl-cyclohex-1-enyl)-thiophene-2-carboxylic acid (compound #43)

EXAMPLE 2

Preparation of 5-cyclohexyl-3-[(trans-4-hydroxy-cyclohexyl)-(trans-4-methyl-cyclohexanecarbonyl)-amino]-thiophene-2-carboxylic acid (Compound#2)

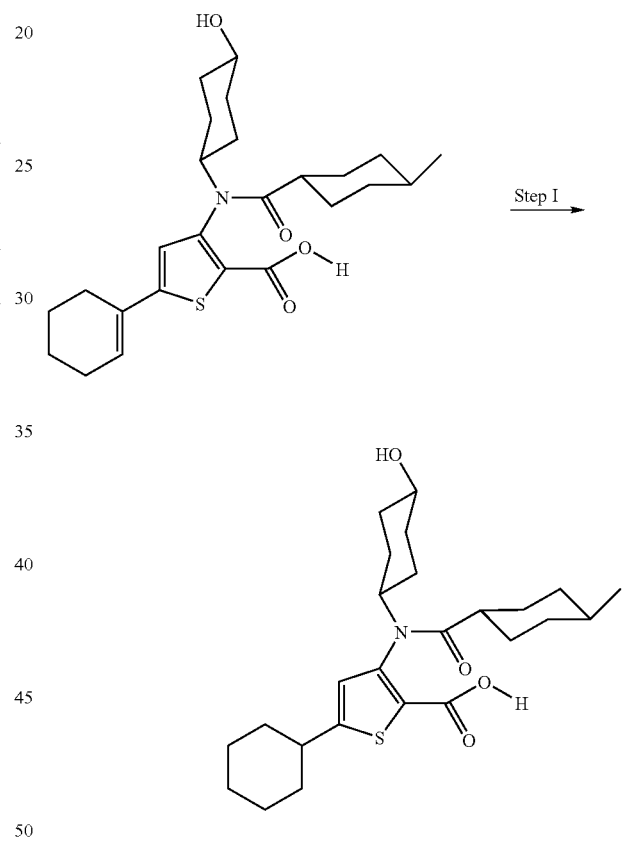

Step I

To a solution of 5-cyclohex-1-enyl-3-[(trans-4-hydroxy-cyclohexyl)-(trans-4-methyl-cyclohexanecarbonyl)-amino]-thiophene-2-carboxylic acid (22 mg, 0.05 mmol) in dry MeOH (1 ml) was added 10% palladium on charcoal (3 mg). The resulting reaction mixture was placed under $H_2$ atmosphere, stirred at room temperature for 16 h, and then filtered on celite and evaporated to dryness. The crude product was purified by flash chromatography using $CH_2Cl_2$:MeOH hexanes as eluent to to give 5-cyclohexyl-3-[(trans-4-hydroxy-cyclohexyl)-(trans-4-methyl-cyclohexanecarbonyl)-amino]-thiophene-2-carboxylic acid (7 mg, 32%).

Using essentially the same procedure described above the following compounds can be prepared:

5-(4,4-Dimethyl-cyclohexyl)-3-[(trans-4-methyl-cyclohexanecarbonyl)-(1-methyl-piperidin-4-yl)-amino]-thiophene-2-carboxylic acid (compound #93)

5-(4,4-dimethyl-cyclohexyl)-3-[(trans-4-methoxymethoxy-cyclohexyl)-(trans-4-methyl-cyclohexanecarbonyl)-amino]-thiophene-2-carboxylic acid (compound #116)

5-(cis/trans-4-hydroxy-cyclohexyl)-3-[(trans-4-hydroxy-cyclohexyl)-(trans-4-methyl-cyclohexanecarbonyl)-amino]-thiophene-2-carboxylic acid (compound #85)

3-[(trans-4-hydroxy-cyclohexyl)-(trans-4-methyl-cyclohexanecarbonyl)-amino]-5-(4-oxo-cyclohexyl)-thiophene-2-carboxylic acid (compound #86)

5-cycloheptyl-3-[(trans-4-hydroxy-cyclohexyl)-(trans-4-methylcyclohexanecarbonyl)-amino]-thiophene-2-carboxylic acid (compound #6)

5-(4,4-dimethyl-cyclohexyl)-3-[(trans-4-methoxy-cyclohexyl)-(trans-4-methyl-cyclohexanecarbonyl)-amino]-thiophene-2-carboxylic acid (compound #21)

5-cyclohexyl-3-[(trans-4-methoxy-cyclohexyl)-(trans-4-methyl-cyclohexanecarbonyl)-amino]-thiophene-2-carboxylic acid (compound #112)

5-(cis/trans-4-fluoro-cyclohexyl)-3-[(trans-4-methoxy-cyclohexyl)-(trans-4-methyl-cyclohexanecarbonyl)-amino]-thiophene-2-carboxylic acid (compound #137)

5-(4,4-Dimethyl-cyclohexyl)-3-[(trans-4-hydroxy-cyclohexyl)-(trans-4-methyl-cyclohexanecarbonyl)-amino]-thiophene-2-carboxylic acid (compound #64)

3-[(trans-4-Hydroxy-cyclohexyl)-(trans-4-methyl-cyclohexanecarbonyl)-amino]-5-(trans-4-methyl-cyclohexyl)-thiophene-2-carboxylic acid (compound #77)

3-[(trans-4-Hydroxy-cyclohexyl)-(trans-4-methyl-cyclohexanecarbonyl)-amino]-5-(cis-4-methyl-cyclohexyl)-thiophene-2-carboxylic acid (compound #78)

EXAMPLE 3

Preparation of 5-(4,4-dimethylcyclohexyl)-3-[(trans-4-methoxy-cyclohexyl)-(trans-4-methyl-cyclohexanecarbonyl)-amino]-thiophene-2-carboxylic acid (compound #21)

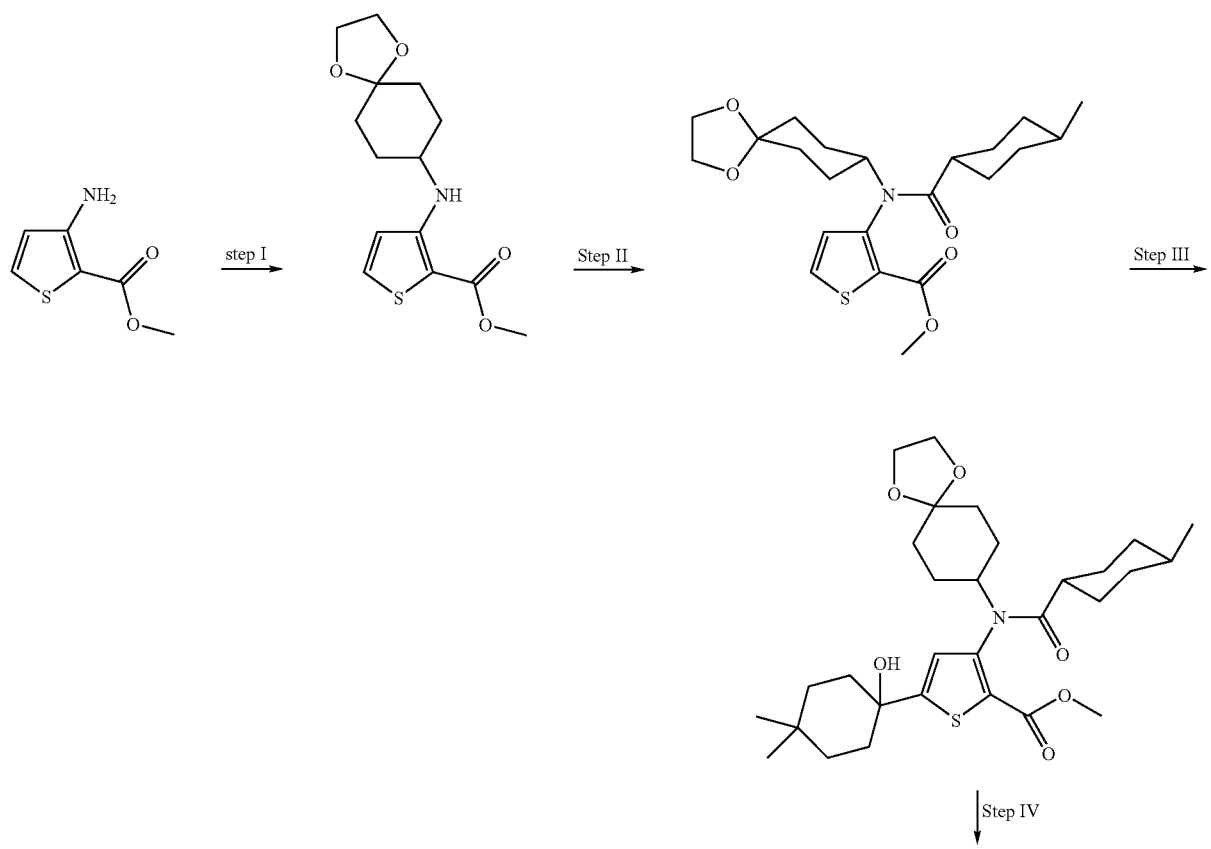

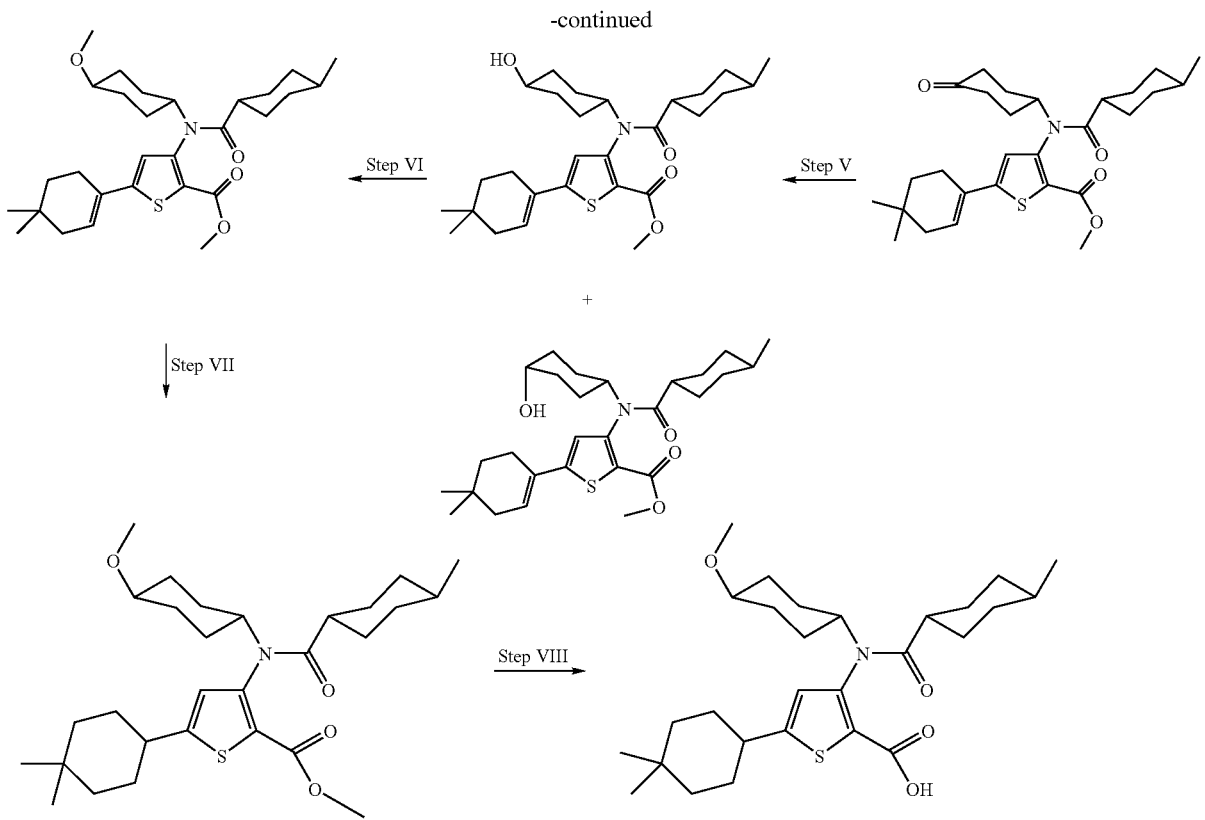

Step I:

A suspension of 3-amino-thiophene-2-carboxylic acid methyl ester (5.0 g, 31.85 mmol) in dry THF (9 mL) was treated with 1,4-cyclohexanedione monoethylene ketal (5.0 g, 32.05 mmol), followed by dibutyltin dichloride (482 mg, 1.59 mmol). After 5 min, phenyl silane (4.3 mL, 34.96 mmol) was added and the reaction mixture was stirred overnight at room temperature. After concentration, the residue was dissolved in EtOAc and washed with NaHCO$_3$ followed by brine. The organic layer was separated, dried (Na$_2$SO$_4$), filtered and concentrated. The residue was purified by column chromatography using 30% ethyl acetate in hexane as eluent to give 3-(1,4-dioxa-spiro[4.5]dec-8-ylamino)-thiophene-2-carboxylic acid methyl ester (4.5 g, 47% yield).

Step II:

A—Preparation of Trans-4-methylcyclohexyl Carboxylic Acid Chloride:

Oxalyl chloride (2M in dichloromethane, 17 mL) was added dropwise to a suspension of trans-4-methylcyclohexyl carboxylic acid (2.3 g, 16.2 mmol) in dichloromethane (5 mL) and DMF (0.1 mL). The reaction mixture was stirred for 3 h at room temperature. The volatiles were removed under reduced pressure to obtain the crude acid chloride which was used directly for the next reaction.

B—trans-4-Methylcyclohexyl carboxylic acid chloride was added to a solution of 3-(1,4-dioxa-spiro[4.5]dec-8-ylamino)-thiophene-2-carboxylic acid methyl ester (2.4 g, 8.08 mmol) in toluene (18 mL) followed by pyridine (0.7 mL). The resulting mixture was then stirred for 16 h at reflux. The reaction mixture was diluted with toluene (7 mL) and cooled to 5° C. After the addition of pyridine 1.5 mL) and MeOH (0.8 mL), the mixture was stirred 2 h at 5° C. The white solid was filtered and washed with toluene. The filtrate was washed with 10% citric acid, aq. NaHCO$_3$, dried (Na$_2$SO$_4$) and concentrated. The solid was purified by silica gel column chromatography using 20% EtOAc:hexane as eluent to obtain 3-[(1,4-dioxa-spiro[4.5]dec-8-yl)-(trans-4-methyl-cyclohexanecarbonyl)-amino]-thiophene-2-carboxylic acid methyl ester (2.3 g, 68%).

Step III:

Diisopropylamine (5.75 g, 56.8 mmol) and dry THF (58 mL) were added to a dry 500 mL 3 neck round bottom flask under nitrogen. The solution was cooled to −40° C. and nBuLi (39 mL, 47.4 mmol) was added slowly while keeping the internal temperature at −40° C. After 15 min, a suspension of 3-[(1,4-dioxa-spiro[4.5]dec-8-yl)-(trans-4-methyl-cyclo-hexanecarbo-nyl)-amino]-thiophene-2-carboxylic acid methyl ester (10.0 g, 23.7 mmol) in THF (70 mL) was added dropwise while maintaining the internal temperature at −40° C. After 30 min at −40° C., 4,4-dimethyl-cyclohexanone (5.88 g, 47.7 mmol) was added in one portion and stirred at −40° C. for 30 min. The reaction mixture was quenched with saturated NH$_4$Cl, partitioned and the aqueous phase extracted with EtOAc. The combined organic phase was washed with brine, dried over MgSO$_4$, filtered and evaporated to obtain crude 3-[(1,4-dioxa-spiro[4.5]dec-8-yl)-(trans-4-methyl-cyclohexanecarbonyl)-amino]-5-(1-hydroxy-4,4-dimethyl-cyclohexyl)-thiophene-2-carboxylic acid methyl ester (14.4 g) which was used for the next step without any purification.

Step IV:

To a solution of 3-[(1,4-dioxa-spiro[4.5]dec-8-yl)-(trans-4-methyl-cyclohexanecarbonyl)-amino]-5-(1-hydroxy-4,4-dimethyl-cyclohexyl)-thiophene-2-carbo-xylic acid methyl ester (14.4 g, previous step) in dry toluene (50 mL) at room temperature was added trifluoroacetic acid (50 mL). The reaction mixture was stirred for 90 min. Water (1.28 g, 71.1 mmol) was added to the mixture and stirred for 90 min. The reaction mixture was evaporated to dryness, extracted with EtOAc and washed with saturated NaHCO$_3$ and brine. The organic phase was dried over MgSO$_4$, filtered and evaporated to obtain crude 5-(4,4-dimethyl-cyclohex-1-enyl)-3-[(trans-4-methyl-cyclohexanecarbonyl)-(4-oxo-cyclohexyl)-amino]-thiophene-2-carboxylic acid methyl ester (13.3 g) which was used for the next step without any purification.

Step V:

To a solution of 5-(4,4-dimethyl-cyclohex-1-enyl)-3-[(trans-4-methyl-cyclohexanecarbonyl)-(4-oxo-cyclohexyl)-amino]-thiophene-2-carboxylic acid methyl ester (13.3 g, previous reaction) in 195 mL of MeOH at 0° C. was added NaBH$_4$ (450 mg, 11.9 mmol) portion wise. The reaction mixture was stirred for 1 hour at 0° C. After completion of the reaction, HCl (1N) was slowly added. The mixture was evaporated to dryness and the residue partitioned in EtOAc and water. The water phase was extracted (3×) and the combined organic phase was washed with brine, dried over Na$_2$SO$_4$ and evaporated to dryness. The residue was purified by silica gel column chromatography using (30:70) EtOAc: hexane as eluent to obtain 5-(4,4-dimethyl-cyclohex-1-enyl)-3-[(trans-4-hydroxy-cyclohexyl)-(trans-4-methyl-cyclohexanecarbonyl)-amino]-thiophene-2-carboxylic acid methyl ester (5155 mg) as a solid and 5-(4,4-dimethyl-cyclohex-1-enyl)-3-[(cis-4-hydroxy-cyclohexyl)-(trans-4-methyl-cyclohexanecarbonyl)-amino]-thiophene-2-carboxylic acid methyl ester (789 mg) as a solid. The overall yield for steps III, IV and V was 51%.

Step VI:

To a solution of 5-(4,4-dimethyl-cyclohex-1-enyl)-3-[(trans-4-hydroxy-cyclohexyl)-(trans-4-methyl-cyclohexanecarbonyl)-amino]-thiophene-2-carboxylic acid methyl ester (2.0 g, 4.1 mmol) and methyl iodide (7.6 mL, 123 mmol) in dry DMF (20 mL) at 0° C. was added NaH (60% suspension in oil, 328 mg, 8.2 mmol) in portion wise. The reaction mixture was stirred for 90 min at 0° C. under nitrogen. The reaction mixture was quenched by addition of aqueous HCl (2N). After extraction with EtOAc, the organic fraction was washed with water, dried over Na$_2$SO$_4$ and concentrated under reduced pressure. The residue was purified by column chromatography on silica gel using hexane-EtOAc (80:20) as eluent affording the 5-(4,4-dimethyl-cyclohex-1-enyl)-3-[(trans-4-methoxy-cyclohexyl)-(trans-4-methyl-cyclohexanecarbonyl)amino]-thiophene-2-carboxylic acid methyl ester 950 mg (46%) as a solid.

Step VII:

To a solution of 5-(4,4-dimethylcyclohex-1-enyl)-3-[(trans-4-methoxy-cyclo-hexyl)-(4-trans-methyl-cyclohexanecarbonyl)-amino]-thiophene-2-carboxylic acid methyl ester (950 mg, 1.89 mmol) in methanol (25 mL) was added 10% palladium on charcoal (100 mg). The resulting reaction mixture was placed under H$_2$ atmosphere, stirred at room temperature for 20 h, and then filtered through a pad of celite. The filtrate was concentrated and then evaporated to dryness to give 5-(4,4-dimethylcyclohexyl)-3-[(trans-4-methoxy-cyclohexyl)-(trans-4-methyl-cyclohexanecarbonyl)-amino]-thiophene-2-carboxylic acid methyl ester (890 mg, 93%) which was used for the next step without any purification.

Step VIII:

5-(4,4-Dimethylcyclohexyl)-3-[(trans-4-methoxy-cyclohexyl)-(trans-4-methyl-cyclohexanecarbonyl)-amino]-thiophene-2-carboxylic acid methyl ester (890 mg, 1.76 mmol) was dissolved in a 3:2:1 mixture of THF: methanol: H$_2$O (50 mL) and treated with a 1N solution of LiOH.H$_2$O (5.29 mL, 5.29 mmol). After stirring for 2 h at 60° C., the reaction mixture was evaporated to dryness and suspended in water. The reaction mixture was acidified to pH 3. After extraction with EtOAc, the organic fraction was washed with water, dried over Na$_2$SO$_4$ and concentrated under reduced pressure. The residue was purified by column chromatography on silica gel using CH$_2$Cl$_2$:MeOH (90:10) as eluent affording the 5-(4,4-dimethyl-cyclohexyl)-3-[(trans-4-methoxy-cyclohexyl)-(trans-4-methylcyclohexane-carbonyl)-amino]-thiophene-2-carboxylic acid (535 mg, 58%) as a solid.

Using essentially the same procedure described above and substituting different ketones the following compounds can be prepared:

5-(4,4-dimethyl-cyclohexyl)-3-[(cis-4-methoxy-cyclohexyl)-(trans-4-methyl-cyclohexanecarbonyl)-amino]-thiophene-2-carboxylic acid (compound #17)

RS-3-[(trans-4-methyl-cyclohexanecarbonyl)-(4-oxo-cyclohexyl)-amino]-5-(2-methyl-cyclohex-2-enyl)-thiophene-2-carboxylic acid (compound #58)

RS-3-[(trans-4-methyl-cyclohexanecarbonyl)-(4-oxo-cyclohexyl)-amino]-5-(6-methyl-cyclohex-1-enyl)-thiophene-2-carboxylic acid (compound #59)

RS-3-[(trans-4-hydroxy-cyclohexyl)-(trans-4-methyl-cyclohexanecarbonyl)-amino]-5-(6-methyl-cyclohex-1-enyl)-thiophene-2-carboxylic acid (compound #60)

RS-3-[(trans-4-hydroxy-cyclohexyl)-(trans-4-methyl-cyclohexanecarbonyl)-amino]-5-(5-methyl-cyclohex-1-enyl)-thiophene-2-carboxylic acid (compound #61)

5-(5,5-dimethyl-cyclohex-1-enyl)-3-[(trans-4-methoxy-cyclohexyl)-(trans-4-methyl-cyclohexanecarbonyl)-amino]-thiophene-2-carboxylic acid (compound #138)

5-bicyclo[2.2.1]hept-2-en-2-yl-3-[(trans-4-hydroxy-cyclohexyl)-(trans-4-methyl-cyclohexanecarbonyl)-amino]-thiophene-2-carboxylic acid (compound #28)

5-(4,4-dimethyl-cyclohex-1-enyl)-3-[(trans-4-methoxy-cyclohexyl)-(trans-4-methyl-cyclohexanecarbonyl)-amino]-thiophene-2-carboxylic acid (compound #20)

5-Cyclohex-1-enyl-3-[(trans-4-methyl-cyclohexanecarbonyl)-(4-oxo-cyclohexyl)-amino]-thiophene-2-carboxylic acid (compound #8)

3-[(trans-4-Methoxy-cyclohexyl)-(trans-4-methyl-cyclohexanecarbonyl)-amino]-5-(4-trifluoromethyl-cyclohexyl)-thiophene-2-carboxylic acid (compound #108)

3-[(trans-4-Methoxy-cyclohexyl)-(trans-4-methyl-cyclohexanecarbonyl)-amino]-5-(4-trifluoromethyl-cyclohex-1-enyl)-thiophene-2-carboxylic acid (compound #124)

EXAMPLE 4

Preparation of 5-cyclohex-1-enyl-3-[(trans-4-methoxy-cyclohexyl)-(trans-4-methyl-cyclohexanecarbonyl)-amino]-thiophene-2-carboxylic acid (compound#12)

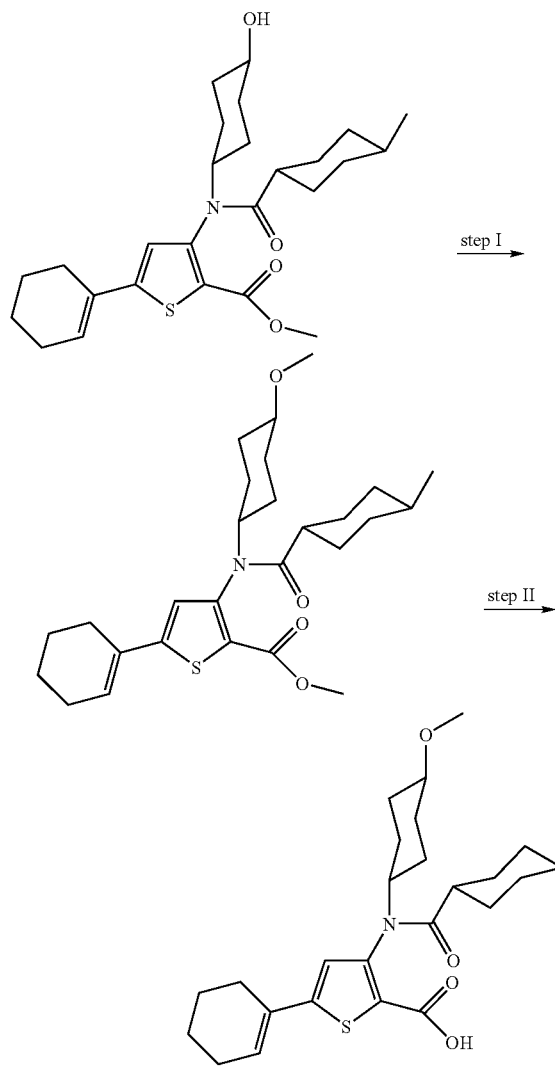

Step I:

To a solution of 5-cyclohex-1-enyl-3-[(trans-4-hydroxy-cyclohexyl)-(trans-4-methyl-cyclohexanecarbonyl)-amino]-thiophene-2-carboxylic acid methyl ester (1.007 g, 2.19 mmol) in dry DMF was added iodomethane (4.10 mL, 65.7 mmol), the mixture was cooled to 0° C., and NaH (60% suspension in oil, 175 mg, 4.38 mmol) was added in portions over 5 min. The mixture was stirred at 0° C. for 1 h 40 min, and it was quenched by addition of water and acidified with 2N HCl. The mixture was diluted with $CH_2Cl_2$ and washed with brine. The organic fraction was separated, dried over $Na_2SO_4$, concentrated under reduced pressure. The residue was purified by column chromatography on silica gel eluting with 0→50% ethyl acetate in hexane to give 5-cyclohex-1-enyl-3-[(trans-4-methoxy-cyclohexyl)-(trans-4-methyl-cyclohexanecarbonyl)-amino]-thiophene-2-carboxylic acid methyl ester (857 mg, 83%). 1H NMR (DMSO-$d_6$, 400 MHz): δ [ppm] 13.1-13.0 (bs, 1H), 6.96 (s, 1H), 6.41 (s, 1H), 4.31-4.24 (m, 1H), 3.12 (s, 3H), 2.90-2.84 (m, 1H), 2.42-2.20 (m, 2H), 2.15 (m, 2H), 1.98-1.78 (m, 4H), 1.68-1.64 (m, 2H), 1.58-1.35 (m, 8H), 1.21-1.02 (m, 5H), 0.87-0.77 (m, 1H), 0.72 (d, J=6.5 Hz, 3H), 0.63-0.46 (m, 2H)

Step II:

The methyl ester from Step I was hydrolysed as previously described (example 3, step VIII) to give 5-cyclohex-1-enyl-3-[(trans-4-methoxy-cyclohexyl)-(trans-4-methyl-yclohexanecarbonyl)-amino]-thiophene-2-carboxylic acid as a solid.

Using essentially the same procedure described above the following compounds can be prepared:

5-Cyclohex-1-enyl-3-[(4-methoxy-cyclohexyl)-(4-methyl-cyclohexanecarbonyl)-mino]-thiophene-2-carboxylic acid (compound #23)

3-[(trans-4-Methoxy-cyclohexyl)-(trans-4-methyl-cyclohexanecarbonyl)-amino]-thiophene-2-carboxylic acid (compound #145)

EXAMPLE 5

3-[(trans-4-Hydroxy-cyclohexyl)-(trans-4-methyl-cyclohexanecarbonyl)-amino]-5-(4-phenoxy-cyclohex-1-enyl)-thiophene-2-carboxylic acid (compound #33)

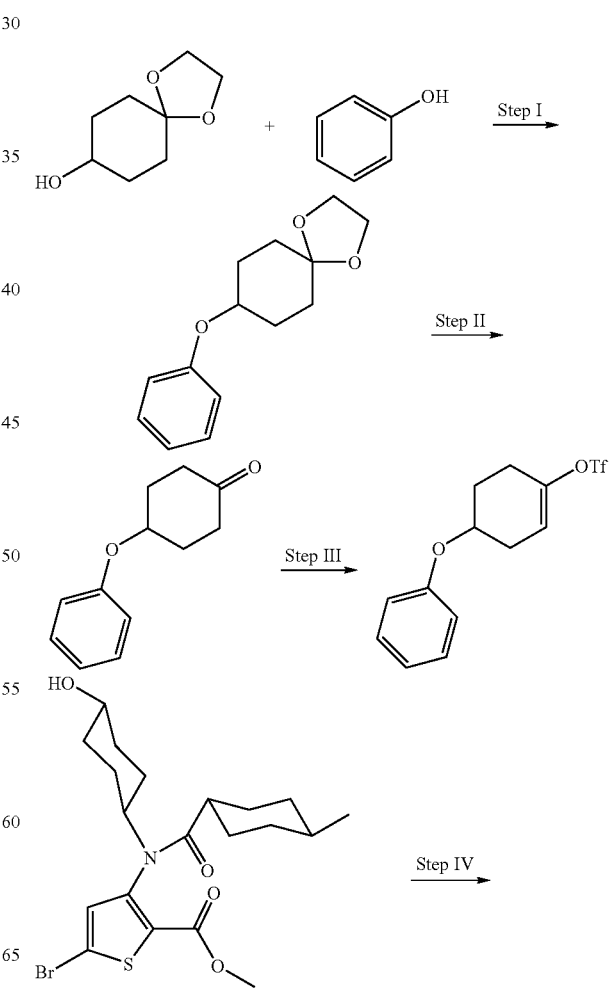

-continued

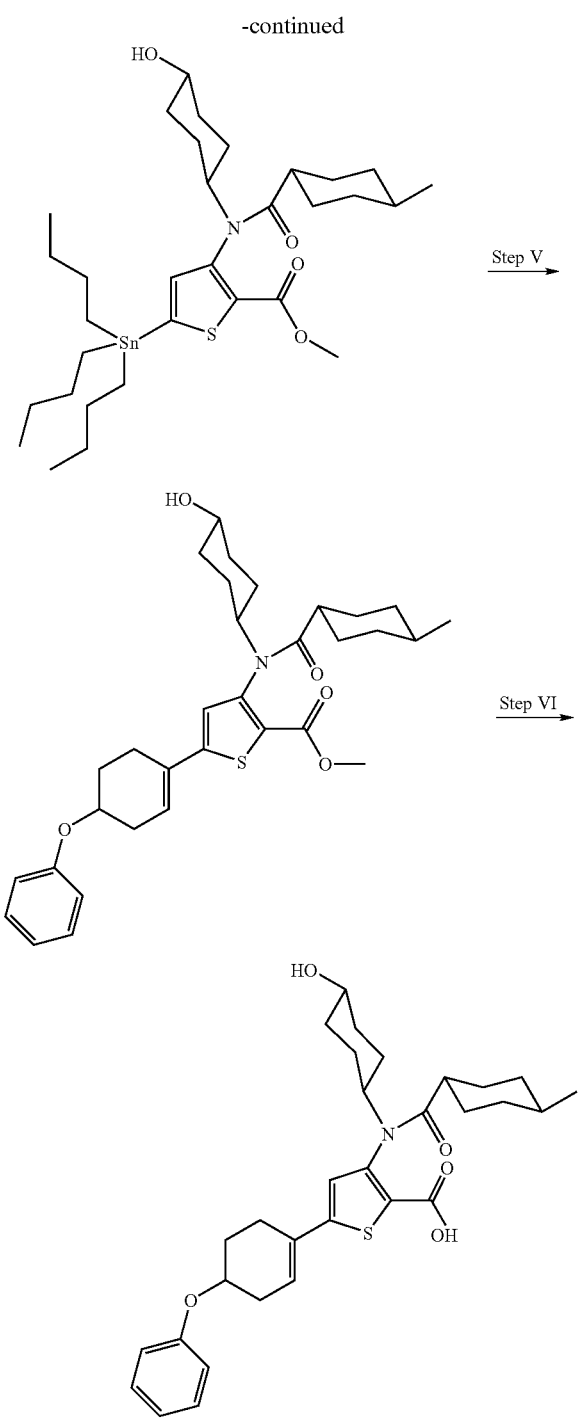

Step I:

To a solution of 1,4-dioxa-spiro[4.5]decan-8-ol (1.85 mg, 11.70 mmol), phenol (1.0 g, 10.64 mmol), PPh$_3$ (3.07 g, 11.70 mmol) in 15 mL of THF at 0° C. was added diisopropyl azodicarboxylate (6 mL, 11.70 mmol, 40% in toluene). The reaction mixture was stirred at room temperature for 48 h. Excess THF was removed in rotary evaporator and the residue was purified by silica gel column chromatography using ethyl acetate and hexane (1:19) to obtain 8-phenoxy-1,4-dioxa-spiro[4.5]decane (1.3 g, 52%) as a solid.

Step II:

To a solution of compound 8-phenoxy-1,4-dioxa-spiro[4.5]decane (2.0 g, 8.55 mmol) in THF (12 mL), 3N HCl (aqueous, 12 mL) was added and the reaction mixture was stirred at 50° C. for 3 h. Excess THF was removed in rotary evaporator and the crude reaction mixture was partitioned between water and ethyl acetate. The organic layer was separated, dried (Na$_2$SO$_4$) and concentrated. The residue was purified by silica gel column chromatography using ethyl acetate and hexane (1:4) to obtain 4-phenoxy-cyclohexanone (900 mg, 56%) as a white solid.

Step III:

To a solution of 4-phenoxy-cyclohexanone (100 mg, 0.53 mmol) in THF (2 mL) cooled to −78° C. was added lithium hexamethyldisilazane (0.6 mL, 0.58 mmol, 1M in THF) and the resulting solution was stirred for 2 h. N-Phenyl-bis(trifluoro-methanesulfonamide) (282 mg, 0.79 mmol) was added and the reaction mixture was allowed to warm at room temperature. Stirring was continued for overnight and solvent was removed and the residue was purified by column chromatography using ethyl acetate and hexane (1:4) to obtain trifluoro-methanesulfonic acid 4-phenoxy-cyclohex-1-enyl ester (120 mg, 71%) as a syrup.

Step IV:

To a stirred solution of 5-bromo-3-[(trans-4-hydroxy-cyclohexyl)-(trans-4-methyl-cyclohexanecarbonyl)-amino]-thiophene-2-carboxylic acid methyl ester (500 mg, 1.09 mmol) in toluene (5 mL) were added (PPh$_3$)$_4$Pd (164 mg, 0.13 mmol) and 1,1,1,2,2,2-hexabutyl-distannane (1.09 mL, 2.18 mmol) under nitrogen. The reaction mixture was stirred and heated to 110° C. during 8 h. The progress of the reaction was monitored by TLC. Filtration and removal of the solvent under reduced pressure on a rotary evaporator followed by flash column chromatographic purification using EtOAc and hexane (1:1), afforded 3-[(trans-4-hydroxy-cyclohexyl)-(trans-4-methyl-cyclohexanecarbonyl)-amino]-5-tributyl-stannanyl-thiophene-2-carboxylic acid methyl ester (150 mg, 21%) as a syrup.

Step V:

To a stirred solution of 3-[(trans-4-hydroxy-cyclohexyl)-(trans-4-methyl-cyclohexanecarbonyl)-amino]-5-tributyl-stannanyl-thiophene-2-carboxylic acid methyl ester (150 mg, 0.23 mmol) in toluene (5 mL) were added (PPh$_3$)$_4$Pd (26 mg), CuBr (2 mg, catalytic) and trifluoro-methanesulfonic acid 4-phenoxy-cyclohex-1-enyl ester (87 mg, 0.27 mmol) under nitrogen. The reaction mixture was stirred and heated to reflux during 5 h. The progress of the reaction was monitored by TLC. Filtration and removal of the solvent under reduced pressure on a rotary evaporator followed by silica gel column chromatography using ethyl acetate and hexane (4:1) afforded 3-[(trans-4-hydroxy-cyclohexyl)-(trans-4-methyl-cyclohexanecarbonyl)-amino]-5-(4-phenoxy-cyclohex-1-enyl)-thiophene-2-carb-oxylic acid methyl ester (30 mg, 24%) as a syrup.

Step VI:

To a stirred solution of 3-[(trans-4-hydroxy-cyclohexyl)-(trans-4-methyl-cyclohexanecarbonyl)-amino]-5-(4-phenoxy-cyclohex-1-enyl)-thiophene-2-carboxylic acid methyl ester (30 mg, 0.05 mmol) in THF:H$_2$O:MeOH (3:1:2) (2 mL), was added LiOH in water (1N) (0.2 mL, 0.2 mmol). The reaction mixture was stirred at 70° C. for 4 h. The reaction mixture was concentrated under reduced pressure on a rotary evaporator. The mixture was partitioned between ethyl acetate and water. The water layer was acidified using 0.1 N HCl. The EtOAc layer was separated and dried over Na$_2$SO$_4$. Filtration and removal of the solvent under reduced pressure on a rotary evaporator followed by HPLC purification afforded 3-[(trans-4-hydroxy-cyclohexyl)-(trans-4-methyl-cyclohexanecarbonyl)-amino]-5-(4-phenoxy-cyclohex-1-enyl)-thiophene-2-carboxylic acid (3 mg, 10%) as a foam.

EXAMPLE 6

5-Cyclohex-1-enyl-3-[[1-(2,2-difluoro-ethyl)-piperidin-4-yl]-(trans-4-methyl-cyclohexanecarbonyl)-amino]-thiophene-2-carboxylic acid (compound #92)

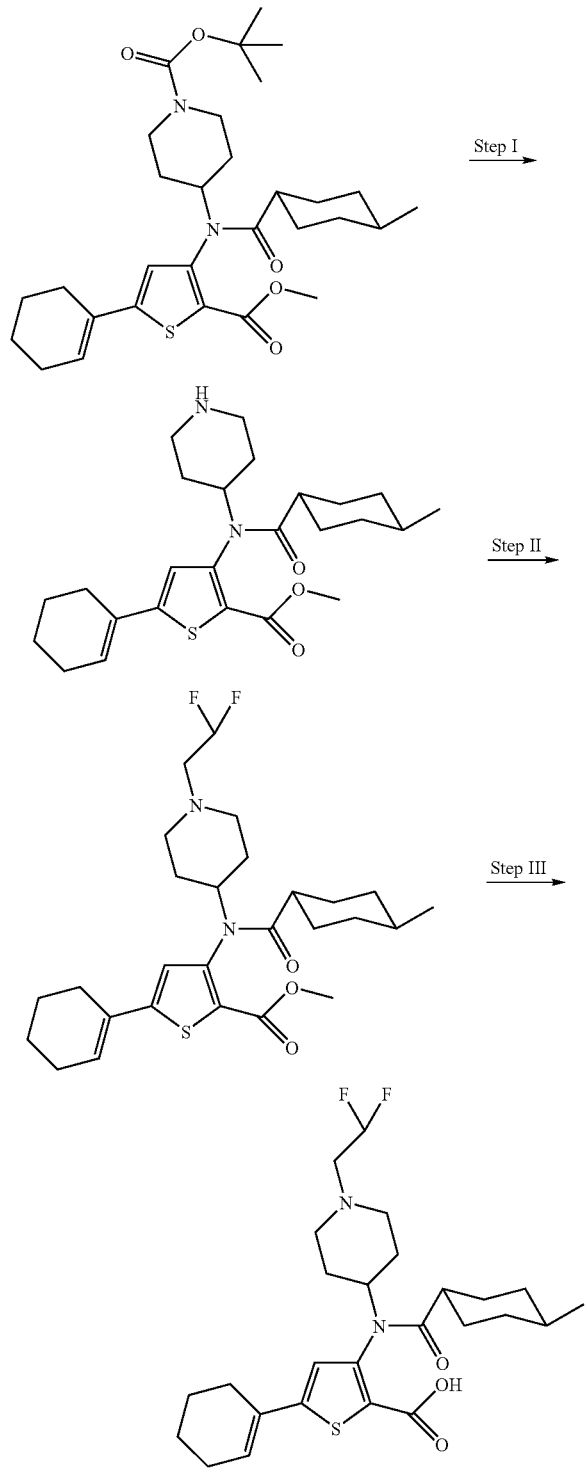

Step I:

A solution of 4-[(5-cyclohex-1-enyl-2-methoxycarbonyl-thiophen-3-yl)-(trans-4-methyl-cyclohexanecarbonyl)-amino]-piperidine-1-carboxylic acid tert-butyl ester (2.3 g, 4.22 mmol) in dichloromethane (15 mL) and trifluoroacetic acid (15 mL) was stirred at room temperature under $N_2$ atmosphere for 4 h. Solvents were removed under reduced pressure and the residue was partitioned between ethyl acetate and saturated $NaHCO_3$. The organic layer was separated, dried ($Na_2SO_4$) and concentrated. The residue was purified by silica gel column chromatography using methanol, chloroform and triethyl amine (10:89:1) as eluent to obtain 5-cyclohex-1-enyl-3-[(trans-4-methyl-cyclohexanecarbonyl)-piperidin-4-yl-amino]-thiophene-2-carboxylic acid methyl ester (1.5 g, 80%) as a solid.

Step II:

To a solution of 5-cyclohex-1-enyl-3-[(trans-4-methyl-cyclohexanecarbonyl)-piperidin-4-yl-amino]-thiophene-2-carboxylic acid methyl ester (100 mg, 0.23 mol) and 2-iodo-1,1-difluoroethane (53 mg, 0.45 mmol) in DMF (2 mL) was added NaH (18 mg, 0.45 mmol, 60%) at 0° C. under $N_2$ atmosphere. The reaction mixture was stirred at 60° C. for 7 h. Excess of NaH was quenched by adding water and the mixture was partitioned between water and ethyl acetate. The organic layer was separated, dried ($Na_2SO_4$) and concentrated. The residue was purified by HPLC to obtain 5-cyclohex-1-enyl-3-[[1-(2,2-difluoro-ethyl)-piperidin-4-yl]-(trans-4-methylcyclohexanecarbonyl)amino]-thiophene-2-carboxylic acid methyl ester (43 mg, 38%) as a white solid.

Step III:

To a stirred solution of 5-cyclohex-1-enyl-3-[[1-(2,2-difluoro-ethyl)-piperidin-4-yl]-(trans-4-methylcyclohexanecarbonyl)amino]-thiophene-2-carboxylic acid methyl ester (40 mg, 0.08 mmol) in THF:$H_2O$:MeOH (3:1:2) (1 mL), was added LiOH in water (1N) (0.16 mL, 0.16 mmol). The reaction mixture was stirred at 70° C. for 5 h. The mixture was concentrated under reduced pressure on a rotary evaporator and the residue was treated with a solution of 0.1 N HCl and extracted in EtOAc. The EtOAc layer was dried over $Na_2SO_4$. Filtration and removal of the solvent under reduced pressure on a rotary evaporator followed by HPLC purification afforded 5-cyclohex-1-enyl-3-[[1-(2,2-difluoro-ethyl)-piperidin-4-yl]-(trans-4-methyl-cyclohexanecarbonyl)-amino]-thiophene-2-carboxylic acid (9.0 mg, 39%) as a foam.

Similarly, was synthesized.

5-(Cyclohex-1-enyl-3-[[1-(2-fluoro-ethyl)-piperidin-4-yl]-(trans-4-methyl-cyclohexanecarbonyl)-amino]-thiophene-2-carboxylic acid (compound #139)

EXAMPLE 7

5-(2,6-Difluoro-cyclohex-1-enyl)-3-[(trans-4-methoxy-cyclohexyl)-(trans-4-methyl-cyclohexanecarbonyl)-amino]-thiophene-2-carboxylic acid (compound #119) and 5-(2,3-Difluoro-cyclohex-1-enyl)-3-[(trans-4-methoxy-cyclohexyl)-(trans-4-methyl-cyclohexanecarbonyl)-amino]-thiophene-2-carboxylic acid (compound #120)

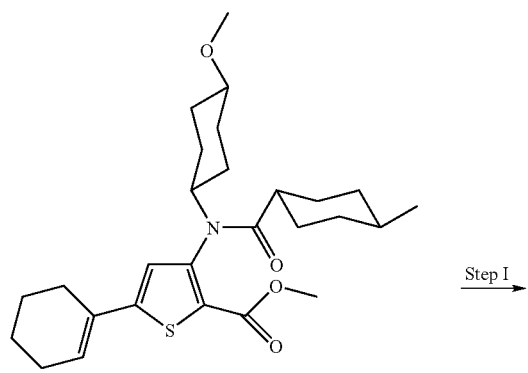

Step I →

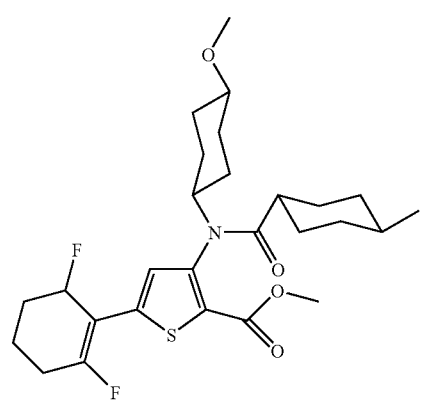

+

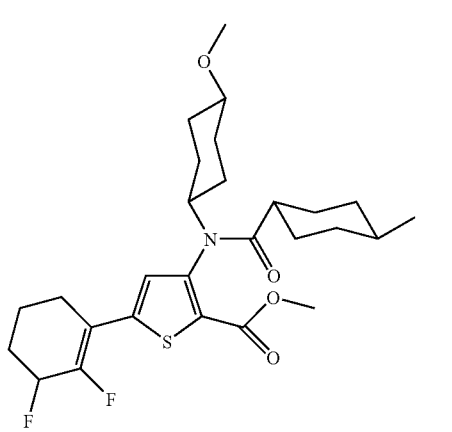

Step II →

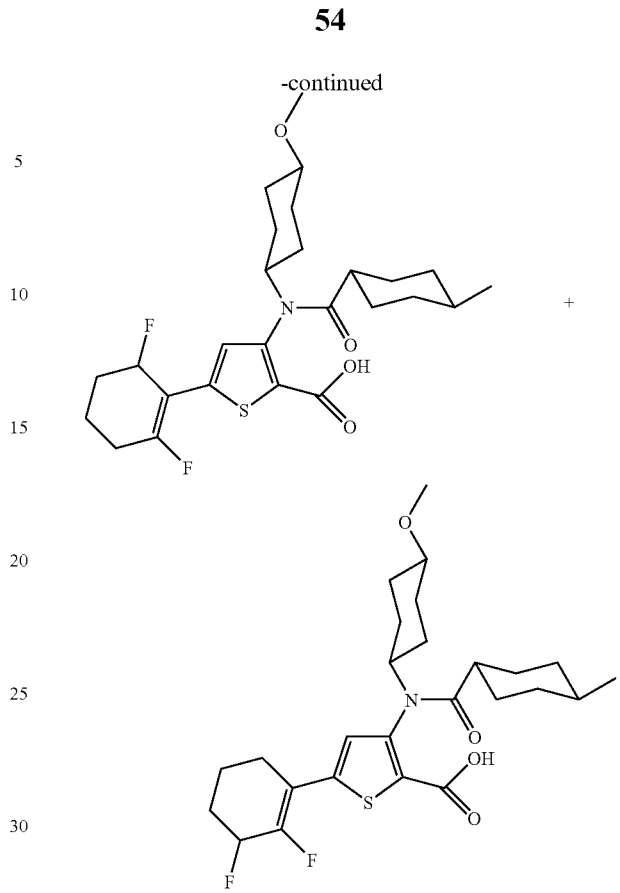

Step I:

To a solution of 5-cyclohex-1-enyl-3-[(trans-4-methoxy-cyclohexyl)-(trans-4-methyl-cyclohexanecarbonyl)-amino]-thiophene-2-carboxylic acid methyl ester (100 mg, 0.21 mmol) in acetonitrile (2 mL) was added selectfluor™ fluorinating reagent and the reaction mixture was stirred at room temperature for 12 h. Solvent was removed and the residue was purified by silica gel column chromatography using ethyl acetate and hexane (1:1) to obtain 5-(2,6-difluoro-cyclohex-1-enyl)-3-[(trans-4-methoxy-cyclohexyl)-(trans-4-methyl-cyclohexanecarbonyl)-amino]-thiophene-2-carboxylic acid methyl ester and 5-(2,3-difluoro-cyclohex-1-enyl)-3-[(trans-4-methoxy-cyclohexyl)-(trans-4-methyl-cyclohexanecarbonyl)amino]-thiophene-2-carboxylic acid methyl ester as a mixture (83 mg, 78%) as a syrup.

Step II:

To a solution of 5-(2,6-difluoro-cyclohex-1-enyl)-3-[(trans-4-methoxy-cyclohexyl)-(trans-4-methyl-cyclohexanecarbonyl)-amino]-thiophene-2-carboxylic acid methyl ester and 5-(2,3-Difluoro-cyclohex-1-enyl)-3-[(trans-4-methoxy-cyclohexyl)-(trans-4-methyl-cyclohexanecarbonyl)-amino]-thiophene-2-carboxylic acid methyl ester (83 mg, 0.16 mmol) in THF:H$_2$O:MeOH (3:1:2) (2 mL), was added LiOH in water (1N) (0.5 mL, 0.5 mmol). The reaction mixture was stirred at 70° C. for 5 h. The mixture was concentrated under reduced pressure on a rotary evaporator and the residue was treated with a solution of 0.1 N HCl and extracted in EtOAc. The EtOAc layer was dried over Na$_2$SO$_4$. Filtration and removal of the solvent under reduced pressure on a rotary evaporator followed by HPLC purification afforded 5-(2,6-difluoro-cyclohex-1-enyl)-3-[(trans-4-methoxy-cyclohexyl)-(trans-4-methyl-cyclohexanecarbonyl)-amino]-thiophene-2-carboxylic acid (3 mg) and 5-(2,3-difluoro-cyclohex-1-enyl)-3-[(trans-4-methoxy-cyclohexyl)-(trans-4-methyl-cyclohexanecarbonyl)-amino]-thiophene-2-carboxylic acid (3 mg) in overall 8% isolated yield.

EXAMPLE 8

5-Cyclohex-1-enyl-3-[(1-isobutyryl-piperidin-4-yl)-(trans-4-methyl cyclohexanecarbonyl)-amino]-thiophene-2-carboxylic acid (compound #141)

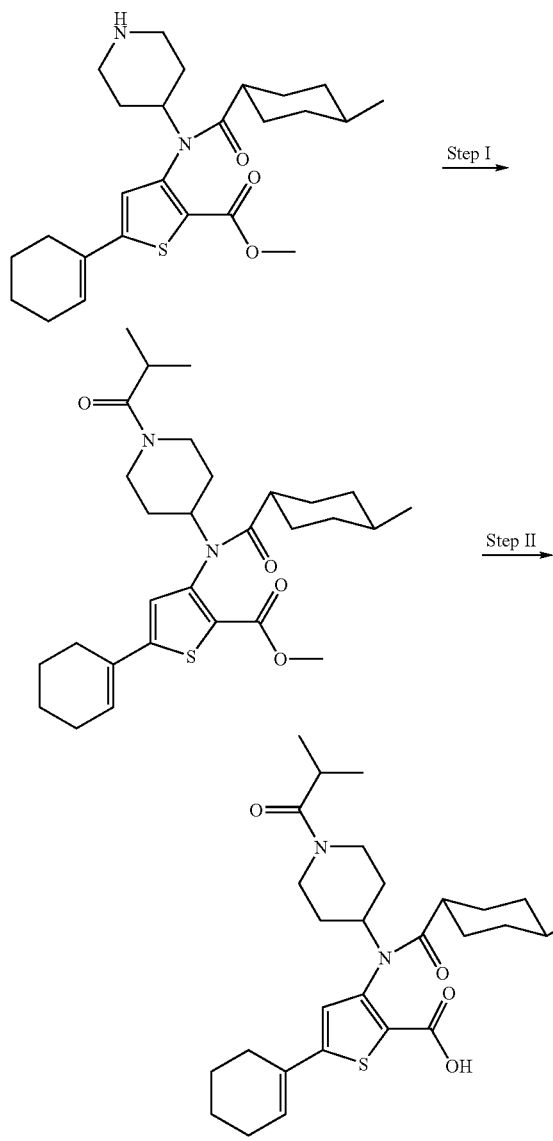

Step I:

To a solution of 5-cyclohex-1-enyl-3-[(trans-4-methylcyclohexanecarbonyl)-piperidin-4-yl-amino]-thiophene-2-carboxylic acid methyl ester (100 mg, 0.23 mmol) in dichloromethane (3 mL) was added triethylamine (3 mL) and isobutyryl chloride (28 μL, 0.27 mmol). The reaction mixture was stirred at room temperature for 12 h and then quenched with a saturated solution of NaHCO₃. The organic layer was separated, dried (Na₂SO₄) and concentrated. The residue was purified by silica gel column chromatography using ethyl acetate and hexane (1:1) as eluent to obtain 5-cyclohex-1-enyl-3-[(1-isobutyryl-piperidin-4-yl)-(trans-4-methyl cyclohexanecarbonyl)-amino]-thiophene-2-carboxylic acid methyl ester (55 mg, 47%) as a white solid.

Step II:

To a stirred solution of 5-cyclohex-1-enyl-3-[(1-isobutyryl-piperidin-4-yl)-(trans-4-methyl cyclohexanecarbonyl)-amino]-thiophene-2-carboxylic acid methyl ester (50 mg, 0.10 mmol) in THF:H₂O:MeOH (3:1:2) (3 mL), was added LiOH in water (1N) (0.3 mL, 0.3 mmol). The reaction mixture was stirred at 70° C. for 5 h. The mixture was concentrated under reduced pressure on a rotary evaporator and the residue was treated with a solution of 0.1 N HCl and extracted in EtOAc. The EtOAc layer was dried over Na₂SO₄. Filtration and removal of the solvent under reduced pressure on a rotary evaporator followed by HPLC purification afforded 5-cyclohex-1-enyl-3-[(1-isobutyryl-piperidin-4-yl)-(trans-4-methyl cyclohexanecarbonyl)-amino]-thiophene-2-carboxylic acid (30.0 mg, 61%) as a foam.

Using essentially the same procedure described above the following compounds can be prepared:

5-Cyclohex-1-enyl-3-[(1-methanesulfonyl-piperidin-4-yl)-(trans-4-methyl-cyclohexanecarbonyl)-amino]-thiophene-2-carboxylic acid (compound #101)

5-Cyclohex-1-enyl-3-{(4-methyl-cyclohexanecarbonyl)-[4-(methyl-propionyl-amino)-cyclohexyl]-amino}-thiophene-2-carboxylic acid (compound #140)

EXAMPLE 9

5-Cyclohex-1-enyl-3-[(trans-4-methoxymethoxy-cyclohexyl)-(trans-4-methyl-yclohexanecarbonyl)-amino]-thiophene-2-carboxylic acid (compound 24)

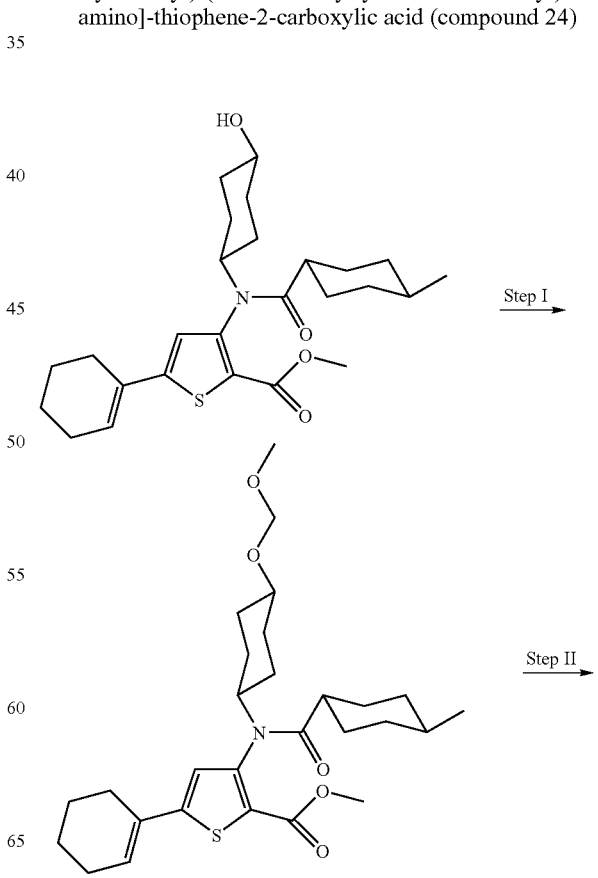

-continued

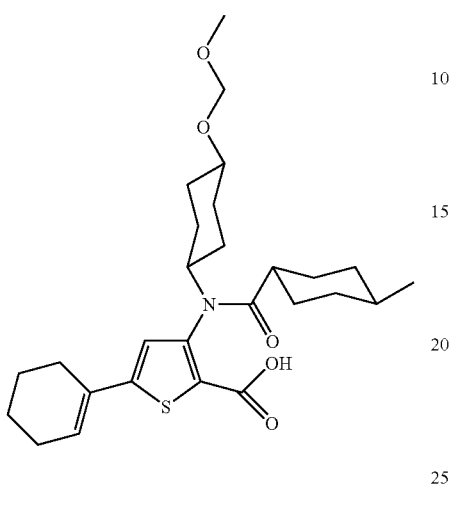

Step I:

To a solution of 5-cyclohex-1-enyl-3-[(trans-4-hydroxy-cyclohexyl)-(trans-4-methyl-cyclohexanecarbonyl)-amino]-thiophene-2-carboxylic acid methyl ester (1 g, 2.18 mmol) in dichloromethane (10 mL) was added diisopropyl ethylamine (0.6 mL, 3.3 mmol), chloromethyl methyl ether (250 μL, 3.3 mmol) and DMAP (40 mg, 0.33 mmol). The reaction mixture was refluxed for 12 h. Solvents were removed and the residue as purified by silica gel column chromatography using ethyl acetate and hexane (1:3) as eluent to obtain 5-cyclohex-1-enyl-3-[(trans-4-methoxymethoxy-cyclohexyl)-(trans-4-methyl-cyclohexanecarbonyl)-amino]-thiophene-2-carboxylic acid methyl ester (780 mg, 71%) as a syrup.

Step II:

To a solution of 5-cyclohex-1-enyl-3-[(trans-4-methoxymethoxy-cyclohexyl)-(trans-methyl-cyclohexanecarbonyl)-amino]-thiophene-2-carboxylic acid methyl ester (775 mg, 1.54 mmol) in THF:H$_2$O:MeOH (3:1:2) (10 mL), was added LiOH in water (1N) (4.6 mL, 4.6 mmol). The reaction mixture was stirred at 70° C. for 5 h. The mixture was concentrated under reduced pressure on a rotary evaporator and the residue was treated with a solution of 0.1 N HCl and extracted in EtOAc. The EtOAc layer was dried over Na$_2$SO$_4$. Filtration and removal of the solvent under reduced pressure on a rotary evaporator followed by HPLC purification afforded 5-cyclohex-1-enyl-3-[(trans-4-methoxymethoxy-cyclohexyl)-(trans-4-methyl-cyclohexanecarbonyl)-amino]-thiophene-2-carboxylic acid (380 mg, 50%) as a foam.

EXAMPLE 10

5-(4,4-Dimethyl-cyclohexyl)-3-[(trans-4-methoxy-cyclohexyl)-(trans-4-methyl-cyclohexanecarbonyl)-amino]-thiophene-2-carboxylate(S)-5-amino-1-carboxy-pentyl-ammonium (compound #100)

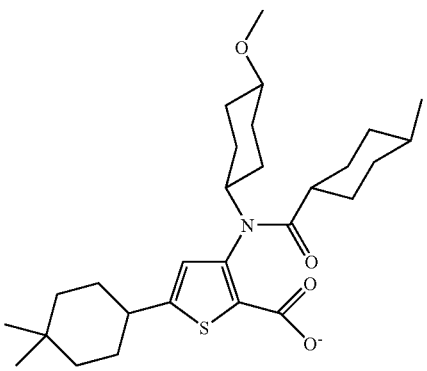

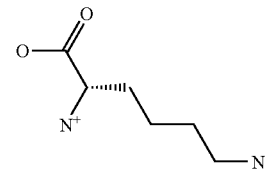

To a solution of 5-(4,4-dimethyl-cyclohexyl)-3-[(trans-4-methoxy-cyclohexyl)-(trans-4-methyl-cyclohexanecarbonyl)-amino]-thiophene-2-carboxylic acid (80 mg, 0.16 mmol) in dioxane and water (1:1, 10 mL), L-lysine was added at 0° C. The solution was stirred at rt for 30 min. Dioxane was removed in the rotary evaporator (partial evaporation) and then the solution was lyophilized to obtain 5-(4,4-dimethyl-cyclohexyl)-3-[(trans-4-methoxy-cyclohexyl)-(trans-4-methyl-cyclohexanecarbonyl)-amino]-thiophene-2-carboxylate (S)-5-amino-1-carboxy-pentyl-ammonium as a foam 104 mg.

Using essentially the same procedure described above the following compounds can be prepared:

5-(4,4-Dimethyl-cyclohexyl)-3-[(trans-4-methoxy-cyclohexyl)-(trans-4-methyl-cyclohexanecarbonyl)-amino]-thiophene-2-carboxylate(2-hydroxy-ethyl)-trimethyl-ammonium (compound #110)

5-(4,4-Dimethyl-cyclohexyl)-3-[(trans-4-methoxy-cyclohexyl)-(trans-4-methyl-cyclohexanecarbonyl)-amino]-thiophene-2-carboxylatemethyl-((2S,3R,4R,5R)-2,3,4,5,6-pentahydroxy-hexyl)-ammonium (compound #109)

EXAMPLE 11

Preparation of RS-5-cyclohex-1-enyl-3-[(trans-4-methyl-cyclohexanecarbonyl)-(3-oxo-octahydro-indolizin-7-yl)-amino]-thiophene-2-carboxylic acid (Compound #87)

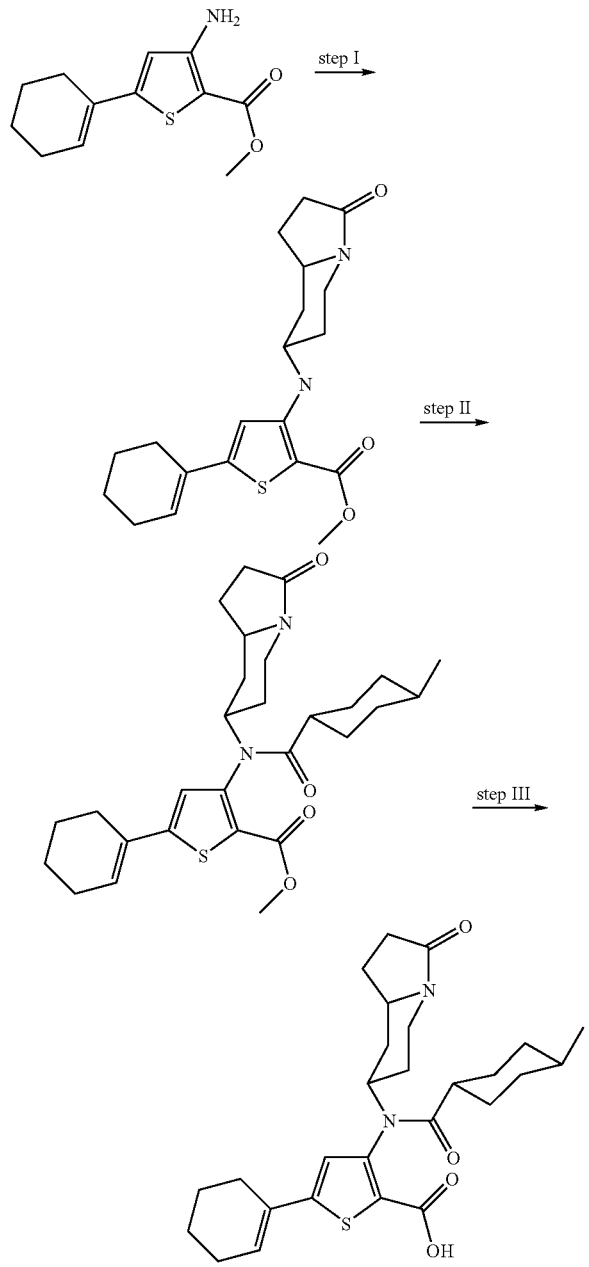

Step I:

To a solution of 5-cyclohex-1-enyl-3-aminothiophene-2-carboxylic acid methyl ester (689 mg, 2.90 mmol) and 3-oxo-octahydro-indolizin-7-one (750 mg, 4.90 mmol; prepared as described in *Tetrahedron*, 1975, 1437) in 3 mL of dry THF was added dibutyltin dichloride (88 mg, 0.29 mmol), and the mixture was stirred for 10 min at room temperature under nitrogen. Then phenylsilane (394 µL, 3.19 mmol) was added, and the mixture was stirred overnight at room temperature. Solvent was evaporated under reduced pressure, and the residue was purified by column chromatography on silica gel using gradient 30-100% EtOAc in hexane to afford 973 mg (90%) of 5-cyclohex-1-enyl-3-[(3-oxo-octahydro-indolizin-7-yl)-amino]-thiophene-2-carboxylic acid methyl ester.

Step II:

trans-4-Methylcyclohexyl carboxylic acid chloride was added to a solution of 5-cyclohex-1-enyl-3-[(3-oxo-octahydro-indolizin-7-yl)-amino]-thiophene-2-carboxylic acid methyl ester (698 mg, 1.86 mmol) and pyridine (166 µL, 2.05 mmol) in dry toluene (8 mL). The mixture was refluxed for 16 h, then it was brought to room temperature, additional amount of pyridine (0.2 mL) and MeOH (1 mL) were added. The mixture was diluted with dichloromethane, washed with brine; organic phase was dried over $Na_2SO_4$, concentrated and purified by column chromatography on silica gel using gradient 0-100% EtOAc in hexane to afford 592 mg (64%) of 5-cyclohex-1-enyl-3-[(trans-4-methyl-cyclohexanecarbonyl)-(3-oxo-octahydro-indolizin-7-yl)-amino]-thiophene-2-carboxylic acid methyl ester.

Step III:

The methyl ester from Step II (565 mg, 1.13 mmol) was hydrolysed with lithium hydroxide as previously described (example 3, step VIII) to give 390 mg (71%) of RS-5-cyclohex-1-enyl-3-[(trans-4-methyl-cyclohexanecarbonyl)-(3-oxo-octahydro-indolizin-7-yl)-amino]-thiophene-2-carboxylic acid as a solid.

Using essentially the same procedure described above the following compounds can be prepared utilizing other ketones in step I:

3-[(trans-4-tert-butyl-cyclohexyl)-(trans-4-methyl-cyclohexanecarbonyl)-amino]-5-cyclohex-1-enyl-thiophene-2-carboxylic acid (compound #44);

3-[(cis-4-tert-butyl-cyclohexyl)-(trans-4-methyl-cyclohexanecarbonyl)-amino]-5-cyclohex-1-enyl-thiophene-2-carboxylic acid (compound #45);

RS-5-cyclohex-1-enyl-3-[(trans-4-methyl-cyclohexanecarbonyl)-(1,2,3,4-tetrahydro-naphthalen-2-yl)-amino]-thiophene-2-carboxylic acid (compound #66);

5-cyclohex-1-enyl-3-[(cis/trans-decahydro-naphthalen-2-yl)-(trans-4-methyl-cyclohexanecarbonyl)-amino]-thiophene-2-carboxylic acid (compound #65);

RS-5-cyclohex-1-enyl-3-[(7-methoxy-1,2,3,4-tetrahydro-naphthalen-2-yl)-(trans-4-methyl-cyclohexanecarbonyl)-amino]-thiophene-2-carboxylic acid (compound #67);

5-cyclohex-1-enyl-3-[(cis/trans-4-methoxymethyl-cyclohexyl)-(trans-4-methyl-cyclohexanecarbonyl)-amino]-thiophene-2-carboxylic acid (compound #126), (ketone for step I can be prepared as described in *Liebigs Annalen der Chemie* (1994), (9), 911-15);

5-cyclohex-1-enyl-3-[(cis-4-methoxymethyl-cyclohexyl)-(trans-4-methyl-cyclohexanecarbonyl)-amino]-thiophene-2-carboxylic acid (compound #131), (ketone for step I can be prepared as described in *Liebigs Annalen der Chemie* (1994), (9), 911-15);

5-cyclohex-1-enyl-3-[(trans-4-methoxymethyl-cyclohexyl)-(trans-4-methyl-cyclohexanecarbonyl)-amino]-thiophene-2-carboxylic acid (compound #132), (ketone for step I can be prepared as described in *Liebigs Annalen der Chemie* (1994), (9), 911-15);

3-[(trans-3-carboxy-trans-4-methylcarbamoyl-cyclohexyl)-(trans-4-methyl-cyclohexanecarbonyl)-amino]-5-cyclohex-1-enyl-thiophene-2-carboxylic acid (compound #68) (ketone for step I can be prepared according to: *Canadian Journal of Chemistry* (1982), 60(4), 419-24).

5-Cyclohex-1-enyl-3-[(trans-4-methyl-cyclohexanecarbonyl)-(tetrahydro-pyran-4-yl)-amino]-thiophene-2-carboxylic acid (compound #29)

5-Cyclohex-1-enyl-3-[(trans-4-methyl-cyclohexanecarbonyl)-(tetrahydro-thiopyran-4-yl)-amino]-thiophene-2-carboxylic acid (compound #42)

5-Cyclohex-1-enyl-3-[(trans-4-methyl-cyclohexanecarbonyl)-(trans-4-methyl-cyclohexyl)-amino]-thiophene-2-carboxylic acid (compound #52)

5-Cyclohex-1-enyl-3-[(trans-4-methyl-cyclohexanecarbonyl)-(cis-4-methyl-cyclohexyl)-amino]-thiophene-2-carboxylic acid (compound #53)

5-Cyclohex-1-enyl-3-[(trans-4-methyl-cyclohexanecarbonyl)-(1-methyl-piperidin-4-yl)-amino]-thiophene-2-carboxylic acid (compound #56)

Sodium; 5-(4,4-dimethyl-cyclohexyl)-3-[(4-methyl-cyclohexanecarbonyl)-(1-methyl-piperidin-4-yl)-amino]-thiophene-2-carboxylate (compound #93)

EXAMPLE 12

Preparation of RS-5-cyclohex-1-enyl-3-[(trans-4-methyl-cyclohexane-carbonyl)-(2-methyl-1,3-dioxo-octahydro-isoindol-5-yl)-amino]-thiophene-2-carboxylic acid (compound #72)

ecarbonyl)-(2-methyl-1,3-dioxo-octahydro-isoindol-5-yl)-amino]-thiophene-2-carboxylic acid as white solid after lyophilization.

EXAMPLE 13

Preparation of 5-(4,4-dimethyl-cyclohex-1-enyl)-3-[(trans-4-methoxy-methoxy-cyclohexyl)-(trans-4-methyl-cyclohexanecarbonyl)-amino]-thiophene-2-carboxylic acid (Compound #114)

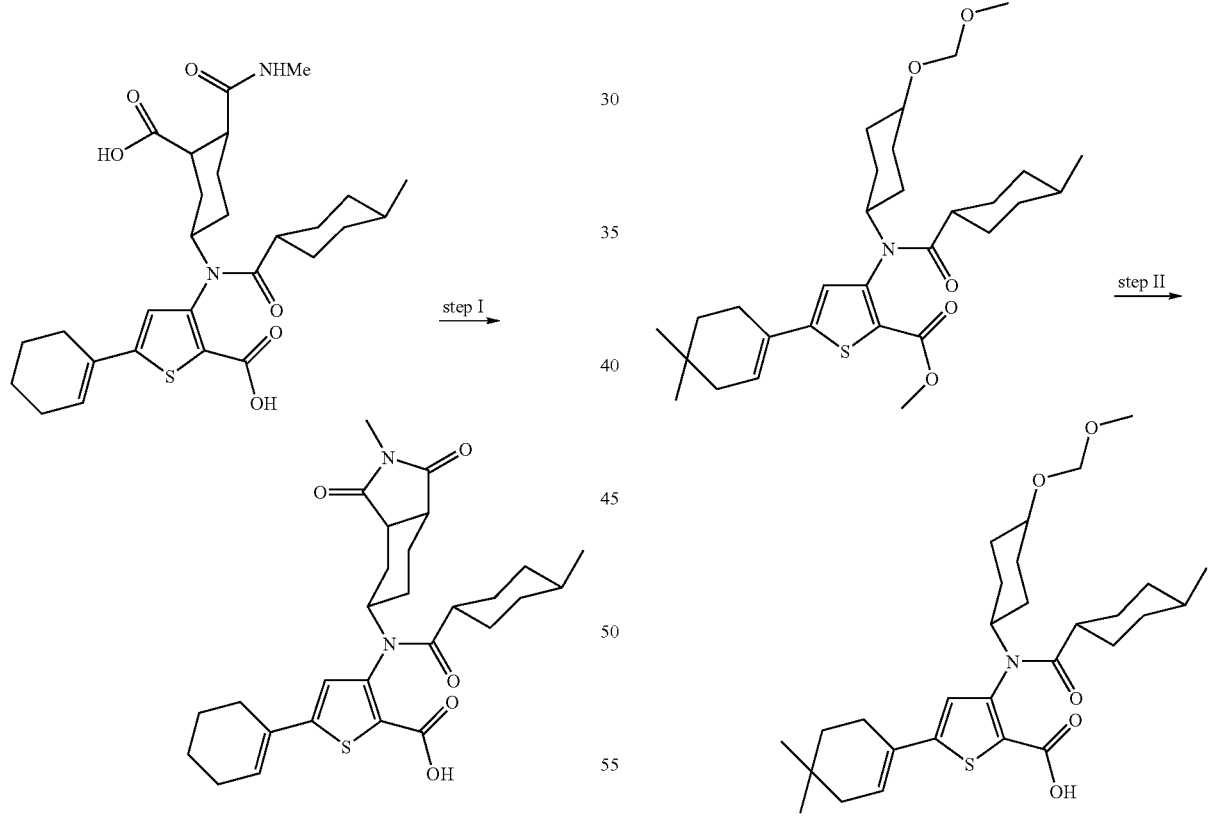

Step I:
To a solution of 3-[(trans-3-carboxy-trans-4-methylcarbamoyl-cyclohexyl)-(trans-4-methyl-cyclohexanecarbonyl)-amino]-thiophene-2-carboxylic acid (44 mg, 0.083 mmol; prepared as described in example 11) in dry $CH_2Cl_2$ (2 mL) were added $iPr_2EtN$ (29 μL, 0.166 mmol) and HATU (33 mg, 0.087 mmol), and the mixture was stirred for 72 h at room temperature. Solvent was evaporated to dryness and the residue was purified by preparative HPLC to obtain 22 mg (52%) of RS-5-cyclohex-1-enyl-3-[(trans-4-methyl-cyclohexan- Step I:
To a solution of 5-(4,4-dimethyl-cyclohex-1-enyl)-3-[(trans-4-hydroxy-cyclohexyl)-(trans-4-methyl-cyclohexanecarbonyl)-amino]-thiophene-2-carboxylic acid methyl ester (406 mg, 0.83 mmol), i-$Pr_2EtN$ (218 μL, 1.25 mmol) and DMAP (15 mg, 0.12 mmol) in dry $CH_2Cl_2$ (20 mL) was added chloromethyl methyl ether (95 μL, 1.25 mmol), and the mixture was stirred at room temperature overnight. Then the mixture was diluted with $CH_2Cl_2$, washed with brine, organic fraction was dried over Na₂SO₄, concentrated under reduced pressure and purified by column chromatography on silica gel eluting with 0-30% EtOAc in hexanes to give 286 mg (65%) of 5-(4,4-dimethyl-cyclohex-1-enyl)-3-[(trans-4-methoxymethoxy-cyclohexyl)-(trans-4-methyl-cyclohexanecarbonyl)-amino]-thiophene-2-carboxylic acid methyl ester.

Step II:

The methyl ester from Step I (285 mg, 0.54 mmol) was dissolved in a 4:2:1 mixture of THF:H₂O:methanol (7 mL), LiOH.H₂O (225 mg, 5.36 mmol) was added to solution, and it was heated in a microwave oven at 120° C. for 5 min, then for an additional 5 min at 130° C. The reaction mixture was diluted with CH₂Cl₂, acidified with 2N HCl, washed with brine, and organic fraction was dried over Na₂SO₄ and evaporated to dryness. The residue was purified by column chromatography on silica gel eluting with 0-10% MeOH in CH₂Cl₂ to give 265 mg (95%) of 5-(4,4-dimethyl-cyclohex-1-enyl)-3-[(trans-4-methoxymethoxy-cyclohexyl)-(trans-4-methyl-cyclohexanecarbonyl)-amino]-thiophene-2-carboxylic acid.

Using essentially the same procedure described above the following compounds can be prepared:
5-Cyclohex-1-enyl-3-[(trans-4-ethoxymethoxy-cyclohexyl)-(trans-4-methyl-cyclohexanecarbonyl)-amino]-thiophene-2-carboxylic acid (compound #125)

EXAMPLE 14

Preparation of 5-(1,4-dioxa-spiro[4.5]dec-7-en-8-yl)-3-[(trans-4-hydroxy-cyclohexyl)-(trans-4-methyl-cyclohexanecarbonyl)-amino]-thiophene-2-carboxylic acid (compound #14)

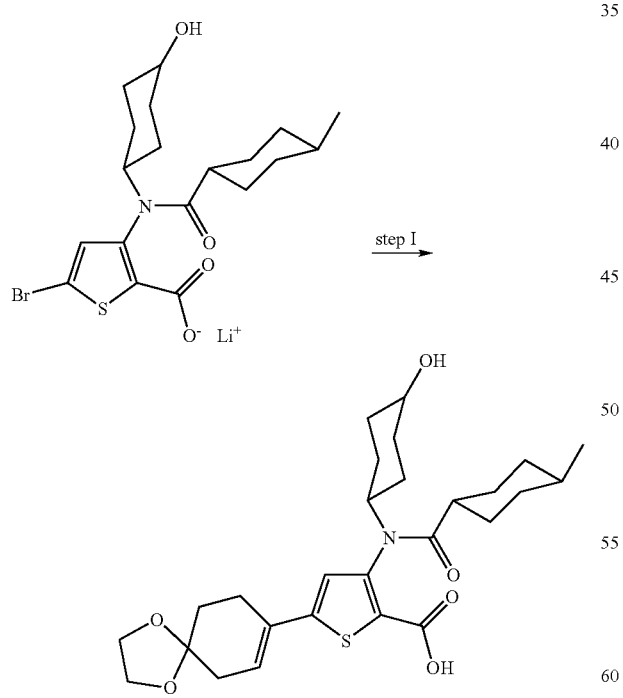

Step I:

To a solution of lithium 5-bromo-3-[(trans-4-hydroxy-cyclohexyl)-(trans-4-methylcyclohexanecarbonyl)-amino]-thiophene-2-carboxylate (498 mg, 1.10 mmol) and 1,4-dioxaspiro[4,5]dec-7-en-8-boronic acid (412 mg, 1.55 mmol) in DMF (6 mL) was added 2M solution of Na₂CO₃ (3 mL), and the mixture was deoxygenated by bubbling nitrogen through solution for 10 min. Then Pd(PPh₃)₄ was added to the mixture, and it was refluxed under nitrogen for 2 h. The mixture was brought to room temperature and filtered through a celite pad washing with EtOAc and H₂O. Filtrate was extracted with EtOAc (4×), then aqueous fraction was separated and acidified with 2N HCl till pH 2-3. The mixture was extracted with CH₂Cl₂ and CH₂Cl₂-MeOH, organic fraction was dried over Na₂SO₄ and evaporated to dryness. Crude compound was recrystallized from CH₃CN to afford 453 mg (82%) of 5-(1,4-dioxa-spiro[4.5]dec-7-en-8-yl)-3-[(trans-4-hydroxy-cyclohexyl)-(trans-4-methyl-cyclohexanecarbonyl)-amino]-thiophene-2-carboxylic acid as a solid.

Using essentially the same procedure described above the following compounds can be prepared utilizing other boronic acids:

5-cyclohept-1-enyl-3-[(trans-4-hydroxy-cyclohexyl)-(trans-4-methyl-cyclohexanecarbonyl)-amino]-thiophene-2-carboxylic acid (compound #5)

RS-3-[(trans-4-hydroxy-cyclohexyl)-(trans-4-methyl-cyclohexanecarbonyl)-amino]-5-(4-methyl-cyclohex-1-enyl)-thiophene-2-carboxylic acid (compound #4)

RS-5-(4-tert-butyl-cyclohex-1-enyl)-3-[(trans-4-hydroxy-cyclohexyl)-(trans-4-methyl-cyclohexanecarbonyl)-amino]-thiophene-2-carboxylic acid (compound #13)

RS-3-[cyclohexyl-(trans-4-methyl-cyclohexanecarbonyl)-amino]-5-(4-methyl-cyclohex-1-enyl)-thiophene-2-carboxylic acid (compound #47) and 5-cyclohept-1-enyl-3-[cyclohexyl-(trans-4-methyl-cyclohexanecarbonyl)-amino]-thiophene-2-carboxylic acid (compound #46) were prepared from lithium 5-bromo-3-[cyclohexyl-(trans-4-methyl-cyclohexanecarbonyl)-amino]-thiophene-2-carboxylate obtained from 5-bromo-3-amino-thiophene-2-carboxylic acid methyl ester.

EXAMPLE 15

Preparation of 3-[(trans-4-hydroxy-cyclohexyl)-(trans-4-methyl-cyclohexanecarbonyl)-amino]-5-(4-oxo-cyclohex-1-enyl)-thiophene-2-carboxylic acid (compound #25)

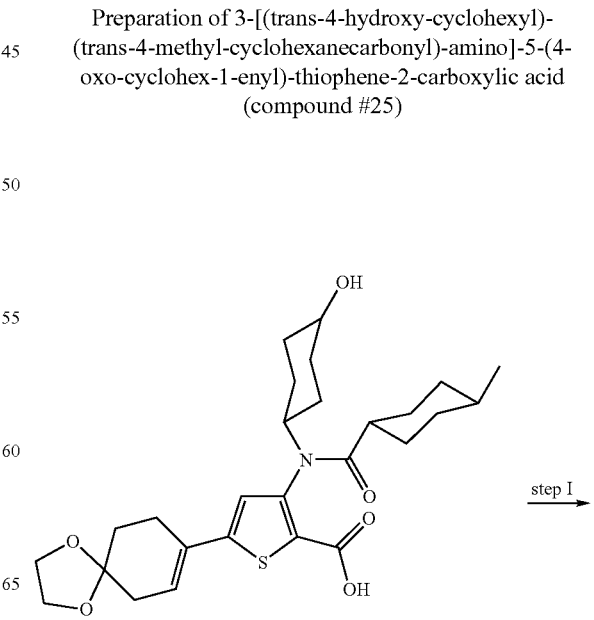

-continued

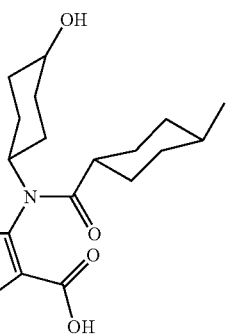

Step I:

To a solution of 5-(1,4-Dioxa-spiro[4.5]dec-7-en-8-yl)-3-[(trans-4-hydroxy-cyclohexyl)-(trans-4-methyl-cyclohexanecarbonyl)-amino]-thiophene-2-carboxylic acid (428 mg, 0.85 mmol) in THF (5 mL) was added 3N HCl (2.5 mL), and the mixture was heated at 40° C. for 5 h. Then it was diluted with $CH_2Cl_2$ (70 mL) and washed with brine and water. Organic fraction was dried over $Na_2SO_4$, concentrated under reduced pressure and the residue was purified by column chromatography on silica gel eluting with 0-10% MeOH in $CH_2Cl_2$ to give 278 mg (71%) of 3-[(trans-4-hydroxy-cyclohexyl)-(trans-4-methyl-cyclohexanecarbonyl)-amino]-5-(4-oxo-cyclohex-1-enyl)-thiophene-2-carboxylic acid.

EXAMPLE 16

Preparation of 5-[4-benzyloxyimino-cyclohex-1-enyl]-3-[(trans-4-hydroxy-yclohexyl)-(trans-4-methyl-cyclohexanecarbonyl)-amino]-thiophene-2-carboxyic acid (compound #26)

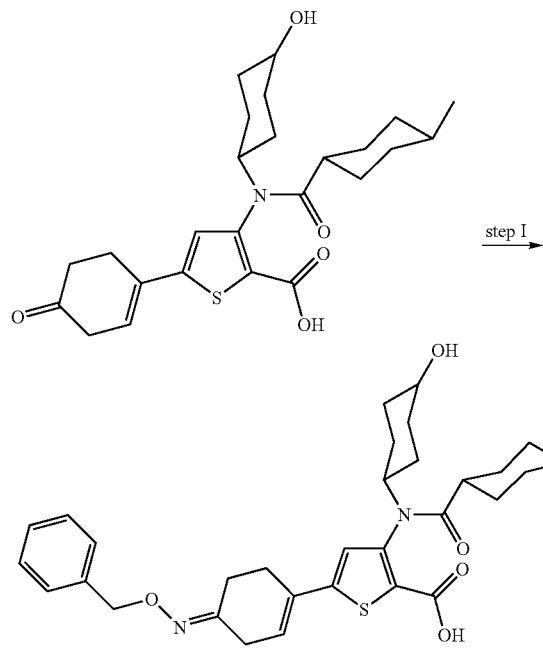

Step I:

To a solution of 3-[(trans-4-hydroxy-cyclohexyl)-(trans-4-methyl-cyclohexanecarbonyl)-amino]-5-(4-oxo-cyclohex-1-enyl)-thiophene-2-carboxylic acid (30 mg, 0.065 mmol) in a 2:1$H_2O$-ethanol mixture (3 mL) were added O-benzylhydroxylamine hydrochloride (21 mg, 0.13 mmol) and sodium acetate (18 mg, 0.13 mmol), and the mixture was stirred at room temperature overnight. Then the mixture was extracted with $CH_2Cl_2$, organic phase was dried over $Na_2SO_4$, concentrated under reduced pressure, and purified by column chromatography on silica gel eluting with 2-15% MeOH in $CH_2Cl_2$ to give 20 mg (54%) of 5-{4-benzyloxyimino-cyclohex-1-enyl}-3-[(trans-4-hydroxy-cyclohexyl)-(trans-4-methyl-yclohexanecarbonyl)-amino]-thiophene-2-carboxylic acid.

5-{4-ethoxyimino-cyclohex-1-enyl}-3-[(trans-4-hydroxy-cyclohexyl)-(trans-4-methyl-yclohexanecarbonyl)-amino]-thiophene-2-carboxylic acid (compound #27) can be prepared in a similar fashion utilizing O-ethylhydroxylamine.

EXAMPLE 17

Preparation of RS-5-(4-hydroxy-cyclohex-1-enyl)-3-[(trans-4-hydroxy-yclohexyl)-(trans-4-methyl-cyclohexanecarbonyl)-amino]-thiophene-2-carboxyic acid (compound #34)

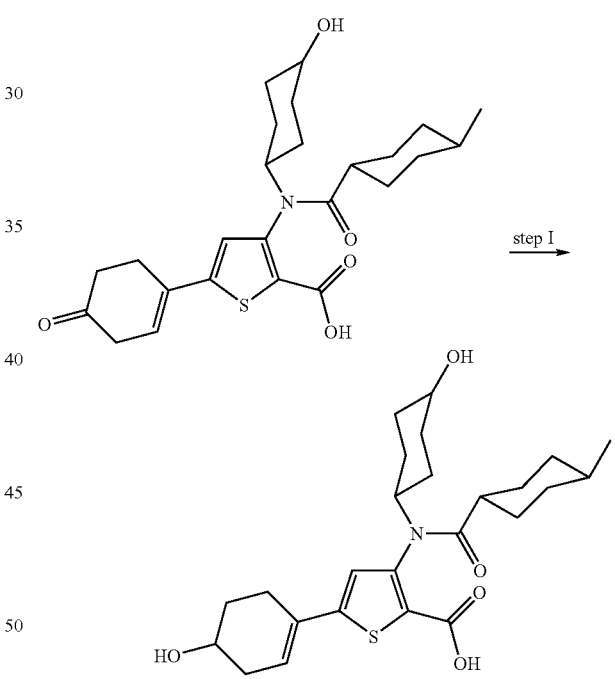

Step I:

To a solution of 3-[(trans-4-hydroxy-cyclohexyl)-(trans-4-methyl-cyclohexanecarbonyl)-amino]-5-(4-oxo-cyclohex-1-enyl)-thiophene-2-carboxylic acid (87 mg, 0.19 mmol) in dry MeOH (5 mL) was added sodium borohydride (4 mg, 0.09 mmol), and the mixture was stirred at room temperature for 4 h. The reaction was quenched by addition of aqueous $NH_4Cl$, acidified till pH 3 and extracted with $CH_2Cl_2$. Organic fraction was washed with brine, dried over $Na_2SO_4$, concentrated under reduced pressure and purified by column chromatography on silica gel eluting with 0-10% MeOH in $CH_2Cl_2$ to give 49 mg (56%) of RS-5-(4-hydroxy-cyclohex-1-enyl)-3-[(trans-4-hydroxy-cyclohexyl)-(trans-4-methyl-cyclohexanecarbonyl)-amino]-thiophene-2-carboxylic acid.

EXAMPLE 18

Preparation of 5-cyclohex-1-enyl-3-[(trans-4-methyl-cyclohexanecarbonyl)-phenyl-amino]-thiophene-2-carboxylic acid (Compound 10)

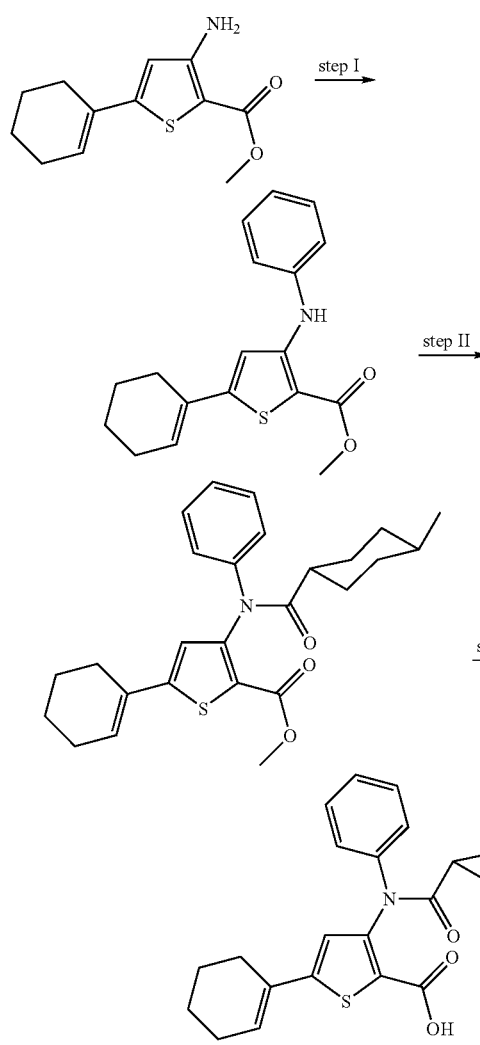

Step I:

To a solution of 5-cyclohex-1-enyl-3-amino-thiophene-2-carboxylic acid methyl ester (111 mg, 0.47 mmol) and bromobenzene (54 µL, 0.51 mmol) in dry dioxane (3 mL) were added cesium carbonate (459 mg, 1.41 mmol) and $Pd_2 dba_3$ (43 mg, 0.047 mmol), and the mixtue was deoxygenated by bubbling nitrogen through solution for 10 min. Then BINAP (47 mg, 0.075 mmol) was added to the mixture, and it was refluxed under nitrogen overnight. The mixture was diluted with $CH_2Cl_2$ and filtered through celite washing with $CH_2Cl_2$. Filtrate was concentrated under reduced pressure and purified by column chromatography on silica gel eluting with 2-30% EtOAc in hexanes to give 111 mg (76%) of 5-cyclohex-1-enyl-3-phenylamino-thiophene-2-carboxylic acid methyl ester.

Step II:

The methyl ester from Step I (565 mg, 1.13 mmol) was acylated with trans-4-methylcyclohexyl carboxylic acid chloride as previously described (example 11, step II) to give 41 mg (27%) of 5-cyclohex-1-enyl-3-[(trans-4-methyl-cyclohexanecarbonyl)-phenyl-amino]-thiophene-2-carboxylic acid methyl ester.

Step III:

The product from Step II (38 mg, 0.09 mmol) was hydrolysed with lithium hydroxide as previously described (example 3, step VIII) to give 32 mg (89%) of 5-cyclohex-1-enyl-3-[(trans-4-methyl-cyclohexanecarbonyl)-phenyl-amino]-thiophene-2-carboxylic acid.

EXAMPLE 19

Preparation of RS-5-cyclohex-1-enyl-3-[cyclohex-3-enyl-(trans-4-methyl-cyclohexanecarbonyl)-amino]-thiophene-2-carboxylic acid (Compound #115)

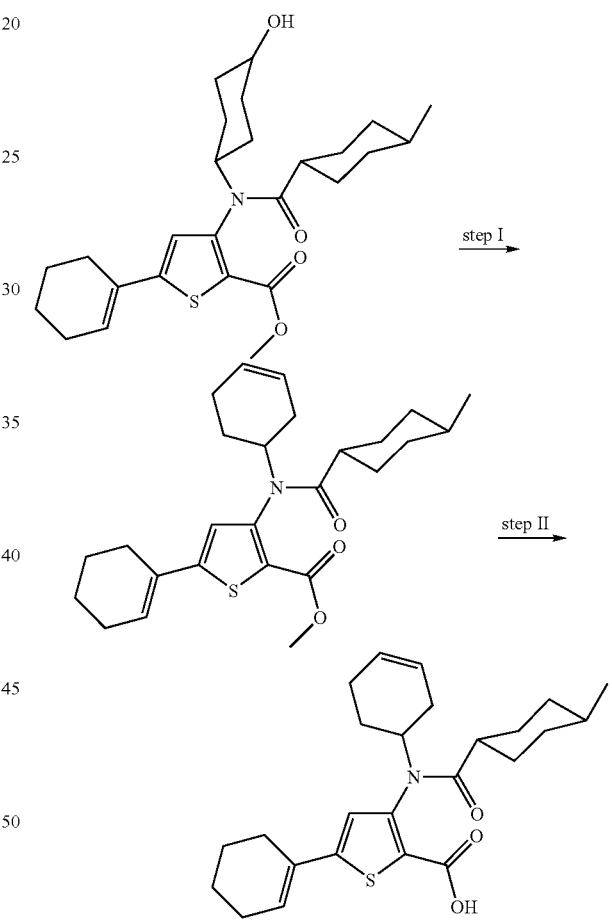

Step I:

To a solution of 5-cyclohex-1-enyl-3-[(trans-4-hydroxy-cyclohexyl)-(trans-4-methyl-cyclohexanecarbonyl)-amino]-thiophene-2-carboxylic acid methyl ester 390 mg, 0.85 mmol) in dry DMF (3 mL) at 0° C. was added 0.34 mL of 10M solution of $CHF_2I$ in benzene, followed by NaH (60% suspension in oil, 68 mg, 1.70 mmol), and the mixture was stirred for 2 h allowing to warm up to room temperature. Then it has been transferred into a sealed tube and heated in a microwave oven for 20 min at 120° C. The mixture was treated as described in example 4, and purified by column chromatography on silica gel eluting with 0→50% ethyl acetate in hexane to give 5-cyclohex-1-enyl-3-[cyclohex-3-enyl-(trans-4-methyl-cyclohexanecarbonyl)-amino]-thiophene-2-carboxylic acid methyl ester (132 mg, 35%).

Step II:

The methyl ester from Step I (132 mg, 0.30 mmol) was hydrolysed with lithium hydroxide as previously described (example 3, step VIII) to give 99 mg (77%) of RS-5-cyclohex-1-enyl-3-[cyclohex-3-enyl-(trans-4-methyl-cyclohexanecarbonyl)-amino]-thiophene-2-carboxylic acid as a solid.

EXAMPLE 20

Preparation of 3-[(trans-4-methoxy-cyclohexyl)-(trans-4-methyl-cyclohexanecarbonyl)-amino]-5-(4-oxo-cyclohexyl)-thiophene-2-carboxylic acid (Compound #113)

Step II:

A solution of 5-(1,4-dioxa-spiro[4.5]dec-7-en-8-yl)-3-[(trans-4-hydroxy-cyclohexyl)-(trans-4-methyl-cyclohexane-carbonyl)-amino]-thiophene-2-carboxylic acid methyl ester (981 mg, 1.89 mmol) in dry MeOH (30 mL) was deoxygenated by bubbling nitrogen through-solution for 5 min, then 10% palladium on charcoal (202 mg) was added, nitrogen was bubbled for another 5 min, then it was displaced by hydrogen, and the mixture was stirred at room temperature overnight. The mixture was filtered through celite washing with MeOH, and filtrate was concentrated under reduced pressure to give 928 mg (95%) of crude 5-(1,4-dioxa-spiro[4.5]dec-8-yl)-3-[(trans-4-hydroxy-cyclohexyl)-(trans-4-methyl-cyclohexane-carbonyl)-amino]-thiophene-2-carboxylic acid methyl ester, which was used in the following step without purification.

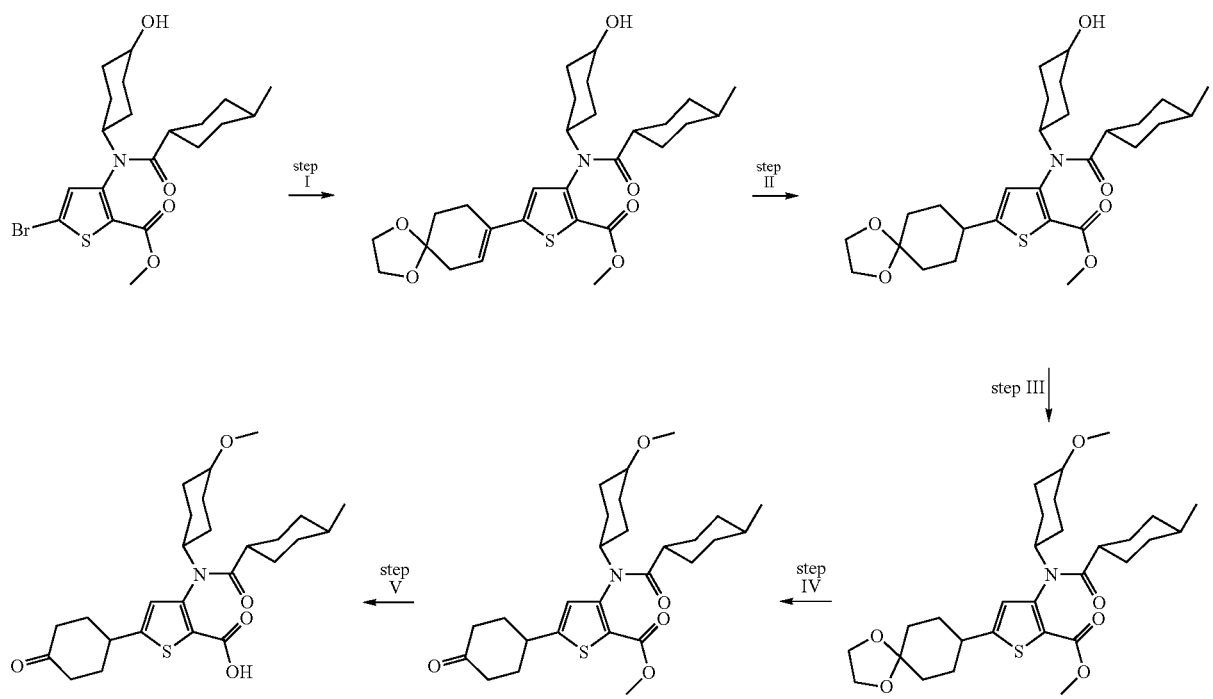

Step I:

To a solution of 5-bromo-3-[(trans-4-hydroxy-cyclohexyl)-(trans-4-methyl-cyclohexanecarbonyl)-amino]-thiophene-2-carboxylic acid methyl ester (1.312 g, 2.86 mmol) and 1,4-dioxaspiro[4,5]dec-7-en-8-boronic acid (1.066 g, 4.01 mmol) in DMF (12 mL) was added 2M solution of Na$_2$CO$_3$ (6 mL), and the mixture was deoxygenated by bubbling nitrogen through solution for 10 min. Then Pd(PPh3)4 was added to the mixture, and it was heated at 100° C. for 40 min. The mixture was brought to room temperature, diluted with CH$_2$Cl$_2$, acidified with 3N HCl till pH 2-3, and extracted with EtOAc. Organic fraction was washed with NaHCO$_3$ and brine, dried over Na$_2$SO$_4$, concentrated under reduced pressure, and the residue was purified by column chromatography on silica gel using hexanes-EtOAc gradient to afford 1.368 g (92%) of 5-(1,4-dioxa-spiro[4.5]dec-7-en-8-yl)-3-[(trans-4-hydroxy-cyclohexyl)-(trans-4-methyl-cyclohexanecarbonyl)-amino]-thiophene-2-carboxylic acid methyl ester as a solid.

Step III:

The product from Step II (922 mg, 1.77 mmol) was treated with methyl iodide (2.21 mL, 35.48 mmol) and 60% oil suspension of sodium hydride (142 mg, 3.54 mmol) using procedure described in step I of example 4 to afford 1.143 g (100%) of crude 5-(1,4-dioxa-spiro[4.5]dec-8-yl)-3-[(trans-4-methoxy-cyclohexyl)-(trans-4-methyl-cyclohexane-carbonyl)-amino]-thiophene-2-carboxylic acid methyl ester.

Step IV:

The product of step III was dissolved in THF (40 mL), 3N HCl (20 mL) was added to this solution, and the mixture was heated for 3 h at 50° C., then for an additional 3 h at 60° C. The mixture was brought to room temperature, extracted with CH$_2$Cl$_2$, washed with sodium bicarbonate and brine, organic fraction was separated, dried over Na$_2$SO$_4$, and concentrated under reduced pressure. Purification by column chromatography on silica gel using hexanes-EtOAc gradient to afford 726 mg (85%) of 3-[(trans-4-methoxy-cyclohexyl)-(trans-4- methyl-cyclohexanecarbonyl)-amino]-5-(4-oxocyclohexyl)-thiophene-2-carboxylic acid methyl ester.

Step V:

The product from step IV (61 mg) was hydrolyzed with lithium hydroxide as described earlier (example 3, step VIII) to afford after column purification on silica gel (CH$_2$Cl$_2$-MeOH) 23 mg (39%) of 3-[(trans-4-methoxy-cyclohexyl)-(trans-4-methyl-cyclohexanecarbonyl)-amino]-5-(4-oxocyclohexyl)-thiophene-2-carboxylic acid.

EXAMPLE 21

Preparation of 5-(4,4-difluoro-cyclohexyl)-3-[(trans-4-methoxy-cyclohexyl)-(trans-4-methyl-cyclohexanecarbonyl)-amino]-thiophene-2-carboxylic acid (Compound #122) and RS-5-(4-fluoro-cyclohex-3-enyl)-3-[(trans-4-methoxy-cyclohexyl)-(trans-4-methyl-cyclohexanecarbonyl)-amino]-thiophene-2-carboxylic acid (Compound #123)

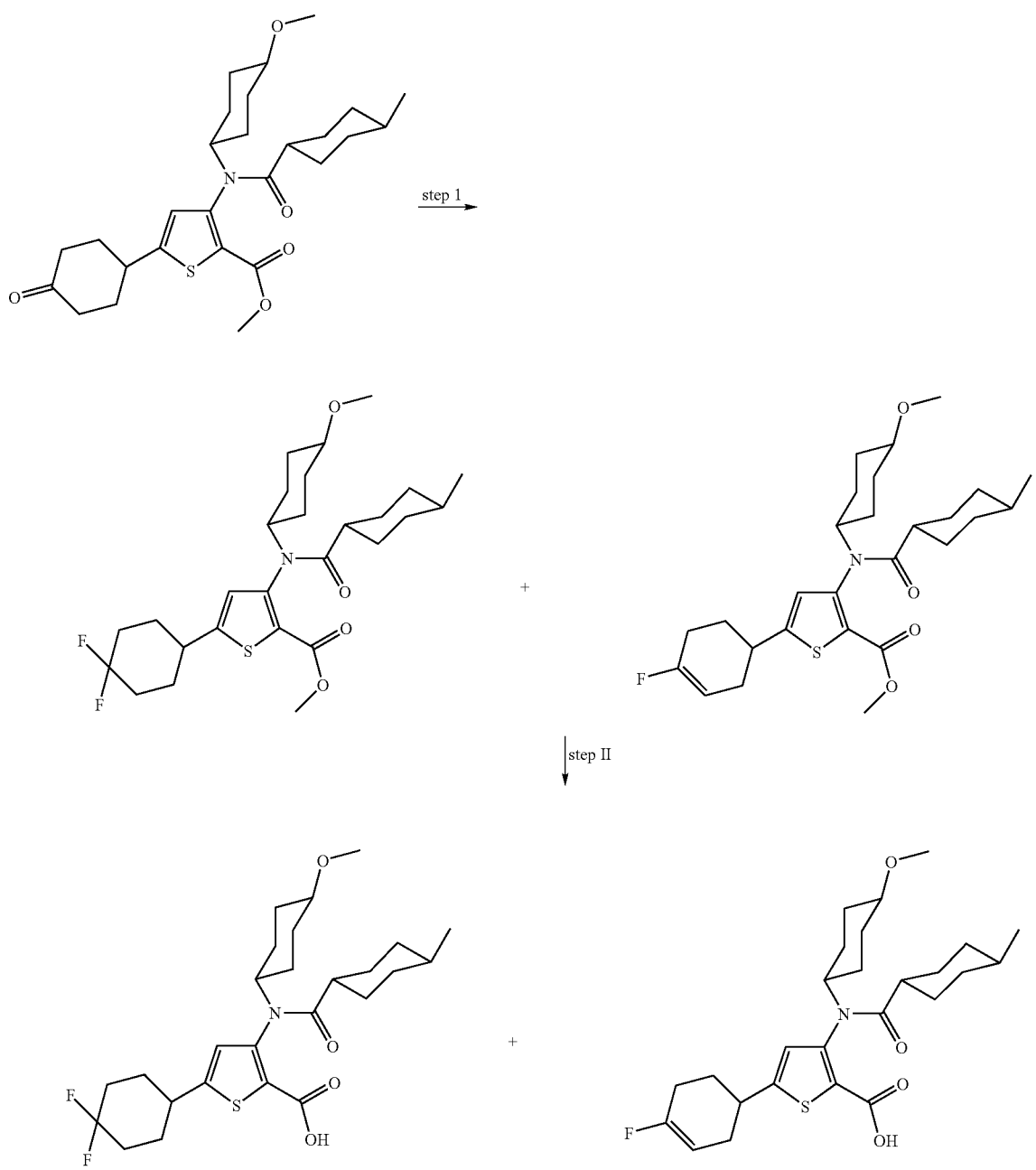

Step I:

To a solution of 3-[(trans-4-methoxy-cyclohexyl)-(trans-4-methyl-cyclohexanecarbonyl)-amino]-5-(4-oxocyclohexyl)-thiophene-2-carboxylic acid methyl ester (652 mg, 1.33 mmol) in dry toluene was added DAST (523 μl, 3.99 mmol), and the mixture was stirred at room temperature overnight. Then the mixture was diluted with dichloromethane and washed with brine. Organic fraction was separated, dried over Na₂SO₄, concentrated under reduced pressure and purified by column chromatography on silica gel using hexanes-EtOAc gradient to afford 600 mg (88%) of 7:3 mixture of 5-(4,4-difluoro-cyclohexyl)-3-[(trans-4-methoxy-cyclohexyl)-(trans-4-methyl-cyclohexanecarbonyl)-amino]-thiophene-2-carboxylic acid methyl ester and 5-(4-fluoro-cyclohex-3-enyl)-3-[(trans-4-methoxy-cyclohexyl)-(trans-4-methyl-cyclohexanecarbonyl)-amino]-thiophene-2-carboxylic acid methyl ester.

Step II:

The product from step I (584 mg) was hydrolyzed with lithium hydroxide as described earlier (example 3, step VIII) to afford after preparative HPLC separation 270 mg of 5-(4,4-difluoro-cyclohexyl)-3-[(trans-4-methoxy-cyclohexyl)-(trans-4-methyl-cyclohexanecarbonyl)-amino]-thiophene-2-carboxylic acid and 55 mg of RS-5-(4-fluoro-cyclohex-3-enyl)-3-[(trans-4-methoxy-cyclohexyl)-(trans-4-methyl-cyclohexanecarbonyl)-amino]-thiophene-2-carboxylic acid.

EXAMPLE 22

Preparation of 3-[(trans-4-hydroxy-cyclohexyl)-(trans-4-methyl-cyclohexanecarbonyl)-amino]-thiophene-2-carboxylic acid (Compound #143)

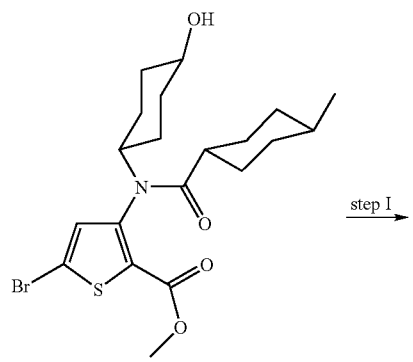

step I

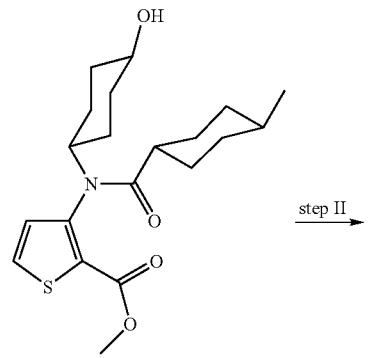

step II

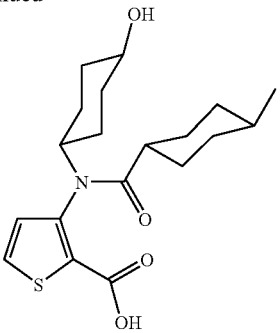

Step I:

To a solution of 5-bromo-3-[(trans-4-hydroxy-cyclohexyl)-(trans-4-methylcyclohexanecarbonyl)-amino]-thiophene-2-carboxylic acid methyl ester (229 mg, 0.50 mmol) in dry MeOH (5 mL) was added 10% palladium on charcoal (53 mg), nitrogen was bubbled through solution for 10 min, then it was displaced by hydrogen, and the mixture was stirred at room temperature for 24 h. The mixture was filtered through celite washing with MeOH, and filtrate was concentrated under reduced pressure to give 199 mg of crude 3-[(trans-4-hydroxy-cyclohexyl)-(trans-4-methylcyclohexanecarbonyl)-amino]-thiophene-2-carboxylic acid methyl ester, which was used in the following step without purification.

Step II:

The product from step I (30 mg) was hydrolyzed with lithium hydroxide as described earlier (example 3, step VIII) to afford after column purification on silica gel (CH₂Cl₂-MeOH) 16 mg (57%) of 3-[(trans-4-hydroxy-cyclohexyl)-(trans-4-methyl-cyclohexanecarbonyl)-amino]-thiophene-2-carboxylic acid.

EXAMPLE 23

Preparation of 5-cyclohex-1-enyl-3-[(trans-4-ethoxy-cyclohexyl)-(trans-4-methyl-cyclohexanecarbonyl)-amino]-thiophene-2-carboxylic acid (compound #22)

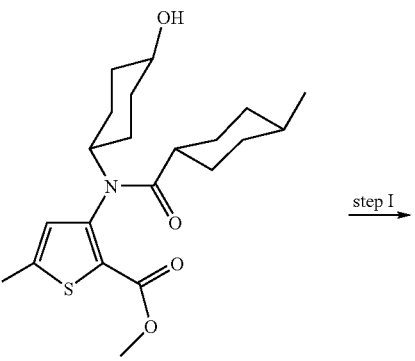

step I

75

-continued

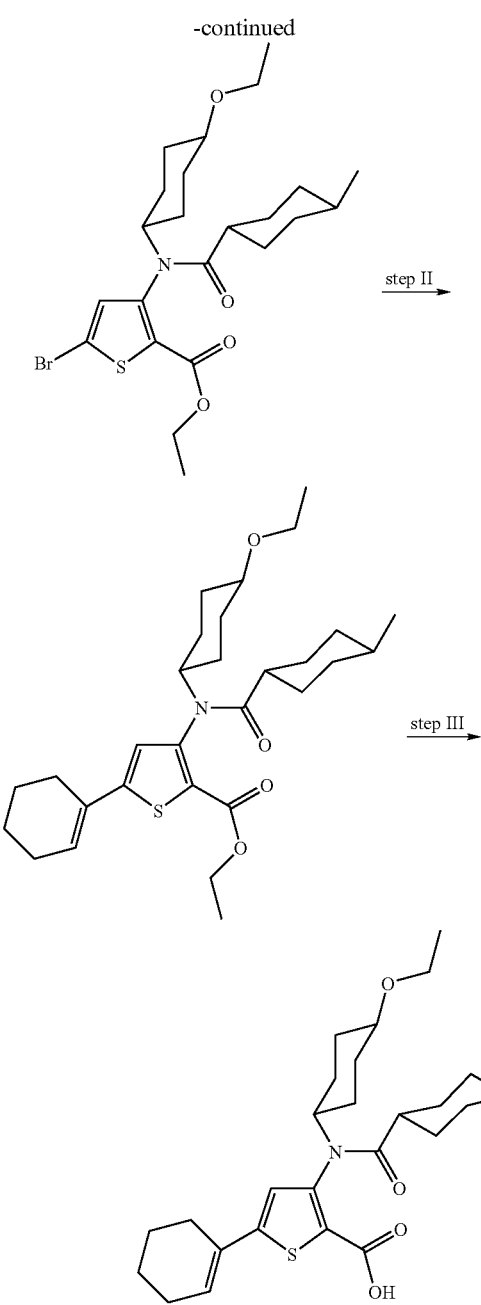

5-bromo-3-[(trans-4-ethoxy-cyclohexyl)-(trans-4-methyl-cyclohexanecarbonyl)-amino]-thiophene-2-carboxylic acid ethyl and methyl esters.

Step II:

The product of step I (277 mg) was reacted with cyclohexene boronic acid (91 mg, 0.72 mmol) to give 173 mg (63%) of 5-bromo-3-[(trans-4-ethoxy-cyclohexyl)-(trans-4-methyl-cyclohexanecarbonyl)-amino]-thiophene-2-carboxylic acid ethyl ester.

Step III:

The ester from Step II (173 mg, 0.34 mmol) was hydrolysed by lithium hydroxide as previously described (example 3, step VIII) to give 91 mg of 5-cyclohex-1-enyl-3-[(trans-4-ethoxy-cyclohexyl)-(trans-4-methyl-cyclohexanecarbonyl)-amino]-thiophene-2-carboxylic acid.

EXEMPLE 24

4-[(2-Carboxy-5-cyclohex-1-enyl-thiophen-3-yl)-(trans-4-methyl-cyclohexanecarbonyl)-amino]-1,1-dimethyl-piperidinium (compound #88)

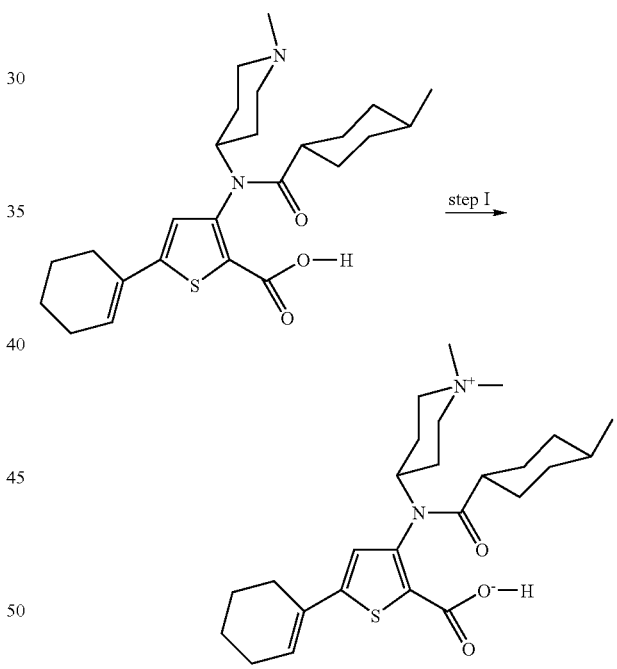

Step I:

To a solution of 5-bromo-3-[(trans-4-hydroxy-cyclohexyl)-(trans-4-methyl-cyclohexanecarbonyl)-amino]-thiophene-2-carboxylic acid methyl ester (269 mg, 0.59 mmol) in dry DMF (2 mL) was added iodoethane (279 μL, 2.95 mmol), the mixture was cooled to 0° C., and NaH (60% suspension in oil, 47 mg, 1.17 mmol) was added in portions over 5 min. The mixture was stirred at 0° C. for 3 h, and it was quenched by addition of water and acidified with 2N HCl. The mixture was diluted with $CH_2Cl_2$ and washed with brine. The organic fraction was separated, dried over $Na_2SO_4$, concentrated under reduced pressure. The residue was purified by column chromatography on silica gel eluting with 0→50% ethyl acetate in hexane to give 176 mg of 2:1 mixture of Step I:

To a solution of 5-cyclohex-1-enyl-3-[(trans-4-methyl-cyclohexanecarbonyl)-(1-methyl-piperidin-4-yl)-amino]-thiophene-2-carboxylic acid (10 mg, 0.02 mmol) in 0.5 mL of dry dichloromethane at 0° C. (ice bath) under nitrogen was added methyl iodide (3.1 mg, 0.02 mmol). The mixture was stirred for 15 min at 0° C. and 150 min at room temperature. The mixture was concentrated under reduced pressure to afford 10 mg (100%) of 4-[(2-Carboxy-5-cyclohex-1-enyl-thiophen-3-yl)-(trans-4-methyl-cyclohexanecarbo-nyl)-amino]-1,1-dimethyl-piperidinium.

Ref: U.S. Pat. No. 4,962,101

EXEMPLE 25

4-[[5-Cyclohex-1-enyl-2-(2,2-dimethyl-propionyloxymethoxy-carbonyl)-thiophen-3-yl]-(trans-4-methyl-cyclohexanecarbonyl)-amino]-1-methyl-piperidinium; chloride (compound #89)

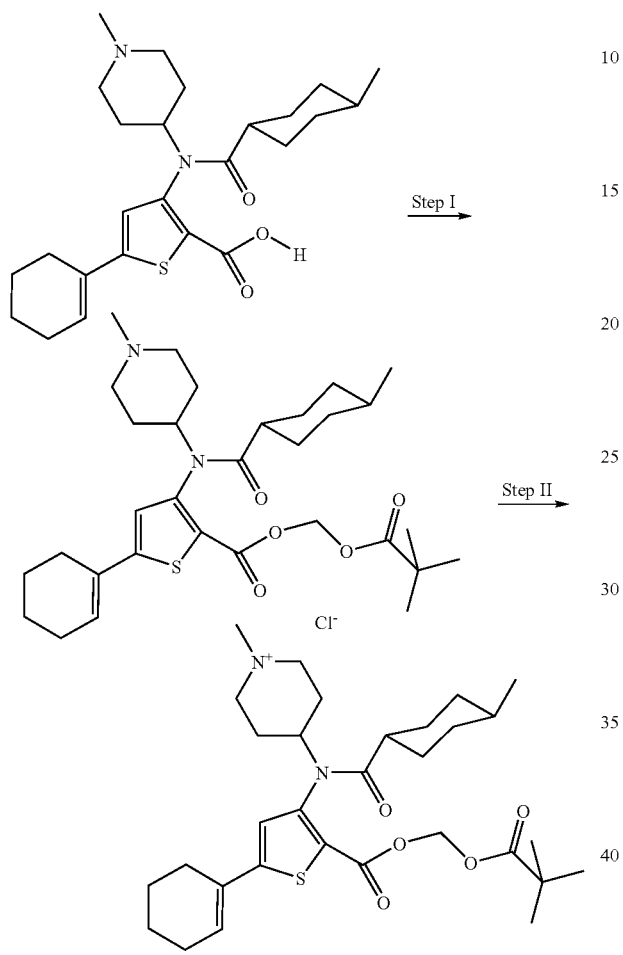

Step I:
To a solution of 5-cyclohex-1-enyl-3-[(4-methyl-cyclohexanecarbonyl)-(1-methyl-piperidin-4-yl)-amino]-thiophene-2-carboxylic acid (130 mg, 0.27 mmol) in 5.0 mL of dry dimethylformamide under nitrogen was added cesium carbonate (351 mg, 1.08 mmol) and 2,2-dimethyl-propionic acid chloromethyl ester (45 mg, 0.297 mmol). The mixture was stirred for 120 min at 60° C. The mixture was partitioned between ethyl acetate and water. The EtOAc layer was separated and was washed 3 times with water, dried over $Na_2SO_4$. Filtration and removal of the solvent under reduced pressure on a rotary evaporator followed by HPLC purification afforded 120 mg (79%) of 5-cyclohex-1-enyl-3-[(trans-4-methyl-cyclohexanecarbonyl)-(1-methyl-piperidin-4-yl)-amino]-thiophene-2-carboxylic acid 2,2-dimethyl-propionyloxymethyl ester.

Step II:
To a solution of 5-cyclohex-1-enyl-3-[(trans-4-methyl-cyclohexanecarbonyl)-(1-methyl-piperidin-4-yl)-amino]-thiophene-2-carboxylic acid 2,2-dimethyl-propionyloxymethyl ester (112 mg, 0.20 mmol) in 5.0 mL of dry methanol under nitrogen at 0° C. (ice bath) was added 3 drops of HCl (6 N). The mixture was stirred for 5 min and evaporated under reduced pressure on a rotary evaporator to afford 109 mg of 4-[[5-cyclohex-1-enyl-2-(2,2-dimethyl-propionyloxymethoxy-carbonyl)-thiophen-3-yl]-(trans-4-methyl-cyclohexane-carbonyl)-amino]-1-methyl-piperidinium hydrochloride.

Using essentially the same procedure described above the following compounds can be prepared:
4-[(5-Cyclohex-1-enyl-2-isopropoxycarbonyloxymethoxy-carbonyl-thiophen-3-yl)-(trans-4-methyl-cyclohexanecarbonyl)-amino]-1-methyl-piperidinium; chloride (compound #90)

EXAMPLE 26

5-Cyclohex-1-enyl-3-[(1,3-dimethyl-2,4-dioxo-1,3-diaza-spiro[4.5]dec-8-yl)-(trans-4-methyl-cyclohexanecarbonyl)-amino]-thiophene-2-carboxylic acid (compound #32)

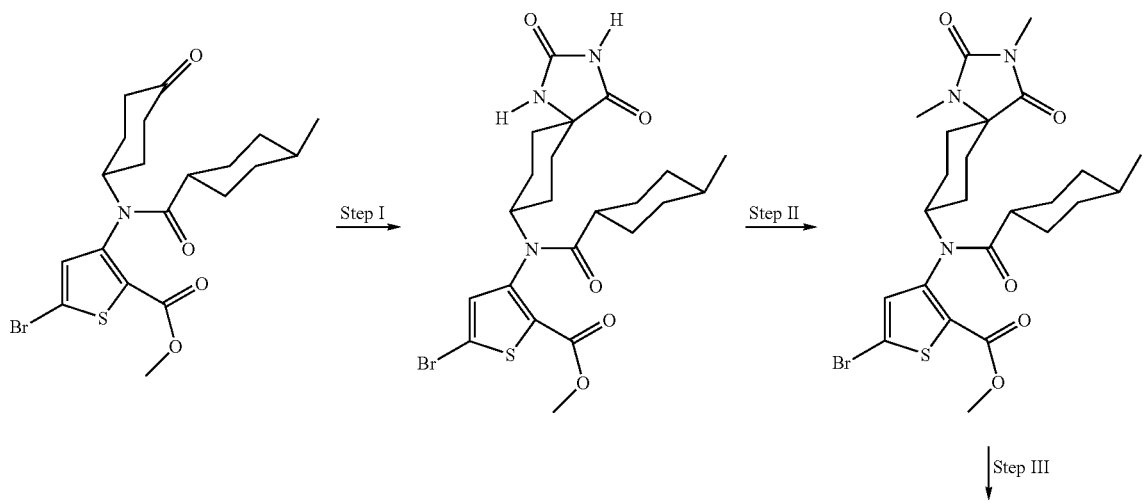

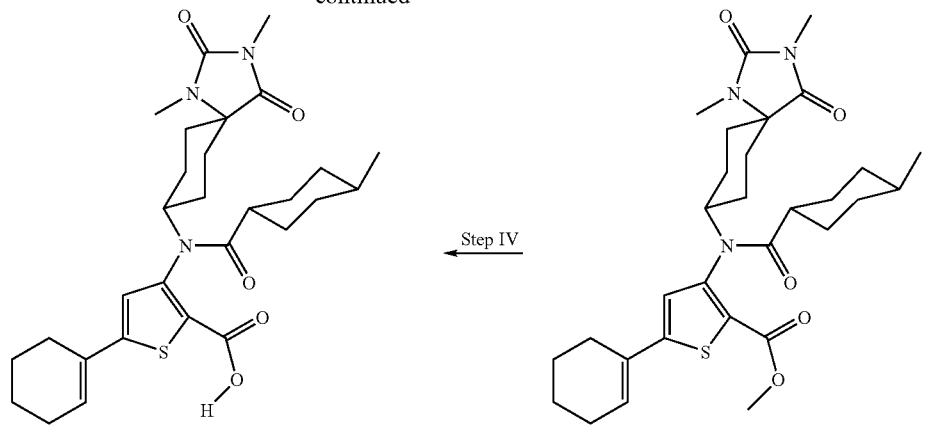

Step I:

To a solution of 5-bromo-3-[(4-methyl-cyclohexanecarbonyl)-(4-oxo-cyclohexyl)-amino]-thiophene-2-carboxylic acid methyl ester (1000 mg, 2.20 mmol) in 30 mL of dry methanol was added a water solution of ammonium carbonate (634 mg, 6.60 mmol, 15 ml $H_2O$) and solid potassium cyanide (634 mg, 6.60 mmol). The mixture was stirred for 16 h at 55° C. under nitrogen. The mixture was partitioned between ethyl acetate and water. The EtOAc layer was separated, washed 3 times with water, dried over $Na_2SO_4$, filtered and concentrated under reduced pressure. The residue was purified by column chromatography on silica gel using 50% EtOAc in hexane to afford 510 mg (45%) of 5-bromo-3-[(2,4-dioxo-1,3-diaza-spiro[4.5]dec-8-yl)-(4-methyl-cyclohexanecarbonyl)-amino]-thiophene-2-carboxylic acid methyl ester.

Step II:

To a solution of 5-bromo-3-[(2,4-dioxo-1,3-diaza-spiro[4.5]dec-8-yl)-(4-methyl-cyclohexanecarbonyl)-amino]-thiophene-2-carboxylic acid methyl ester (360 mg, 0.68 mmol) in 5 mL of dry dimethylformamide at 0° C. was added sodium hydride 60% (82 mg, 2.05 mmol) and methyl iodide (291 mg, 1.36 mmol). The mixture was stirred for 16 h at room temperature under nitrogen. The mixture was partitioned between ethyl acetate and water. The EtOAc layer was separated, washed 3 times with water, dried over $Na_2SO_4$, filtered and concentrated under reduced pressure. The residue was purified by column chromatography on silica gel using 30% EtOAc in hexane to afford 200 mg (50%) of 5-bromo-3-[(1,3-dimethyl-2,4-dioxo-1,3-diaza-spiro[4.5]dec-8-yl)-(4-methyl-cyclohexanecarbonyl)-amino]-thiophene-2-carboxylic acid methyl ester.

Step III

The same procedure followed as described in Example 20, step I.

Step IV

The same procedure followed from Example 3, step VIII.

Using essentially the same procedure described above the following compounds can be prepared:

5-(4,4-Dimethyl-cyclohexyl)-3-[(1,3-dimethyl-2,4-dioxo-1,3-diaza-spiro[4.5]dec-8-yl)-(trans-4-methyl-cyclohexanecarbonyl)-amino]-thiophene-2-carboxylic acid (compound #79)

5-(4,4-Dimethyl-cyclohex-1-enyl)-3-[(1,3-dimethyl-2,4-dioxo-1,3-diaza-spiro[4.5]dec-8-yl)-(trans-4-methyl-cyclohexanecarbonyl)-amino]-thiophene-2-carboxylic acid (compound #75)

EXEMPLE 27

5-Cyclohex-1-enyl-3-[(1-oxo-hexahydro-thiopyran-4-yl)-(trans-4-methyl-cyclohexanecarbonyl)-amino]-thiophene-2-carboxylic acid (compound #63+compound #69)

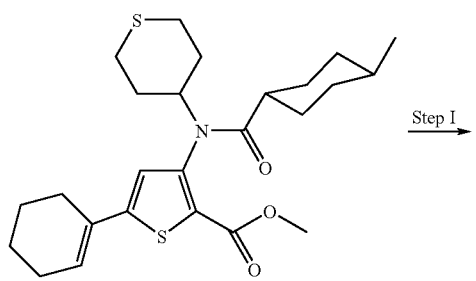

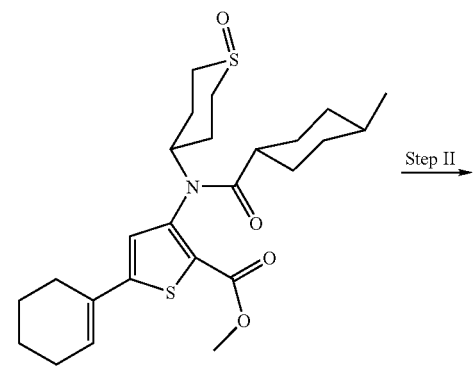

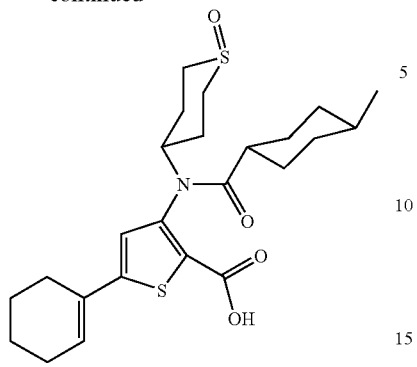

Step I:

To a mixture 5-cyclohex-1-enyl-3-[(trans-4-methyl-cyclohexanecarbonyl)-(tetrahydrothiopyran-4-yl)-amino]-thiophene-2-carboxylic acid methyl ester (100 mg, 0.22 mmol) in 2 mL of EtOH, was added magnesium bis(monoperoxyphthalate) hexahydrate (53 mg, 0.11 mmol). The reaction mixture was stirred 16 h at room temperature. After evaporation to dryness, the residue was partitioned between ethyl acetate and water. The organic layer was separated, dried ($Na_2SO_4$) and concentrated. The residue was purified by silica gel column chromatography using acetone/hexane (1:5) to afford 12 mg of the major isomer and 8 mg of a mixture (30:70) of the minor isomer of 5-cyclohex-1-enyl-3-[(1-oxo-hexahydro-thiopyran-4-yl)-(trans-4-methylcyclohexanecarbonyl)-amino]-thiophene-2-carboxylic acid methyl ester.

Step II:

The same procedure followed from Example 3, step VIII.

EXEMPLE 28

Morpholine-4-carboxylic acid 4-[(2-carboxy-5-cyclohex-1-enyl-thiophen-3-yl)-(trans-4-methyl-cyclohexanecarbonyl)-amino]-cyclohexyl ester (compound #18)

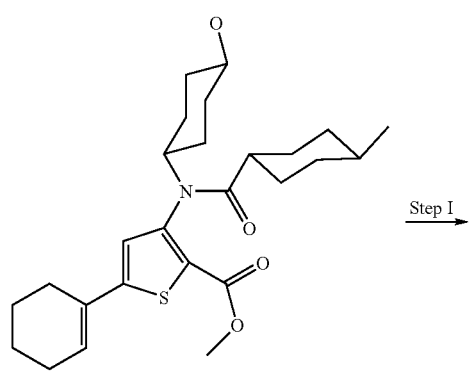

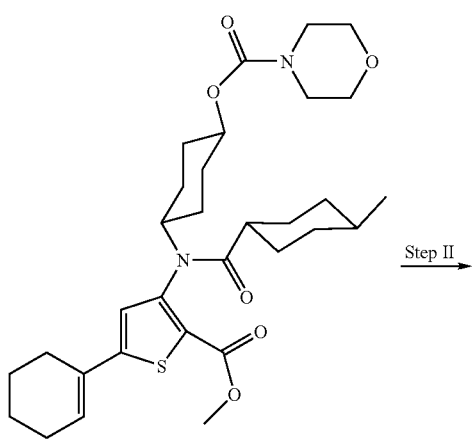

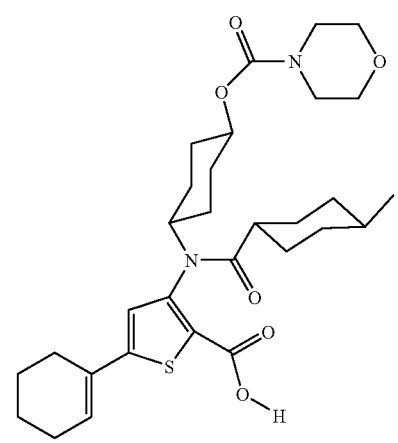

Step I:

To a cold (−20° C.) solution of 5-cyclohex-1-enyl-3-[(trans-4-hydroxy-cyclohexyl)-(trans-4-methyl-cyclohexanecarbonyl)-amino]-thiophene-2-carboxylic acid methyl ester (75 mg, 0.16 mmol) in 5 ml of THF was added LiHMDS (33 mg, 0.20 mmol). After ½ h, the reaction mixture was treated with morpholine-4-carbonyl chloride (24 mg, 0.16 mmol). The reaction mixture was stirred for 3 h at room temperature. The residue was partitioned between ethyl acetate and 5 ml saturated water solution of $NH_4Cl$. The organic layer was separated, dried ($Na_2SO_4$) and concentrated. The residue was purified by silica gel column chromatography to afford 35 mg (37%) of morpholine-trans-4-carboxylic acid 4-[(5-cyclohex-1-enyl-2-methoxycarbonyl-thiophen-3-yl)-(trans-4-methyl-cyclohexanecarbonyl)-amino]-cyclohexyl ester.

Step II:

The same procedure followed from Example 3, step VIII.

EXAMPLE 29

5-cyclohex-1-enyl-3-[(4-ethyoxyimino-cyclohexyl)-(trans-4-methyl-cyclohexanecarbonyl)-amino]-thiophene-2-carboxylic acid (compound #54)

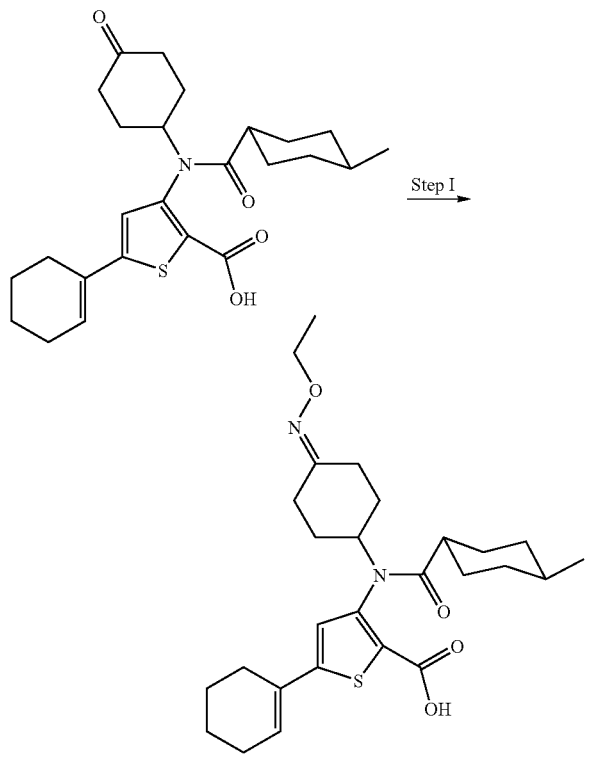

Step I:

To a solution of 5-Cyclohex-1-enyl-3-[(trans-4-methyl-cyclohexanecarbonyl)-(4-oxo-cyclohexyl)-amino]-thiophene-2-carboxylic acid (0.055 g, 0.12 mmol) in 1 ml of $H_2O$/EtOH (2:1) was added ethoxyamine hydrochloride (0.024 g, 0.24 mmol) and sodium acetate (0.032 g, 0.24 mmol). The reaction mixture was stirred at room temperature for 24 h and treated with water. The aqueous layer was extracted with $CH_2Cl_2$ (3×) and the organic layer was dried with sodium sulfate, filtered and concentrated under reduce pressure. The residue was purified by HPLC to obtain 5-cyclohex-1-enyl-3-[(4-ethyoxyimino-cyclohexyl)-(trans-4-methyl-cyclohexanecarbonyl)-amino]-thiophene-2-carboxylic acid (0.015 g, 26%).

EXAMPLE 30

5-(4,4-dimethyl-cyclohex-1-enyl)-3-[(trans-4-methyl-cyclohexanecarbonyl)-(cis-4-[1,2,4]triazol-1-yl-cyclohexyl)-amino]-thiophene-2-carboxylic acid hydrochloride (compound #94) and 5-(4,4-dimethyl-cyclohex-1-enyl)-3-[(trans-4-methyl-cyclohexanecarbonyl)-(trans-4-[1,2,4]triazol-1-yl-cyclohexyl)-amino]-thiophene-2-carboxylic acid hydrochloride (compound #95)

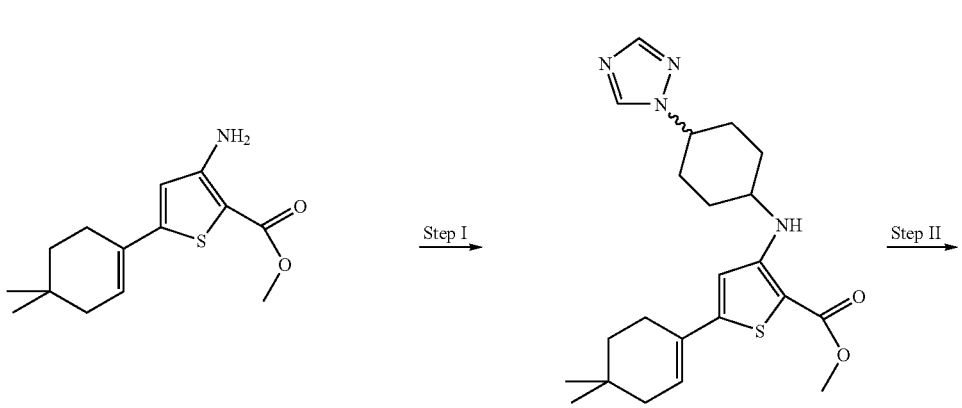

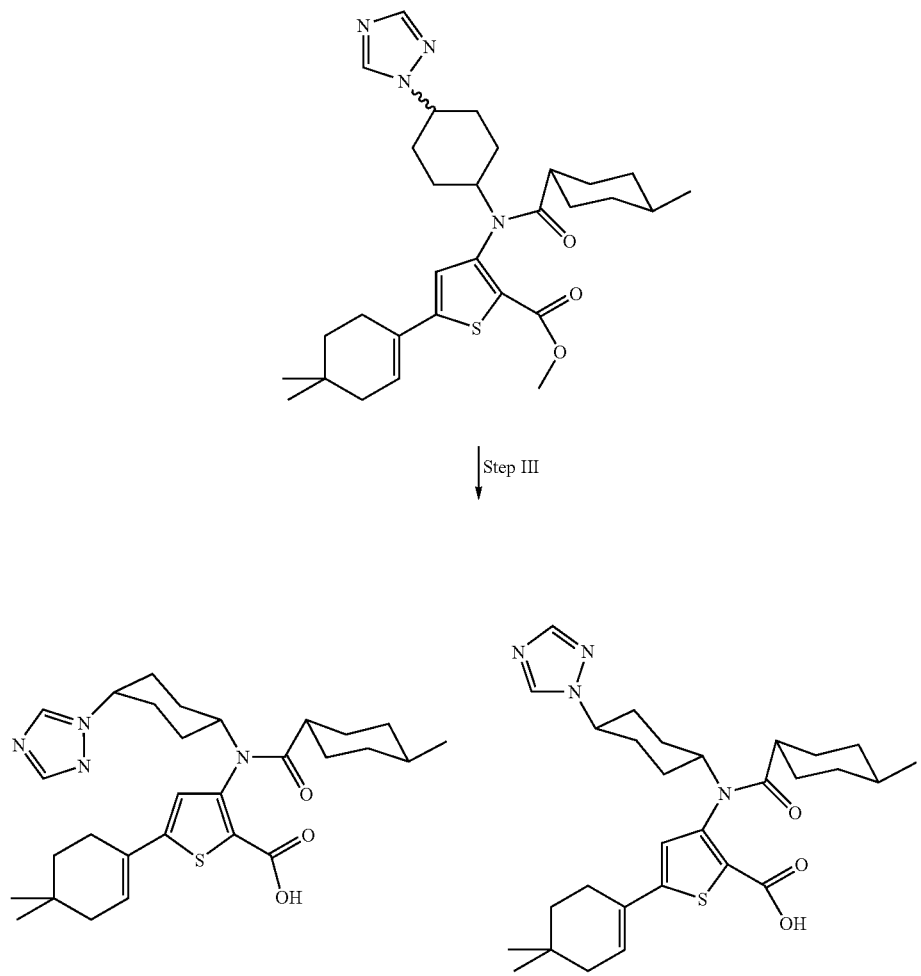

Step I:

Reductive amination of 3-amino-5-(4,4-dimethyl-cyclohex-1-enyl)-thiophene-2-carboxylic acid methyl ester (0.630 g, 2.37 mmol) and 5-[1,2,4]triazol-1-yl-heptan-2-one (0.560 g, 3.39 mmol) was performed under the same conditions previously described (example 3, step I) using dibutyltin dichloride and phenylsilane to give 5-(4,4-Dimethyl-cyclohex-1-enyl)-3-(trans-4-[1,2,4]triazol-1-yl-cyclohexylamino)-thiophene-2-carboxylic acid methyl ester (0.800 g, 64%).

Step II:

5-(4,4-Dimethyl-cyclohex-1-enyl)-3-(4-[1,2,4]triazol-1-yl-cyclohexylamino)thiophene-2-carboxylic acid methyl ester (0.800 g, 2 mmol) was acylated with with trans-4-methylcyclohexyl carboxylic acid chloride as previously described (example 1, step II) to give 5-(4,4-Dimethyl-cyclohex-1-enyl)-3-[(trans-4-methyl-cyclohexanecarbonyl)-(4-[1,2,4]triazol-1-yl-cyclohexyl)-amino]-thiophene-2-carboxylic acid methyl ester (0.640 g, 60%).

Step III:

5-(4,4-Dimethyl-cyclohex-1-enyl)-3-[(trans-4-methyl-cyclohexanecarbonyl)-(4-[1,2,4]triazol-1-yl-cyclohexyl)-amino]-thiophene-2-carboxylic acid methyl ester (0.073 g, 0.13 mmol) was hydrolysed with lithium hydroxide as previously described (example 3, step VIII) to give after HPLC purification the pure isomer 5-(4,4-dimethyl-cyclohex-1-enyl)-3-[(trans-4-methyl-cyclohexanecarbonyl)-(cis-4-[1,2,4]triazol-1-yl-cyclohexyl)-amino]-thiophene-2-carboxylic acid hydrochloride compound #94 (0.0024 g, 4%) and 5-(4,4-dimethyl-cyclohex-1-enyl)-3-[(trans-4-methyl-cyclohexanecarbonyl)-(trans-4-[1,2,4]triazol-1-yl-cyclohexyl)-amino]-thiophene-2-carboxylic acid hydrochloride compound #95 (0.005 g, 8%).

EXAMPLE 31

5-(4,4-dimethyl-cyclohexyl)-3-[(trans-4-methyl-cyclohexanecarbonyl)-(cis-4-[1,2,4]triazol-1-yl-cyclohexyl)-amino]-thiophene-2-carboxylic acid hydrochloride (compound #117 and 5-(4,4-dimethyl-cyclohexyl)-3-[(trans-4-methyl-cyclohexanecarbonyl)-(trans-4-[1,2,4]triazol-1-yl-cyclohexyl)-amino]-thiophene-2-carboxylic acid hydrochloride (compound #118)

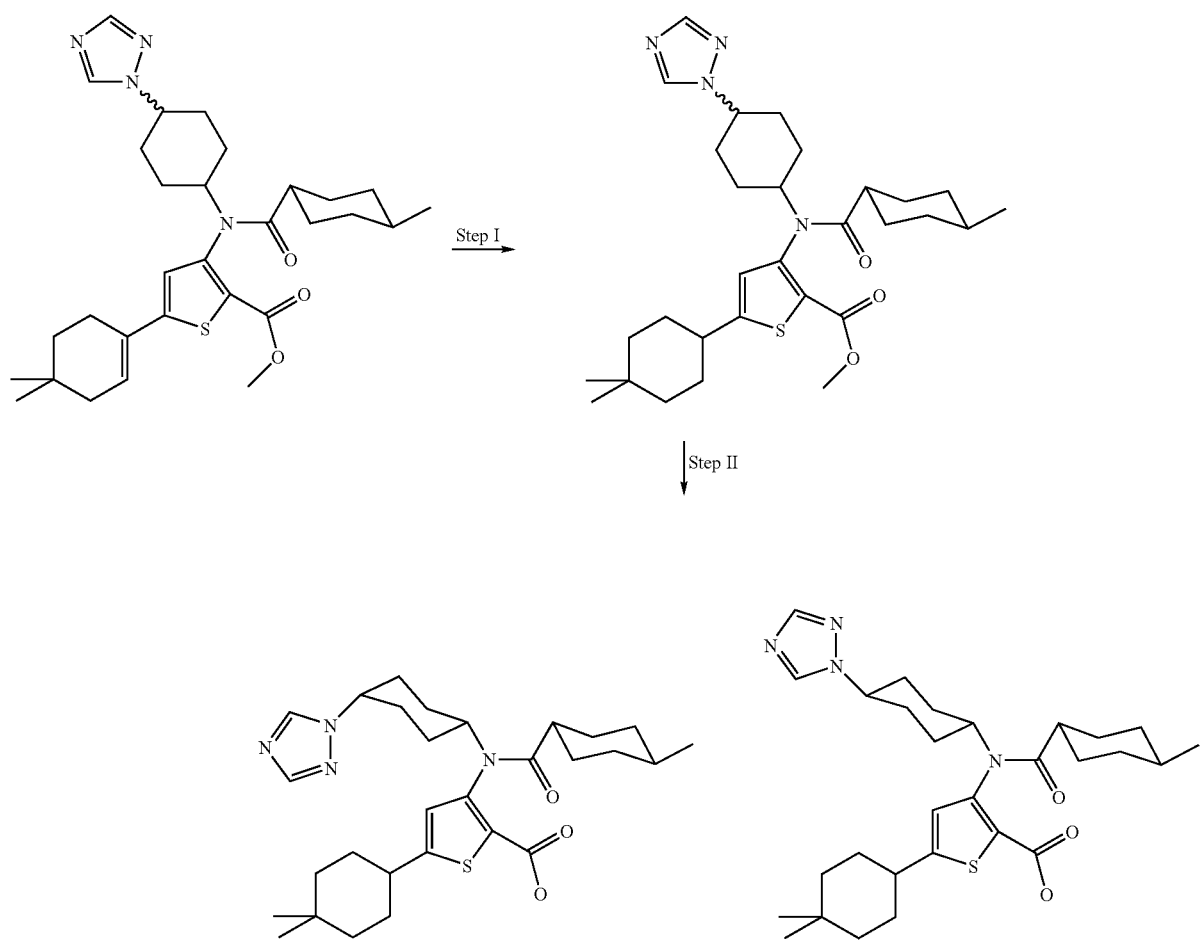

Step I:

To a solution of 5-(4,4-dimethyl-cyclohex-1-enyl)-3-[(trans-4-methyl-cyclohexanecarbonyl)-(4-[1,2,4]triazol-1-yl-cyclohexyl)-amino]-thiophene-2-carboxylic acid methyl ester (0.472 g, 0.88 mmol) in acetic acid (4.4 ml) was added 20% wet palladium hydroxide on charcoal (0.141 g). The resulting reaction mixture was placed under $H_2$ atmosphere, stirred at room temperature for 16 h, and then filtered through celite and evaporated to dryness to obtain 5-(4,4-dimethyl-cyclohexyl)-3-[(trans-4-methyl-cyclohexanecarbonyl)-(4-[1,2,4]triazol-1-yl-cyclohexyl)-amino]-thiophene-2-carboxylic acid methyl ester (0.470 g, 95%).

Step II:

5-(4,4-Dimethyl-cyclohexyl)-3-[(trans-4-methyl-cyclohexanecarbonyl)-(4-[1,2,4]triazol-1-yl-cyclohexyl)-amino]-thiophene-2-carboxylic acid methyl ester (0.470 g, 0.88 mmol) was hydrolysed with lithium hydroxide as previously described (example 3, step VIII) to give after HPLC purification the pure isomer 5-(4,4-dimethyl-cyclohexyl)-3-[(trans-4-methyl-cyclohexanecarbonyl)-(cis-4-[1,2,4]triazol-1-yl-cyclohexyl)-amino]-thiophene-2-carboxylic acid hydrochloride (0.011 g, 2.4%) and 5-(4,4-dimethyl-cyclohexyl)-3-[(trans-4-methyl-cyclohexanecarbonyl)-(trans-4-[1,2,4]triazol-1-yl-cyclohexyl)-amino]-thiophene-2-carboxylic acid hydrochloride (0.020 g, 4.3%).

EXAMPLE 32

5-(4,4-dimethyl-cyclohexyl)-3-[(trans-4-methyl-cyclohexanecarbonyl)-(trans-4-[1,2,3]triazol-1-yl-cyclohexyl)-amino]-thiophene-2-carboxylic acid hydrochloride (compound #135)

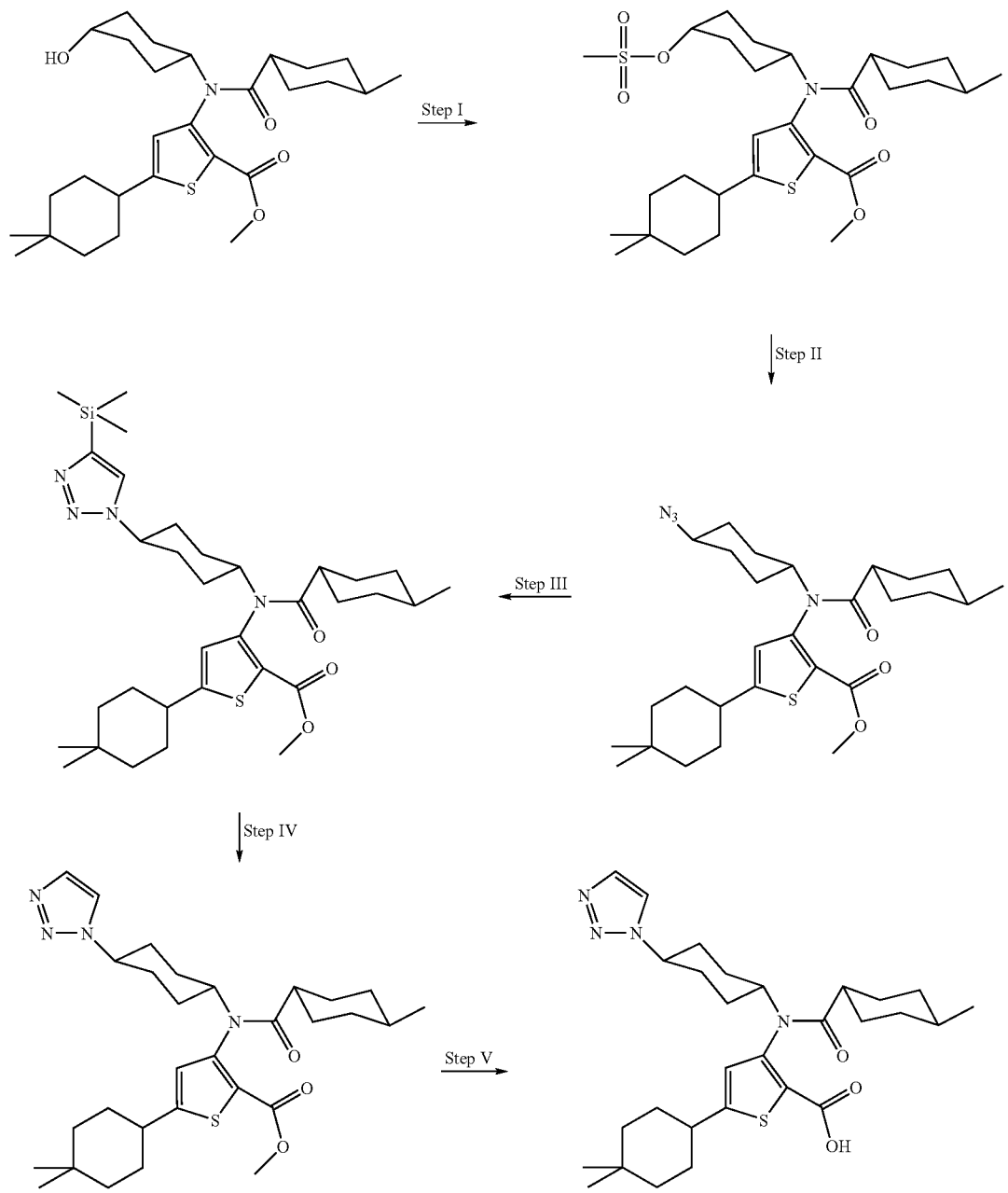

Step I:

To a solution of 5-(4,4-Dimethyl-cyclohexyl)-3-[(cis-4-hydroxy-cyclohexyl)-(trans-4-methyl-cyclohexanecarbonyl)-amino]-thiophene-2-carboxylic acid methyl ester (2.25 g, 4.60 mmol) in 23 ml of $CH_2Cl_2$ was added at 0° C. methanesulfonyl chloride (1.05 g, 9.20 mmol) followed by triethylamine (1.28 ml, 9.20 mmol). The reaction mixture was stirred at room temperature for 24 h and treated with water. The aqueous Layer was extracted with ethyl acetate and the organic layer was washed with water and brine. The organic layer was dried with sodium sulfate, filtered and concentrated under reduce pressure to give 5-(4,4-Dimethyl-cyclohexyl)-3-[(cis-4-methanesulfonyloxy-cyclohexyl)-(trans-4-methyl-cyclohexanecarbonyl)-amino]-thiophene-2-carboxylic acid methyl ester (2.56 g, 98%)

Step II:

To a solution of 5-(4,4-dimethyl-cyclohexyl)-3-[(cis-4-methanesulfonyloxy-cyclohexyl)-(trans-4-methyl-cyclohexanecarbonyl)-amino]-thiophene-2-carboxylic acid methyl ester (2.56 g, 4.50 mmol) in 30 ml of DMF was added sodium azide (1.5 g, 23 mmol). The reaction mixture was stirred for 48 h at 50° C. The mixture was diluted with diethyl ether and washed 3 time with water and 1 time with brine. The organic layer was dried with sodium sulfate, filtered and concentrated under reduce pressure. The residue was purified by silica gel column chromatography (20% ethyl acetate/hexane to 100% ethyl acetate followed by 10% MeOH/CH$_2$Cl$_2$) to give 3-[(trans-4-Azido-cyclohexyl)-(trans-4-methyl-cyclohexanecarbonyl)-amino]-5-(4,4-dimethyl-cyclohexyl)-thiophene-2-carboxylic acid methyl ester (1.6 g, 69%).

Step III:

A solution of 3-[(trans-4-azido-cyclohexyl)-(trans-4-methyl-cyclohexanecarbonyl)-amino]-5-(4,4-dimethyl-cyclohexyl)-thiophene-2-carboxylic acid methyl ester (0.90 g, 1.7 mmol) in trimethylsilylacetylene (1.2 ml, 6.8 mmol) was treated in microwave at 120° C. for 2 h. The mixture was concentrated under reduce pressure and the residue purified by silica gel column chromatography (1% MeOH/CH$_2$Cl$_2$ to 10% MeOH/CH$_2$Cl$_2$) to obtain 5-(4,4-Dimethyl-cyclohexyl)-3-{(trans-4-methyl-cyclohexanecarbonyl)-[trans-4-(4-trimethylsilany-[1,2,3]triazol-1-yl)-cyclohexyl]-amino}-thiophene-2-carboxylic acid methyl ester (1.1 g, 58%)

Step IV:

To a solution of 5-(4,4-dimethyl-cyclohexyl)-3-{(trans-4-methyl-cyclohexanecarbonyl)-[trans-4-(4-trimethylsilany-[1,2,3]triazol-1-yl)cyclohexyl]-amino}-thiophene-2-carboxylic acid methyl ester (1.1 g, 1.8 mmol) in THF (4.4 ml) was added TBAF 1.0 M in THF (0.270 ml, 2.70 mmol). The reaction mixture was stirred for 24 h and treated with water and saturated ammonium chloride solution. The aqueous layer was extracted with ethyl acetate. The organic layer was washed with brine, dried with sodium sulfate, filtered and concentrated under reduce pressure. The residue was purified by silica gel column chromatography (50% ethyl acetate/hexane to 100% ethyl acetate) to give 5-(4,4-Dimethyl-cyclohexyl)-3-[(trans-4-methyl-cyclohexanecarbonyl)-(trans-4-[1,2,3]triazol-1-yl-cyclohexyl)-amino]-thiophene-2-carboxylic acid methyl ester (0.534 g, 55%).

Step V:

5-(4,4-Dimethyl-cyclohexyl)-3-[(trans-4-methyl-cyclohexanecarbonyl)-(trans-4-[1,2,3]triazol-1-yl-cyclohexyl)-amino]-thiophene-2-carboxylic acid methyl ester (0.53 g, 0.99 mmol) was hydrolysed with lithium hydroxide as previously described (example 3, step VIII) to give without any purification 5-(4,4-dimethyl-cyclohexyl)-3-[(trans-4-methyl-cyclohexanecarbonyl)-(trans-4-[1,2,3]triazol-1-yl-cyclohexyl)-amino]-thiophene-2-carboxylic acid hydrochloride (0.48 g, 95%).

EXAMPLE 33

5-cyclohex-1-enyl-3-[(trans,4-methyl-cyclohexanecarbonyl)-piperidin-4-yl-amino]-thiophene-2-carboxylic acid (compound #107)

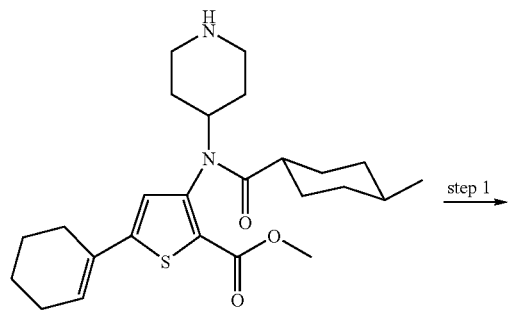

-continued

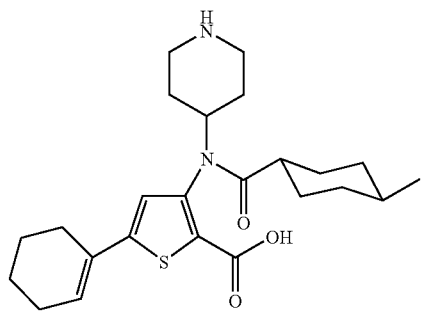

Step I was followed from Example 3, step VIII.

EXAMPLE 34

5-Cyclohex-1-enyl-3-[(trans,4-methyl-cyclohexanecarbonyl)-(1-pyrimidin-5-yl-piperidin-4-yl)-amino]-thiophene-2-carboxylic acid (Compound #96)

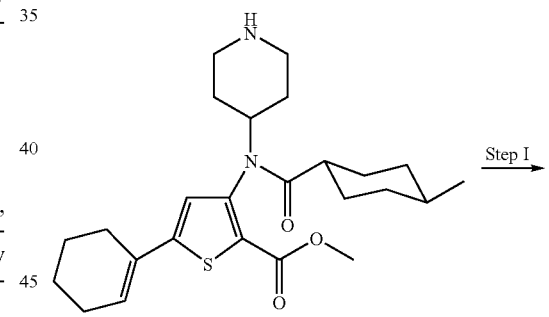

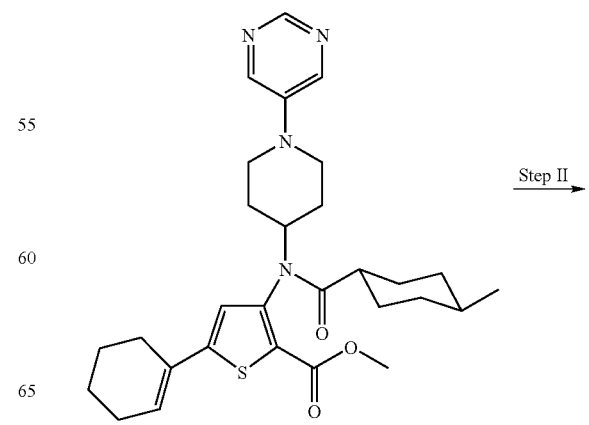

-continued

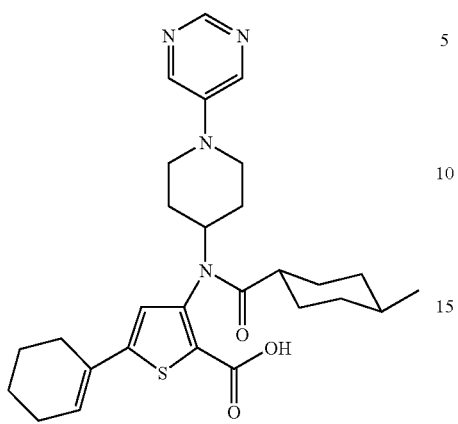

Step I:

To a solution of tris(dibenzylideneacetone)dipalladium (Pd$_2$(dba)$_3$) (10 mg, 0.01 mmol, 5 mol %) and rac 2,2'bis(diphenylphosphonium)1,1'-binapthyl (BINAP) (6.8 mg, 0.01 mmol) in dry toluene (9 mL) at ambient temperature, under nitrogen, was added a solid mixture of 5-cyclohex-1-enyl-3-[(trans-4-methyl-cyclohexanecarbonyl)-piperidin-4-yl-amino]thiophene-2-carboxylic acid methyl ester (100 mg, 0.22 mmol) and 5-bromo 1,3 pyrimidine (143 mg, 0.89 mmol) and cesium carbonate (79 mg, 0.24 mmol). The resulting dirty brown mixture was heated to 110° C. for 19.5 h. The reaction mixture was stripped off solvent and the residue dissolved in EtOAc and washed with water brine dried and evaporated to a brown foam (123 mg). The crude material was purified by chromatography using CH$_2$Cl$_2$:CH$_3$CN:MeOH=3:1:0.1 as eluent to give 5-cyclohex-1-enyl-3-[(trans-4-methyl-cyclohexanecarbonyl)-(1-pyrimidin-5-yl-piperidin-4-yl)-amino]-thiophene-2-carboxylic acid methyl ester (65 mg, 57%).

Step II:

To a solution of 5-Cyclohex-1-enyl-3-[(4-methyl-cyclohexanecarbonyl)-(1-pyrimidin-5-yl-piperidin-4-yl)-amino]-thiophene-2-carboxylic acid methyl ester (45 mg, 0.09 mmol) in dioxan:water=4:1, 1 mL) was added solid lithium hydroxide (11 mg, 0.26 mmol) in one portion. The solution was stirred at 21° C. for 25 h then stripped-off solvent and the residue taken into water (2 mL), cooled to 0° C. and slowly acidified to pH 1.5 with 6N HCl. The resulting pale yellow precipitate was filtered, washed with water (3 ml) and ether and dried in vacuuo to give the 5-Cyclohex-1-enyl-3-[(trans, 4-methyl-cyclohexanecarbonyl)-(1-pyrimidin-5-yl-piperidin-4-yl)-amino]-thiophene-2-carboxylic acid as a pale yellow solid (35 mg, 79%)

Using essentially the same procedure described above the following compounds can be prepared:

5-Cyclohex-1-enyl-3-[(trans-4-methyl-cyclohexanecarbonyl)-(1-phenyl-piperidin-4-yl)-amino]-thiophene-2-carboxylic acid (compound #127)

EXAMPLE 35

5-Cyclohex-1-enyl-3-[(trans-4-methyl-cyclohexanecarbonyl)-(1-pyrimidin-2-yl-piperidin-4-yl)-amino]-thiophene-2-carboxylic acid (compound #103

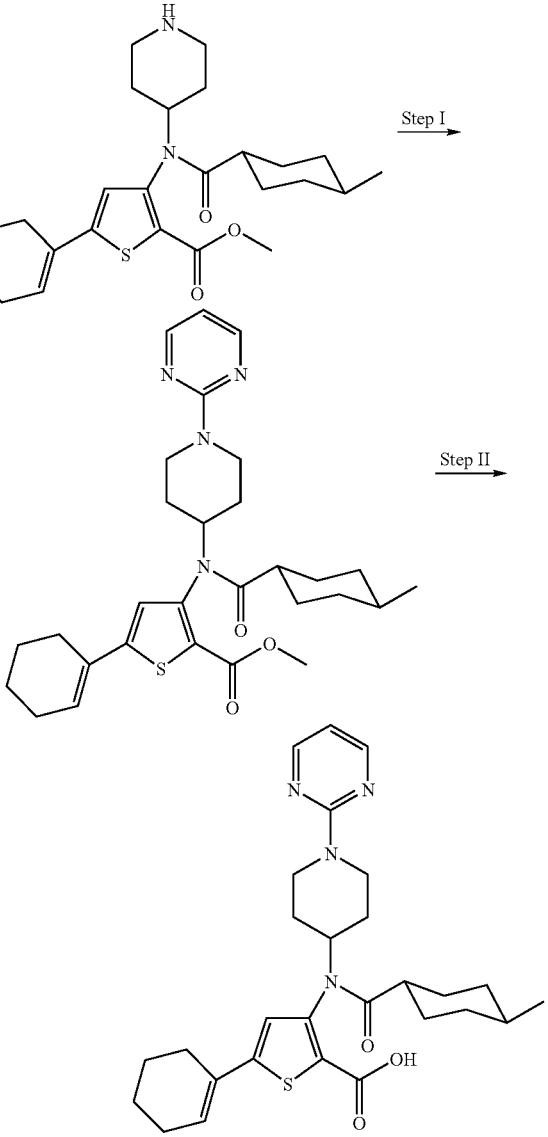

Step 1:

A solution of Pd$_2$(dba)$_3$ (6 mg, 0.01 mmol, 3 mol %) and 2-dicyclohexylphosphino-2'-(N,N-dimethylamino)biphenyl (3.4 mg, 0.01 mmol, 4.5 mol %) in dry toluene (4.6 mL) at 21° C. under nitrogen was added a mixture of 2-bromo-1,2-pyrimidine (107 mg, 0.68 mmol), 5-cyclohex-1-enyl-3-[(trans-4-methyl-cyclohexanecarbonyl)-piperidin-4-yl-amino]thiophene-2-carboxylic acid methyl ester (100 mg, 0.22 mmol) and cesium carbonate (80 mg, 0.25 mmol). The resulting dirty green mixture was stirred at 21° C. for 64 h. The dirty green opaque reaction mixture was stripped off solvent and the residue taken into EtOAc and washed with water, brine dried (Na$_2$SO$_4$) and evaporated to a gum (136 mg). The crude material was purified by column chromatography using methylene chloride:acetonitrile:methanol=9:1:0.1 as eluent to give 5-cyclohex-1-enyl-3-[(trans-4-methyl-cyclohexanecarbonyl)-(1-pyrimidin-2-yl-piperidin-4-yl)-amino]-thiophene-2-carboxylic acid methyl ester as a pale yellow foam (58 mg, 49%).

Step II:
5-Cyclohex-1-enyl-3-[(trans-4-methyl-cyclohexanecarbonyl)-(1-pyrimidin-2-yl-piperidin-4-yl)-amino]-thiophene-2-carboxylic acid methyl ester was hydrolysed with lithium hydroxide as described before (example 3, step VIII) to give the title compound #103

EXAMPLE 36

5-Cyclohex-1-enyl-3-[(1-formyl-piperidin-4-yl)-(trans-4-methycyclo-hexanecarbonyl)-amino]-thiophene-2-carboxylic acid (compound #98)

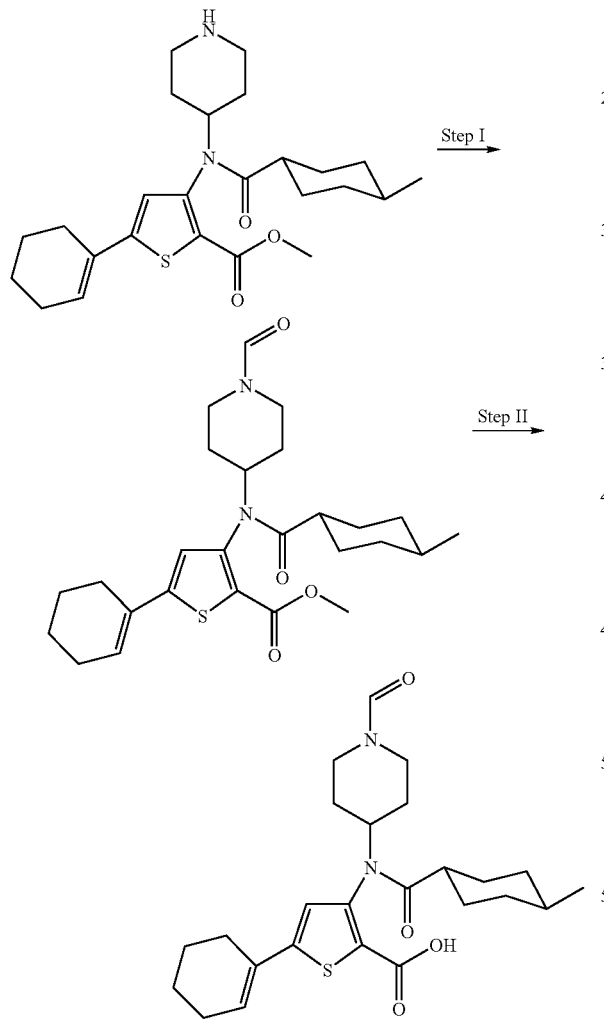

Step I:
A solution of 5-cyclohex-1-enyl-3-[(trans-4-methyl-cyclohexanecarbonyl)-piperidin-4-yl-amino]thiophene-2-carboxylic acid methyl ester (100 mg, 0.22 mmol) in ethyl formate (1.5 mL) under nitrogen, was placed in a bath at 65° C. for 20 h after which was added 1,2-dichloroethane (2.5 mL) and another portion of ethyl formate (2 mL). The bath temperature was raised to 95° C. and the reaction refluxed for a further 21 h. Tlc showed ca 80% conversion. The reaction was stripped off solvent and the residue purified by column chromatography using methylene chloride:acetonitrile:methanol=9:1:0.1 as eluent to give 5-Cyclohex-1-enyl-3-[(1-formyl-piperidin-4-yl)-(trans-4-methyl-cyclohexanecarbonyl)-amino]-thiophene-2-carboxylic acid methyl ester (42 mg, 41%)

Step II:
5-Cyclohex-1-enyl-3-[(1-formyl-piperidin-4-yl)-(trans-4-methyl-cyclohexane-carbonyl)-amino]-thiophene-2-carboxylic acid methyl ester was hydrolysed with lithium hydroxide according to previously described procedures (example 3, step VIII) to give the title compound.

EXAMPLE 37

5-Cyclohex-1-enyl-3-[(trans-4-methyl-cyclohexanecarbonyl)-(1-Pyridin-3-ylmethyl-piperidin-4-yl)-amino]-thiophene-2-carboxylic acid (compound #121)

Alkylation of 5-cyclohex-1-enyl-3-[(trans-4-methyl-cyclohexanecarbonyl)-piperidin-4-yl-amino]-thiophene-2-carboxylic acid methyl ester with 3-bromomethylpyridine and subsequent hydrolysis of the derived ester afforded the title compound compound #121

Using essentially the same procedure described above the following compounds can be prepared:

3-[(1-Cyano-piperidin-4-yl)-(trans-4-methyl-cyclohexanecarbonyl)-amino]-5-cyclohex-1-enyl-thiophene-2-carboxylic acid compound #102

EXAMPLE 38

5-Cyclohex-1-enyl-3-[[1,3]dioxan-5-yl-(trans-4-methyl-cyclohexane-carbonyl)-amino]-thiophene-2-carboxylic acid (compound #30)

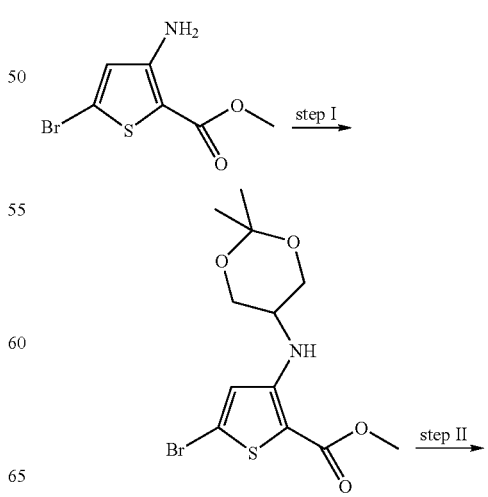

-continued

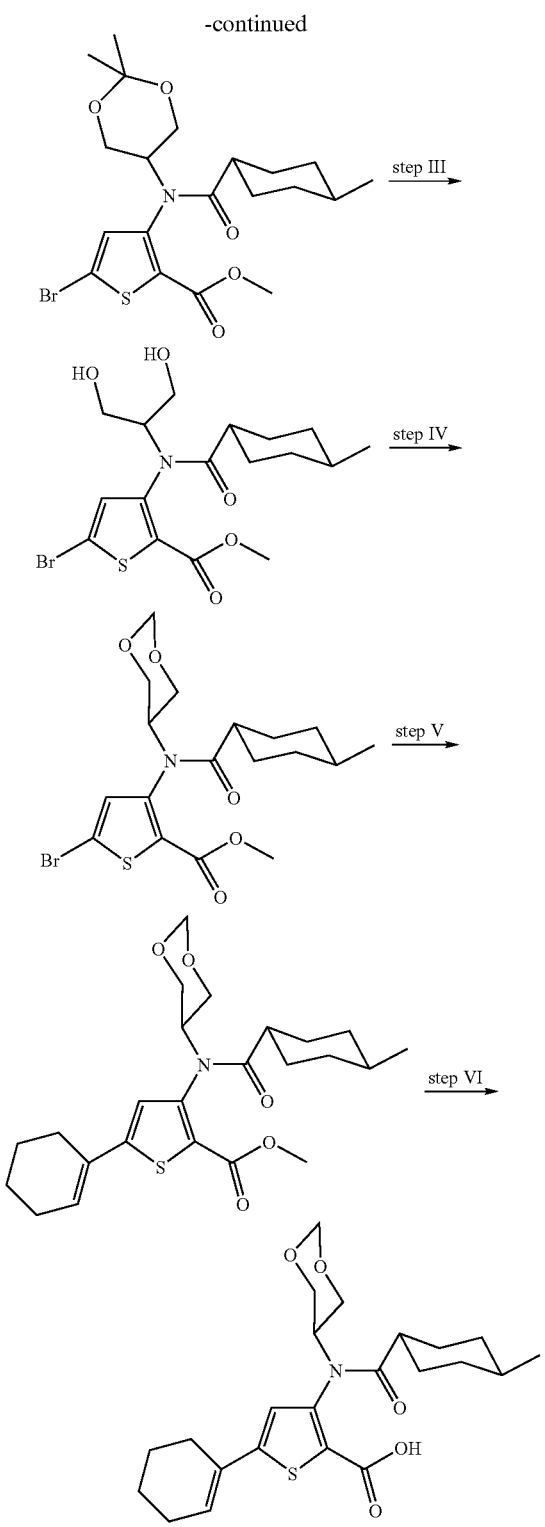

Step I:

A suspension of 3-amino-5-bromo-thiophene-2-carboxylic acid methyl ester (0.5 g, 2.12 mmol) in dry THF (0.6 mL) was treated with 2,2-dimethyl-[1,3]dioxan-5-one (253 µl, 2.12 mmol), followed by dibutyltin dichloride (32 mg, 0.11 mmol). After 5 min phenyl silane (280 µl, 2.27 mmol) was added and the reaction was stirred at room temperature for 3 days. It was dissolved in ethyl acetate (100 mL), washed with NaHCO$_3$ solution and brine. The organic layer was separated, dried over MgSO$_4$, evaporated and left on vacuum pump overnight. The residue was triturated with hexane-ether (4:1) mixture (2×100 mL). The soluble portion was evaporated and purified by chromatography over silica gel (hexane:ethyl acetate—95:5) yielding pure 5-bromo-3-(2,2-dimethyl-[1,3] dioxan-5-ylamino)-thiophene-2-carboxylic acid methyl ester (220 mg, 29%).

Step II:

Oxalyl chloride (2M in DCM, 2.7 mL) was added dropwise to a suspension of the trans-4-methyl cyclohexyl carboxylic acid (365 mg, 2.57 mmol) in DCM and a drop of DMF. The mixture was stirred at room temperature for 3 h and evaporated. Hexane (4 mL) was added and the mixture was evaporated. This was repeated once more. The residue was diluted with dry toluene (2.3 mL) (total volume became 2.7 mL) and used for the next step.

To a mixture of 5-bromo-3-(2,2-dimethyl-[1,3]dioxan-5-ylamino)-thiophene-2-carboxylic acid methyl ester (200 mg, 0.57 mmol) in toluene (1 mL) and pyridine (100 µl, 1.23 mmol), acid chloride in toluene prepared above (1.1 mL, 1.05 mmol) was added. The reaction mixture was refluxed for 16 h. TLC showed the presence of starting material. Pyridine (50 µl, 0.62 mmol) and acid chloride in totuene (0.5 mL, 0.47 mmol) were added and the refluxing was continued for 24 h. The mixture was cooled to 5° C. Toluene (2 mL) and pyridine (0.2 mL) were added. After stirring for 5 min MeOH (0.5 mL) was added and the mixture was stirred for 10 min. It was diluted with ethyl acetate, washed with saturated NaHCO$_3$ and brine, dried and evaporated. The crude reaction mixture was chromatographed over silica gel (hexane-ethyl acetate mixtures as eluents) yielding 5-bromo-3-[(2,2-dimethyl-[1,3]dioxan-5-yl)-(trans-4-methyl-cyclohexanecarbonyl)-amino]-thiophene-2-carboxylic acid methyl ester (35 mg) contaminated with a small impurity. This material was used for the next step.

Step III:

A mixture of 5-bromo-3-[(2,2-dimethyl-[1,3]dioxan-5-yl)-(trans-4-methyl-cyclohexanecarbonyl)-amino]-thiophene-2-carboxylic acid methyl ester (35 mg) contaminated with a small impurity in THF (1.1 mL) and 3N HCl (0.75 mL) was stirred at room temperature for 16 h. It was neutralized with solid NaHCO$_3$ and evaporated down to dryness. The residue was triturated with ethyl acetate (3×8 mL). The ethyl acetate extracts were combined, evaporated and chromatographed over silica gel (hexane:EtOAc—1:1) yielding pure 5-bromo-3-[(2-hydroxy-1-hydroxymethyl-ethyl)-(trans-4-methyl-cyclohexanecarbonyl)-amino]-thiophene-2-carboxylic acid methyl ester (18 mg; 7.2% in two steps).

Step IV:

A mixture of 5-bromo-3-[(2-hydroxy-1-hydroxymethyl-ethyl)-(trans-4-methyl-cyclohexanecarbonyl)-amino]-thiophene-2-carboxylic acid methyl ester (18 mg, 0.041 mmol), paraformaldehyde (6 mg) and boron trifluoride-diethyl etherate (15 µl, 0.12 mmol) in dry dioxane (0.6 mL) was stirred at 80° C. for 14 min. It was cooled and added to ice and NaHCO$_3$ solution mixture, extracted with ethyl acetate, washed with brine, dried and evaporated. Pure 5-bromo-3-[[1,3]dioxan-5-yl-(trans-4-methyl-cyclohexanecarbonyl)-amino]-thiophene-2-carboxylic acid methyl ester was obtained after chromatography over silica gel (hexane:ethyl acetate—9:1 as eluent) (15 mg; 81%).

Step V:

Nitrogen was bubbled through a solution of 5-bromo-3-[[1,3]dioxan-5-yl-(trans-4-methyl-cyclohexanecarbonyl)-amino]-thiophene-2-carboxylic acid methyl ester (15 mg, 0.034 mmol) containing cyclohexen-1-ylboronic acid (8 mg, 0.063 mmol) in 2M aqueous Na₂CO₃ (0.9 mL) and DME (1.8 mL) for 10 min. Pd(PPh₃)₄ (3 mg) was added and the mixture was refluxed for 1 h 10 min. It was cooled, diluted with ethyl acetate (50 mL), washed with water and brine, dried and evaporated yielding the crude 5-cyclohex-1-enyl-3-[[1,3]dioxan-5-yl-(trans-4-methyl-cyclohexanecarbonyl)-amino]-thiophene-2-carboxylic acid methyl ester (24 mg) which was used in the next step without further purification.

Step VI:

Crude 5-cyclohex-1-enyl-3-[[1,3]dioxan-5-yl-(trans-4-methyl-cyclohexane-carbonyl)-amino]-thiophene-2-carboxylic acid methyl ester (24 mg) was dissolved in a mixture of THF, MeOH and H₂O (3:2:1) (1.8 mL) and 1N LiOH (0.15 mL) was added. Rest of the procedure has been described earlier (example 3, step VIII). Pure 5-cyclohex-1-enyl-3-[[1,3]dioxan-5-yl-(trans-4-methyl-cyclohexanecarbonyl)-amino]-thiophene-2-carboxylic acid was obtained by preparative HPLC.

Using essentially the same procedure described above the following compounds can be prepared:

5-Cyclohex-1-enyl-3-[(trans-4-methyl-cyclohexanecarbonyl)-(2-methyl-[1,3]dioxan-5-yl)-amino]-thiophene-2-carboxylic acid (compound #36)

EXAMPLE 39

5-Cyclohex-1-enyl-3-[(cis-4-fluoro-cyclohexyl)-(trans-4-methyl-cyclohexanecarbonyl)-amino]-thiophene-2-carboxylic acid (compound #57)

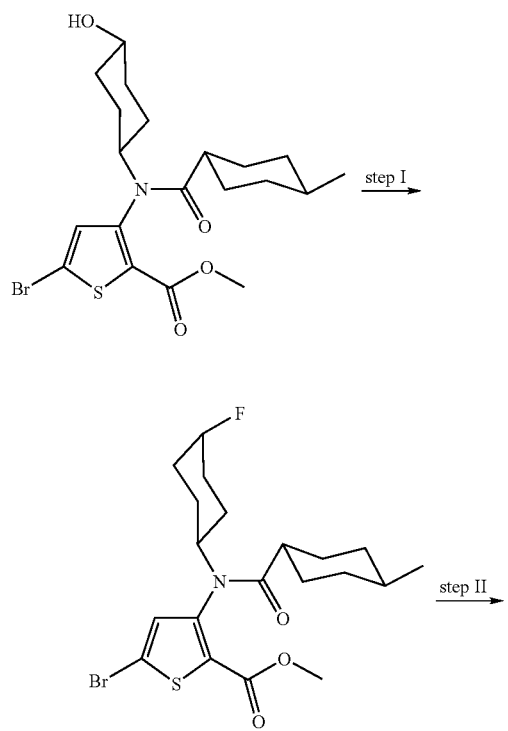

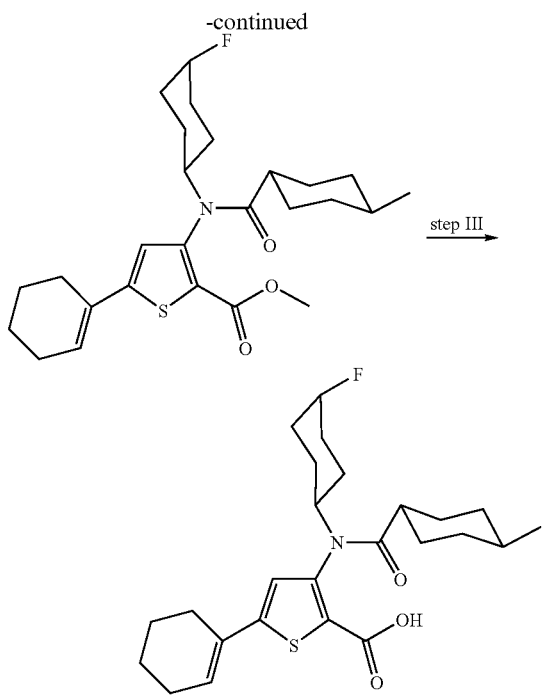

Stpe I:

To a solution of (diethylamino)sulfur trifluoride (0.24 mL, 1.82 mmol) in DCM (2.7 mL) pyridine (0.27 mL, 3.34 mmol) was added followed by dropwise addition of 5-bromo-3-[(trans-4-hydroxy-cyclohexyl)-(trans-4-methyl-cyclohexanecarbonyl)-amino]-thiophene-2-carboxylic acid methyl ester (150 mg, 0.32 mmol) in DCM (2.0 mL) during 10 min. The mixture was stirred for 16 h at room temperature. It was cooled in ice-bath and saturated NaHCO₃ was added slowly to neutralize the excess reagent. The mixture was stirred at room temperature for 3 h. It was extracted with DCM (100 mL), washed with brine, dried (MgSO₄) and evaporated. The crude was chromatographed over silica gel (hexane:EtOAc—95:5 and 90:10 as eluents) yielding pure 5-bromo-3-[(cis-4-fluoro-cyclohexyl)-(trans-4-methyl-cyclohexanecarbonyl)-amino]-thiophene-2-carboxylic acid methyl ester (28 mg, 18%) and 5-bromo-3-[(trans-4-fluoro-cyclohexyl)-(trans-4-methyl-cyclohexanecarbonyl)-amino]-thiophene-2-carboxylic acid methyl ester (22 mg, 14%).

Step II:

Nitrogen was bubbled through a solution of 5-bromo-3-[(cis-4-fluoro-cyclohexyl)-(trans-4-methyl-cyclohexanecarbonyl)-amino]-thiophene-2-carboxylic acid methyl ester (20 mg, 0.043 mmol) and cyclohexen-1-ylboronic acid (13 mg, 0.103 mmol) in 2M Na₂CO₃ (1.3 mL) and DME (2.6 mL) for 6 min. Pd(PPh₃)₄ (4.4 mg) was added and the mixture was refluxed for 1 h and 30 min. It was cooled, diluted with ethyl acetate, washed with water and brine, dried (MgSO₄) and evaporated. The crude was purified by chromatography over silica gel (hexane:EtOAc—9:1 and 4:1 as eluents) yielding pure 5-cyclohex-1-enyl-3-[(cis-4-fluoro-cyclohexyl)-(trans-4-methyl-cyclohexanecarbonyl)-amino]-thiophene-2-carboxylic acid methyl ester (10 mg, 50%).

Step III:

5-cyclohex-1-enyl-3-[(cis-4-fluoro-cyclohexyl)-(trans-4-methyl-cyclohexane-carbonyl)-amino]-thiophene-2-carboxylic acid methyl ester (10 mg, 0.021) was dissolved in a mixture of THF, MeOH and H₂O (3:2:1) (2 mL) and 1N LiOH (0.1 mL) was added. Rest of the procedure has been described earlier (example 3, step VIII). Pure 5-cyclohex-1-enyl-3-[(cis-4-fluoro-cyclohexyl)-(trans-4-methyl-cyclohexanecarbonyl)-amino]-thiophene-2-carboxylic acid was obtained after chromatography over silica gel (5% MeOH in DCM as eluent) (5 mg, 51%).

Using essentially the same procedure described above the following compounds can be prepared:

5-Cyclohex-1-enyl-3-[(trans-4-fluoro-cyclohexyl)-(trans-4-methyl-cyclohexanecarbonyl)-amino]-thiophene-2-carboxylic acid (compound #70)

5-(4,4-Dimethyl-cyclohexyl)-3-[(trans-4-fluoro-cyclohexyl)-(trans-4-methyl-cyclohexanecarbonyl)-amino]-thiophene-2-carboxylic acid (compound #83)

5-Cyclohex-1-enyl-3-[(4,4-difluoro-cyclohexyl)-(trans-4-methyl-cyclohexanecarbonyl)-amino]-thiophene-2-carboxylic acid (compound #91) can be prepared from 5-Bromo-3-[(trans-4-methyl-cyclohexanecarbonyl)-(4-oxo-cyclohexyl)-amino]-thiophene-2-carboxylic acid methyl ester using synthetic steps described in is example 39.

EXAMPLE 40

5-(3-Hydroxy-cyclohex-1-enyl)-3-[(trans-4-hydroxy-cyclohexyl)-(trans-4-methyl-cyclohexanecarbonyl)-amino]-thiophene-2-carboxylic acid (compound #82)

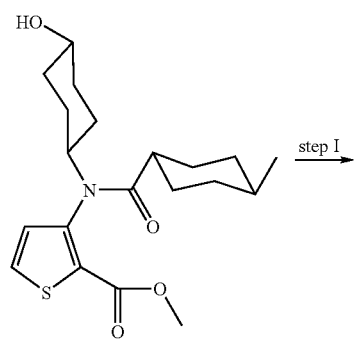

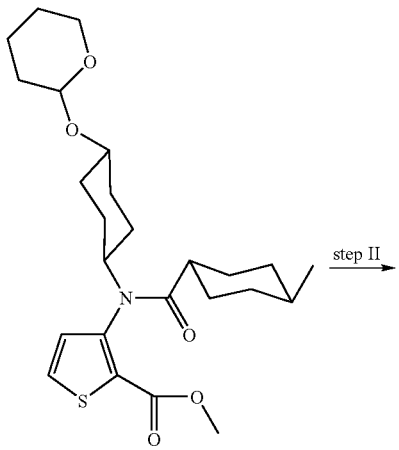

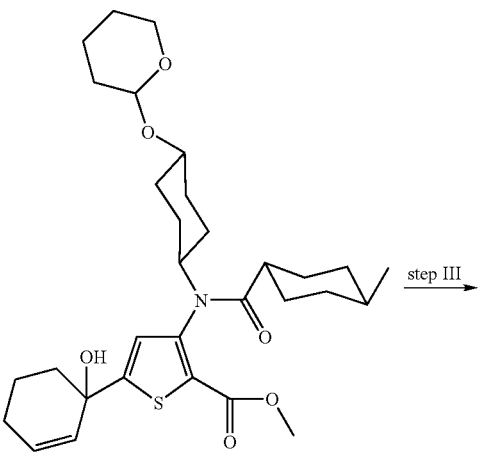

-continued

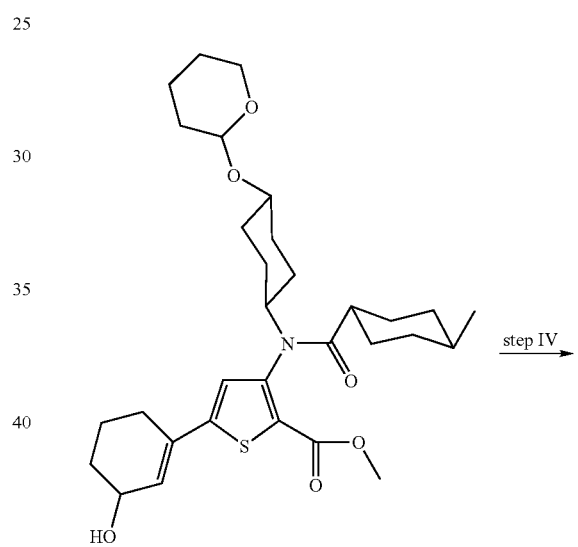

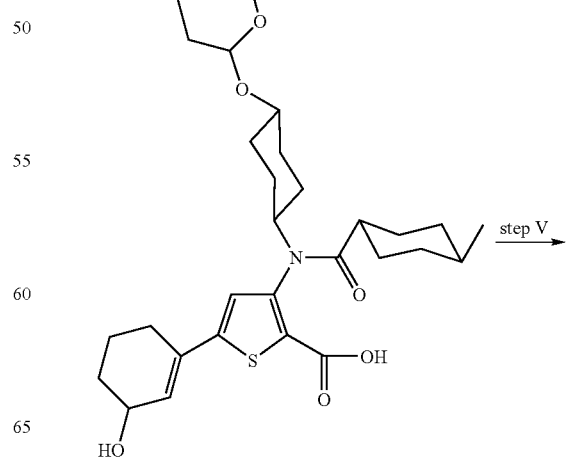

-continued

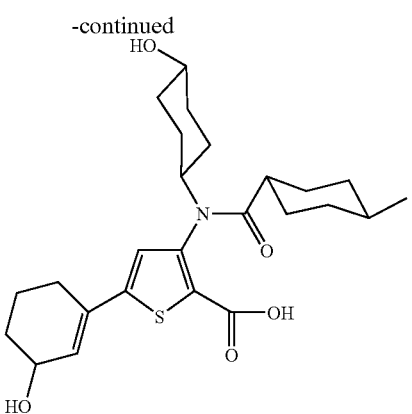

Step I:

To a solution of 3-[(trans-4-hydroxy-cyclohexyl)-(trans-4-methyl-cyclohexanecarbonyl)-amino]-thiophene-2-carboxylic acid methyl ester (140 mg, 0.37 mmol) in DCM (4 mL) p-toluenesulfonic acid monohydrate (6 mg) and 3,4-dihydro-2H-pyran (38 μl, 0.42 mmol) were added at room temperature. After stirring for 1 h and min saturated NaHCO₃ was added. It was extracted with DCM, washed with brine, dried (MgSO₄) and evaporated. The crude material was chromatographed over silica gel (prewashed with Et₃N) (hexane:EtOAc—9:1 as eluent) yielding pure 3-{(trans-4-methyl-cyclohexanecarbonyl)-[trans-4-(tetrahydro-pyran-2-yloxy)-cyclohexyl]-amino}-thiophene-2-carboxylic acid methyl ester (83 mg, 48%).

Step II:

To a mixture of THF (0.5 mL) and diisopropylamine (31 μl, 0.22 mmol) cooled to −40° C. n-BuLi (1.3 M, 165 μl, 0.21 mmol) was added dropwise. After stirring at this temperature for 30 min it was cooled to −78° C. and 3-{(trans-4-methyl-cyclohexanecarbonyl)-[trans-4-(tetrahydro-pyran-2-yloxy)-cyclohexyl]-amino}-thiophene-2-carboxylic acid methyl ester (82 mg, 0.18 mmol) in THF (0.5 mL) was added dropwise. The mixture was stirred at this temperature for 30 min. Cyclohex-2-enone (20 μl, 0.21 mmol) was added quickly and it was stirred for 20 min at −78° C. Saturated NH₄Cl solution was added and the mixture was allowed to come to room temperature. It was extracted with EtOAc. The extract was washed with brine, dried (MgSO₄) and evaporated. Pure 5-(1-hydroxy-cyclohex-2-enyl)-3-{(trans-4-methyl-cyclohexanecarbonyl)-[trans-4-(tetrahydro-pyran-2-yloxy)-cyclohexyl]-amino}-thiophene-2-carboxylic acid methyl ester was obtained after chromatography over silica gel (hexane:EtOAc—80:20 as eluent) (48 mg, 48%).

Step III:

A solution of 5-(1-hydroxy-cyclohex-2-enyl)-3-{(trans-4-methyl-cyclohexanecarbonyl)-[trans-4-(tetrahydro-pyran-2-yloxy)-cyclohexyl]-amino}-thiophene-2-carboxylic acid methyl ester (48 mg, 0.086 mmol) in DCM (1 mL) was cooled to −50° C. Triethylsilane (43 μl, 0.27 mmol) was added followed by gradual addition of trifluoroacetic acid (total 22 μl, 0.28 mmol) (4 μl to 6 μl every 30 min). The mixture was stirred at −40° C. to −50° C. for 3.5 h. Aqueous NaHCO₃ was added and the mixture was allowed to come to room temperature. It was extracted with DCM, washed with brine, dried (MgSO₄) and evaporated. The crude was left at room temperature for 2 days and purified by chromatography over silica gel (hexane-EtOAc mixtures) yielding 5-(3-Hydroxy-cyclohex-1-enyl)-3-{(trans-4-methyl-cyclohexanecarbonyl)-[trans-4-(tetrahydro-pyran-2-yloxy)-cyclohexyl]-amino}-thiophene-2-carboxylic acid methyl ester (22 mg, 45%).

Step IV:

A mixture of 5-(3-hydroxy-cyclohex-1-enyl)-3-{(trans-4-methyl-cyclohexanecarbonyl)-[trans-4-(tetrahydro-pyran-2-yloxy)-cyclohexyl]-amino}-thiophene-2-carboxylic acid methyl ester (22 mg; 0.039 mmol) in THF:MeOH:H₂O (3:2:1) (2.5 mL) and 1N LiOH (0.2 mL) was stirred at 50° C. for 4 h. Following the procedure described earlier (example 3, step VIII) pure 5-(3-Hydroxy-cyclohex-1-enyl)-3-{(trans-4-methyl-cyclohexanecarbonyl)-[trans-4-(tetrahydro-pyran-2-yloxy)-cyclohexyl]-amino}-thiophene-2-carboxylic acid (10 mg, 46%) was obtained by chromatography over silica gel.

Step V:

A solution of 5-(3-hydroxy-cyclohex-1-enyl)-3-{(trans-4-methyl-cyclohexane-carbonyl)-[trans-4-(tetrahydro-pyran-2-yloxy)-cyclohexyl]-amino}-thiophene-2-carboxylic acid (4 mg, 0.007 mmol) in acetic acid:THF:H₂O (4:2:1) (0.7 mL) was stirred at 45° C. for 3.5 h. The mixture was evaporated to dryness and triturated with CHCl₃ and hexane yielding 5-(3-hydroxy-cyclohex-1-enyl)-3-[(trans-4-hydroxy-cyclohexyl)-(trans-4-methyl-cyclohexanecarbonyl)-amino]-thiophene-2-carboxylic acid (1.6 mg, 47%).

Using essentially the same procedure described above the following compounds can be prepared:

5-(3-Hydroxy-cyclohex-1-enyl)-3-{(trans-4-methyl-cyclohexanecarbonyl)-[trans-4-(tetrahydro-pyran-2-yloxy)-cyclohexyl]-amino}-thiophene-2-carboxylic acid (compound #55)

EXAMPLE 41

5-(4,4-Dimethyl-cyclohexyl)-3-[[1,3]dioxan-5-yl-(trans-4-methyl-cyclohexanecarbonyl)-amino]-thiophene-2-carboxylic acid (compound #97)

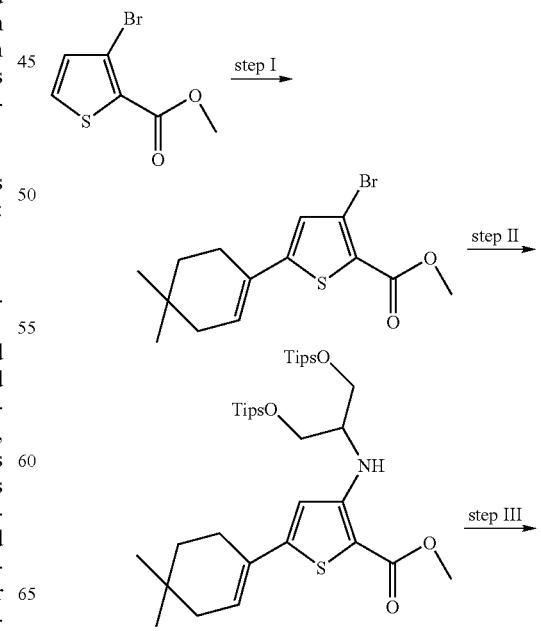

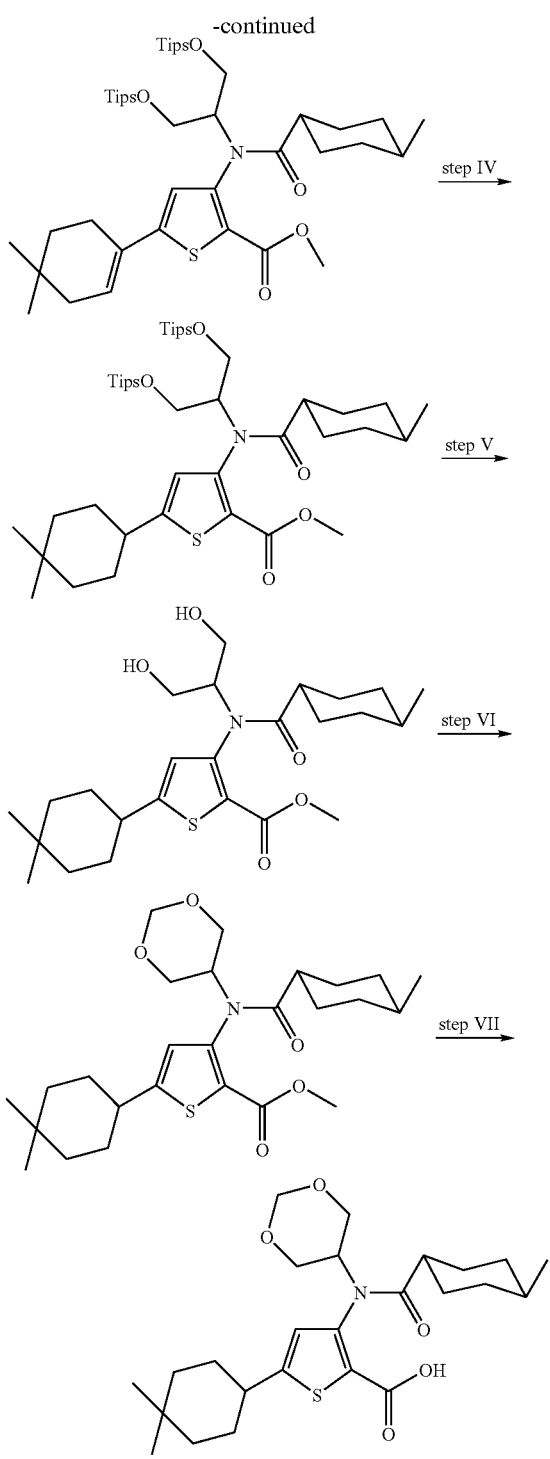

Step I:
3-Bromo-5-(4,4-dimethyl-cyclohex-1-enyl)-thiophene-2-carboxylic acid methyl ester was prepared from 3-bromo-thiophene-2-carboxylic acid methyl ester following a procedure described earlier (example 3, steps III and IV).

Step II:
Nitrogen was bubbled through a mixture of 2-triisopropyl-silanyloxy-1-triisopropylsilanyloxymethyl-ethylamine (prepared from serinol using triisopropylsilyl chloride) (420 mg, 1.04 mmol) and 3-bromo-5-(4,4-dimethyl-cyclohex-1-enyl)-thiophene-2-carboxylic acid methyl ester (350 mg, 1.06 mmol) in dioxane (3.5 mL) containing $Cs_2CO_3$ (1 g, 3.07 mmol) and $Pd_2(dba)_3$ (96 mg, 0.1 mmol) for 6 min. 2,2'-Bis(diphenylphosphino)-1,1'-binaphthyl (105 mg, 0.17 mmol) was added and the mixture was stirred at 80° C. for 24 h. It was diluted with DCM, filtered through celite and evaporated. 5-(4,4-Dimethyl-cyclohex-1-enyl)-3-(2-triisopropylsilanyloxy-1-triisopropylsilanyloxymethyl-ethylamino)-thiophene-2-carboxylic acid methyl ester was obtained by chromatography over silica gel (hexane:EtOAc—95:5) (500 mg, 72%).

Step III:
5-(4,4-Dimethyl-cyclohex-1-enyl)-3-[(trans-4-methyl-cyclohexanecarbonyl)-(2-triisopropylsilanyloxy-1-triisopropylsilanyloxymethyl-ethyl)-amino]-thiophene-2-carboxylic acid methyl ester was prepared from 5-(4,4-Dimethyl-cyclohex-1-enyl)-3-(2-triisopropylsilanyloxy-1-triisopropylsilanyloxymethyl-ethylamino)-thiophene-2-carboxylic acid methyl ester following a procedure described earlier (example 38, step II).

Step IV:
5-(4,4-Dimethyl-cyclohex-1-enyl)-3-[(trans-4-methyl-cyclohexanecarbonyl)-(2-triisopropylsilanyloxy-1-triisopropylsilanyloxymethyl-ethyl)-amino]-thiophene-2-carboxylic acid methyl ester was hydrogenated with 10% Pd/C following a procedure described (example 2).

Step V:
A solution of 3-[(1-diisopropylsilanyloxymethyl-2-triisopropylsilanyloxy-ethyl)-(trans-4-methyl-cyclohexanecarbonyl)-amino]-5-(4,4-dimethyl-cyclohexyl)-thiophene-2-carboxylic acid methyl ester (60 mg, 0.078 mmol) in THF (1 mL) was treated with HF.pyridine (0.1 mL). The mixture was stirred at room temperature for 16 h. The mixture was diluted with EtOAc and added to solid $NaHCO_3$. It was stirred at room temperature for 2 h, filtered and evaporated. Pure 5-(4,4-dimethyl-cyclohexyl)-3-[(2-hydroxy-1-hydroxymethyl-ethyl)-(trans-4-methyl-cyclohexanecarbonyl)-amino]-thiophene-2-carboxylic acid methyl ester was obtained on chromatography over silica gel (EtOAc as eluent) (32 mg, 89%).

Step VI:
5-(4,4-Dimethyl-cyclohexyl)-3-[[1,3]dioxan-5-yl-(trans-4-methyl-cyclohexanecarbonyl)-amino]-thiophene-2-carboxylic acid methyl ester was prepared from 5-(4,4-dimethyl-cyclohexyl)-3-[(2-hydroxy-1-hydroxymethyl-ethyl)-(trans-4-methyl-cyclohexanecarbonyl)-amino]-thiophene-2-carboxylic acid methyl ester using paraformaldehyde following a procedure described earlier (example 38, step IV).

Step VII:
5-(4,4-Dimethyl-cyclohexyl)-3-[[1,3]dioxan-5-yl-(trans-4-methyl-cyclohexane-carbonyl)-amino]-thiophene-2-carboxylic acid was prepared from 5-(4,4-dimethyl-cyclohexyl)-3-[[1,3]dioxan-5-yl-(trans-4-methyl-cyclohexanecarbonyl)-amino]-thiophene-2-carboxylic acid methyl ester following a procedure described earlier (example 3, step VIII).

Using essentially the same procedure described above the following compounds can be prepared:

5-Cyclohex-1-enyl-3-[cyclopropyl-(trans-4-methyl-cyclohexanecarbonyl)-amino]-thiophene-2-carboxylic acid (compound #51)

3-[Benzo[1,3]dioxol-5-yl-(trans-4-methyl-cyclohexanecarbonyl)-amino]-5-cyclohex-1-enyl-thiophene-2-carboxylic acid (compound #136)

EXAMPLE 42

5-Cyclohex-1-enyl-3-[(trans-4-methyl-cyclohexanecarbonyl)-(trans-4-methylsulfanylmethoxy-cyclohexyl)-amino]-thiophene-2-carboxylic acid (compound #142)

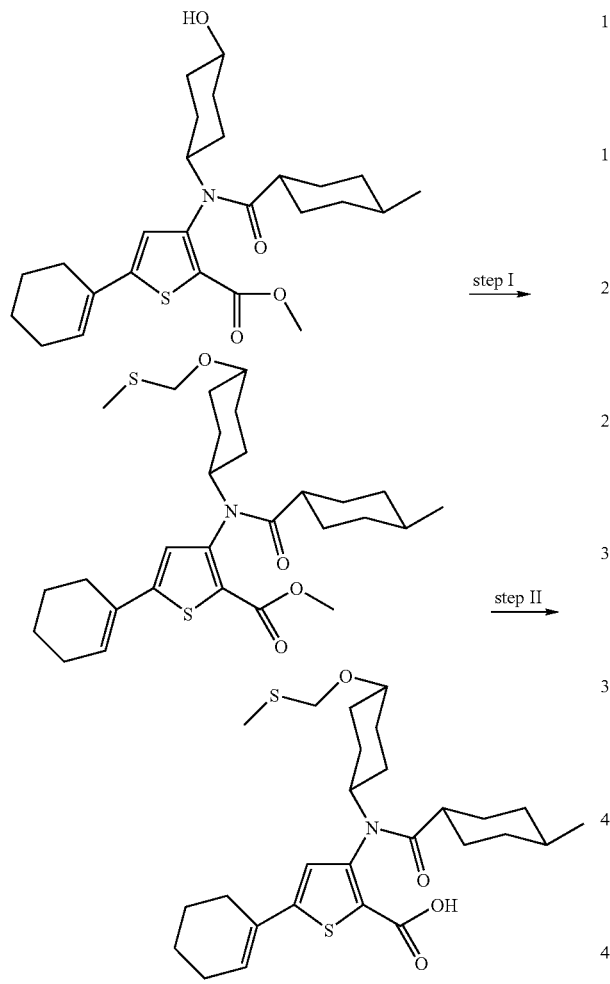

Step I:

To a solution of 5-cyclohex-1-enyl-3-[(trans-4-hydroxy-cyclohexyl)-(trans-4-methyl-cyclohexanecarbonyl)-amino]-thiophene-2-carboxylic acid methyl ester (25 mg, 0.054 mmol) in DMSO (0.2 mL) was added a mixture of acetic acid and acetic anhydride (1:5.6) (0.17 mL). After stirring for 1.5 h at room temperature it was held at 40° C. for 5 h. It was cooled to room temperature and stirred for 16 h. The mixture was cooled in ice-bath and NaHCO₃ solution was added carefully. It was extracted with ether. The extract was washed with water and brine, dried over MgSO₄ and evaporated. Xs Pure 5-cyclohex-1-enyl-3-[(trans-4-methyl-cyclohexanecarbonyl)-(trans-4-methylsulfanylmethoxy-cyclohexyl)-amino]-thiophene-2-carboxylic acid methyl ester was obtained by chromatography over silica gel (hexane:EtOAc=-4:1) (22 mg, 77%).

Step II:

5-cyclohex-1-enyl-3-[(trans-4-methyl-cyclohexanecarbonyl)-(trans-4-methylsulfanylmethoxy-cyclohexyl)-amino]-thiophene-2-carboxylic acid methyl ester was hydrolyzed to the corresponding acid following a procedure described earlier (example 3, step VIII).

EXAMPLE 43

5-Cyclohex-2-enyl-3-[(trans-4-hydroxy-cyclohexyl)-(trans-4-methyl-cyclohexanecarbonyl)-amino]-thiophene-2-carboxylic acid (compound #146) and 5-cyclohex-1-enyl-3-[(trans-4-hydroxy-cyclohexyl)-(trans-4-methyl-cyclohexanecarbonyl)-amino]-thiophene-2-carboxylic acid (compound #4) as a 5:6 mixture

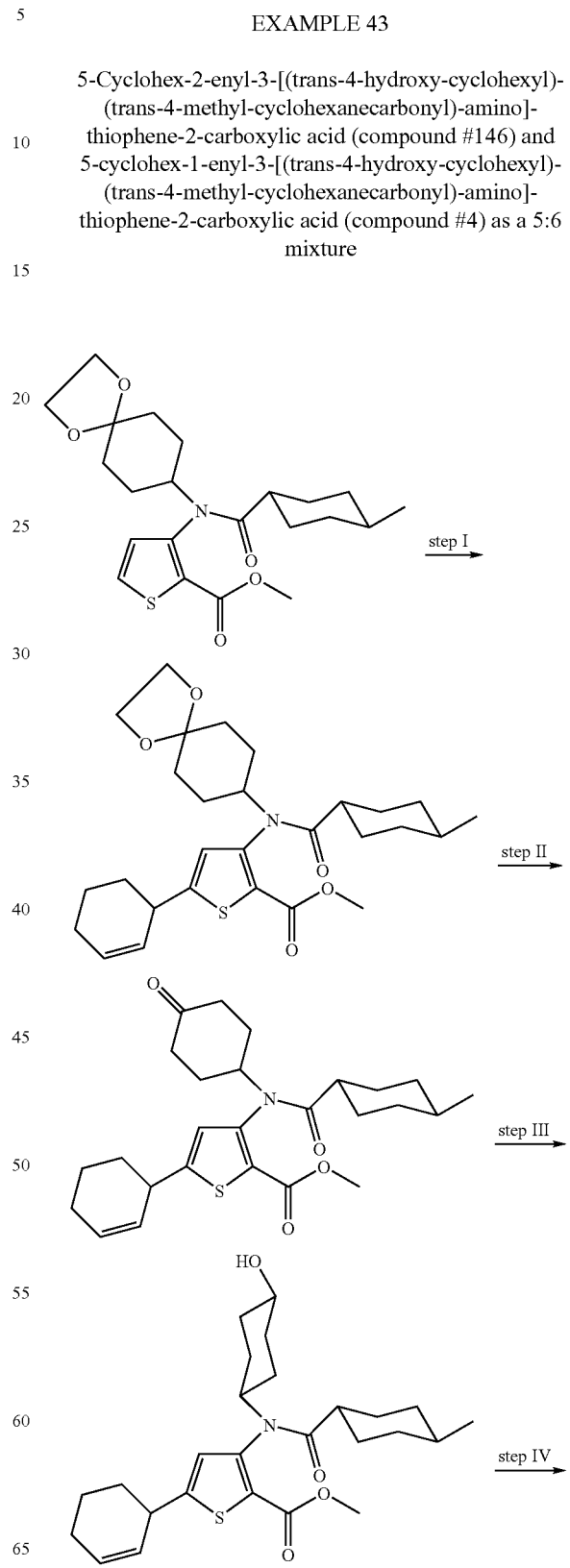

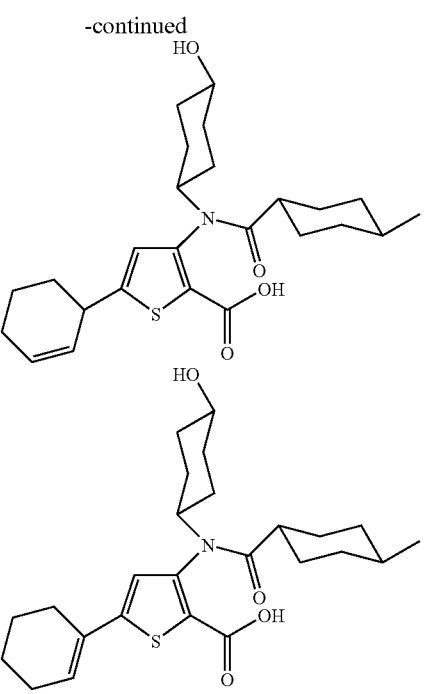

Step I:

In a small RB flask THF (1.5 mL) was placed followed by diisopropylamine (80 μl, 0.57 mmol) and the mixture was cooled to −40° C. n-BuLi (1.6 M, 0.34 mL, 0.54 mmol) was added dropwise. It was stirred at this temperature for 20 min. The mixture was cooled to −78° C. and 3-[(1,4-dioxa-spiro [4.5]dec-8-yl)-(trans-4-methyl-cyclohexanecarbonyl)-amino]-thiophene-2-carboxylic acid methyl ester (200 mg, 0.47 mmol) in THF (2 mL) was added dropwise. Stirring at −78° C. was continued for 30 min. Tributyl borane (1M in ether, 0.48 mL) was added and the mixture was allowed to come to room temperature over a period of 1 h. This solution was added to a suspension of CuCN (47 mg) in THF (1 mL) cooled to −30° C. The mixture was stirred at this temperature for 20 min. 3-Bromocyclohexene (90%, 60 μl, 0.47 mmol) was added and the mixture was allowed to come to room temperature slowly. It was stirred at this temperature for 16 h. The mixture was cooled to 0° C. and 10% NaOH (0.8 mL) was added followed by dropwise addition of 30% H₂O₂ (0.27 mL). The mixture was stirred for 10 min. It was diluted with EtOAc, washed with water and brine, dried (MgSO₄) and evaporated. Pure 5-cyclohex-2-enyl-3-[(1,4-dioxa-spiro[4.5] dec-8-yl)-(trans-4-methyl-cyclohexanecarbonyl)-amino]-thiophene-2-carboxylic acid methyl ester was obtained on chromatography over silica gel (hexane:EtOAc—9:1, 4:1 and 7:3 eluents) (153 mg, 64%).

Step II:

A mixture of 5-cyclohex-2-enyl-3-[(1,4-dioxa-spiro[4.5] dec-8-yl)-(trans-4-methyl-cyclohexanecarbonyl)-amino]-thiophene-2-carboxylic acid methyl ester (50 mg, 0.1 mmol) in DCM (4 mL), trifluoroacetic acid (0.4 mL) and water (20 μl) was stirred for 16 h at room temperature. Trifluoroacetic acid ((0.2 mL) was added and it was stirred for another 3 h. Saturated NaHCO₃ solution was added and it was extracted with DCM. The extract was washed with brine, dried over MgSO₄ and evaporated yielding crude 5-cyclohex-2-enyl-3-[(trans-4-methyl-cyclohexanecarbonyl)-(4-oxo-cyclohexyl)-amino]-thiophene-2-carboxylic acid methyl ester (40 mg) which was used in the next step.

Step III:

To a mixture of 5-cyclohex-2-enyl-3-[(trans-4-methyl-cyclohexanecarbonyl)-(4-oxo-cyclohexyl)-amino]-thiophene-2-carboxylic acid methyl ester (40 mg) and MeOH (3 mL) cooled to 0° C. was added NaBH₄ (15 mg) in one portion. Reaction was complete in 5 min. HCl (0.1 N, 0.5 mL) was added until it was acidic. It was evaporated and then extracted with DCM, washed with saturated NaHCO₃ solution, brine, dried (MgSO₄) and evaporated. The crude was purified by chromatography over silica gel (hexane:EtOAc—1:1 as eluent) yielding pure 5-Cyclohex-2-enyl-3-[(trans-4-hydroxy-cyclohexyl)-(trans-4-methyl-cyclohexanecarbonyl)-amino]-thiophene-2-carboxylic acid methyl ester (12 mg, 26%) in two steps.

Step IV:

To a solution of 5-Cyclohex-2-enyl-3-[(trans-4-hydroxy-cyclohexyl)-(trans-4-methyl-cyclohexanecarbonyl)-amino]-thiophene-2-carboxylic acid methyl ester (12 mg, 0.026 mmol) in a mixture of THF:MeOH:H₂O (3:2:1) (1.6 mL) was added 1N LiOH (0.1 mL). The mixture was stirred at 50° C. for 4.5 h. The mixture was concentrated and dissolved in water. It was transferred to a separatory funnel. Ethyl acetate was added followed by addition of 0.1 N HCl (1 mL). The product was extracted into EtOAc. The extract was washed with water and brine, dried (MgSO₄) and evaporated. The crude was chromatographed over silica gel (DCM containing 1 to 8% MeOH as eluents) yielding 5:6 mixture of 5-cyclohex-2-enyl-3-[(trans-4-hydroxy-cyclohexyl)-(trans-4-methyl-cyclohexanecarbonyl)-amino]-thiophene-2-carboxylic acid and 5-cyclohex-1-enyl-3-[(trans-4-hydroxy-cyclohexyl)-(trans-4-methyl-cyclohexanecarbonyl)-amino]-thiophene-2-carboxylic acid (4.5 mg).

EXAMPLE 44

5-Cyclohex-1-enyl-3-[{trans-4-(1-methoxycarbonyl-2-methyl-propyl-carbamoyloxy)-cyclohexyl}-(trans-4-methyl-cyclohexanecarbonyl)-amino]-thiophene-2-carboxylic acid (compound #19)

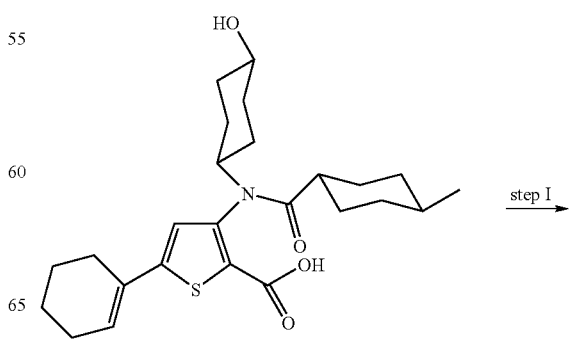

-continued

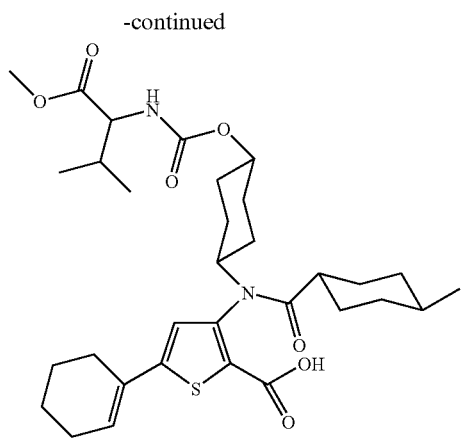

Step I:

A mixture of 5-cyclohex-1-enyl-3-{(trans-4-hydroxy-cyclohexyl)-(trans-4-methyl-cyclohexane-carbonyl)-amino}-thiophene-2-carboxylic acid (20 mg, 0.045 mmol) and methyl (S)-(−)-2-isocyanato −3-methylbutyrate (10 µl, 0.07 mmol) in toluene (1 mL) was stirred at 70° C. for 2 h. It was cooled and water (1 mL) was added. The mixture was stirred at room temperature for one h. It was extracted with EtOAc (50 mL), washed with brine, dried (MgSO$_4$) and evaporated. Pure 5-cyclohex-1-enyl-3-[{trans-4-(1-methoxycarbonyl-2-methyl-propylcarbamoyloxy)-cyclohexyl}-(trans-4-methyl-cyclohexanecarbonyl)-amino]-thiophene-2-carboxylic acid was obtained by chromatography over silica gel (hexane-EtOAc mixtures, pure EtOAc and 5% acetone in DCM as eluent) (12.4 mg, 45%).

EXAMPLE 45

Preparation of 5-cyclohex-1-enyl-3-[(trans-4-methyl-cyclohexanecarbonyl))-(cis-4-[1,2,4]triazol-1-yl-cyclohexyl)-amino]-thiophene-2-carboxylic acid hydrochloride (compound #41) and 5-cyclohex-1-enyl-3-[(trans-4-methyl-cyclohexanecarbonyl))-(trans-4-[1,2,4]triazol-1-yl-cyclohexyl)-amino]-thiophene-2-carboxylic acid hydrochloride (compound #48)

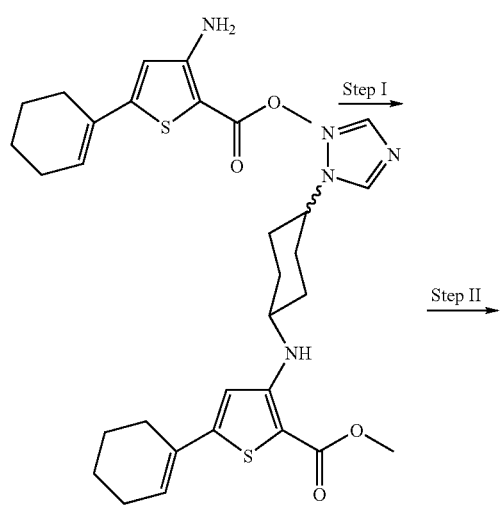

-continued

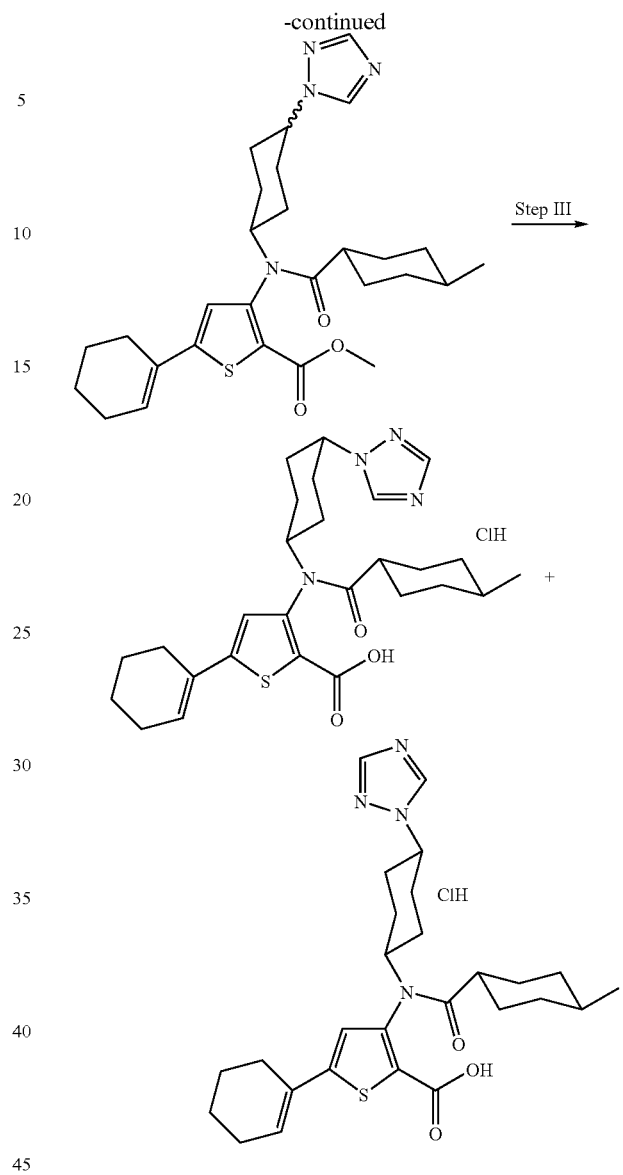

Step I:

A mixture of intermediate 1, 4-[1,2,4]triazol-1-yl-cyclohexanone (257 mg, 1.55 mmol) and 3-Amino-5-cyclohex-1-enyl-thiophene-2-carboxylic acid methyl ester (compound x, see Irina) (368 mg, 1.55 mmol) was treated by dibutyltin dichloride (24 mg, 0.078 mmol). The resulting mixture was stirred 5 min at room temperature and phenylsilane (210 µl, 1.70 mmol) was added. The reaction mixture was stirred at room temperature under nitrogen for 40 h. Solvent was removed and the crude was purified by silica gel column chromatography using a gradient from 50% EtOAc:hexanes to 100% EtOAc as eluent to give 5-cyclohex-1-enyl-3-(4-[1,2,4]triazol-1-yl-cyclohexylamino)-thiophene-2-carboxylic acid methyl ester (555 mg, 92%) as a yellow mixture of cis and trans isomers.

Step II:

5-cyclohex-1-enyl-3-(4-[1,2,4]triazol-1-yl-cyclohexylamino)-thiophene-2-carboxylic acid methyl ester (555 mg, 1.436 mmol) was treated with a 1M solution of trans-4-methylcyclohexanecarbonyl chloride in toluene (2.87 mL, 2.87 mmol). Pyridine (128 µl, 1.58 mmol) was added and the mixture was stirred at reflux overnight under nitrogen. It was cooled to room temperature and dilute with EtOAc. The resulting mixture was washed twice with a saturated aqueous sodium bicarbonate and once with brine, dried over $Na_2SO_4$ and concentrated. The crude was purified by silica gel column chromatography using a gradient from 50% EtOAc:hexanes to 100% EtOAc as eluent to afford 5-cyclohex-1-enyl-3-[(trans-4-methyl-cyclohexanecarbonyl)-(4-[1,2,4]triazol-1-yl-cyclohexyl)-amino]-thiophene-2-carboxylic acid methyl ester (494 mg, 67%) as a yellow mixture of cis and trans isomers.

Step III:

5-cyclohex-1-enyl-3-[(trans-4-methyl-cyclohexanecarbonyl)-(4-[1,2,4]triazol-1-yl-cyclohexyl)-amino]-thiophene-2-carboxylic acid methyl ester (494 mg, 0.967) was saponified as described before (example 3, step VIII). The final compound was purified by HPLC preparative to afford 5-cyclohex-1-enyl-3-[(trans-4-methyl-cyclohexanecarbonyl))-(cis-4-[1,2,4]triazol-1-yl-cyclohexyl)-amino]-thiophene-2-carboxylic acid hydrochloride (92 mg, 18%) and 5-cyclohex-1-enyl-3-[(trans-4-methyl-cyclohexanecarbonyl))-(trans-4-[1,2,4]triazol-1-yl-cyclohexyl)-amino]-thiophene-2-carboxylic acid hydrochloride (141 mg, 26%) both as white solid.

Using essentially the same procedure described above the following compounds can be prepared according to example 45 using intermediate 1, 2, 3, 5, 6 and commercial 1,3-dimethoxyacetone respectively:

5-cyclohex-1-enyl-3-[(trans-4-methyl-cyclohexanecarbonyl))-(cis-4-[1,2,3]triazol-1-yl-cyclohexyl)-amino]-thiophene-2-carboxylic (compound #104), 5-cyclohex-1-enyl-3-[(trans-4-methyl-cyclohexanecarbonyl))-(trans-4-[1,2,3]triazol-1-yl-cyclohexyl)-amino]-thiophene-2-carboxylic (compound #105), 5-cyclohex-1-enyl-3-[cis-(1,3-dimethyl-2-oxo-1,3-diaza-spiro[4.5]dec-8-yl)-(trans-4-methyl-cyclohexanecarbonyl)-amino]-thiophene-2-carboxylic acid (compound #73), 5-cyclohex-1-enyl-3-[trans-(1,3-dimethyl-2-oxo-1,3-diaza-spiro[4.5]dec-8-yl)-(trans-4-methyl-cyclohexanecarbonyl)-amino]-thiophene-2-carboxylic acid (compound #74), 3-[(cis-4-cyano-4-methyl-cyclohexyl)-(trans-4-methyl-cyclohexanecarbonyl)-amino]-5-cyclohex-1-enyl-thiophene-2-carboxylic acid (compound #99), 3-[(trans-4-cyano-4-methyl-cyclohexyl)-(trans-4-methyl-cyclohexanecarbonyl)-amino]-5-cyclohex-1-enyl-thiophene-2-carboxylic acid (compound #106), 3-[bicyclo[3.2.1]oct-3-yl-(trans-4-methyl-cyclohexanecarbonyl)-amino]-5-cyclohexe-1-enyl-thiophene-2-carboxylic acid (compound #40) and 5-cyclohex-1-enyl-3-[(2-methoxy-1-methoxymethyl-ethyl)-(trans-4-methyl-cyclohexanecarbonyl)-amino]-thiophene-2-carboxylic acid (compound #111)

EXAMPLE 46

Preparation of 5-cyclohex-1-enyl-3-[(trans-4-methyl-cyclohexanecarbonyl))-cis-(3-oxo-2-aza-spiro[4.5]dec-8-yl)-amino]-thiophene-2-carboxylic (compound #80) and 5-cyclohex-1-enyl-3-[(trans-4-methyl-cyclohexanecarbonyl))-trans-(3-oxo-2-aza-spiro[4.5]dec-8-yl)-amino]-thiophene-2-carboxylic (compound #81)

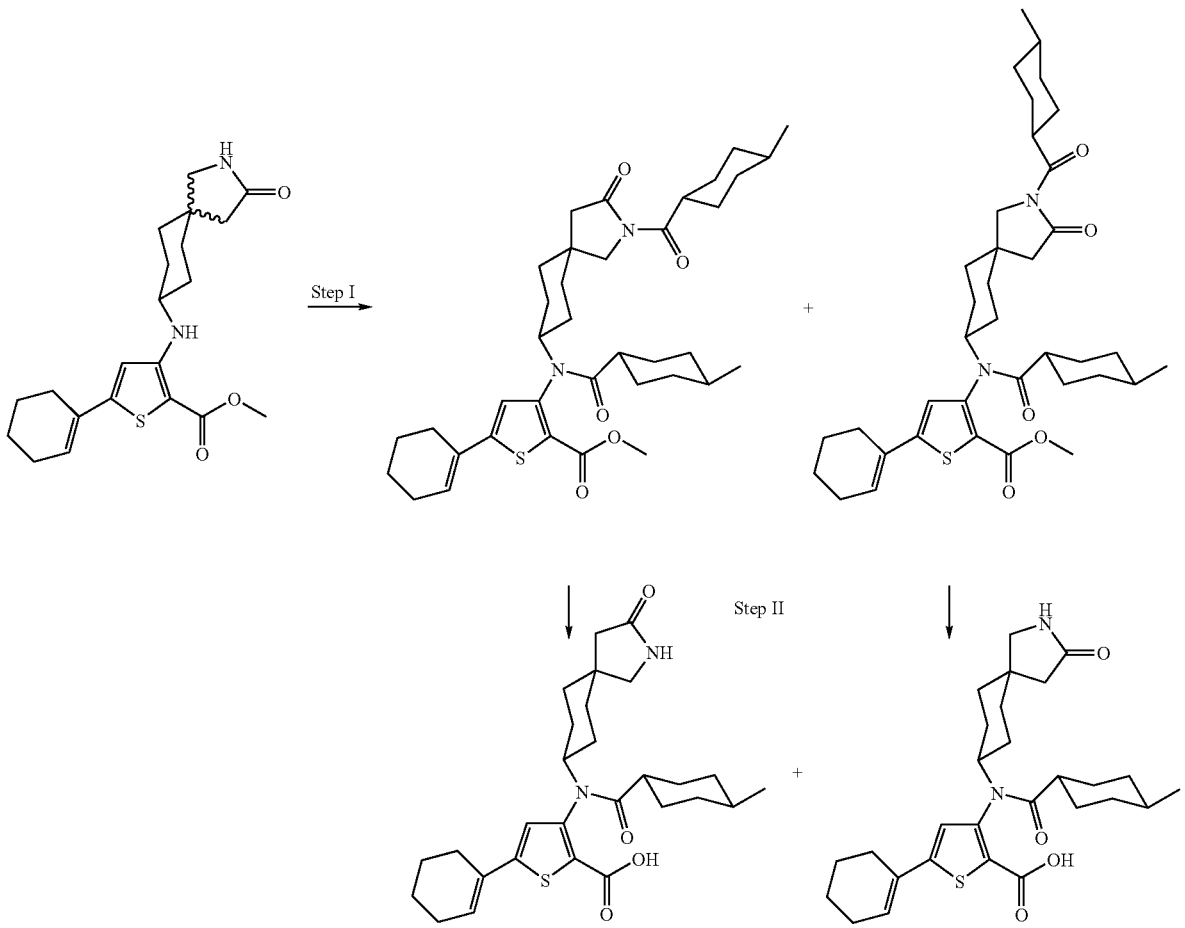

Step I:

A mixture of cis and trans 5-Cyclohex-1-enyl-3-(3-oxo-2-aza-spiro[4.5]dec-8-ylamino)-thiophene-2-carboxylic acid methyl ester (1.08 g, 2.78 mmol), prepared with intermediate 4 was treated with a 1M solution of trans-4-methylcyclohexanecarbonyl chloride in toluene (5.56 mL, 5.56 mmol). Pyridine (248 µL, 3.06 mmol) was added and the mixture was stirred at reflux overnight under nitrogen. It was cooled to room temperature and dilute with EtOAc. The resulting mixture was washed twice with a saturated aqueous sodium bicarbonate and once with brine, dried over $Na_2SO_4$ and concentrated. The crude was purified by silica gel column chromatography using a gradient from 15% EtOAc:hexanes to 30% EtOAc:hexanes as eluent, to afford 5-cyclohex-1-enyl-3-{(trans-4-methyl-cyclohexanecarbonyl)-[2-(trans-4-methyl-cyclohexanecarbonyl)-cis-3-oxo-2-aza-spiro[4.5]dec-8-yl]-amino}-thiophene-2-carboxylic acid methyl ester (543 mg, 31%) and 5-cyclohex-1-enyl-3-{(trans-4-methyl-cyclohexanecarbonyl)-[2-(trans-4-methyl-cyclohexanecarbonyl)-trans-3-oxo-2-aza-spiro[4.5]dec-8-yl]-amino}-thiophene-2-carboxylic acid methyl ester (319 mg, 18%)

Step II:

Each separate isomer from step I were submitted to the standard saponification conditions (example 3, step VIII) to afford both title compounds.

EXAMPLE 47

Preparation of 5-cyclohex-1-enyl-3-[(trans-4-methyl-cyclohexanecarbonyl))-cis-(2-methyl-3-oxo-2-aza-spiro[4.5]dec-8-yl)-amino]-thiophene-2-carboxylic (compound #84)

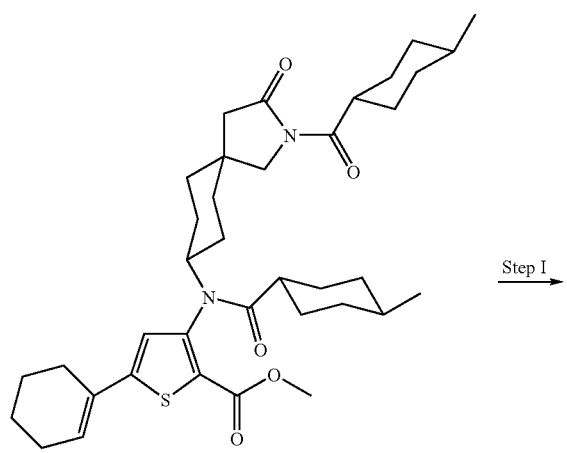

Step I

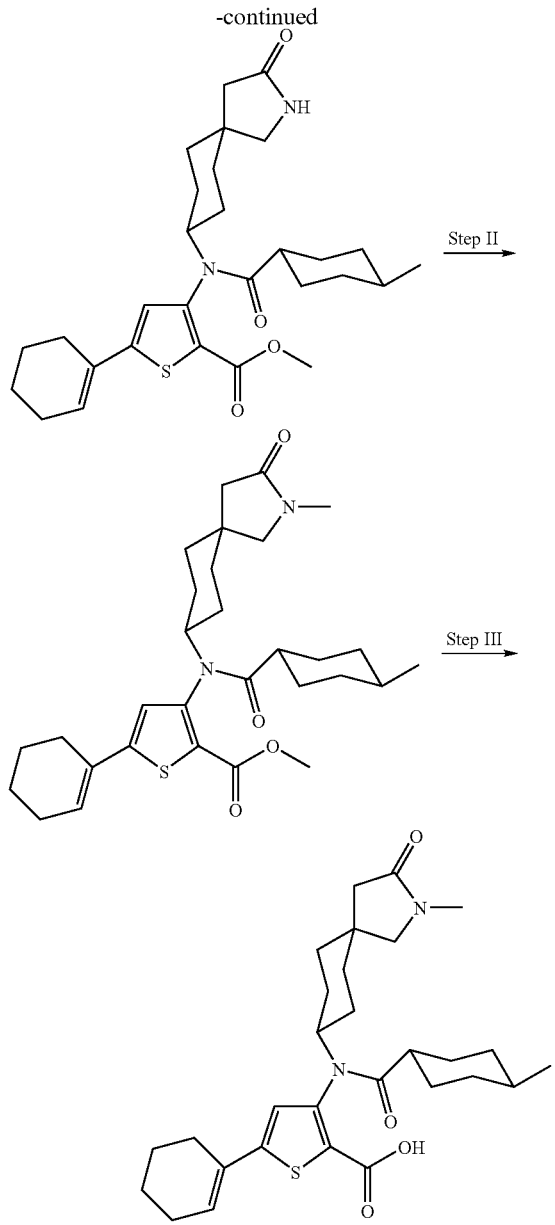

Step 1:

A solution of 5-cyclohex-1-enyl 3-{(trans-4-methyl-cyclohexanecarbonyl)-[2-(trans-4-methyl-cyclohexanecarbonyl)-cis-3-oxo-2-aza-spiro[4.5]dec-8-yl]-amino}-thiophene-2-carboxylic acid methyl ester (445 mg, 0.699 mmol) in 4 mL of methanol anhydrous was treated by a solution of sodium methoxide 25% in methanol (151 µl, 0.669 mmol). The resulting mixture was stirred under nitrogen at room temperature for 2 h. Solvent was removed under vacuum. A portion of 30 mL of dichloromethane was added. It was washed with 20 mL of 1N solution of aqueous HCl, dried over $Na_2SO_4$ and concentrated. The crude was purified by silica gel column chromatography using 100% EtOAc as eluent to afford 5-cyclohex-1-enyl-3-[(trans-4-methyl-cyclohexanecarbonyl)-cis-(3-oxo-2-aza-spiro[4.5]dec-8-yl)-amino]-thiophene-2-carboxylic acid methyl ester (150 mg, 42%) as a pale yellow solid.

Step II:

A solution of 5-cyclohex-1-enyl-3-[(trans-4-methyl-cyclohexanecarbonyl)-cis-(3-oxo-2-aza-spiro[4.5]dec-8-yl)-amino]-thiophene-2-carboxylic acid methyl ester (145 mg, 0.283 mmol) in 2.5 mL of dry DMF was treated with sodium hydride 60% (34 mg, 0.85 mmol). The mixture was stirred at room temperature for 20 min after witch iodomethane (53 μL, 0.85 mmol) was added. The reaction mixture was stirred overnight. Water was added and it was acidified using 1 N HCl aqueous. Then, it was extracted with EtOAc. The organic portion was washed with brine, dried over $Na_2SO_4$ and concentrated to afford crude 5-cyclohex-1-enyl-3-[(4-methyl-cyclohexanecarbonyl)-(2-methyl-3-oxo-2-aza-spiro[4.5]dec-8-yl)-amino]-thiophene-2-carboxylic acid methyl ester.

Step III:

The crude material obtained in step II was diluted in 6 mL of a 3:2:1 solution of THF, methanol, water. It was treated by lithium hydroxide monohydrate (48 mg, 1.1 mmol). The resulting mixture was stirred 3 h at 50° C. It was then acidified with 1N HCl aqueous, concentrated and purified by HPLC preparative to afford 5-cyclohex-1-enyl-3-[(trans-4-methyl-cyclohexanecarbonyl))-cis-(2-methyl-3-oxo-2-aza-spiro[4.5]dec-8-yl)-amino]-thiophene-2-carboxylic (24 mg, 16%) as a white solid.

Using essentially the same procedure described above the following compounds can be prepared:
5-cyclohex-1-enyl-3-[(trans-4-methyl-cyclohexanecarbonyl))-trans-(2-methyl-3-oxo-2-aza-spiro[4.5]dec-8-yl)-amino]-thiophene-2-carboxylic (compound #128),
5-cyclohex-1-enyl-3-[cis-(2-ethyl-3-oxo-2-aza-spiro[4.5]dec-8-yl)-(trans-4-methyl-cyclohexanecarbonyl)-amino]-thiophene-2-carboxylic acid (compound #130)
5-cyclohex-1-enyl-3-[trans-(2-ethyl-3-oxo-2-aza-spiro[4.5]dec-8-yl)-(trans-4-methyl-cyclohexanecarbonyl)-amino]-thiophene-2-carboxylic acid (compound #129).

EXAMPLE 48

Preparation of 3-[(cis-4-cyanocyclohexyl)-(trans-4-methyl-cyclohexanecarbonyl)-amino]-5-cyclohex-1-enyl-thiophene-2-carboxylic (compound #49) and 3-[(trans-4-cyanocyclohexyl)-(trans-4-methyl-cyclohexanecarbonyl)-amino]-5-cyclohex-1-enyl-thiophene-2-carboxylic (compound #50)

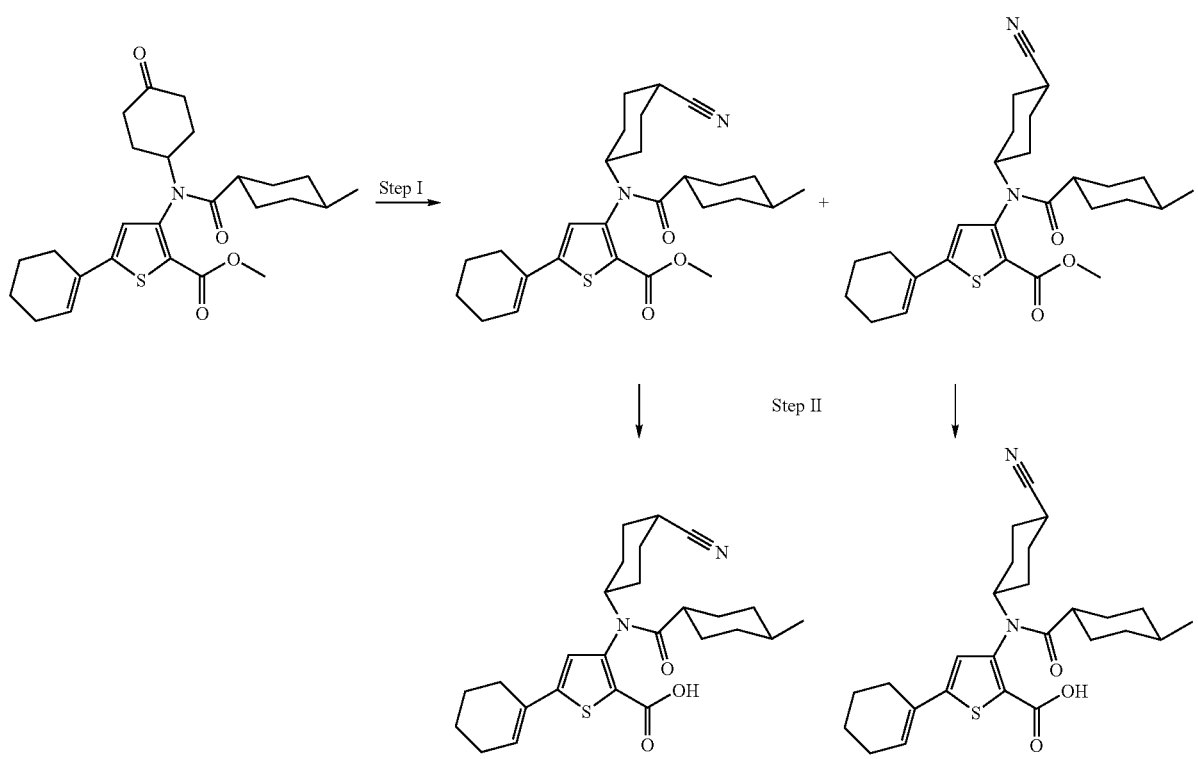

Step 1:

5-Cyclohex-1-enyl-3-[(trans-4-methyl-cyclohexanecarbonyl)-(4-oxo-cyclohexyl)-amino]-thiophene-2-carboxylic acid methyl ester (1.00 g, 2.25) was submitted to the same procedure as for intermediate 1 step I. The final mixture obtained was purified by silica gel column chromatography using 30% EtOAc:hexanes as eluent to afford 3-[(cis-4-cyano-cyclohexyl)-(trans-4-methyl-cyclohexanecarbonyl)-amino]-5-cyclohex-1-enyl-thiophene-2-carboxylic acid methyl ester (256 mg, 25%) and 3-[(trans-4-cyano-cyclohexyl)-(trans-4-methyl-cyclohexanecarbonyl)-amino]-5-cyclohex-1-enyl-thiophene-2-carboxylic acid methyl ester (352 mg, 34%).

Step II:

Each separate isomer from step I were submitted to the standard saponification conditions (example 3, step VIII) to afford both title compounds.

EXAMPLE 49

Preparation of 5-cyclohex-1-enyl-3-{(trans-4-methyl-cyclohexanecarbonyl)-[trans-4-(1H-tetrazol-5-yl)-cyclohexyl]-amino}-thiophene-2-carboxylic (compound #62)

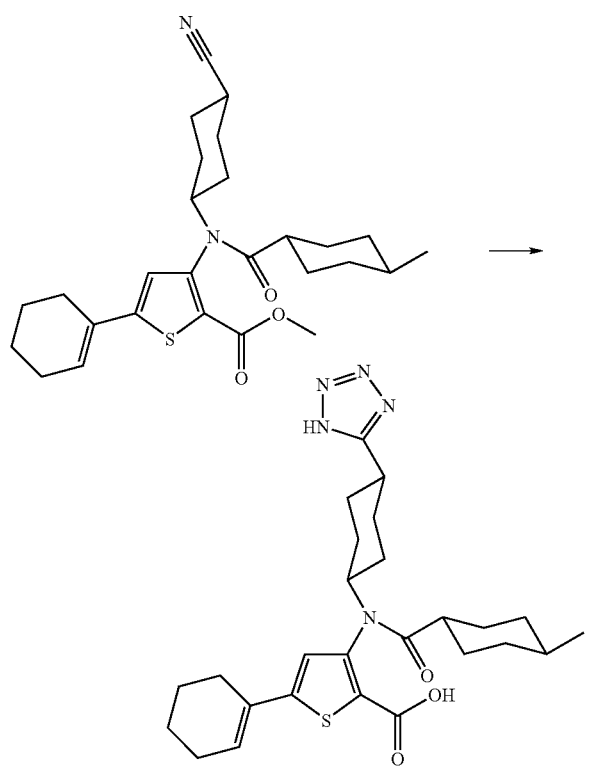

A mixture of 3-[(trans-4-cyano-cyclohexyl)-(trans-4-methyl-cyclohexanecarbonyl)-amino]-5-cyclohex-1-enyl-thiophene-2-carboxylic acid methyl ester (100 mg, 0.220 mmol), ammonium chloride (74 mg, 1.4 mmol) and sodium azide (91 mg, 1.4 mmol) in 2.0 mL of dry DMF was stirred at 150° C. under nitrogen for two days. Water was added and it was extracted with EtOAc. The organic portion was dried over $Na_2SO_4$ and concentrated. The crude was purified by HPLC to afford the title compound (9.0 mg, 8.2%).

EXAMPLE 50

Preparation of 5-cyclohex-1-enyl-3-[(cis-4-isobutyrylamino-cyclohexyl)-(trans-4-(methyl-cyclohexanecarbonyl)-amino]-thiophene-2-carboxylic (compound #133) and 5-cyclohex-1-enyl-3-[(trans-4-isobutyrylamino-cyclohexyl)-(trans-4-(methyl-cyclohexanecarbonyl)-amino]-thiophene-2-carboxylic (compound #134)

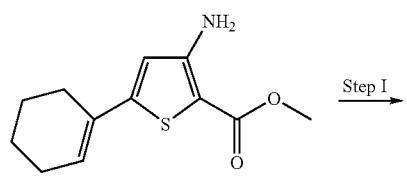

-continued

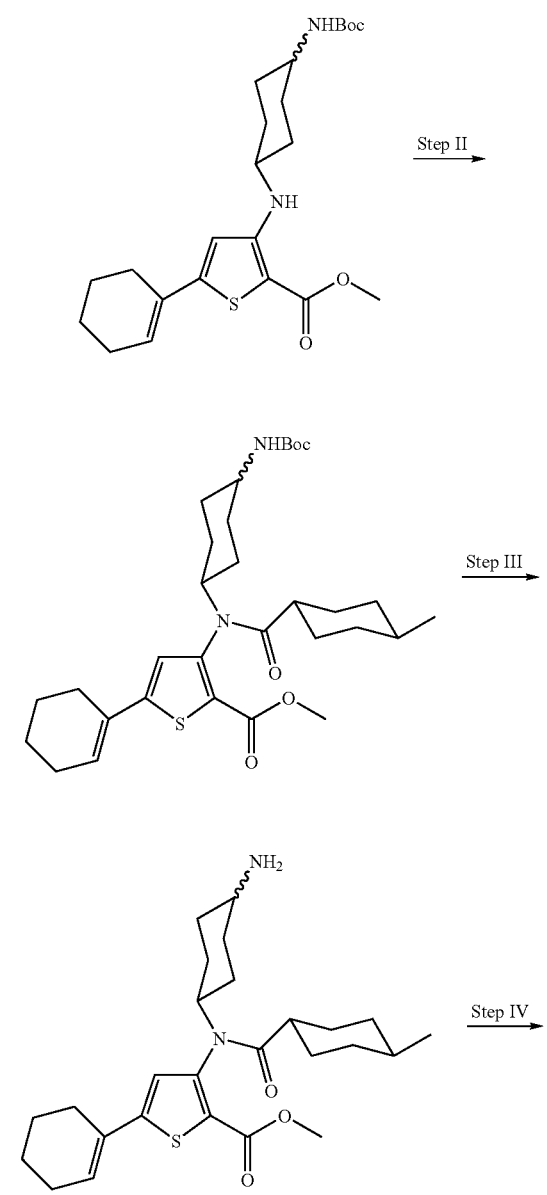

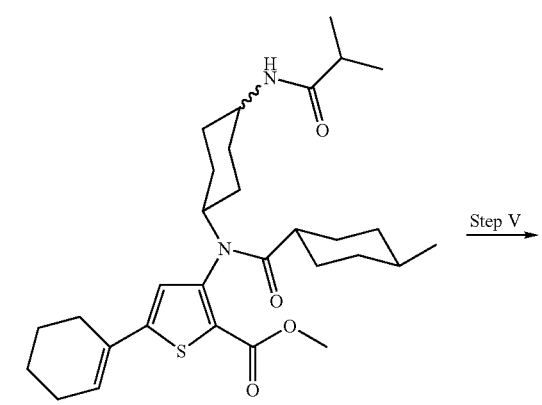

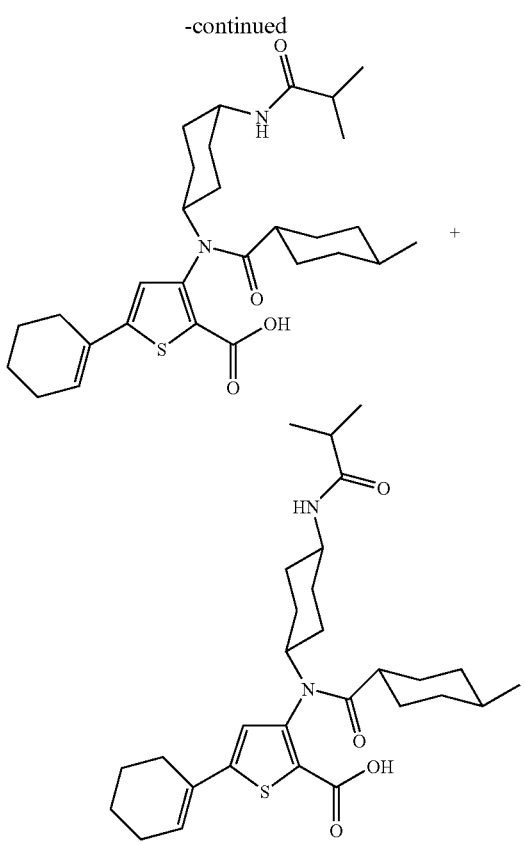

Step I and step II were performed as described before (example 1, step I and II) using N-4-Boc-aminocyclohexanone as intermediate Step III:

To a solution of cis and trans 3-[(4-tert-Butoxycarbonylamino-cyclohexyl)-(trans-4-methyl-cyclohexanecarbonyl)-amino]-5-cyclohex-1-enyl-thiophene-2-carboxylic acid methyl ester (2.21 g, 3.95 mmol) in 17 mL of dichloromethane was added 17 mL of trifluoroacetic acid. The mixture was stirred at room temperature for 15 h. Solvent and trifluoroacetic acid were removed in vacuo. The crude was diluted with ether. It was washed with a 1N NaOH aqueous solution and with brine, dried over $Na_2SO_4$ and concentrated to afford a crude mixture of cis and trans 3-[(4-amino-cyclohexyl)-(trans-4-methyl-cyclohexanecarbonyl)-amino]-5-cyclohex-1-enyl-thiophene-2-carboxylic acid methyl ester (1.62 g, 3.51 mmol) as a brown yellow solid.

Step IV:

A solution of cis and trans 3-[(4-amino-cyclohexyl)-(trans-4-methyl-cyclohexanecarbonyl)-amino]-5-cyclohex-1-enyl-thiophene-2-carboxylic acid methyl ester (100 mg, 0.218 mmol) and triethylamine (46 μl, 0.33 mmol) in 1 mL of dichloromethane was treated with isobutyryl chloride (30 μl, 0.28 mmol). The mixture was stirred overnight at room temperature under nitrogen. Solvent was removed. EtOAc was added. It was washed twice with water and once with brine, dried over $Na_2SO_4$ and concentrated to give a crude mixture of cis and trans 5-cyclohex-1-enyl-3-[(4-isobutyrylamino-cyclohexyl)-(trans-4-methyl-cyclohexanecarbonyl)-amino]-thiophene-2-carboxylic acid methyl ester.

Step V:

The crude material obtained in step IV was diluted in 4.3 mL of a 3:2:1 solution of THF, methanol, water. It was treated by lithium hydroxide monohydrate (37 mg, 0.87 mmol). The resulting mixture was stirred 24 h at room temperature. It was then acidified with 10% HCl aqueous solution, concentrated and purified by HPLC preparative to afford 5-cyclohex-1-enyl-3-[(cis-4-isobutyrylamino-cyclohexyl)-(trans-4-(methyl-cyclohexanecarbonyl)-amino]-thiophene-2-carboxylic (7.6 mg, 6.7%) and 5-cyclohex-1-enyl-3-[(trans-4-isobutyrylamino-cyclohexyl)-(trans-4-(methyl-cyclohexanecarbonyl)-amino]-thiophene-2-carboxylic (26.3 mg, 23%) both as white solid.

Preparation of Intermediates 1 to 8

Intermediate 1: 4-[1,2,4]triazol-1-yl-cyclohexanone

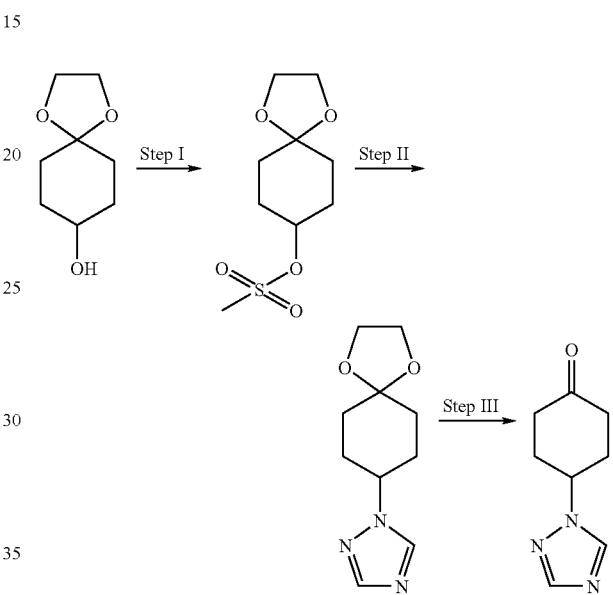

Step I:

Methanesulfonic acid 1,4-dioxa-spiro[4.5]dec-8-yl ester was prepared according to: Cheng, Chen Yu; Wu, Shou Chien; Hsin, Ling Wei; Tam, S. William. *Coll. Med., Natl.* Taiwan Univ., Taipei, Taiwan. *Journal of Medicinal Chemistry* (1992), 35(12), 2243-7.

Step II:

A solution of methanesulfonic acid 1,4-dioxa-spiro[4.5]dec-8-yl ester (567 mg, 2.40 mmol) and 1,2,4-triazole (232 mg, 3.36 mmol) in dry DMF (5.00 mL) was treated with sodium hydride 60% (125 mg, 3.12 mmol) at room temperature under nitrogen. The resulting mixture was stirred at 65° C. for 72 h. It was poured in ice water (75 mL), extracted 3 portions of 75 mL of EtOAc. The organic portions were combined, dried over anhydrous $Na_2SO_4$ and concentrated. The solid was purified by silica gel column chromatography using a gradient from 100% EtOAc to 5% MeOH:EtOAc as eluent to furnished the final compound 1-(1,4-dioxa-spiro[4.5]dec-8-yl)-1H-[1,2,4]triazole as a white solid (247 mg, 49%).

Step III:

1-(1,4-dioxa-spiro[4.5]dec-8-yl)-1H-[1,2,4]triazole (379 mg, 1.81 mmol) was dissolved in a 1:1 mixture of THF and 3N HCl aqueous solution (9 mL). The resulting mixture was stirred at 40° C. for 5 h. Most of the THF was removed under vacuum then the remaining mixture was neutralized using a 3N NaOH aqueous solution until a basic pH was reached. It was extracted with 3 portions of 10 mL of dichloromethane. The organic portions were combined, dried over anhydrous Na₂SO₄ and concentrated to afford 4-[1,2,4]triazol-1-yl-cyclohexanone as a white waxy solid (257 mg, 86%).

Intermediate 2: 4-[1,2,3]triazol-1-yl-cyclohexanone

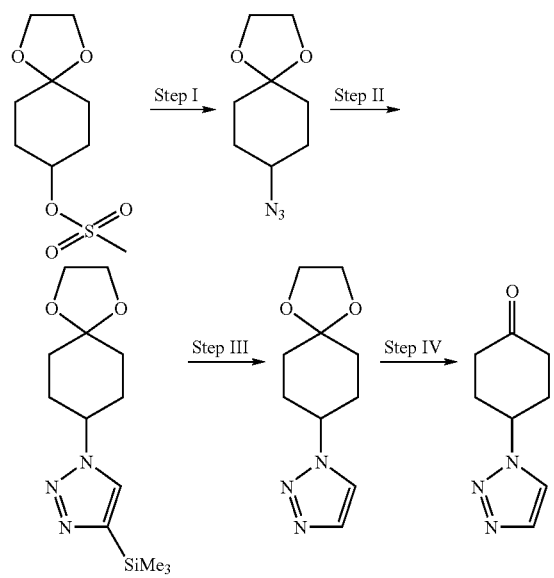

Step I:

A mixture of methanesulfonic acid 1,4-dioxa-spiro[4.5]dec-8-yl ester (2.80 g, 11.9 mmol) and sodium azide (3.86 g, 59.3 mmol) in 50 mL of dry DMF was stirred for 20 h at 100° C. under nitrogen. The final mixture was cooled to room temperature dilute with brine and extracted with three portions of ether. The organic portions were combined, dried over Na₂SO₄ and concentrated to give 8-azido-1,4-dioxa-spiro[4.5]decane (2.2 g, 100%).

Step II:

A mixture of 8-Azido-1,4-dioxa-spiro[4.5]decane (1.00 g, 5.43 mmol) and 1-(trimethylsilyl)propyne (3.76 mL, 27.1 mmol) was submitted to microwave at 120° C. for 2 h. The mixture was concentrated under vacuum to remove the excess of 1-(trimethylsilyl)propyne and crude 1-(1,4-dioxa-spiro[4.5]dec-8-yl)-4-trimethylsilanyl-1H-[1,2,3]triazole (1.6 g, 105%) was obtained.

Step III:

A solution of 1-(1,4-dioxa-spiro[4.5]dec-8-yl)-4-trimethylsilanyl-1H-[1,2,3]-triazole (1.60 g, 5.68) in 41 mL of dry THF was treated by a 1M solution of tetrabutylammonium fluoride in THF (9.0 mL, 9.0 mmol). The resulting mixture was stirred for 48 h at room temperature under nitrogen. It was diluted with EtOAc, washed with saturated aqueous ammonium chloride, water and brine, dried over Na₂SO₄ and concentrated to give 1-(1,4-dioxa-spiro[4.5]dec-8-yl)-1H-[1,2,3]triazole (1.06 g, 89%).

Step IV:

1-(1,4-dioxa-spiro[4.5]dec-8-yl)-1H-[1,2,3]triazole (1.06 g, 5.06 mmol) was submitted to the same procedure as for intermediate 1 step III to afford 4-[1,2,3]triazol-1-yl-cyclohexanone (479 mg, 57%) as a white solid.

Intermediate 3: 9,12-dioxa-1,3-diaza-dispiro[4.2.4.2]tetradecane-2,4-dione

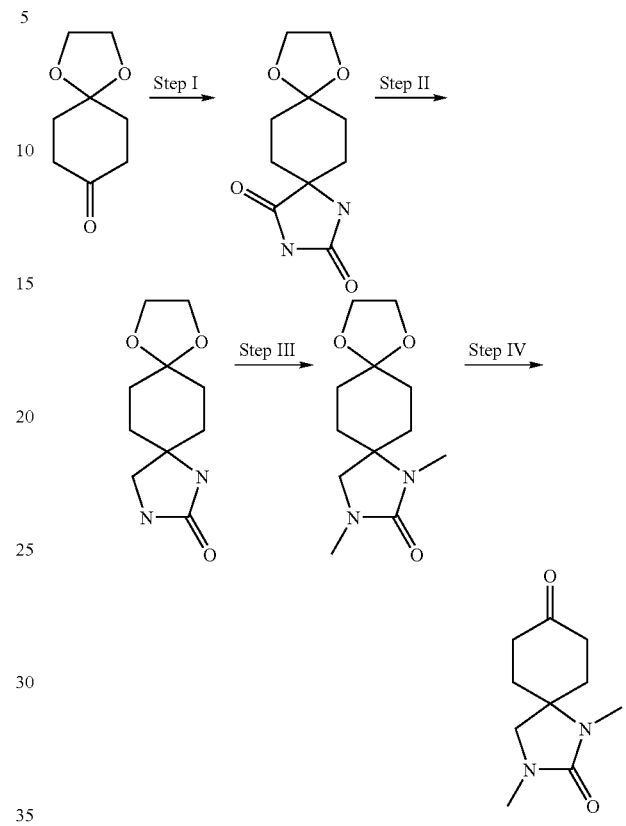

Step I:

A suspension of 1,4-dioxa-spiro[4.5]decan-8-one (10.0 g, 64.0 mmol) in 64 mL of methanol was treated with a solution of ammonium carbonate (18.4 g, 192 mmol) in 64 mL of water. Potassium cyanide (6.14 g, 96.0 mmol) was added and the mixture was stirred at 65° C. for 18 h. It was cooled to room temperature and a precipitate was formed. The precipitate was collected by filtration to give a white solid and the filtrate was extracted with ethyl acetate. The portion of ethyl acetate was concentrated to afford also a white solid. Both solids were combined to afford 9,12-dioxa-1,3-diaza-dispiro[4.2.4.2]tetradecane-2,4-dione (9.80 g g, 68%)

Step II:

A suspension of 9,12-dioxa-1,3-diaza-dispiro[4.2.4.2]tetradecane-2,4-dione (9.64 g, 42.6 mmol) in 143 mL of dry THF was treated at 0° C. with a solution of LiAlH₄ 1M in THF (94.0 mL, 94.0 mmol). The resulting mixture was stirred overnight at room temperature under nitrogen. An aqueous saturated solution of Rochelle's salt was added. It was stirred for 3 h, extracted 4× with EtOAc and 3× with dichloromethane. Organic portions were combined and concentrated. The crude was purified by silica gel column chromatography using a gradient from 1% CH₂Cl₂:MeOH to 10% CH₂Cl₂:MeOH as eluent to afford 9,12-Dioxa-1,3-diaza-dispiro[4.2.4.2]tetradecan-2-one (5.20 g, 57%) as a white solid.

Step III:

A solution of 9,12-dioxa-1,3-diaza-dispiro[4.2.4.2]tetradecan-2-one (4.70 g, 22.1 mmol) in 110 mL of dioxane was treated with sodium hydride 60% (2.92 g, 73.0 mmol) at room temperature. The mixture was heated at 55° C. and stirred for 4 h under nitrogen. Methyl iodide (8.20 mL, 132 mmol) was added and the resulting mixture was stirred overnight at reflux. The reaction was quenched with water. It was extracted with five portions of ether and two portions of dichloromethane. The organic portions were combined and concentrated. The crude was purified by silica gel column chromatography using a gradient from 10% EtOAc:hexanes to 100% EtOAc as eluent to give 1,3-dimethyl-9,12-dioxa-1,3-diaza-dispiro[4.2.4.2]tetradecan-2-one (3.1 g, 58%).

Step IV:

1,3-Dimethyl-9,12-dioxa-1,3-diaza-dispiro[4.2.4.2]tetradecan-2-one (3.16 g, 13.2 mmol) was dissolved in 66 mL of THF and a portion of 130 mL of 3N HCl aqueous solution was added. The resulting mixture was stirred at 50° C. for two days. THF was removed under vacuum then the remaining mixture was extracted with two portions of dichloromethane. The organic portions were combined, dried over anhydrous Na$_2$SO$_4$ and concentrated. The crude was purified by silica gel column chromatography using a gradient from 2% CH$_2$Cl$_2$:MeOH to 10% CH$_2$Cl$_2$:MeOH as eluent to afford 1,3-dimethyl-1,3-diaza-spiro[4.5]decane-2,8-dione (1.7 g, 66%).

Intermediate 4: 2-aza-spiro[4.5]decane-3,8-dione

Intermediate 4 was prepared following a synthetic pathway described for different similar substate in: *Przewosny, Michael Thomas; Puetz, Claudia* US2005043565.

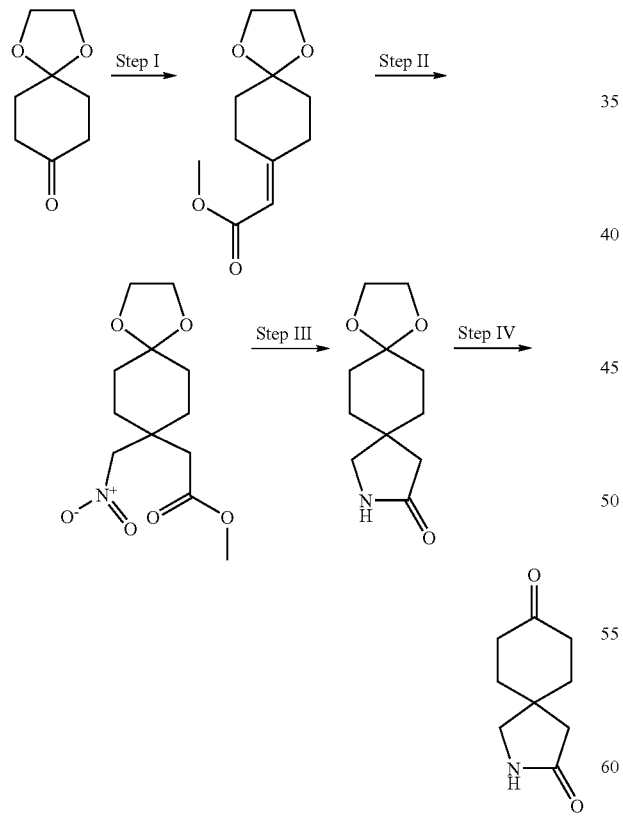

Step I:

A solution of 1,4-dioxa-spiro[4.5]decan-8-one (5.00 g, 32.0 mmol) in 65 mL of anhydrous toluene was treated with methyl(triphenylphosphoranylidene)acetate (13.9 g, 41.6 mmol). The mixture was stirred at reflux for 18 h under nitrogen. Solvent was removed and the crude was purified by silica gel column chromatography using a 20% EtOAc:hexanes mixture as eluent to afford (1,4-dioxa-spiro[4.5]dec-8-ylidene)-acetic acid methyl ester (5.51 g, 81%) as a colorless oil.

Step II:

A solution of (1,4-dioxa-spiro[4.5]dec-8-ylidene)-acetic acid methyl ester (5.50 g, 25.9 mmol) in 14 mL of dry THF was treated by nitromethane (2.10 mL, 38.9 mmol) followed by a 1M solution of tetrabutylammonium fluoride in THF (26.5 mL, 26.5 mmol). The resulting mixture was stirred at reflux for 20 h under nitrogen. After cooling, the mixture was diluted with water and extracted with three portions of ether. The etheral portions were combined, washed with a 10% aqueous solution of potassium hydrogensulfate, dried over anhydrous Na$_2$SO$_4$ and concentrated. The crude was purified by silica gel column chromatography using a 20% EtOAc:hexanes mixture as eluent to afford (8-Nitromethyl-1,4-dioxa-spiro[4.5]dec-8-yl)-acetic acid methyl ester (5.34 g, 75%) as a colorless oil.

Step III:

A solution of (8-nitromethyl-1,4-dioxa-spiro[4.5]dec-8-yl)-acetic acid methyl ester (5.34 g, 19.5 mmol) in 35 mL of methanol was purged with nitrogen. A portion of about 430 mg of Raney 2800 nickel was added. The reaction mixture was purged with hydrogen and a positive pressure of hydrogen was maintained overnight using a balloon. Then, the final mixture was purged with nitrogen and filtered through a pad of celite washing with methanol. The filtrate was concentrated to afford 1,4-dioxa-10-aza-dispiro[4.2.4.2]tetradecan-11-one (3.95 g, 96%) as a white solid.

Step IV:

To a solution of 1,4-dioxa-10-aza-dispiro[4.2.4.2]tetradecan-11-one (3.95 g, 18.7 mmol) in 160 mL of acetone was added 16 mL of water and pyridinium p-toluenesulfonate (1.41 g, 5.61 mmol). The resulting mixture was stirred at reflux for 20 h. Then, it was cooled and concentrated. The crude was purified by silica gel column chromatography using a 5% MeOH:EtOAc mixture as eluent to afford 2-aza-spiro[4.5]decane-3,8-dione (1.80 g, 58%) as a white solid.

Intermediates 5:
8-methyl-1,4-dioxa-spiro[4.5]decane-8-carbonitrile

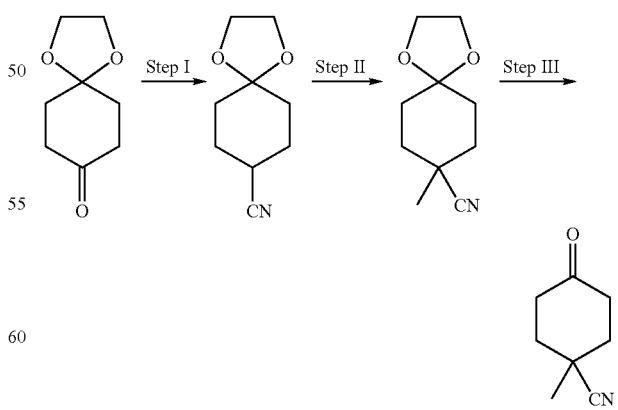

Step I:

1,4-Dioxa-spiro[4.5]decane-8-carbonitrile was prepared according to: Becker, Daniel P.; Flynn, Daniel L. *Gas-* trointest. Dis. Res. Dep., Searle Res. Dev., Skokie, Ill., USA. Synthesis (1992), (11), 1080-2.

Step II:

A 1.6M solution of Butyllithium in THF (14.6 mL, 23.3 mmol) was slowly added over 10 min to a solution of diisopropylamine (3.54 mL, 25.15 mmol) in 11 mL of anhydrous THF at −40° C. under nitrogen. The resulting mixture was stirred for 30 min at −40° C. and the solution of lithium diisopropylamide obtained was transferred dropwise over 15 min to a 0° C. solution of 1,4-Dioxa-spiro[4.5]decane-8-carbonitrile (3.00 g, 17.9 mmol) in 25 of anhydrous THF. The reaction mixture was stirred 15 min at 0° C. and methyl iodide (3.35 mL, 53.8 mmol) was added dropwise over 15 min. The resulting mixture was stirred 30 min at 0° C. then, 30 min at room temperature. A portion of 20 mL of saturated aqueous ammonium chloride was added. It was extracted with ether (3×150 mL). The organic portions were combined, dried over anhydrous $Na_2SO_4$ and concentrated. Drying under vacuum for 30 min afforded the desired 8-methyl-1,4-ioxa-spiro[4.5]decane-8-carbonitrile as a yellow solid (3.29 g, 101%).

Step III:

8-methyl-1,4-dioxa-spiro[4.5]decane-8-carbonitrile (3.29 g, 18.1 mmol) was dissolved in a 1:1 mixture of THF and 3N HCl aqueous solution (60 mL). The resulting mixture was stirred at 40° C. for 5 h, cooled to 0° C. and neutralized using about 30 mL of a 3N NaOH aqueous solution until a basic pH was reached. It was extracted with ether (4×75 mL). The organic portions were combined, dried over anhydrous $Na_2SO_4$ and concentrated. The crude was purified by silica gel column chromatography using a gradient from 15% EtOAc:hexanes to 20% EtOAc:hexanes as eluent to afford 1-Methyl-4-oxo-cyclohexanecarbonitrile as a white solid (1.82 g, 73%).

Intermediate 6: 4-[1,2,4]triazol-1-yl-cyclohexanone

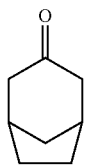

Prepared as described in: Jefford, C. W.; Gunsher, J.; Hill, D. T.; Brun, P.; Le Gras, J.; Waegell, B. *Chem. Dep.*, Temple Univ., Philadelphia, Pa., USA. *Organic Syntheses* (1971), 51 60-5.

Intermediate 7

3-Amino-5-cyclohex-1-enyl-thiophene-2-carboxylic acid methyl ester

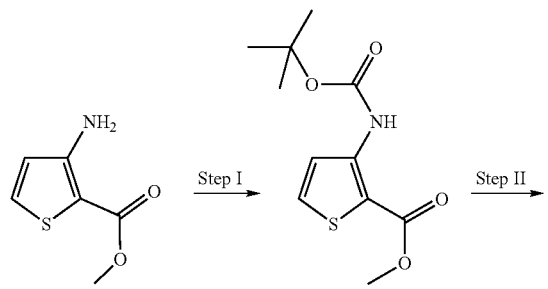

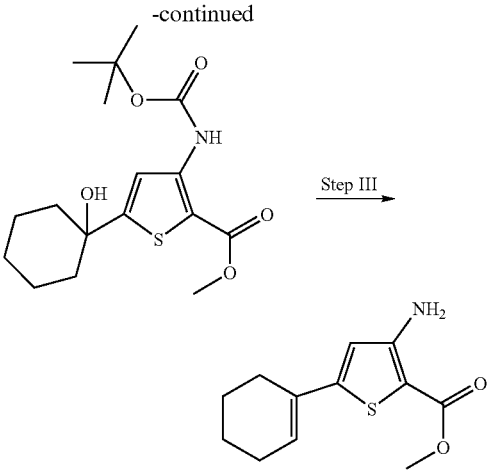

Step I:

In a 3 L 3 neck flask with a mechanical stirrer, DMAP (11.5 g, 0.10 mmol) was added to a solution of 3-amino-thiophene-2-carboxylic acid methyl ester (105 g, 0.95 mmol) and in pyridine (750 mL). A solution of $(BOC)_2O$ (222 g, 1.02 mol) in pyridine (750 mL) was slowly added to the previous solution while the temperature was kept between 20 and 25° C. The mixture was stirred under nitrogen for 20 h. The reaction mixture was evaporated to dryness then triturated in 500 mL of MeOH at rt for 3 h then 30 min at 0° C. The suspension was filtered on a buchner funnel and washed with cold ethanol. The white solid was dried to afford 175 g (70%) of 3-tert-Butoxycarbonylamino-thiophene-2-carboxylic acid methyl ester.

Step II:

Diisopropylamine (140 g, 1.39 mol) and 800 mL dry THF were added to a dry 12 L 4 neck flask with a mechanical stirrer under nitrogen. The solution was cooled to −40° C. and n-BuLi (1.29 mol) was added slowly while keeping the inside temperature around −40° C. The mixture was stirred for 45 min at −40° C. and then cooled to −78° C. To this solution, a solution of 3-tert-butoxycarbonylamino-thiophene-2-carboxylic acid methyl ester (99 g, 0.384 mmol) in 3.2 L THF was added drop wise. The mixture was stirred for 60 min at −78° C. and then cyclohexanone (118 g, 1.19 mmol) was added in 30 seconds. The mixture was stirred for 30 min at −78° C. The reaction mixture was quenched with 0.75 L of $NH_4Cl$ (sat). The aqueous phase was extract with 0.75 L of EtOAc. Combined the organic phase and washed them with 5 L of brine, Dried over $Na_2SO_4$, filtered and evaporated to a residue to afford 115 g (84%) of 3-tert-Butoxycarbonylamino-5-(1-hydroxy-cyclohexyl)-thiophene-2-carboxylic acid methyl ester.

Step III:

To a solution of 3-tert-butoxycarbonylamino-5-(1-hydroxy-cyclohexyl)-thiophene-2-carboxylic acid methyl ester (68 g, 0.192 mol) in 400 mL of dichloromethane at 0° C. (ice bath) was added trifluoroacetic acid (400 mL). The mixture was stirred for 30 min at 0° C. and followed by TLC. After completion, the reaction mixture was evaporated to dryness and partitioned between ethyl acetate and saturated water solution of $NaHCO_3$. The organic layer was separated, dried ($Na_2SO_4$) and concentrated. The residue was triturated in 4.4 volume of hexane for 30 min. Then filtered and washed with cold hexane. Dried in the vacuum oven to afford 35 g (76%) of 3-Amino-5-cyclohex-1-enyl-thiophene-2-carboxylic acid methyl ester.

Intermediate 8

3-Amino-5-bromo-thiophene-2-carboxylic acid methyl ester

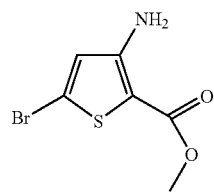

Intermediate 8 was prepared following the same procedure mentioned for intermediate 7.

General Schemes for the Production of Compounds in Accordance with this Invention In provisional application U.S. Ser. No. 60/680,482 it is stated that Compound# 16 and Compound#19 (which were both incorrectly numbered and are renumbered as Compounds 146 and 149 respectively) can be prepared according to the following Scheme A. Applicant wishes to point that Compound #146 was obtained using the synthetic scheme depicted in Example 43.

SCHEME A

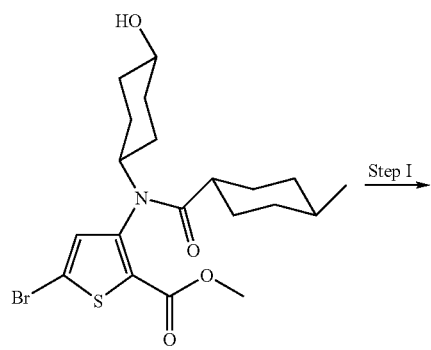

Step I

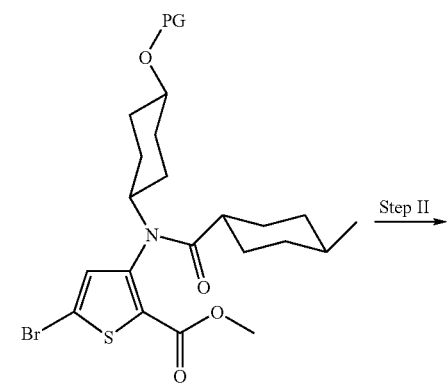

Step II

-continued

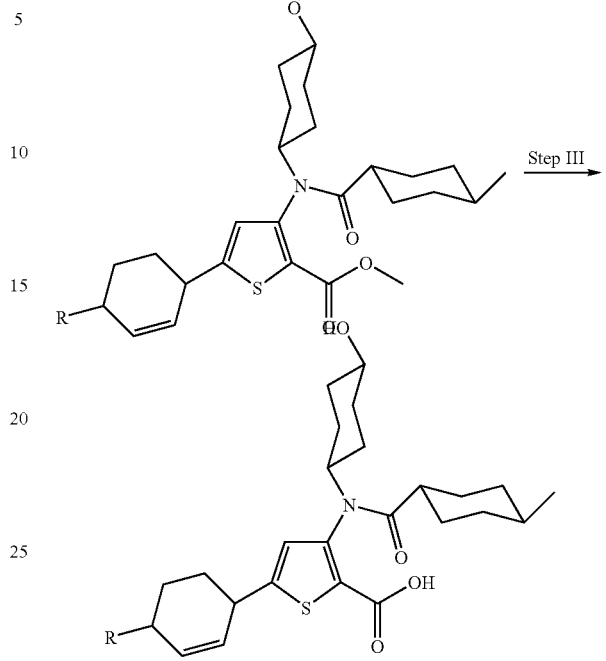

Step III

PG = Protecting group
R = H or Me

For example, compounds such as 149 and 150 can be prepared according to the following Scheme B:

SCHEME B

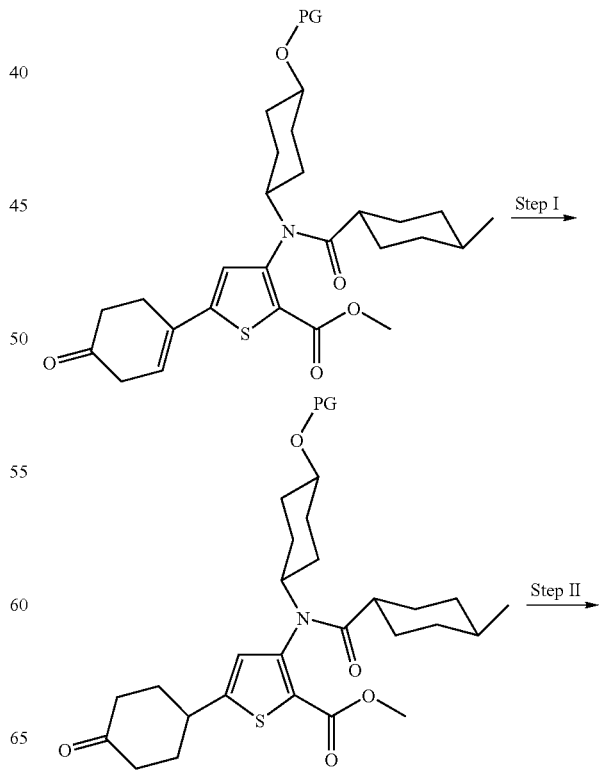

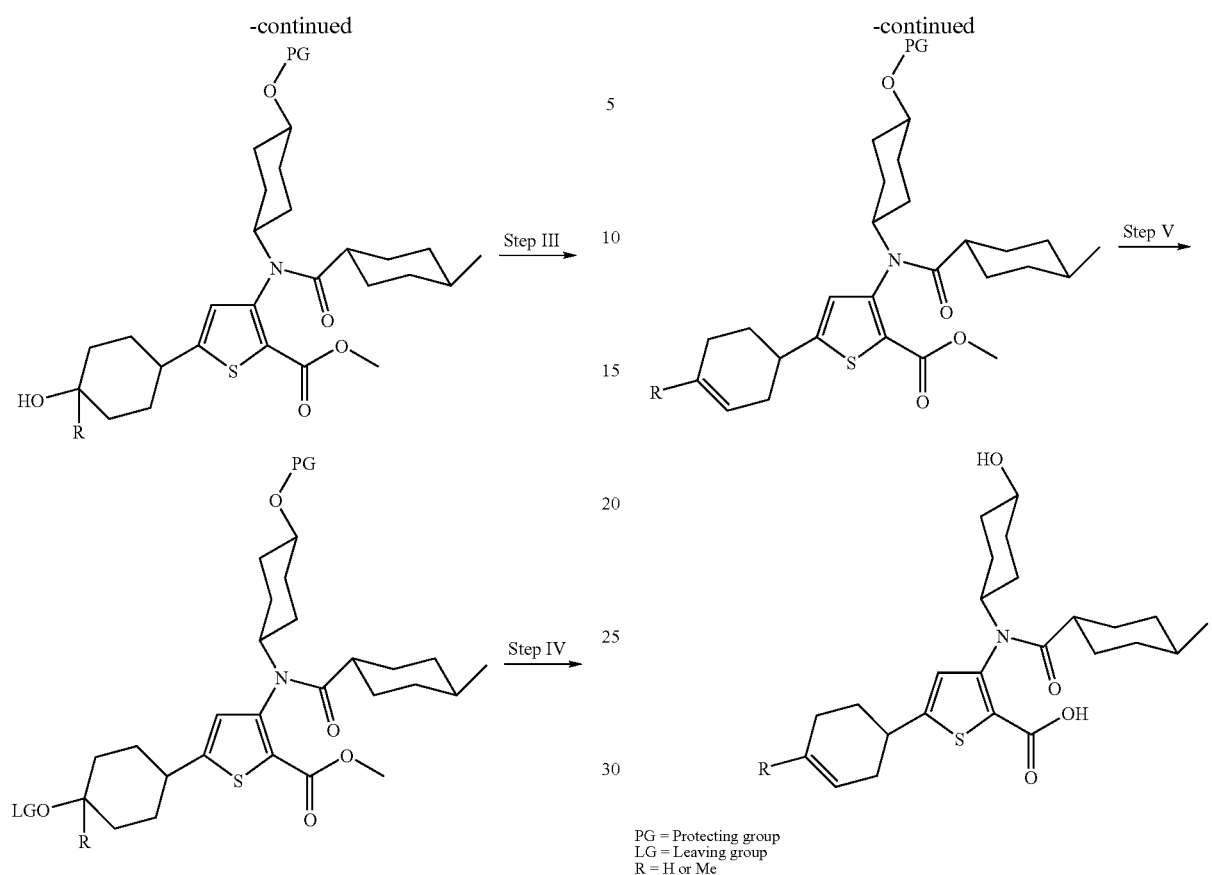
PG = Protecting group
LG = Leaving group
R = H or Me
TABLE 1
List of compounds in accordance with the present invention
| Compound# | Structure | m/z* (M + H)+ | IC50 |
|---|---|---|---|
| 1 | 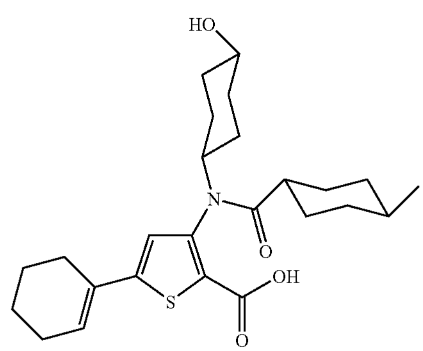 | 446.1 | A |

TABLE 1-continued

List of compounds in accordance with the present invention

| Compound# | Structure | m/z* (M + H)+ | IC50 |
|---|---|---|---|
| 2 | 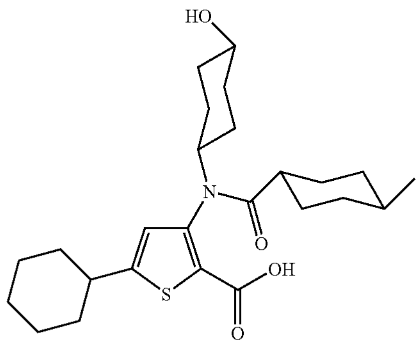 | 448.1 | A |
| 3 | 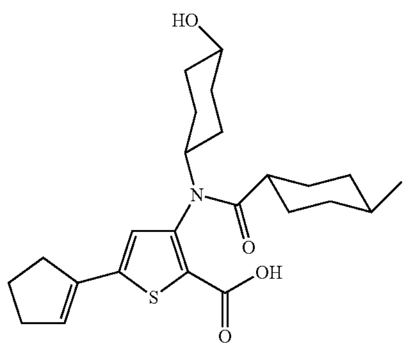 | | A |
| 4 | 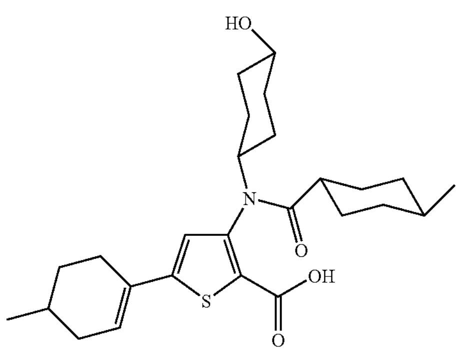 | 460.2 | A |
| 5 | 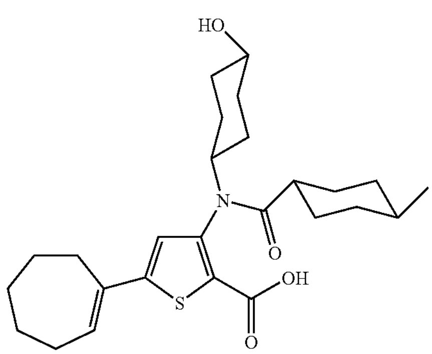 | 460.2 | A |

TABLE 1-continued

List of compounds in accordance with the present invention

| Compound# | Structure | m/z* (M + H)+ | IC50 |
|---|---|---|---|
| 6 | 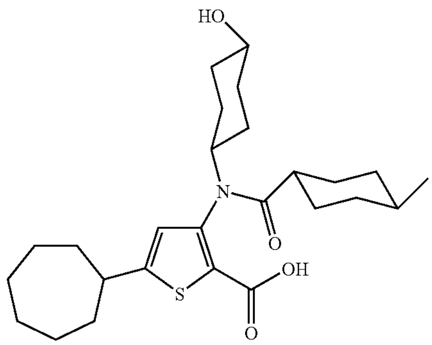 | 462.3 | A |
| 7 | 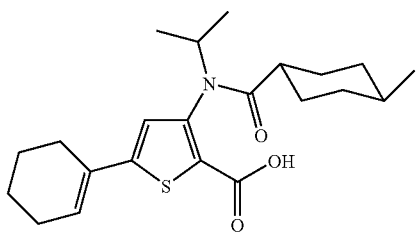 | 390.1 | A |
| 8 | 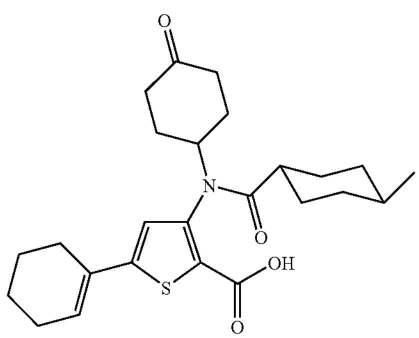 | 444.2 | A |
| 9 | 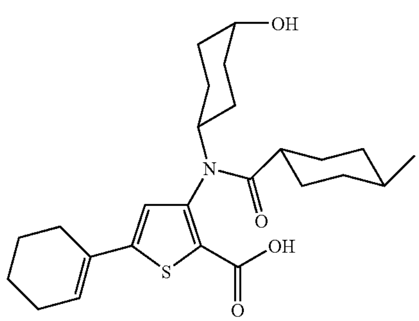 | 446.2 | A |
| 10 | 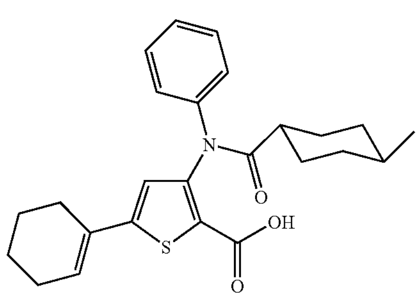 | 424.1 | A |

TABLE 1-continued

List of compounds in accordance with the present invention

| Compound# | Structure | m/z* (M + H)+ | IC50 |
|---|---|---|---|
| 11 | 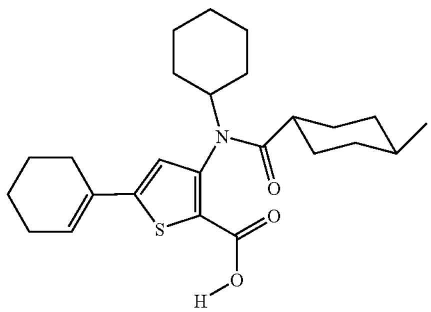 | 430.2 | A |
| 12 | 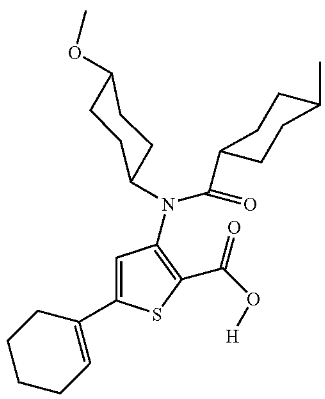 | 460.4 | A |
| 13 | 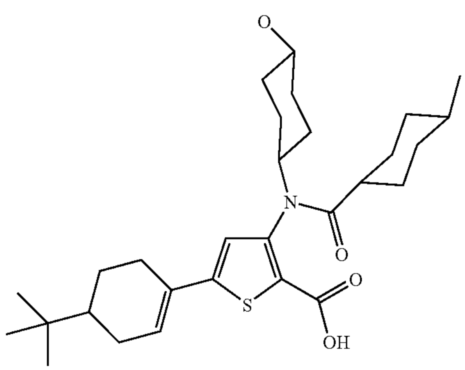 | 502.3 | A |
| 14 | 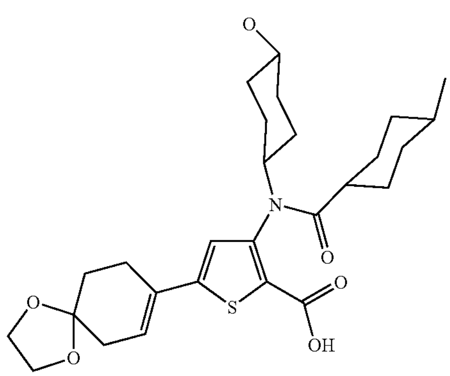 | 504.2 | A |

TABLE 1-continued

List of compounds in accordance with the present invention

| Compound# | Structure | m/z* (M + H)+ | IC50 |
|---|---|---|---|
| 15 | 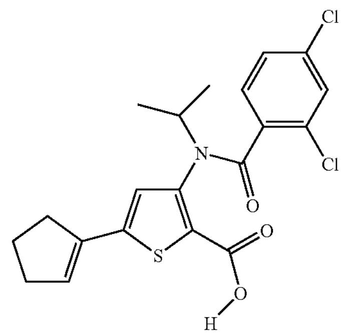 | 425.4 | C |
| 16 | 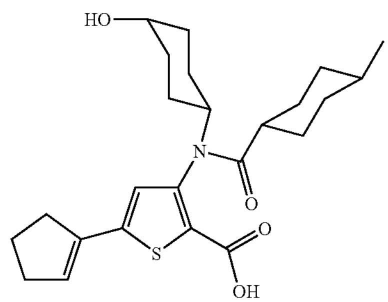 | 432.2 | A |
| 17 | 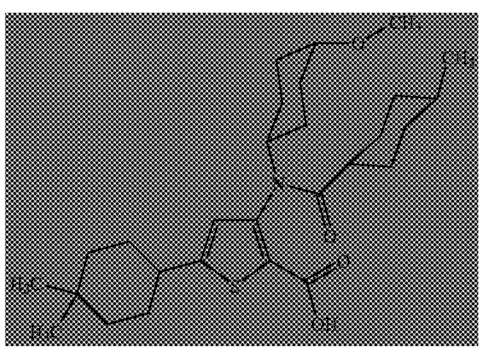 | | |
| 18 | 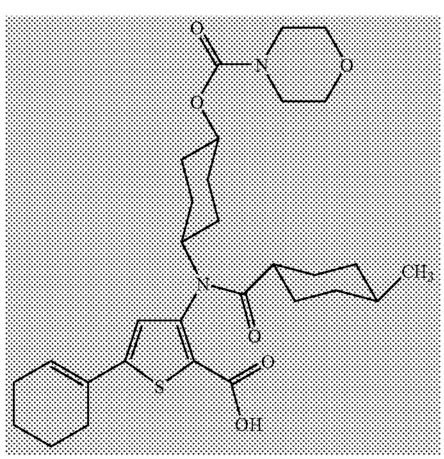 | 559.5 | A |

TABLE 1-continued

List of compounds in accordance with the present invention

| Compound# | Structure | m/z* (M + H)+ | IC50 |
|---|---|---|---|
| 19 | 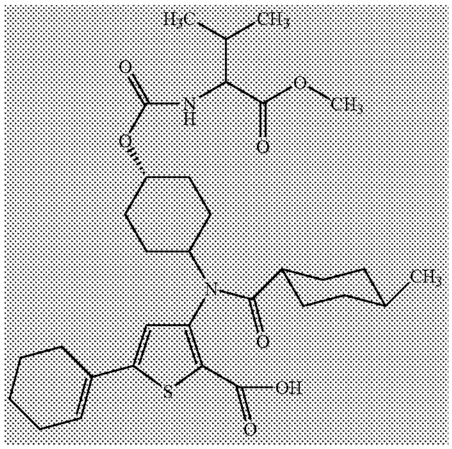 | 603.5 | A |
| 20 | 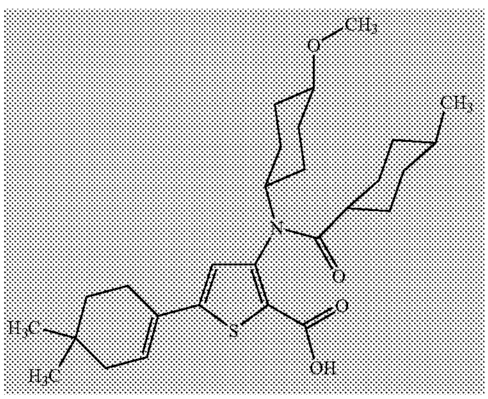 | 488.4 | A |
| 21 | 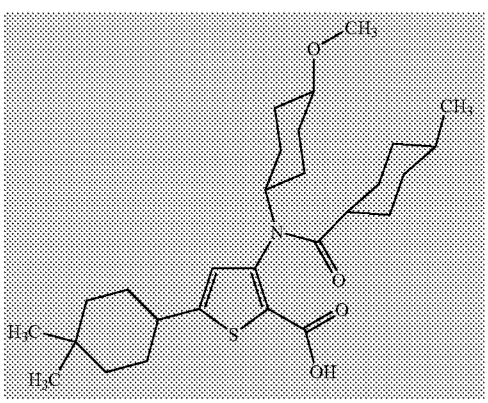 | 490.5 | A |

TABLE 1-continued

List of compounds in accordance with the present invention

| Compound# | Structure | m/z* (M + H)+ | IC50 |
|---|---|---|---|
| 22 | 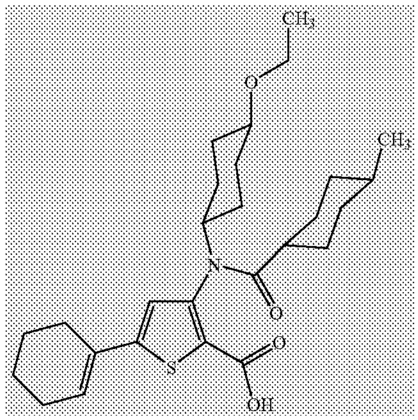 | 474.4 | A |
| 23 | 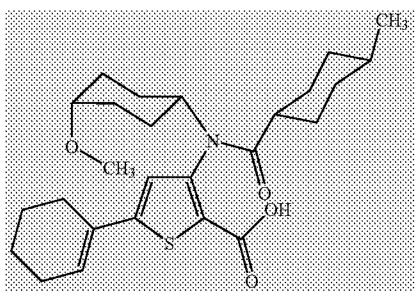 | 460.3 | A |
| 24 | 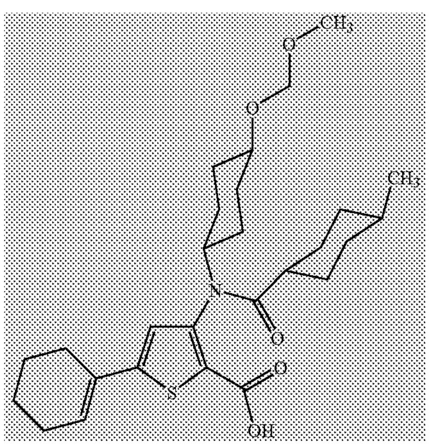 | 490.4 | A |

TABLE 1-continued

List of compounds in accordance with the present invention

| Compound# | Structure | m/z* (M + H)+ | IC50 |
|---|---|---|---|
| 25 | 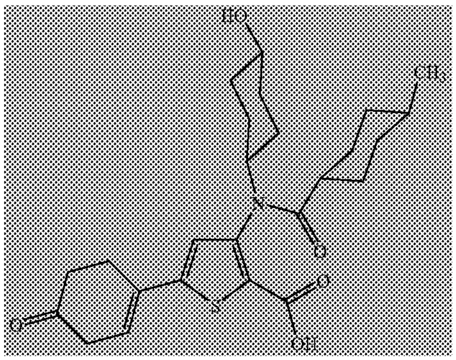 | 460.2 | B |
| 26 | 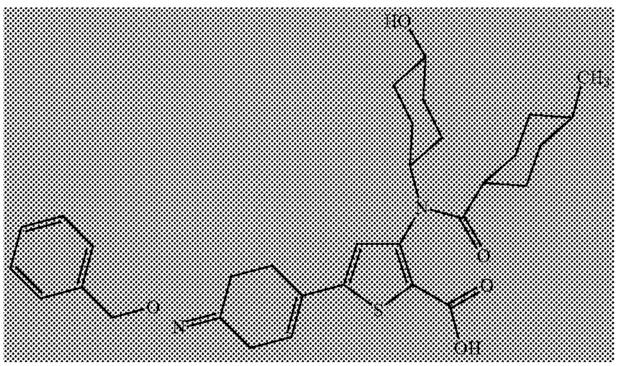 | 565.3 | A |
| 27 | 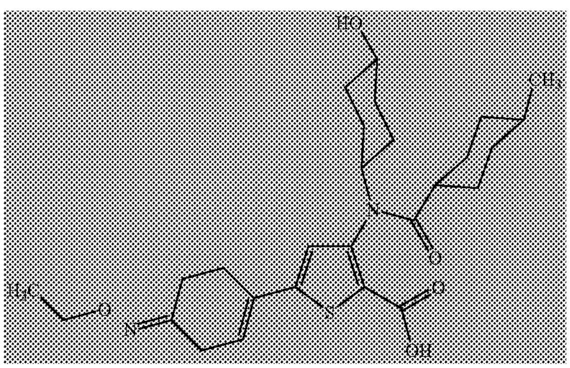 | 503.3 | A |
| 28 | 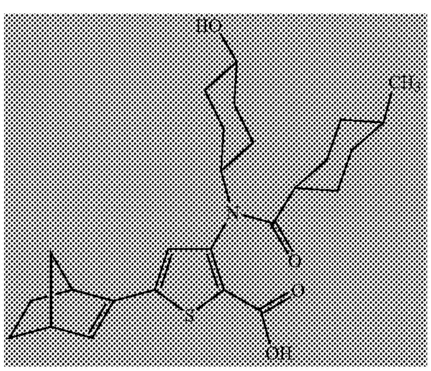 | 458.1 | C |

TABLE 1-continued

List of compounds in accordance with the present invention

| Compound# | Structure | m/z* (M + H)+ | IC50 |
|---|---|---|---|
| 29 | 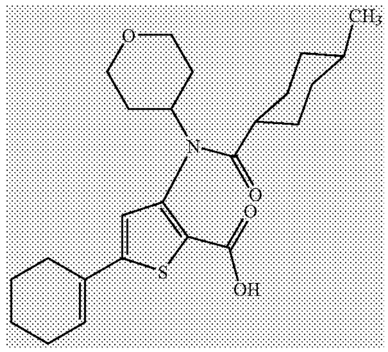 | 432.4 | A |
| 30 | 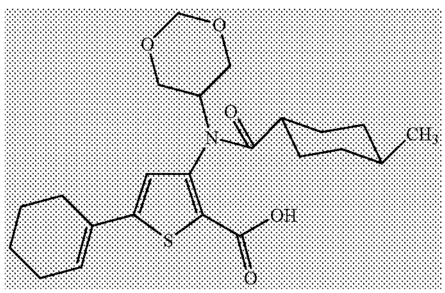 | 434.1 | A |
| 31 | 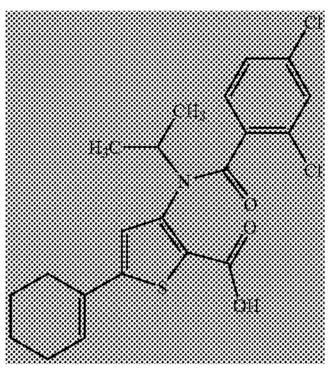 | 439.1 | B |
| 32 | 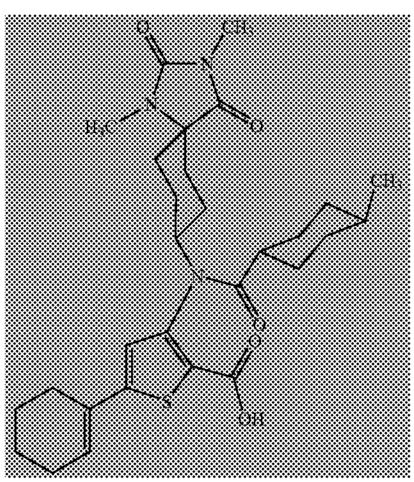 | | A |

TABLE 1-continued

List of compounds in accordance with the present invention

| Compound# | Structure | m/z* (M + H)+ | IC50 |
|---|---|---|---|
| 33 | 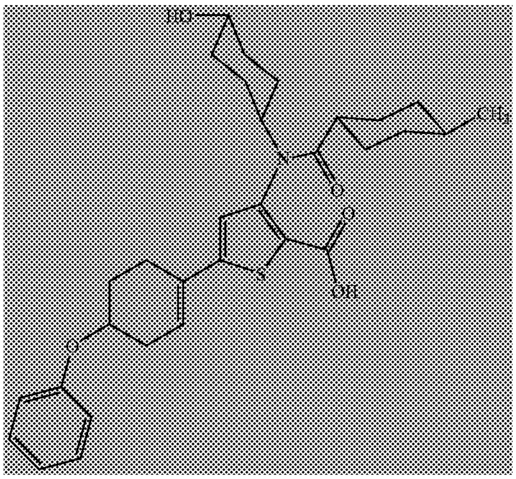 | 538.4 | A |
| 34 | 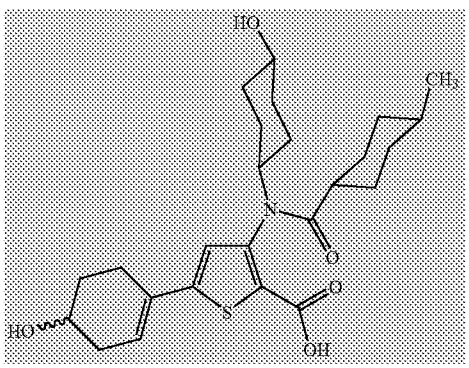 | 462.3 | A |
| 35 | 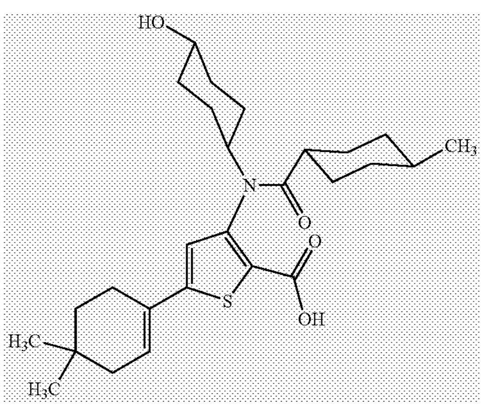 | 474.4 | A |

TABLE 1-continued

List of compounds in accordance with the present invention

| Compound# | Structure | m/z* (M + H)+ | IC50 |
|---|---|---|---|
| 36 | 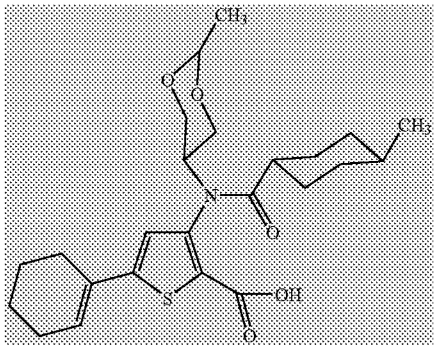 | 448.4 | A |
| 37 | 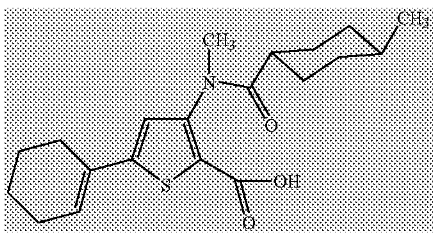 | 362.3 | B |
| 38 | 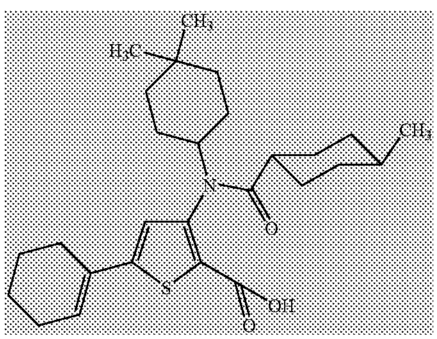 | 458.4 | A |
| 39 | 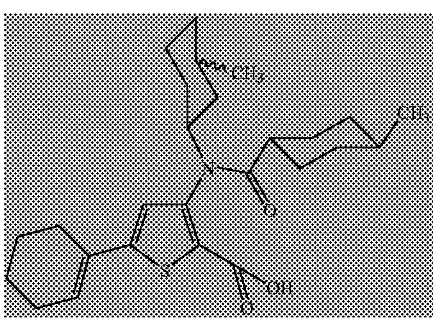 | 444.4 | A |

TABLE 1-continued

List of compounds in accordance with the present invention

| Compound# | Structure | m/z* (M + H)+ | IC50 |
|---|---|---|---|
| 40 | 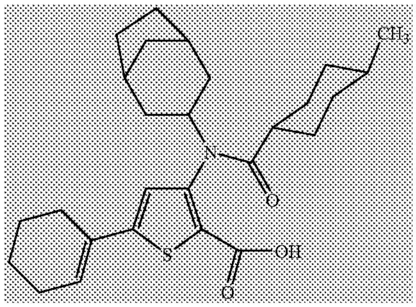 | 456.4 | A |
| 41 | 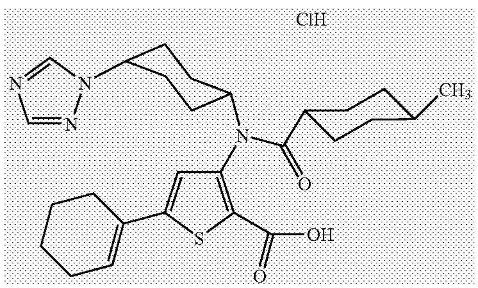 | 497.4 | A |
| 42 | 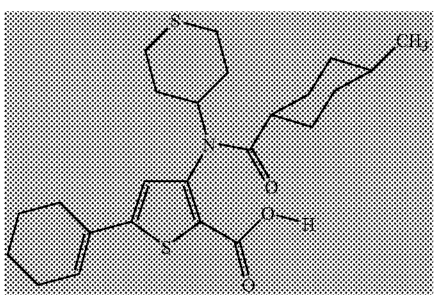 | 448.3 | A |
| 43 | 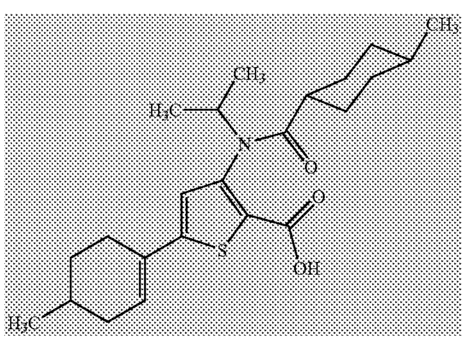 | 404.3 | A |

TABLE 1-continued

List of compounds in accordance with the present invention

| Compound# | Structure | m/z* (M + H)+ | IC50 |
|---|---|---|---|
| 44 | 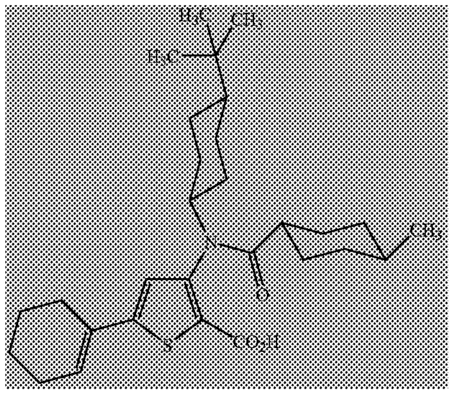 | 486.4 | B |
| 45 | 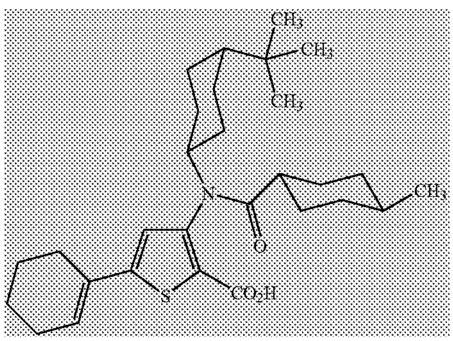 | 486.5 | A |
| 46 | 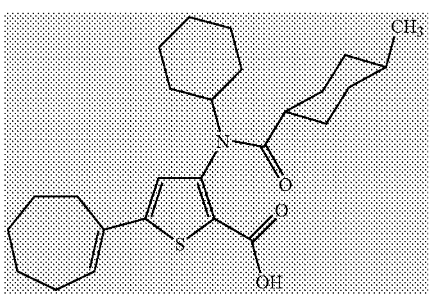 | 444.4 | A |
| 47 | 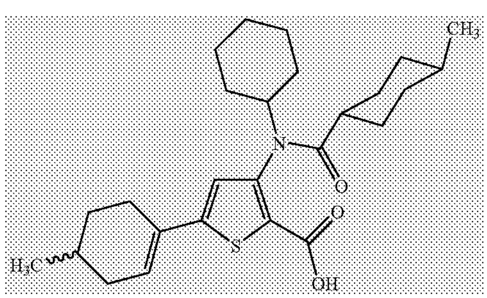 | 444.3 | A |

TABLE 1-continued

List of compounds in accordance with the present invention

| Compound# | Structure | m/z* (M + H)+ | IC50 |
|---|---|---|---|
| 48 | 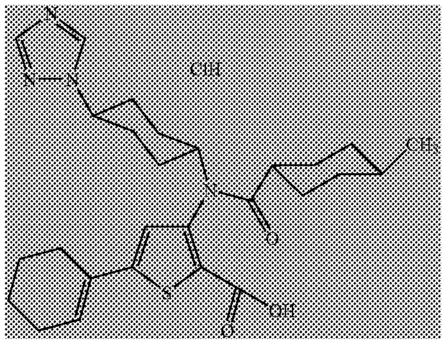 | 497.4 | A |
| 49 | 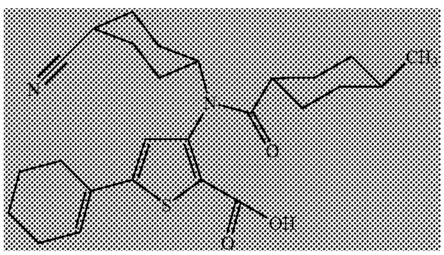 | 455.3 | A |
| 50 | 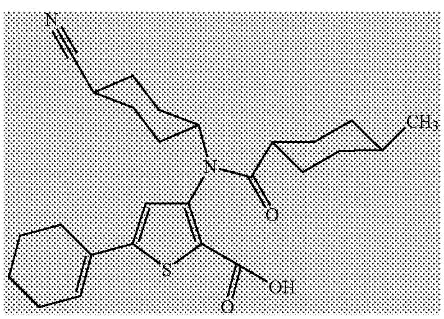 | 455.4 | A |
| 51 | 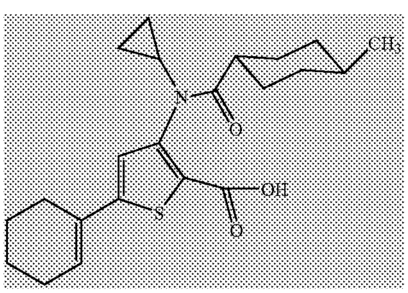 | 388.3 | B |

TABLE 1-continued
List of compounds in accordance with the present invention
| Compound# | Structure | m/z* (M + H)+ | IC50 |
|---|---|---|---|
| 52 | 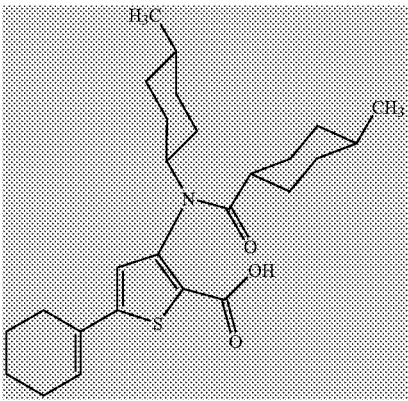 | 444.4 | A |
| 53 | 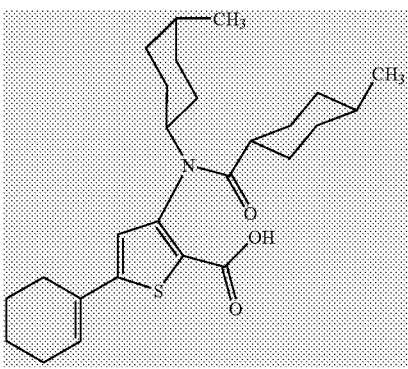 | 444.4 | A |
| 54 | 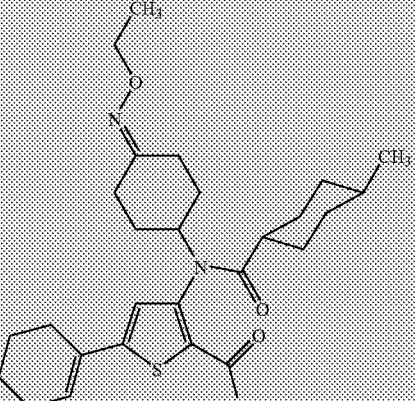 | 487.7 | A |

TABLE 1-continued

List of compounds in accordance with the present invention

| Compound# | Structure | m/z* (M + H)+ | IC50 |
|---|---|---|---|
| 55 | 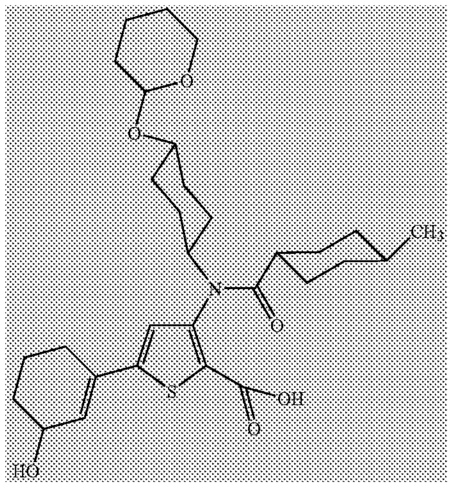 | 546.4 | A |
| 56 | 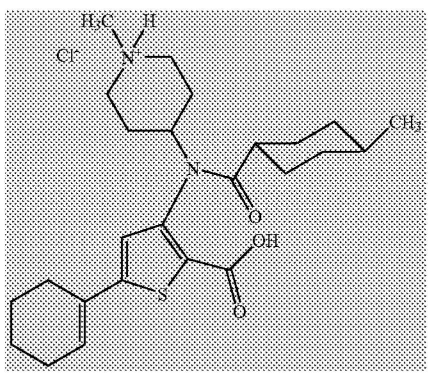 | 445.4 (M+) | A |
| 57 | 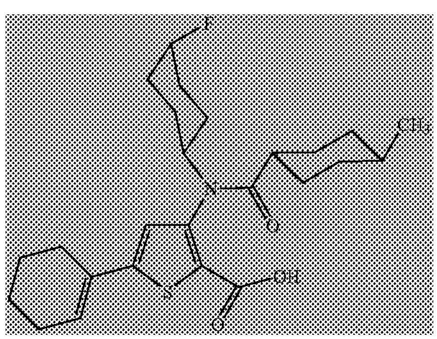 | 448.3 | A |

TABLE 1-continued
List of compounds in accordance with the present invention
| Compound# | Structure | m/z* (M + H)+ | IC50 |
|---|---|---|---|
| 58 | 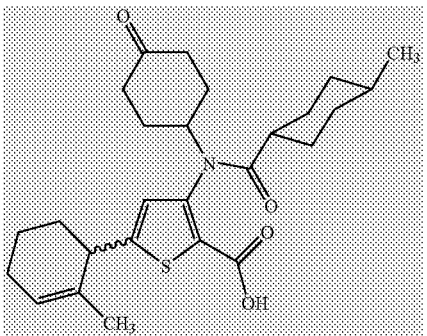 | 458.4 | B |
| 59 | 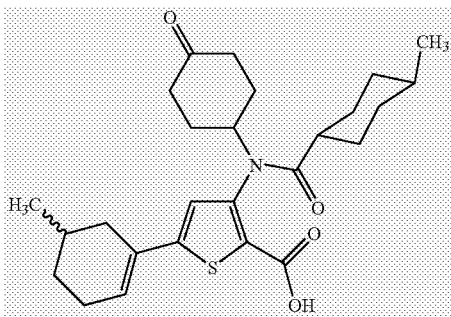 | 458.4 | A |
| 60 | 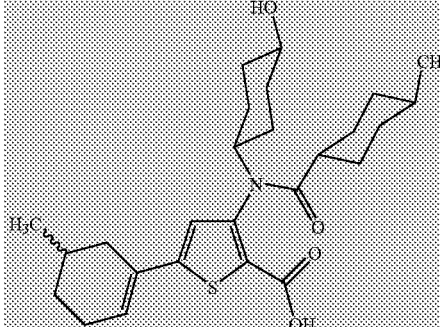 | 460.4 | A |
| 61 | 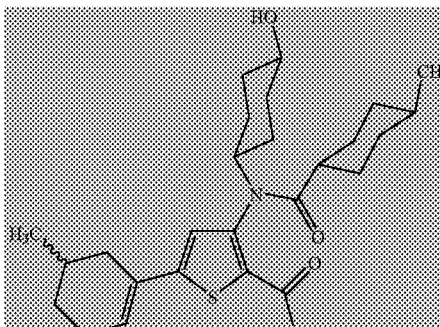 | 460.4 | A |

TABLE 1-continued

List of compounds in accordance with the present invention

| Compound# | Structure | m/z* (M + H)+ | IC50 |
|---|---|---|---|
| 62 | 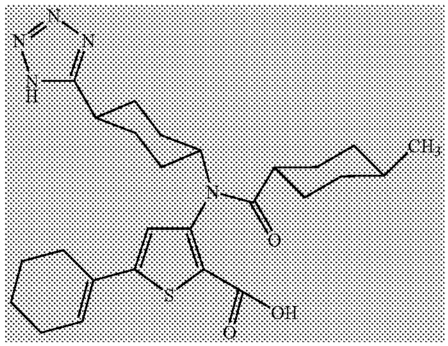 | 498.4 | A |
| 63 | 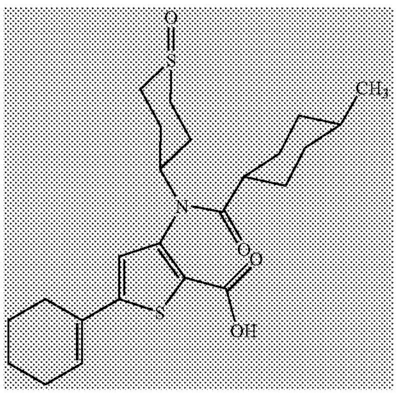 | 464.3 | A |
| 64 | 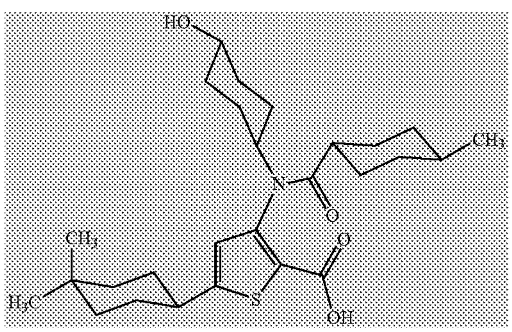 | 476.4 | A |
| 65 | 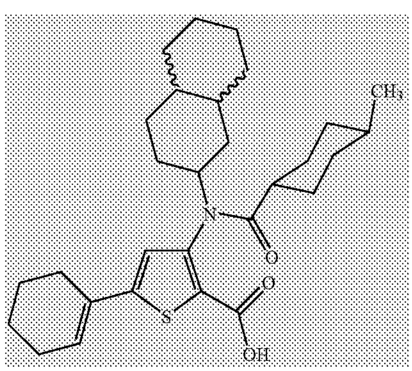 | 484.4 | A |

TABLE 1-continued

List of compounds in accordance with the present invention

| Compound# | Structure | m/z* (M + H)+ | IC50 |
|---|---|---|---|
| 66 | 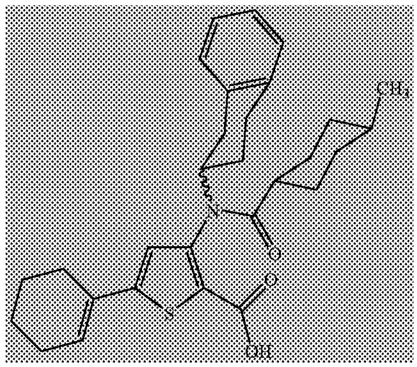 | 478.4 | A |
| 67 | 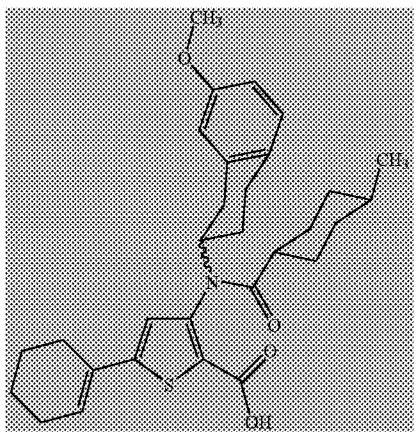 | 508.4 | A |
| 68 | 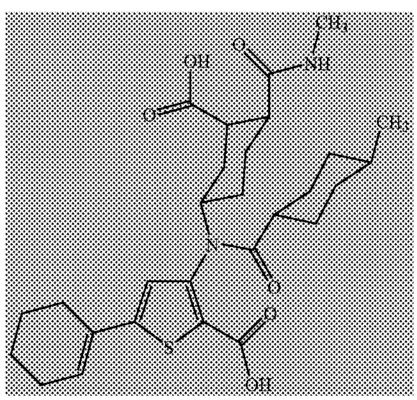 | 531.4 | A |

TABLE 1-continued
List of compounds in accordance with the present invention
| Compound# | Structure | m/z* (M + H)+ | IC50 |
|---|---|---|---|
| 69 | 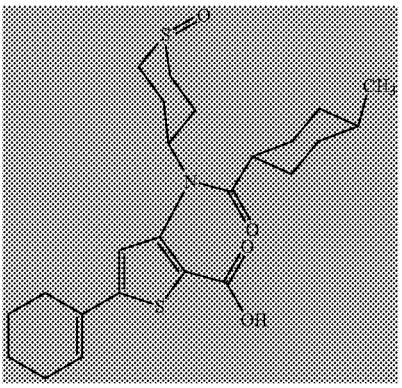 | 464.3 | A |
| 70 | 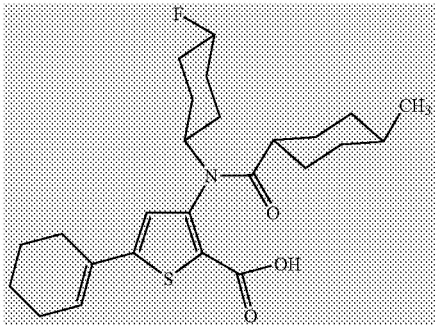 | 448.3 | A |
| 71 | 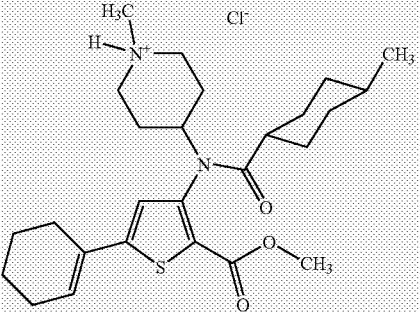 | 460.4 (M+) | A |
| 72 | 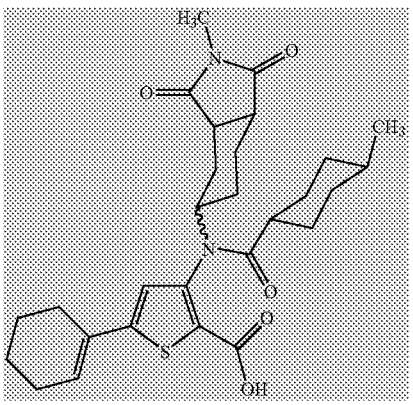 | 513.4 | A |

TABLE 1-continued
List of compounds in accordance with the present invention
| Compound# | Structure | m/z* (M + H)+ | IC50 |
|---|---|---|---|
| 73 | 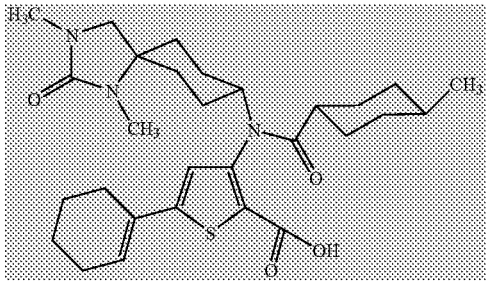 | 528.4 | A |
| 74 | 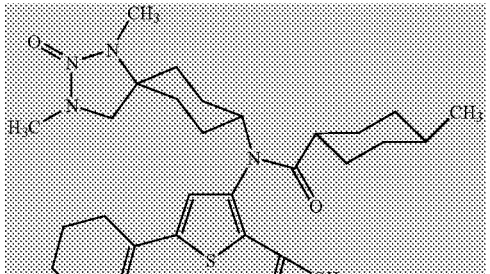 | 528.4 | A |
| 75 | 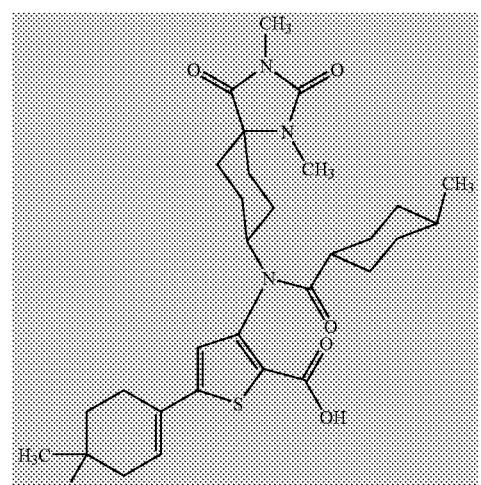 | 570.3 | A |
| 76 | 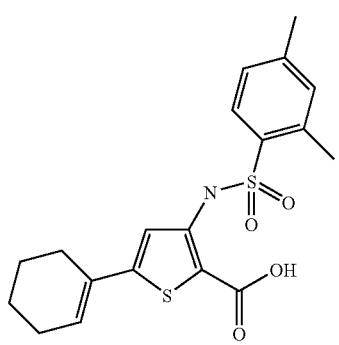 | | |

TABLE 1-continued

List of compounds in accordance with the present invention

| Compound# | Structure | m/z* (M + H)+ | IC50 |
|---|---|---|---|
| 77 | 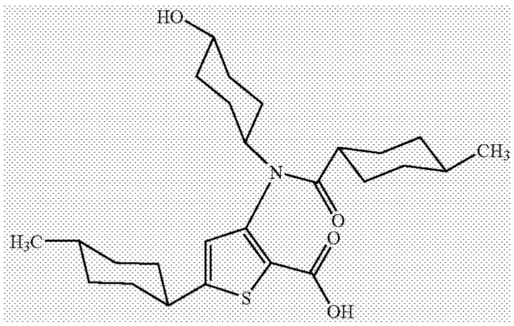 | 462.3 | A |
| 78 | 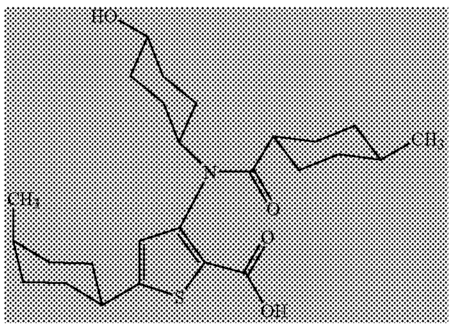 | 462.3 | A |
| 79 | 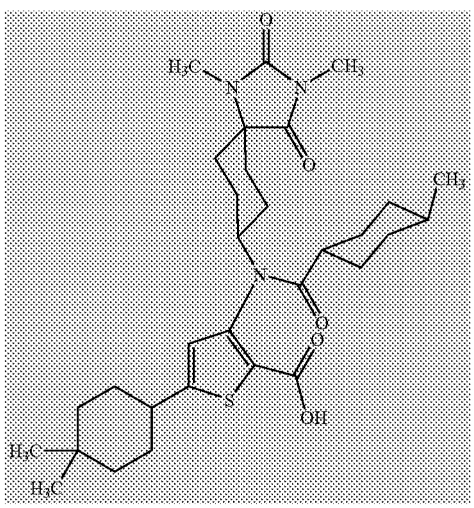 | 572.5 | A |
| 80 | 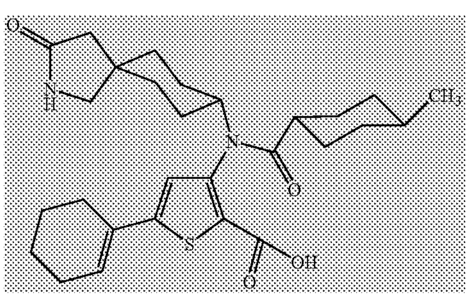 | 499.4 | A |

TABLE 1-continued

List of compounds in accordance with the present invention

| Compound# | Structure | m/z* (M + H)+ | IC50 |
|---|---|---|---|
| 81 | 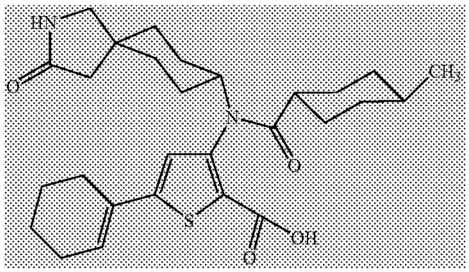 | 499.4 | A |
| 82 | 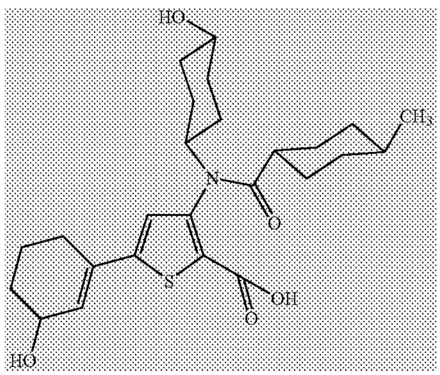 | 462.3 | B |
| 83 | 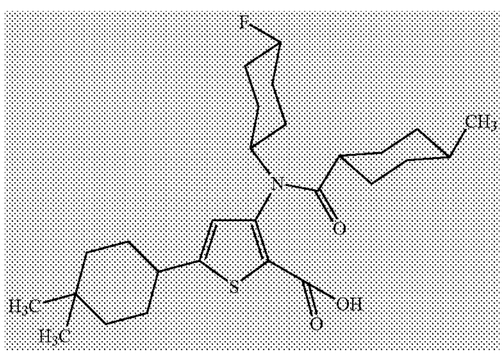 | 478.4 | A |
| 84 | 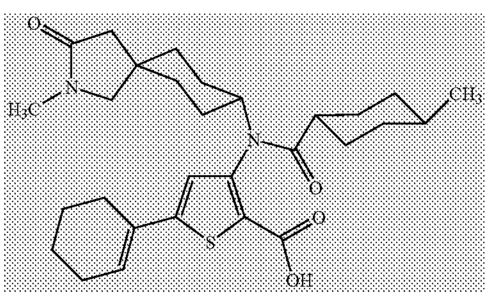 | 513.4 | A |

TABLE 1-continued

List of compounds in accordance with the present invention

| Compound# | Structure | m/z* (M + H)+ | IC50 |
|---|---|---|---|
| 85 | 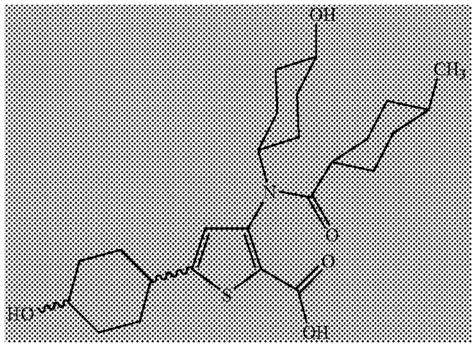 | 464.4 | B |
| 86 | 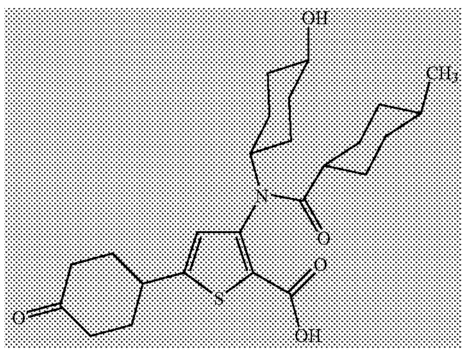 | 462.4 | B |
| 87 | 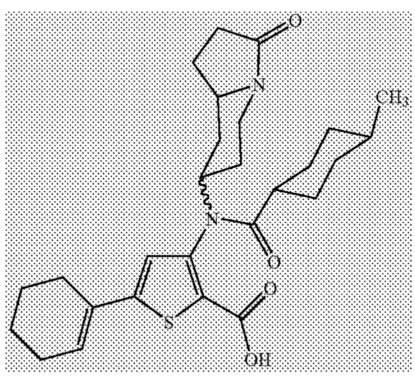 | 485.3 | A |
| 88 | 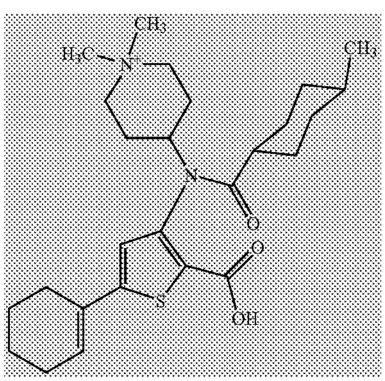 | 459.2 (M+) | A |

TABLE 1-continued

List of compounds in accordance with the present invention

| Compound# | Structure | m/z* (M + H)+ | IC50 |
|---|---|---|---|
| 89 | 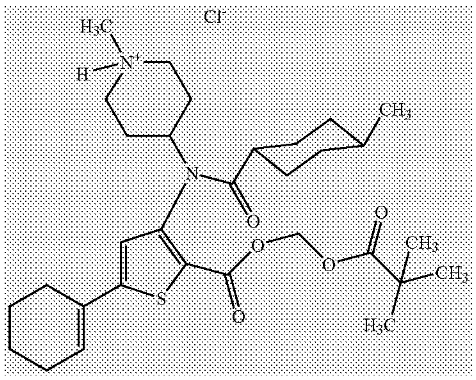 | 559.5 (M+) | |
| 90 | 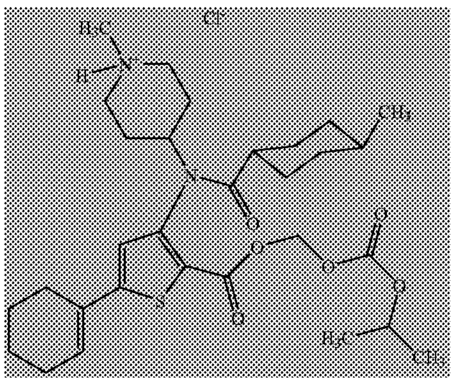 | 561.5 (M+) | |
| 91 | 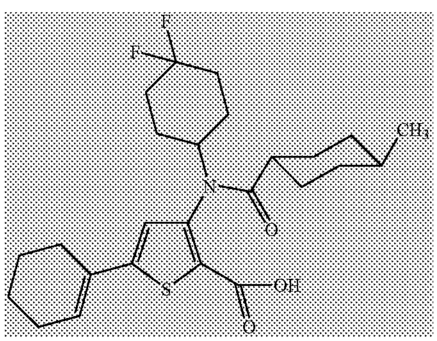 | 466.3 | |
| 92 | 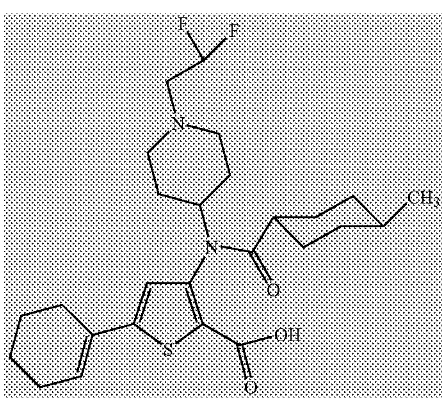 | 495.4 | |

TABLE 1-continued
List of compounds in accordance with the present invention
| Compound# | Structure | m/z* (M + H)+ | IC50 |
|---|---|---|---|
| 93 | 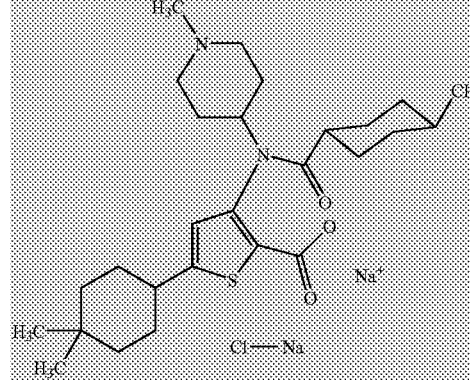 | | A |
| 94 | 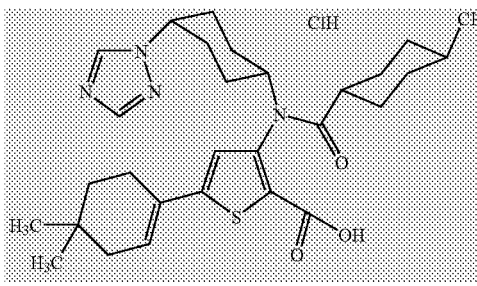 | 525.5 | A |
| 95 | 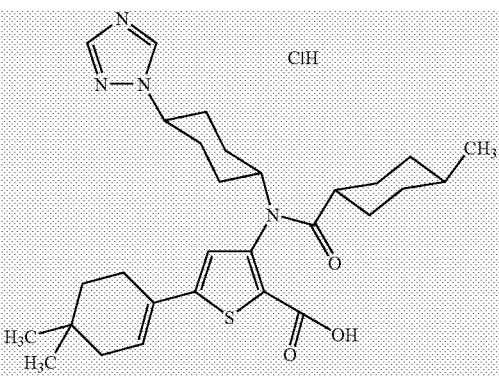 | 525.5 | A |
| 96 | 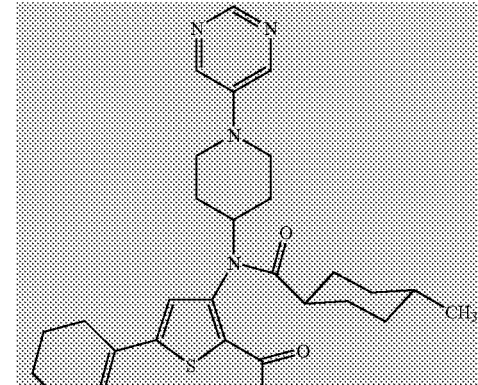 | 509.4 | A |

TABLE 1-continued

List of compounds in accordance with the present invention

| Compound# | Structure | m/z* (M + H)+ | IC50 |
|---|---|---|---|
| 97 | 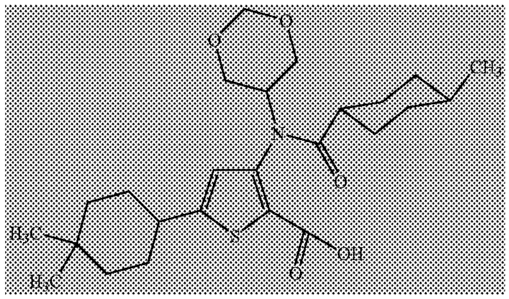 | 464.4 | A |
| 98 | 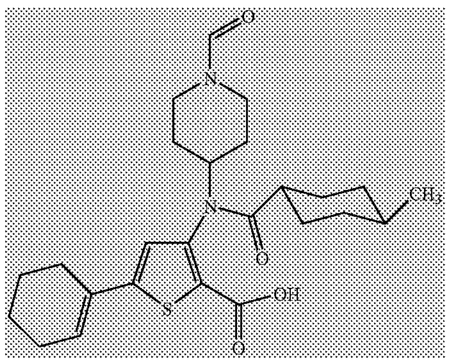 | | A |
| 99 | 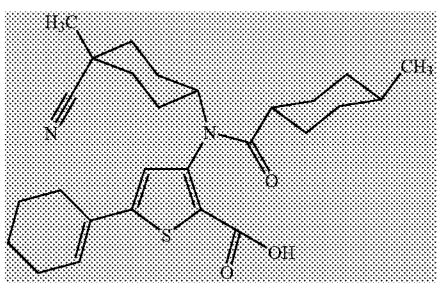 | 469.4 | A |
| 100 | 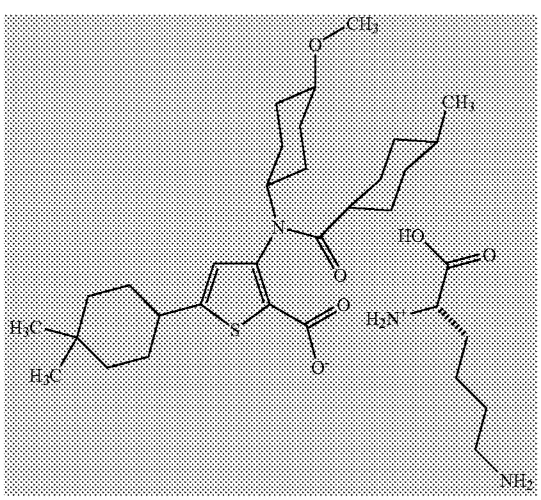 | | |

TABLE 1-continued

List of compounds in accordance with the present invention

| Compound# | Structure | m/z* (M + H)+ | IC50 |
|---|---|---|---|
| 101 | 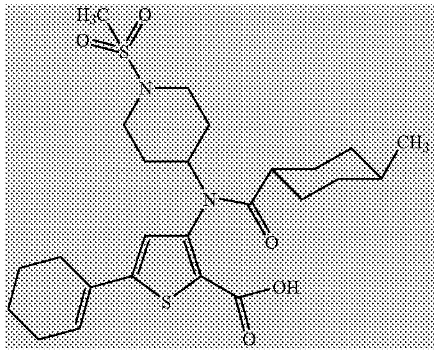 | 509.4 | A |
| 102 | 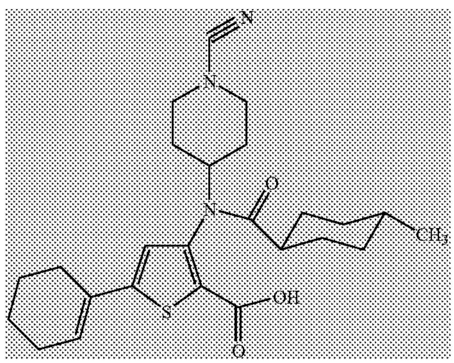 | | A |
| 103 | 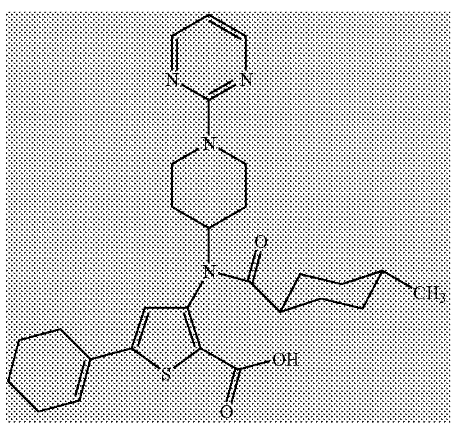 | 509.4 | A |
| 104 | 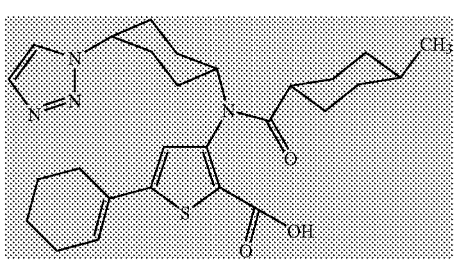 | 497.4 | A |

TABLE 1-continued
List of compounds in accordance with the present invention
| Compound# | Structure | m/z* (M + H)+ | IC50 |
|---|---|---|---|
| 105 | 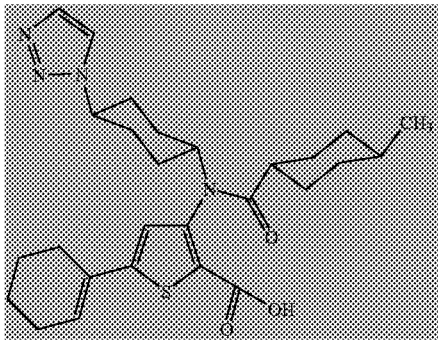 | 497.4 | A |
| 106 | 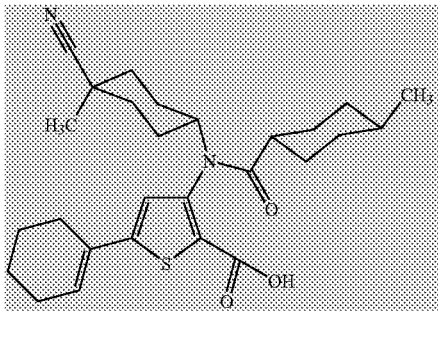 | 469.4 | A |
| 107 | 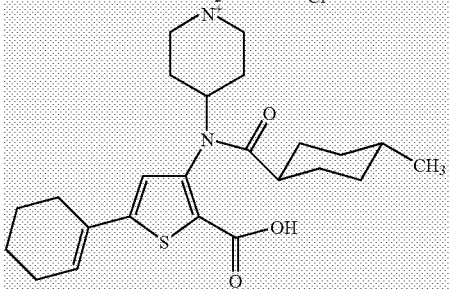 | 430.4 (M+) | A |
| 108 | 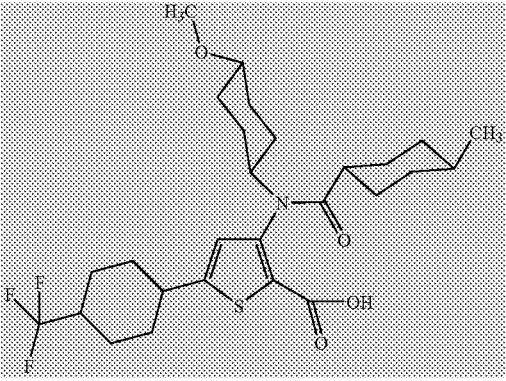 | 530.4 | A |

TABLE 1-continued

List of compounds in accordance with the present invention

| Compound# | Structure | m/z* (M + H)+ | IC50 |
|---|---|---|---|
| 109 | 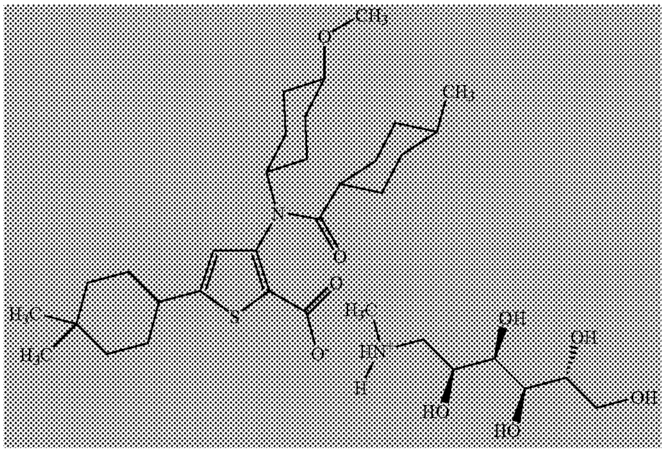 | | |
| 110 | 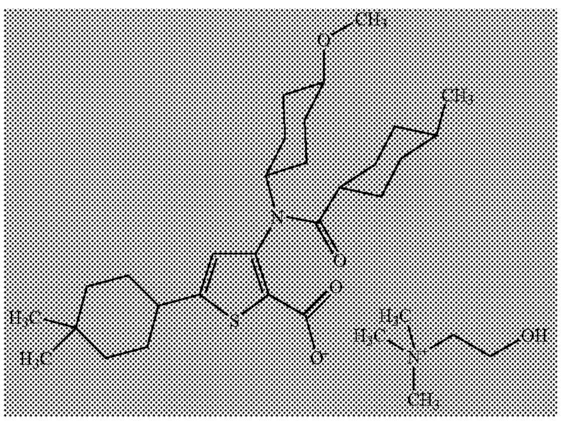 | | |
| 111 | 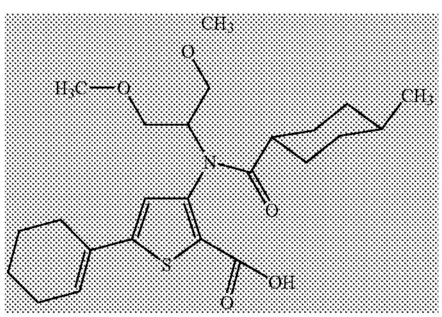 | 450.3 | A |

TABLE 1-continued

List of compounds in accordance with the present invention

| Compound# | Structure | m/z* (M + H)+ | IC50 |
|---|---|---|---|
| 112 | 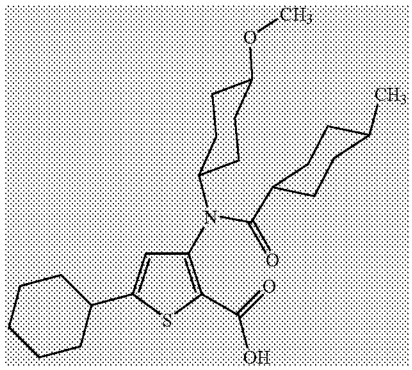 | 462.4 | A |
| 113 | 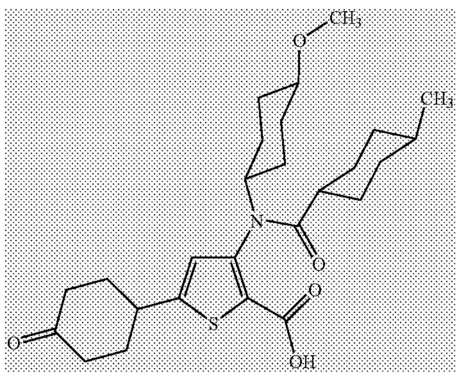 | 476.4 | A |
| 114 | 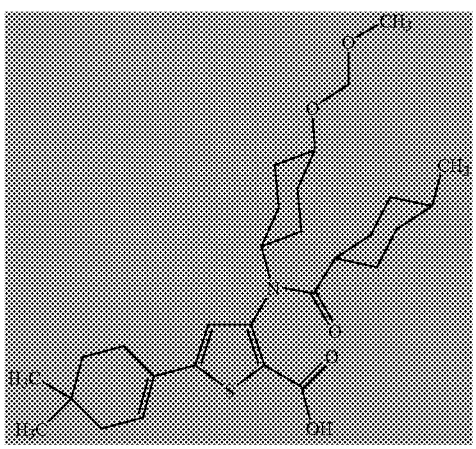 | 518.5 | A |
| 115 | 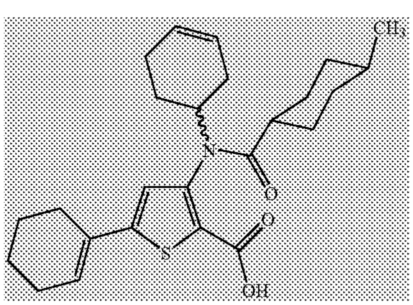 | 428.3 | A |

TABLE 1-continued

List of compounds in accordance with the present invention

| Compound# | Structure | m/z* (M + H)+ | IC50 |
|---|---|---|---|
| 116 | 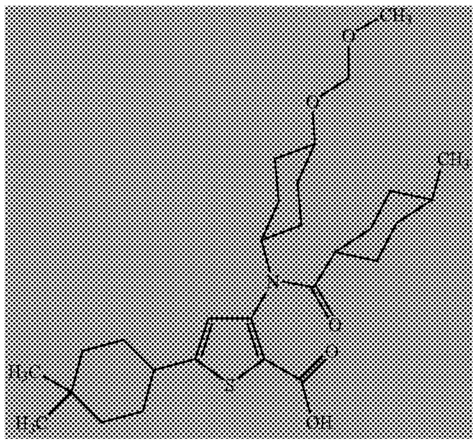 | 520.4 | A |
| 117 | 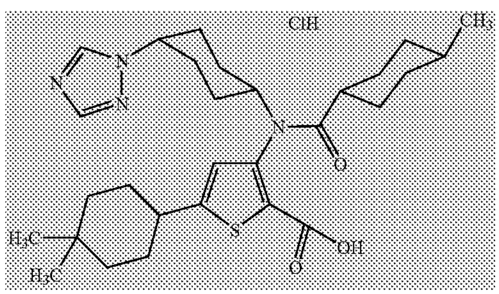 | 527.4 | A |
| 118 | 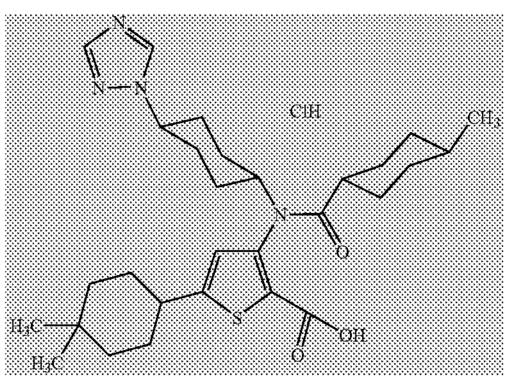 | 527.4 | A |

TABLE 1-continued

List of compounds in accordance with the present invention

| Compound# | Structure | m/z* (M + H)+ | IC50 |
|---|---|---|---|
| 119 | 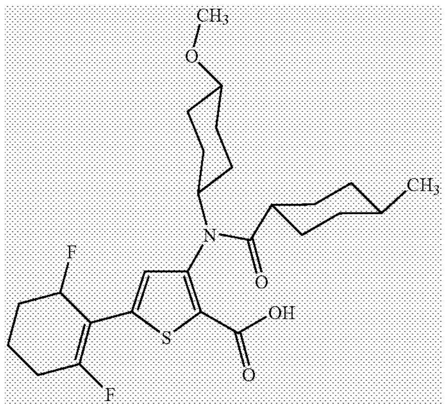 | 496.4 | A |
| 120 | 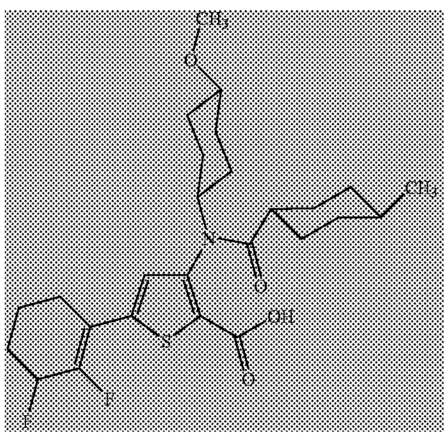 | 496.4 | A |
| 121 | 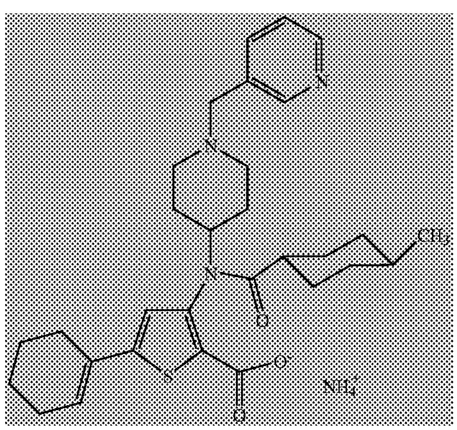 | 522.4 | A |

TABLE 1-continued

List of compounds in accordance with the present invention

| Compound# | Structure | m/z* (M + H)+ | IC50 |
|---|---|---|---|
| 122 | 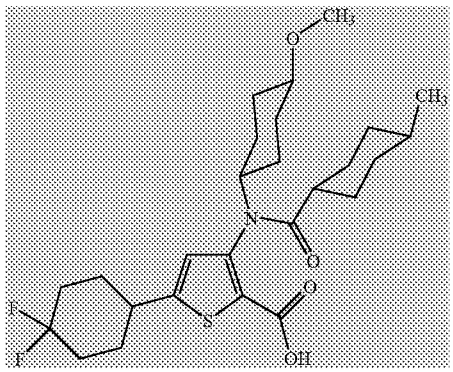 | 498.4 | A |
| 123 | 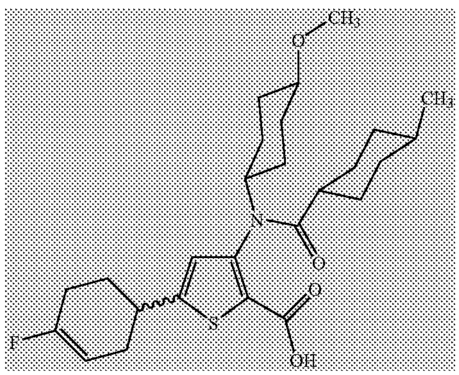 | 478.4 | A |
| 124 | 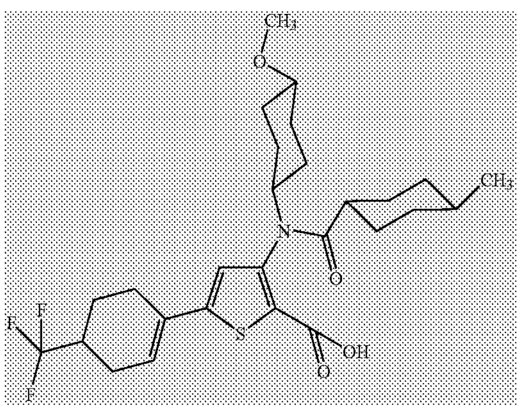 | 528.4 | A |
| 125 | 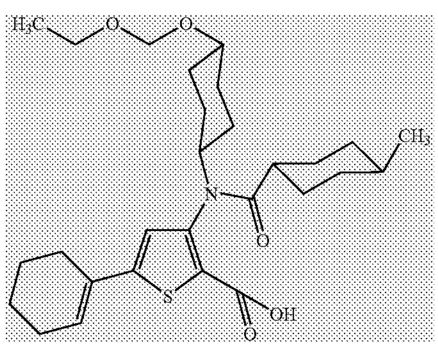 | 504.4 | A |

TABLE 1-continued

List of compounds in accordance with the present invention

| Compound# | Structure | m/z* (M + H)+ | IC50 |
|---|---|---|---|
| 126 | 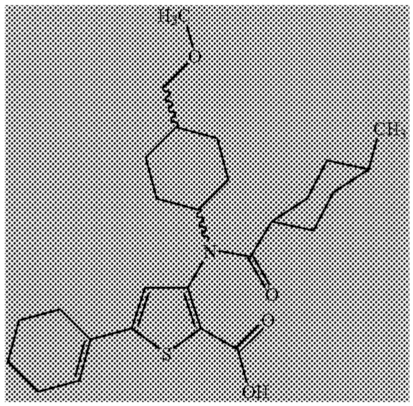 | 474.4 | A |
| 127 | 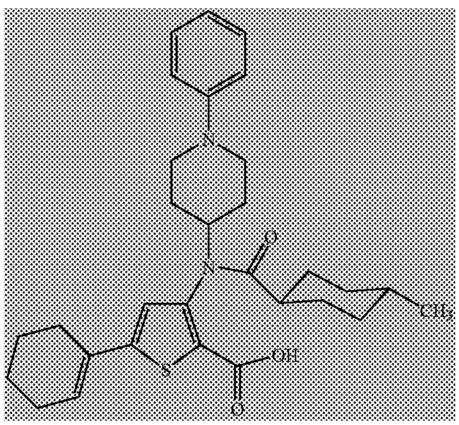 | 507.4 | A |
| 128 | 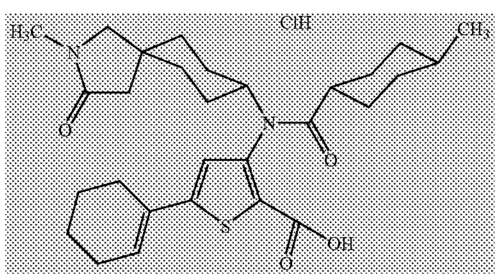 | 513.4 | A |
| 129 | 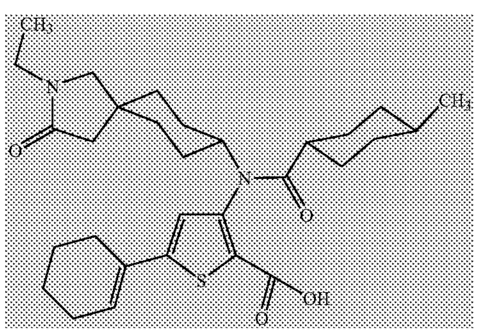 | 527.4 | A |

TABLE 1-continued
List of compounds in accordance with the present invention
| Compound# | Structure | m/z* (M + H)+ | IC50 |
|---|---|---|---|
| 130 | 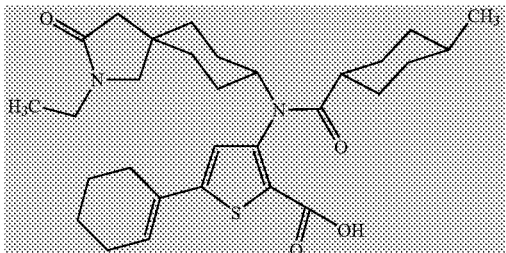 | 527.4 | A |
| 131 | 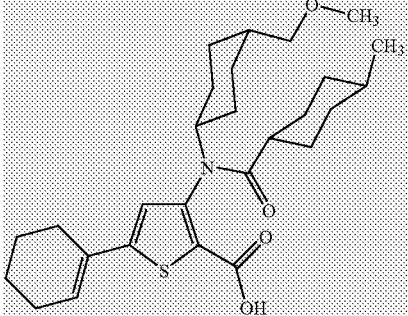 | 474.4 | A |
| 132 | 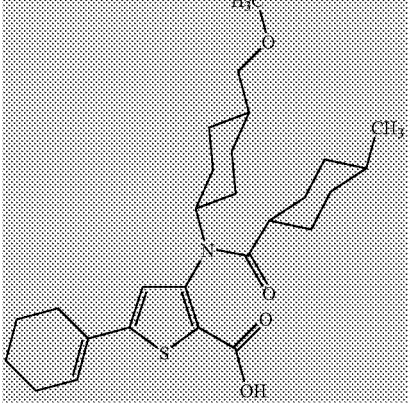 | 474.4 | A |
| 133 | 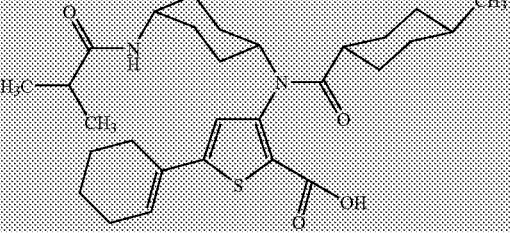 | 515.4 | A |

TABLE 1-continued

List of compounds in accordance with the present invention

| Compound# | Structure | m/z* (M + H)+ | IC50 |
|---|---|---|---|
| 134 | 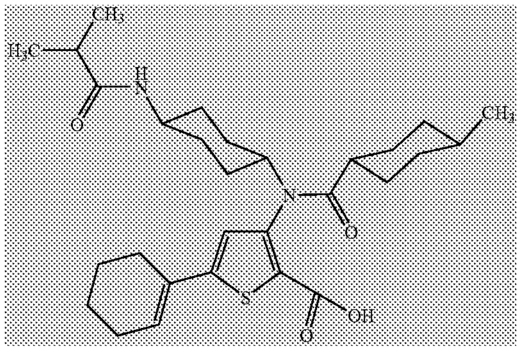 | 515.4 | A |
| 135 | 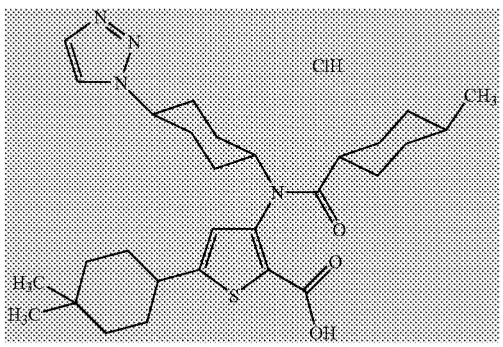 | | A |
| 136 | 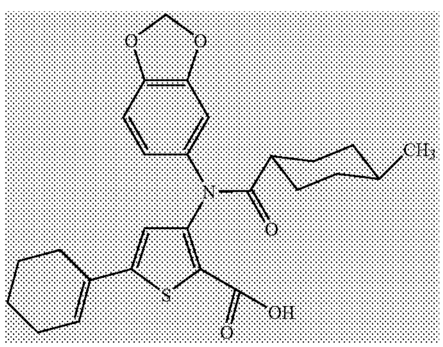 | 468.0 | A |
| 137 | 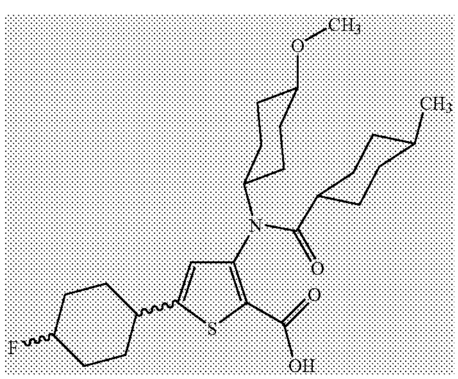 | 480.3 | A |

TABLE 1-continued

List of compounds in accordance with the present invention

| Compound# | Structure | m/z* (M + H)+ | IC50 |
|---|---|---|---|
| 138 | 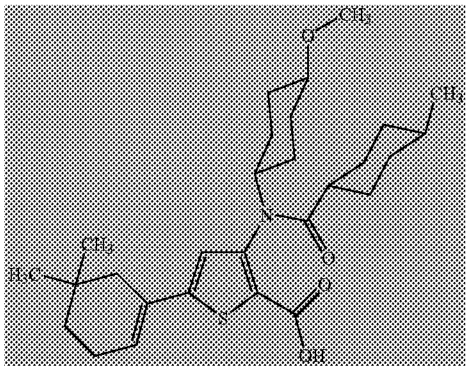 | 488.3 | A |
| 139 | 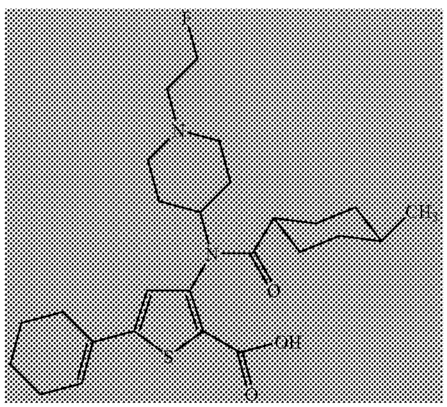 | 477.3 | A |
| 140 | 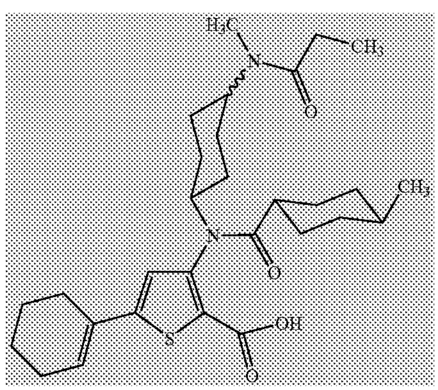 | 515.4 | A |

TABLE 1-continued

List of compounds in accordance with the present invention

| Compound# | Structure | m/z* (M + H)+ | IC50 |
|---|---|---|---|
| 141 | 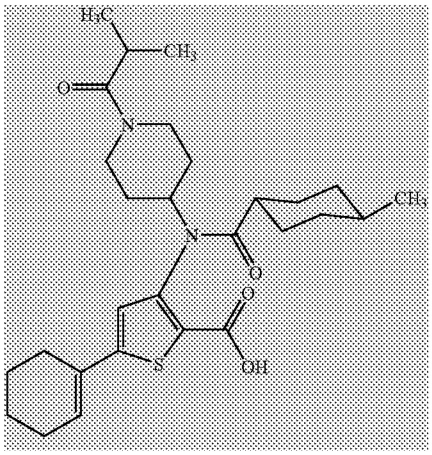 | 501.3 | A |
| 142 | 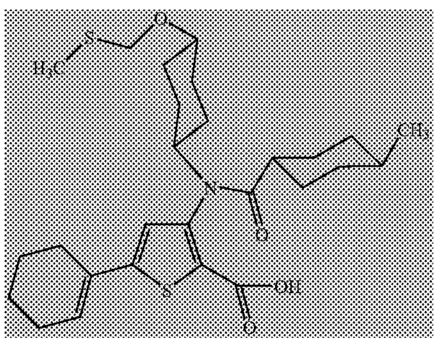 | 506.3 | A |
| 143 | 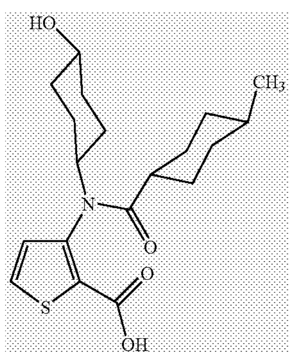 | 366.1 | |
| 144 | 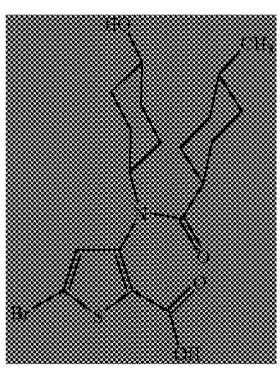 | | |

TABLE 1-continued

List of compounds in accordance with the present invention

| Compound# | Structure | m/z* (M + H)+ | IC50 |
|---|---|---|---|
| 145 | 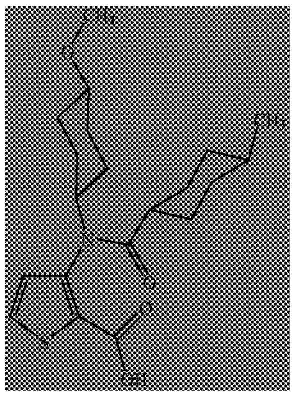 | 380.1 | |
| 146 | 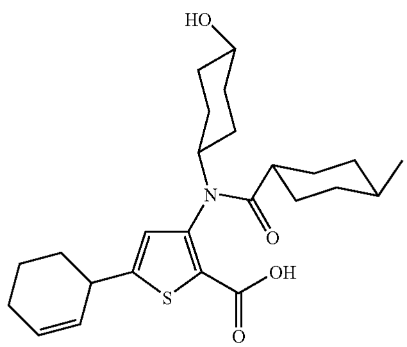 | | |
| 147 | 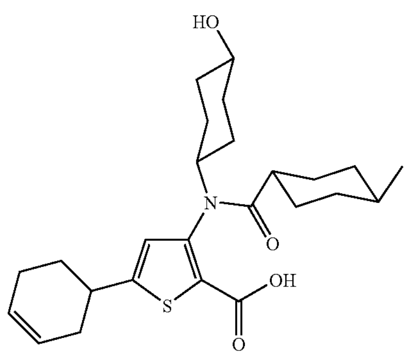 | | |
| 148 | 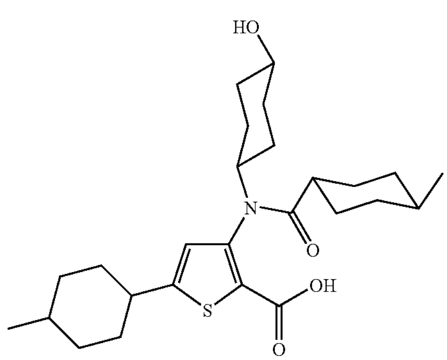 | | |

TABLE 1-continued

List of compounds in accordance with the present invention

| Compound# | Structure | m/z* (M + H)+ | IC50 |
|---|---|---|---|
| 149 | 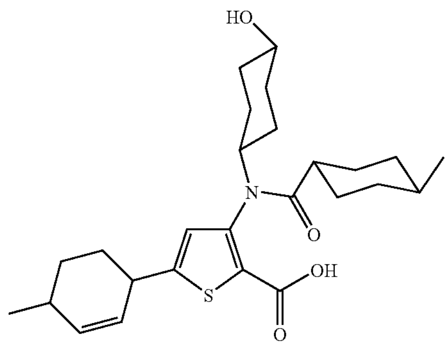 | | |
| 150 | 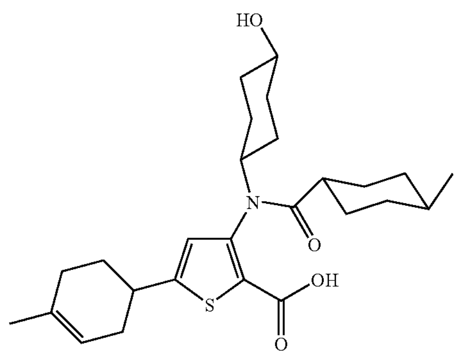 | | |
| 151 | 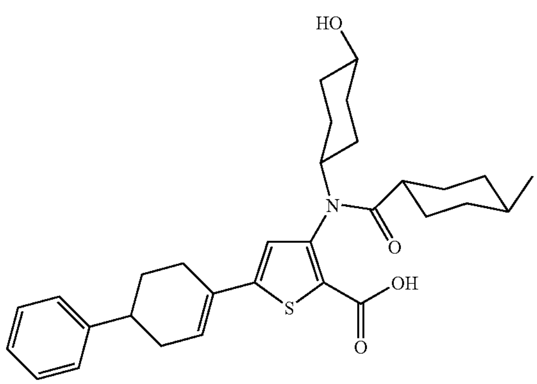 | | |
| 152 | 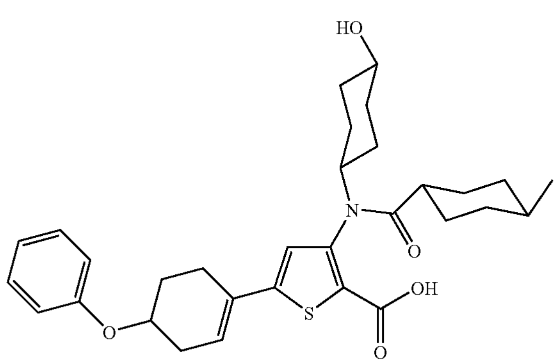 | | |

TABLE 1-continued

List of compounds in accordance with the present invention

| Compound# | Structure | m/z* (M + H)+ | IC50 |
|---|---|---|---|
| 153 | 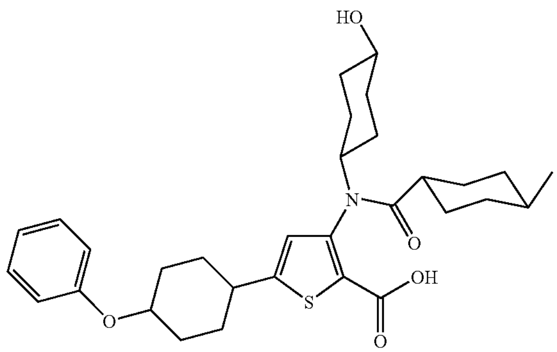 | | |
| 154 | 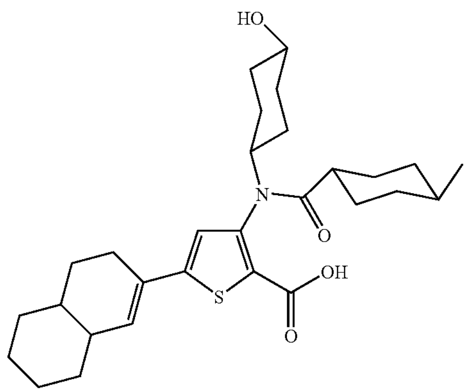 | | |
| 155 | 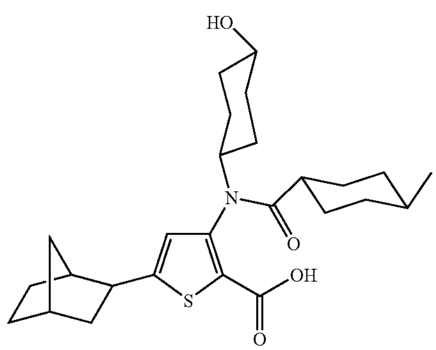 | | |
| 156 | 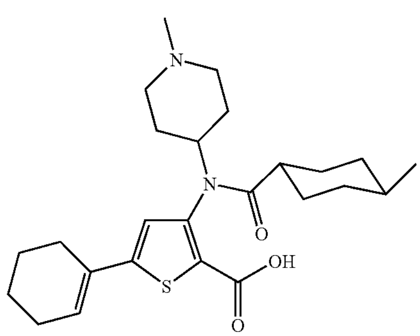 | | |

TABLE 1-continued

List of compounds in accordance with the present invention

| Compound# | Structure | m/z* (M + H)⁺ | IC50 |
|---|---|---|---|
| 157 | 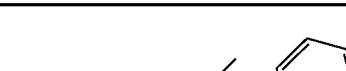 | | |

*mass spectral analysis are recorded using electrospray mass spectrometry. Unless otherwise specified are mass spectral data are (M + H)⁺.

EXAMPLE 51

Evaluation of Compounds in The HCV RNA-Dependent RNA Polymerase Assay

The following references are all incorporated by reference:
1. Behrens, S., Tomei, L., De Francesco, R. (1996) *EMBO* 15, 12-22
2. Harlow, E, and lane, D. (1988) *Antibodies: A Laboratory Manual*. Cold Spring Harbord Laboratory. Cold Spring Harbord. NY.
3. Lohmann, V., Körner, F., Herian, U., and Bartenschlager, R. (1997) *J. Virol.* 71, 8416-8428
4. Tomei, L., Failla, C., Santolini, E., De Francesco, R., and La Monica, N. (1993) *J Virol* 67, 4017-4026

Compounds were evaluated using an in vitro polymerase assay containing purified recombinant HCV RNA-dependent RNA polymerase (NS5B protein). HCV NS5B was expressed in insect cells using a recombinant baculovirus as vector. The experimental procedures used for the cloning, expression and purification of the HCV NS5B protein are described below. Follows, are details of the RNA-dependent RNA polymerase assays used to test the compounds.

Expression of the HCV NS5B Protein in Insect Cells:

The cDNA encoding the entire NS5B protein of HCV-Bk strain, genotype 1b, was amplified by PCR using the primers NS5Nhe5' (5'-GCTAGCGCTAGCTCAATGTCCTACACATGG-3') and XhoNS53' (5'-CTCGAGCTCGAGCGTCCATCGGTTGGGGAG-3') and the plasmid pCD 3.8-9.4 as template (Tomei et al, 1993). NS5Nhe5' and XhoNS53' contain two NheI and XhoI sites (underlined sequences), respectively, at their 5' end. The amplified DNA fragment was cloned in the bacterial expression plasmid pET-21b (Novagen) between the restriction sites NheI and XhoI, to generate the plasmid pET/NS5B. This plasmid was later used as template to PCR-amplify the NS5B coding region, using the primers NS5B-H9 (5'-ATACATATGGCTAGCATGTCAATGTCCTACACATGG-3') and NS5B-R₄ (5'-GGATCCGGATCCCGTTCATCGGTTGGGGAG-3'). NS5B-H9 spans a region of 15 nucleotides in the plasmid pET-21 b followed by the translation initiation codon (ATG) and 8 nucleotides corresponding to the 5' end of the NS5B coding region (nt. 7590-7607 in the HCV sequence with the accession number M58335). NS5B-R₄ contains two BamHI sites (underlined) followed by 18 nucleotides corresponding to the region around the stop codon in the HCV genome (nt. 9365-9347). The amplified sequence, of 1.8 kb, was digested with NheI and BamHI and ligated to a predigested pBlue-BacII plasmid (Invitrogen). The resulting recombinant plasmid was designated pBac/NS5B. Sf9 cells were co-transfected with 3 μg of pBac/NS5B, together with 1 μg of linearized baculovirus DNA (Invitrogen), as described in the manufacturer's protocol. Following two rounds of plaque purification, an NS5B-recombinant baculovirus, BacNS5B, was isolated. The presence of the recombinant NS5B protein was determined by western blot analysis (Harlow and lane, 1988) of BacNS5B-infected Sf9 cells, using a rabbit polyclonal antiserum (anti-NS5B) raised against a His-tagged version of the NS5B protein expressed in *E. coli*. Infections of Sf9 cells with this plaque purified virus were performed in one-liter spinner flasks at a cell density of 1.2×10⁶ cells/ml and a multiplicity of infection of 5.

Preparation of a Soluble Recombinant NS5B Protein:

Sf9 cells were infected as described above. Sixty hours post-infection, cells were harvested then washed twice with phosphate buffer saline (PBS). Total proteins were solubilized as described in Lohmann et al. (1997) with some modifications. In brief, proteins were extracted in three steps, S1, S2, S3, using lysis buffers (LB) I, LB II and LB III (Lohmann et al, 1997). The composition of LBII was modified to contain 0.1% triton X-100 and 150 mM NaCl to reduce the amount of solubilized NS5B protein at this step. In addition, sonication of cell extracts was avoided throughout the protocol to preserve the integrity of the protein structure.

Purification of Recombinant NS5B Using Fast Protein Liquid Chromatography (FPLC):

Soluble NS5B protein in the S3 fraction was diluted to lower the NaCl concentration to 300 mM, then it incubated batchwise with DEAE sepharose beads (Amersham-Pharmacia) for 2 hrs at 4° C., as described by Behrens et al. (1996). Unbound material was cleared by centrifugation for 15 min at 4° C., at 25 000 rpm using a SW41 rotor (Beckman). The supernatant was further diluted to lower the NaCl concentration to 200 mM and subsequently loaded, with a flow rate of 1 ml/min, on a 5 ml HiTrap® heparin column (Amersham-Pharmacia) connected to an FPLC® system (Amersham-Pharmacia). Bound proteins were eluted in 1 ml fractions, using a continuous NaCl gradient of 0.2 to 1 M, over a 25 ml volume. NS5B-containing fractions were identified by sodium dodecyl sulfate polyacrylamide gel electrophoresis (SDS-PAGE), followed by western blotting using the anti-NS5B antiserum at a dilution of 1:2000. Positive fractions were pooled and the elution buffer was exchanged against a 50 mM NaPO$_4$ pH 7.0, 20% glycerol, 0.5% triton X-100 and 10 mM DTT, using a PD-10 column (Amersham-Pharmacia). The sample was then loaded onto a 1 ml HiTrap® SP column (Amersham-Pharmacia), with a flow rate of 0.1 ml/min. Bound proteins were eluted using a continuous 0 to 1 M NaCl gradient over a 15 ml volume. Eluted fractions were analyzed by SDS-PAGE and western blotting. Alternatively, proteins were visualized, following SDS-PAGE, by silver staining using the Silver Stain Plus kit (BioRad) as described by the manufacturer. Positive fractions were tested for RhRp activity (see below) and the most active ones were pooled, and stored as a 40% glycerol solution at −70° C.

In Vitro HCV RhRp Flashplate Scintillation Proximity Assay (STREP-FLASH ASSAY) Used to Evaluate Analogues:

This assay consists on measuring the incorporation of [$^3$H] radiolabelled UTP in a polyrA/biotinylated-oligo dT template-primer, captured on the surface of streptavidin-coated scintillant-embeded microtiter Flashplates™ (NEN Life Science Products inc, MA, USA, SMP 103A). In brief, a 400 ng/µl polyrA solution (Amersham Pharmacia Biotech) was mixed volume-to-volume with 5' biotin-oligo dT$_{15}$ at 20 pmol/µl. The template and primers were denatured at 95 C for 5 minutes then incubated at 37 C for 10 minutes. Annealed template-primers were subsequently diluted in a Tris-HCl containing buffer and allowed to bind to streptavidin-coated flashplates overnight. Unbound material was discarded, compounds were added in a 10 µl solution followed by a 10 µl of a solution containing 50 mM MgCl$_2$, 100 mM Tris-HCl pH 7.5, 250 mM NaCl and 5 mM DTT. The enzymatic reaction was initiated upon addition of a 30 µl solution containing the enzyme and substrate to obtain the following concentrations: 25 µM UTP, 1 µCi [$^3$H] UTP and 100 nM recombinant HCV NS5B. RhRp reactions were allowed to proceed for 2 hrs at room temperature after which wells were washed three times with a 250 µL of 0.15 M NaCl solution, air dried at 37 C, and counted using a liquid scintillation counter (Wallac Microbeta Trilex, Perkin-Elmer, MA, USA).

EXAMPLE 52

Cell-Based Luciferase Reporter HCV RNA Replication Assay Cell Culture

Replicon cell lines Huh-7, 5.2 and ET which are derived from the Huh-7 hepatocarcinoma cell line were maintained in culture as generally described in Krieger, N; Lohmann, V; Bartenschlager, R. Enhancement of hepatitis C virus RNA replication by cell culture-adaptive mutations. *J. Virol.* 2001, 75, 4614-4624. The Huh-7, 5.2 cells contain the highly cell culture-adapted replicon I$_{389}$luc-ubi-neo/NS3-3'/5.1 construct that carries, in addition to the neomycin gene, an integrated copy to the firefly luciferase gene (Krieger, N; Lohmann, V; Bartenschlager, R. Enhancement of hepatitis C virus RNA replication by cell culture-adaptive mutations. *J. Virol.* 2001, 75, 4614-4624). This cell line allows measurement of HCV RNA replication and translation by measuring luciferase activity. It has been previously shown that the luciferase activity tightly follows the replicon RNA level in these cells (Krieger, N; Lohmann, V; Bartenschlager, R. Enhancement of hepatitis C virus RNA replication by cell culture-adaptive mutations. *J. Virol.* 2001, 75, 4614-4624). The Huh-7, ET cell line has the same features as those mentioned for Huh-7, 5.2 cell line, except that ET cells are more robust and contain an adaptative mutation in the HCV NS4B gene instead of NS5A. Both cell lines were maintained in cultures at a sub-confluent level (<85%) as the level of replicon RNA is highest in actively proliferating cells. The culture media used for cell passaging consist of DMEM (Gibco BRL Laboratories, Mississauga, ON, Canada) supplemented with 10% foetal bovine serum with 1% penicilin/streptomycin, 1% glutamine, 1% sodium pyruvate, 1% non-essential amino acids, and 350 ug/ml of G418 final concentration. Cells were incubated at 37° C., in an atmosphere of 5% CO$_2$ and passaged twice a week to maintain sub-confluence.

Approximately 3000 viable Huh-7, 5.2 or ET cells (100 µl) were plated per well in a white opaque 96-well microtiter plate. The cell culture media used for the assay was the same as described above except that it contains no G418 and no phenol red. After an incubation period of 3-4 hours at 37° C. in a 5% CO$_2$ incubator, compounds (100 µl) were added at various concentrations. Cells were then further incubated for 4 days at 37° C. in a 5% CO$_2$ incubator. Thereafter, the culture media was removed and cells were lysed by the addition of 95 µl of the luciferase buffer (luciferin substrate in buffered detergent). Cell lysates were incubated at room temperature and protected from direct light for at least 10 minutes. Plates were read for luciferase counts using a luminometer (Wallac MicroBeta Trilux, Perkin Elmer™, MA, USA).

The 50% inhibitory concentrations (IC$_{50}$s) for inhibitory effect was determined from dose response curves using eleven concentrations per compound in duplicate. Curves were fitted to data points using nonlinear regression analysis, and IC$_{50}$s were interpolated from the resulting curve using GraphPad Prism software, version 2.0 (GraphPad Software Inc., San Diego, Calif., USA).

Table 1 lists compounds representative of the invention. Most Compounds listed in table 1 were tested for Cell-Based Luciferase Reporter HCV RNA Replication Assay Cell Culture and activity is included in the table as follows:

A: IC50 below 5 µM
B: IC50 between 5 µM and 25 µM
C: IC50 above 25 µM

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A thiophene compound according to formula IB:

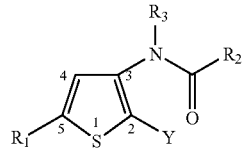

(IB)

wherein:

R$_1$ is optionally substituted C$_{3-12}$ cycloalkyl, optionally substituted C$_{4-12}$ cycloalkenyl, optionally substituted —C(O)—C$_{3-12}$ cycloalkyl, optionally substituted —C(O)—C$_{4-12}$ cycloalkenyl, optionally substituted 5 to 12 member spiroheterocycloalkyl, or optionally substituted 8 to 12 member spiroheterocycloalkenyl, wherein when R$_1$ is optionally substituted 5 to 12 member spiroheterocycloalkyl the cycloalkyl moiety is directly attached to the 5-position of the thiophene ring, and when R$_1$ is optionally substituted 8 to 12 member spiroheterocycloalkenyl the cycloalkenyl moiety is directly attached to the 5-position of the thiophene ring;

R$_2$ and R$_3$ are each independently H, optionally substituted C$_{1-12}$ alkyl, optionally substituted C$_{2-12}$ alkenyl, optionally substituted C$_{2-12}$ alkynyl, optionally substituted C$_{6-14}$ aryl, optionally substituted C$_{7-16}$ aralkyl, optionally substituted 5-12 member heteroaryl, optionally substituted 6-18 member heteroaralkyl, optionally substituted 3-12 member heterocycle, or optionally substituted 4-18 member heterocycle-alkyl;

Y is COOR$_9$, COCOOR$_9$, P(O)OR$_a$OR$_b$, S(O)OR$_9$, S(O)$_2$OR$_9$, tetrazole, CON(R$_9$)CH(R$_9$)COOR$_9$, CONR$_{10}$R$_{11}$, CON(R$_9$)—SO$_2$—R$_9$, CONR$_9$OH, or halogen;

R$_9$, R$_{10}$ and R$_{11}$ are each independently H, optionally substituted C$_{1-12}$ alkyl, optionally substituted C$_{2-12}$ alkenyl, optionally substituted C$_{2-12}$ alkynyl, optionally substituted C$_{6-14}$ aryl, optionally substituted C$_{7-16}$ aralkyl, optionally substituted 5-12 member heteroaryl, optionally substituted 6-18 member heteroaralkyl, optionally substituted 3-12 member heterocycle, or optionally substituted 4-18 member heterocycle-alkyl, or R$_{10}$ and R$_{11}$ are taken together with the nitrogen atom to form an optionally substituted 3 to 10 member heterocycle or an optionally substituted 5-12 member heteroaryl; and R$_a$ and R$_b$ are each independently H, optionally substituted C$_{1-12}$ alkyl, optionally substituted C$_{2-12}$ alkenyl, optionally substituted C$_{2-12}$ alkynyl, optionally substituted C$_{6-14}$ aryl, optionally substituted C$_{7-16}$ aralkyl, optionally substituted 5-12 member heteroaryl, optionally substituted 6-18 member heteroaralkyl, optionally substituted 3-12 member heterocycle, or optionally substituted 4-18 member heterocycle-alkyl, or R$_a$ and R$_b$ are taken together with the oxygen atoms to form an optionally substituted 5 to 10 member heterocycle, or an optionally substituted 5-12 member heteroaryl; or a pharmaceutically acceptable salt thereof, a pharmaceutically acceptable solvate thereof, or a solvate of a pharmaceutically acceptable salt thereof.

2. A compound according to claim 1, wherein Y is COOH.

3. A compound according to claim 1, wherein, R$_a$, R$_b$, R$_9$, R$_{10}$, and R$_{11}$ are each independently H or optionally substituted C$_{1-6}$ alkyl.

4. A compound according to claim 1, wherein R$_a$, R$_b$, R$_9$, R$_{10}$, R$_{11}$ and R$_9$ are each H.

5. A compound according to claim 1 wherein

R$_1$ is C$_{3-12}$ cycloalkyl unsubstituted or substituted one or more times by R$_{17}$, C$_{4-12}$ cycloalkenyl unsubstituted or substituted one or more times by R$_{17}$, —C(O)—C$_{3-12}$ cycloalkyl unsubstituted or substituted one or more times by R$_{17}$, —C(O)—C$_{4-12}$ cycloalkenyl unsubstituted or substituted one or more times by R$_{17}$, 5 to 12 member spiroheterocycloalkyl unsubstituted or substituted one or more times by R$_{17}$, or 8 to 12 member spiroheterocycloalkenyl unsubstituted or substituted one or more times by R$_{17}$; and R$_{17}$ is halogen, oxo, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —C(O)H, —C(O)C$_{1-4}$ alkyl, carboxy, —C(O)O C$_{1-4}$ alkyl, hydroxyl, C$_{1-4}$ alkoxy, nitro, nitroso, azido, cyano, —S(O)$_{0-2}$H, —S(O)$_{0-2}$C$_{1-4}$ alkyl, —SO$_2$NH$_2$, —SO$_2$NH(C$_{1-4}$ alkyl), —SO$_2$N(C$_{1-4}$ alkyl)$_2$, —NHSO$_2$H, —N(C$_{1-4}$ alkyl)SO$_2$H, —N(C$_{1-4}$ alkyl)SO$_2$C$_{1-4}$ alkyl, or —NHSO$_2$C$_{1-4}$ alkyl.

6. A compound according to claim 1, wherein

R$_2$ is C$_{1-12}$ alkyl unsubstituted or substituted one or more times by R$_{17}$, C$_{2-12}$ alkenyl unsubstituted or substituted one or more times by R$_{17}$, C$_{2-12}$ alkynyl unsubstituted or substituted one or more times by R$_{17}$, C$_{6-14}$ aryl which is unsubstituted or substituted one or more times by R$_{18}$, C$_{7-16}$ aralkyl unsubstituted or substituted one or more times by R$_{18}$, 5-12 member heteroaryl unsubstituted or substituted one or more times by R$_{19}$, 6-18 member heteroaralkyl unsubstituted or substituted one or more times by R$_{19}$, 3-12 member heterocycle unsubstituted or substituted one or more times by R$_{20}$, or 4-18 member heterocycle-alkyl unsubstituted or substituted one or more times by R$_{20}$;

R$_{17}$ is halogen, oxo, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —C(O)H, —C(O)C$_{1-4}$ alkyl, carboxy, —C(O)O C$_{1-4}$ alkyl, hydroxyl, C$_{1-4}$ alkoxy, nitro, nitroso, azido, cyano, —S(O)$_{0-2}$H, —S(O)$_{0-2}$C$_{1-4}$ alkyl, —SO$_2$NH$_2$, —SO$_2$NH(C$_{1-4}$ alkyl), —SO$_2$N(C$_{1-4}$ alkyl)$_2$, —NHSO$_2$H, —N(C$_{1-4}$ alkyl)SO$_2$H, —N(C$_{1-4}$ alkyl)SO$_2$C$_{1-4}$ alkyl, or —NHSO$_2$C$_{1-4}$ alkyl;

R$_{18}$ is halogen, C$_{1-6}$ alkyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —C(O)H, —C(O)C$_{1-4}$ alkyl, carboxy, —C(O)O C$_{1-4}$ alkyl, hydroxyl, C$_{1-6}$ alkoxy, nitro, nitroso, azido, cyano, —S(O)$_{0-2}$H, —S(O)$_{0-2}$C$_{1-4}$ alkyl, —SO$_2$NH$_2$, —SO$_2$NH(C$_{1-4}$ alkyl), —SO$_2$N(C$_{1-4}$ alkyl)$_2$, —NHSO$_2$H, —N(C$_{1-4}$ alkyl)SO$_2$H, —N(C$_{1-4}$ alkyl)SO$_2$C$_{1-4}$ alkyl, —NHSO$_2$C$_{1-4}$ alkyl, 5-12 member heteroaryl unsubstituted or substituted by R$_{21}$, 6-18 member heteroaralkyl unsubstituted or substituted by R$_{21}$, 3-12 member heterocycle unsubstituted or substituted by R$_{17}$, or 4-18 member heterocycle-alkyl unsubstituted or substituted by R$_{17}$;

R$_{19}$ is halogen, C$_{1-6}$ alkyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —C(O)H, —C(O)C$_{1-4}$ alkyl, carboxy, —C(O)O C$_{1-4}$ alkyl, hydroxyl, C$_{1-6}$ alkoxy, nitro, nitroso, azido, cyano, —S(O)$_{0-2}$H, —S(O)$_{0-2}$C$_{1-4}$ alkyl, —SO$_2$NH$_2$, —SO$_2$NH(C$_{1-4}$ alkyl), —SO$_2$N(C$_{1-4}$ alkyl)$_2$, —NHSO$_2$H, —N(C$_{1-4}$ alkyl)SO$_2$H, —N(C$_{1-4}$ alkyl)SO$_2$C$_{1-4}$ alkyl, —NHSO$_2$C$_{1-4}$ alkyl, C$_{6-10}$ aryl unsubstituted or substituted by R$_{21}$, C$_{6-10}$ aryloxy unsubstituted or substituted by R$_{21}$, or C$_{7-10}$ arylalkyl unsubstituted or substituted by R$_{21}$;

R$_{20}$ is halogen, oxo, C$_{1-6}$ alkyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —C(O)H, —C(O)C$_{1-4}$ alkyl, carboxy, —C(O)O C$_{1-4}$ alkyl, hydroxyl, C$_{1-6}$ alkoxy, nitro, nitroso, azido, cyano, —S(O)$_{0-2}$H, —S(O)$_{0-2}$C$_{1-4}$ alkyl, —SO$_2$NH$_2$, —$SO_2NH(C_{1-4}$ alkyl), —$SO_2NC_{1-4}$ alkyl)$_2$, —$NHSO_2H$, —$N(C_{1-4}$ alkyl)$SO_2H$, —$N(C_{1-4}$ alkyl)$SO_2C_{1-4}$ alkyl, —$NHSO_2C_{1-4}$ alkyl, $C_{6-10}$ aryl unsubstituted or substituted by $R_{17}$, $C_{6-10}$ aryloxy unsubstituted or substituted by $R_{17}$, or $C_{7-10}$ arylalkyl unsubstituted or substituted by $R_{17}$; and $R_{21}$ is halogen, —$NH_2$, —$NH(C_{1-4}$ alkyl), —$N(C_{1-4}$ alkyl)$_2$, —$CONH_2$, —$CONH(C_{1-4}$ alkyl),—$CON(C_{1-4}$ alkyl)$_2$, —$NHCOH$, —$N(C_{1-4}$ alkyl)$COH$, —$N(C_{1-4}$ alkyl)$COC_{1-4}$ alkyl, —$NHCOC_{1-4}$ alkyl, —$C(O)H$, —$C(O)C_{1-4}$ alkyl, carboxy, —$C(O)O$ $C_{1-4}$ alkyl, hydroxyl, $C_{1-4}$ alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$NHSO_2H$, —$N(C_{1-4}$ alkyl)$SO_2H$, —$N(C_{1-4}$ alkyl)$SO_2C_{1-4}$ alkyl, or —$NHSO_2C_{1-4}$ alkyl.

7. A compound according to claim 1, wherein $R_3$ is $C_{1-12}$ alkyl unsubstituted or substituted one or more times by $R_{17}$, $C_{2-12}$ alkenyl unsubstituted or substituted one or more times by $R_{17}$, $C_{2-12}$ alkynyl unsubstituted or substituted one or more times by $R_{17}$, $C_{6-14}$ aryl which is unsubstituted or substituted one or more times by $R_{18}$, $C_{7-16}$ aralkyl unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{19}$, or 4-18 member heterocycle-alkyl unsubstituted or substituted one or more times by $R_{19}$;

$R_{17}$ is halogen, oxo, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —$NHCOH$, —$N(C_{1-4}$ alkyl)$COH$, —$N(C_{1-4}$ alkyl)$COC_{1-4}$ alkyl, —$NHCOC_{1-4}$ alkyl, —$C(O)H$, —$C(O)C_{1-4}$ alkyl, carboxy, —$C(O)O$ $C_{1-4}$ alkyl, hydroxyl, $C_{1-4}$ alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$NHSO_2H$, —$N(C_{1-4}$ alkyl)$SO_2H$, —$N(C_{1-4}$ alkyl)$SO_2C_{1-4}$ alkyl, or —$NHSO_2C_{1-4}$ alkyl;

$R_{18}$ is halogen, $C_{1-6}$ alkyl, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —$NHCOH$, —$N(C_{1-4}$ alkyl)$COH$, —$N(C_{1-4}$ alkyl)$COC_{1-4}$ alkyl, —$NHCOC_{1-4}$ alkyl, —$C(O)H$, —$C(O)C_{1-4}$ alkyl, carboxy, —$C(O)O$ $C_{1-4}$ alkyl, hydroxyl, $C_{1-6}$ alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$NHSO_2H$, —$N(C_{1-4}$ alkyl)$SO_2H$, —$N(C_{1-4}$ alkyl)$SO_2C_{1-4}$ alkyl, —$NHSO_2C_{1-4}$ alkyl, 5-12 member heteroaryl unsubstituted or substituted by $R_{21}$, 6-18 member heteroaralkyl unsubstituted or substituted by $R_{21}$, 3-12 member heterocycle unsubstituted or substituted by $R_{17}$, or 4-18 member heterocycle-alkyl unsubstituted or substituted by $R_{17}$;

$R_{19}$ is halogen, $C_{1-6}$ alkyl, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —$NHCOH$, —$N(C_{1-4}$ alkyl)$COH$, —$N(C_{1-4}$ alkyl)$COC_{1-4}$ alkyl, —$NHCOC_{1-4}$ alkyl, —$C(O)H$, —$C(O)C_{1-4}$ alkyl, carboxy, —$C(O)O$ $C_{1-4}$ alkyl, hydroxyl, $C_{1-6}$ alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$NHSO_2H$, —$N(C_{1-4}$ alkyl)$SO_2H$, —$N(C_{1-4}$ alkyl)$SO_2C_{1-4}$ alkyl, —$NHSO_2C_{1-4}$ alkyl, $C_{6-10}$ aryl unsubstituted or substituted by $R_{21}$, $C_{6-10}$ aryloxy unsubstituted or substituted by $R_{21}$, or $C_{7-10}$ arylalkyl unsubstituted or substituted by $R_{21}$;

$R_{20}$ is halogen, oxo, $C_{1-6}$ alkyl, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —$NHCOH$, —$N(C_{1-4}$ alkyl)$COH$, —$N(C_{1-4}$ alkyl)$COC_{1-4}$ alkyl, —$NHCOC_{1-4}$ alkyl, —$C(O)H$, —$C(O)C_{1-4}$ alkyl, carboxy, —$C(O)O$ $C_{1-4}$ alkyl, hydroxyl, $C_{1-6}$ alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2NC_{1-4}$ alkyl)$_2$, —$NHSO_2H$, —$N(C_{1-4}$ alkyl)$SO_2H$, —$N(C_{1-4}$ alkyl)$SO_2C_{1-4}$ alkyl, —$NHSO_2C_{1-4}$ alkyl, $C_{6-10}$ aryl unsubstituted or substituted by $R_{17}$, $C_{6-10}$ aryloxy unsubstituted or substituted by $R_{17}$, or $C_{7-10}$ arylalkyl unsubstituted or substituted by $R_{17}$; and $R_{21}$ is halogen, —$NH_2$, —$NH(C_{1-4}$ alkyl), —$N(C_{1-4}$ alkyl)$_2$, —$CONH_2$, —$CONH(C_{1-4}$ alkyl),—$CON(C_{1-4}$ alkyl)$_2$, —$NHCOH$, —$N(C_{1-4}$ alkyl)$COH$, —$N(C_{1-4}$ alkyl)$COC_{1-4}$ alkyl, —$NHCOC_{1-4}$ alkyl, —$C(O)H$, —$C(O)C_{1-4}$ alkyl, carboxy, —$C(O)O$ $C_{1-4}$ alkyl, hydroxyl, $C_{1-4}$alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$NHSO_2H$, —$N(C_{1-4}$ alkyl)$SO_2H$, —$N(C_{1-4}$ alkyl)$SO_2C_{1-4}$ alkyl, or —$NHSO_2C_{1-4}$ alkyl.

8. A compound according to claim 1, wherein $R_3$ is cyclohexyl unsubstituted or substituted by one or more substituents independently chosen from halogen, $SO_2Rf$, $CONRgRh$, $C_{1-6}$ alkyl, $C_{7-12}$ aralkyl, $C_{6-12}$ aryl, $C_{1-6}$ alkyloxy, $C_{2-6}$ alkenyloxy, $C_{2-6}$ alkynyloxy, $C(O)C_{1-6}$ alkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NRgRh$, $C(O)ORf$ and cyano;

wherein Rf, Rg and Rh in each case are independently H, $C_{1-6}$ alkyl, $C_{2-6}$ alkenyl, or alkynyl.

9. A compound according to claim 1, wherein $R_3$ is cyclohexyl, N-methyl-4-piperidinyl, hydroxycyclohexyl, 4-hydroxycyclohexyl, methoxycyclohexyl, 4-methoxycyclohexyl, dioxolanyl, isopropyl, cyclopentyl, phenyl, H, methyl, benzyl, thiophenylmethyl, or furanylmethyl.

10. A compound according to claim 1, wherein $R_2$ is cyclopropyl, cyclobutyl, cyclopentyl, cyclopentenyl cyclohexyl, cycloheptyl, 2-(cyclopentyl)-ethyl, methyl, ethyl, vinyl, propyl, propenyl, isopropyl, butyl, butenyl isobutyl, pentyl, neopentyl or t-butyl, which in each case is optionally substituted by one or more substituents chosen from halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 3-18 member heteroaralkyl, and $C_{7-18}$ aralkyl, or Rc and Rd are taken together with the oxygen atoms to form an optionally substituted 5 to 10 member heterocycle or an optionally substituted 5-12 member heteroaryl, or $R_{13}$ and $R_{14}$ are taken together with the nitrogen atom to form an optionally substituted 3 to 10 member heterocycle or an optionally substituted 5-12 member heteroaryl.

11. A compound according to claim 1, wherein $R_2$ is cyclohexyl substituted by one or more substituents independently chosen from $C_{1-6}$ alkyl, halogen, $C_{2-6}$ alkenyl, $C_{2-6}$ alkynyl or $C_{1-6}$ alkyloxy, $C_{2-6}$ alkenyloxy, and $C_{2-6}$ alkynyloxy.

12. A compound according to claim 1, wherein $R_1$ is $C_{5-7}$ cycloalkyl or $C_{5-7}$ cycloalkenyl, which in each case is unsubstituted or substituted by one or more substituents chosen from halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl, or Rc and Rd are taken together with the oxygens to form an optionally substituted 5 to 10 member heterocycle or an optionally substituted 5-12 member heteroaryl, or $R_{13}$ and $R_{14}$ are taken together with the nitrogen to form an optionally substituted 3 to 10 member heterocycle or an optionally substituted 5-12 member heteroaryl.

13. A compound according to claim 1, wherein $R_1$ is cyclopropyl, cyclobutyl, cyclopentyl, cyclohexyl cycloheptyl, cyclooctanyl, cyclocyclononanyl, cyclodecanyl, cycloundecanyl, cyclopentenyl, cyclohexenyl, cycloheptenyl, cyclooctenyl, cyclocyclononenyl, cyclodecenyl, cycloundecenyl, cyclopentadienyl, cyclohexadienyl, cycloheptadienyl, cyclooctadienyl, cyclodadienyl, cycloundecadienyl, bicyclohexyl, bicycloheptanyl, bicyclootanyl, bicyclocyclononanyl, bicyclodecanyl, bicycloundecanyl, bicyclohexenyl, bicycloheptenyl, bicyclooctenyl, bicyclocyclononenyl, bicyclodecenyl, and bicycloundecenyl;

each of which is unsubstituted or substituted by one or more substituent chosen from halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, 3-12 member heterocycle, 6-18 member heteroaralkyl, and $C_{7-18}$ aralkyl, or Rc and Rd are taken together with the oxygens to form an optionally substituted 5 to 10 member heterocycle or an optionally substituted 5-12 member heteroaryl, or $R_{13}$ and $R_{14}$ are taken together with the nitrogen to form an optionally substituted 3 to 10 member heterocycle or an optionally substituted 5-12 member heteroaryl.

14. A compound according to claim 1, wherein $R_1$ is cycloalkenyl, whererein the cycloalkenyl ring has one double bond.

15. A compound according to claim 14, wherein the double bond of the cycloalkenyl $R_1$ group is between the carbons in positions 1 and 2 of the ring.

16. A compound according to claim 5, wherein $R_1$ is cyclohexyl or cyclohexenyl which in each case is unsubstituted or substituted.

17. A compound according to claim 1, wherein $R_1$ is $C_{3-12}$ cycloalkyl unsubstituted or substituted one or more times by $R_{17}$, or $C_{4-12}$ cycloalkenyl which is unsubstituted or substituted one or more times by $R_{18}$;

$R_2$ is $C_{3-12}$ cycloalkyl unsubstituted or substituted one or more times by $R_{17}$, or $C_{6-14}$ aryl which is unsubstituted or substituted one or more times by $R_{18}$;

$R_3$ is $C_{1-12}$ alkyl unsubstituted or substituted one or more times by $R_{17}$, or $C_{6-14}$ aryl which is unsubstituted or substituted one or more times by $R_{18}$;

$R_{17}$ is halogen, oxo, $-NH_2$, $-NH(C_{1-4}$ alkyl), $-N(C_{1-4}$ alkyl)$_2$, $-CONH_2$, $-CONH(C_{1-4}$ alkyl), $-CON(C_{1-4}$ alkyl)$_2$, $-NHCOH$, $-N(C_{1-4}$ alkyl)COH, $-N(C_{1-4}$ alkyl)COC$_{1-4}$ alkyl, $-NHCOC_{1-4}$ alkyl, $-C(O)H$, $-C(O)C_{1-4}$ alkyl, carboxy, $-C(O)O$ $C_{1-4}$ alkyl, hydroxyl, $C_{1-4}$ alkoxy, nitro, nitroso, azido, cyano, $-S(O)_{0-2}H$, $-S(O)_{0-2}C_{1-4}$ alkyl, $-SO_2NH_2$, $-SO_2NH(C_{1-4}$ alkyl), $-SO_2N(C_{1-4}$ alkyl)$_2$, $-NHSO_2H$, $-N(C_{1-4}$ alkyl)SO$_2$H, $-N(C_{1-4}$ alkyl)SO$_2C_{1-4}$ alkyl, or $-NHSO_2C_{1-4}$ alkyl;

$R_{18}$ is halogen, $C_{1-6}$ alkyl, $-NH_2$, $-NH(C_{1-4}$ alkyl), $-N(C_{1-4}$ alkyl)$_2$, $-CONH_2$, $-CONH(C_{1-4}$ alkyl), $-CON(C_{1-4}$ alkyl)$_2$, $-NHCOH$, $-N(C_{1-4}$ alkyl)COH, $-N(C_{1-4}$ alkyl)COC$_{1-4}$ alkyl, $-NHCOC_{1-4}$ alkyl, $-C(O)H$, $-C(O)C_{1-4}$ alkyl, carboxy, $-C(O)O$ $C_{1-4}$ alkyl, hydroxyl, $C_{1-6}$ alkoxy, nitro, nitroso, azido, cyano, $-S(O)_{0-2}H$, $-S(O)_{0-2}C_{1-4}$ alkyl, $-SO_2NH_2$, $-SO_2NH(C_{1-4}$ alkyl), $-SO_2N(C_{1-4}$ alkyl)$_2$, $-NHSO_2H$, $-N(C_{1-4}$ alkyl)SO$_2$H, $-N(C_{1-4}$ alkyl)SO$_2C_{1-4}$ alkyl, $-NHSO_2C_{1-4}$ alkyl, 5-12 member heteroaryl unsubstituted or substituted by $R_{21}$, 6-18 member heteroaralkyl unsubstituted or substituted by $R_{21}$, 3-12 member heterocycle unsubstituted or substituted by $R_{17}$, or 4-18 member heterocycle-alkyl unsubstituted or substituted by $R_{17}$; and $R_{21}$ is halogen, $-NH_2$, $-NH(C_{1-4}$ alkyl), $-N(C_{1-4}$ alkyl)$_2$, $-CONH_2$, $-CONH(C_{1-4}$alkyl), $-CON(C_{1-4}$ alkyl)$_2$, $-NHCOH$, $-N(C_{1-4}$ alkyl)COH, $-N(C_{1-4}$ alkyl)COC$_{1-4}$ alkyl, $-NHCOC_{1-4}$ alkyl, $-C(O)H$, $-C(O)C_{1-4}$ alkyl, carboxy, $-C(O)O$ $C_{1-4}$ alkyl, hydroxyl, $C_{1-4}$ alkoxy, nitro, nitroso, azido, cyano, $-S(O)_{0-2}H$, $-S(O)_{0-2}C_{1-4}$ alkyl, $-SO_2NH_2$, $-SO_2NH(C_{1-4}$ alkyl), $-SO_2N(C_{1-4}$ alkyl)$_2$, $-NHSO_2H$, $-N(C_{1-4}$ alkyl)SO$_2$H, $-N(C_{1-4}$ alkyl)SO$_2C_{1-4}$ alkyl, or $-NHSO_2C_{1-4}$ alkyl.

18. A compound according to claim 1, wherein said compound is:

5-Cyclohex-1-enyl-3-[(trans-4-hydroxy-cyclohexyl)-cyclohexyl)-(trans-4-methyl -cyclohexanecarbonyl)-amino]-thiophene-2-carboxylic acid;

5-Cyclohexyl-3-[(trans-4-hydroxy-cyclohexyl)-(trans-4-methyl-cylohexanecarbonyl) -amino]-thiophene-2-carboxylic acid;

5-Cyclopent-1-enyl-3-[(trans-4-hydroxy-cyclohexyl)-(trans-4-methyl -cyclohexanecarbonyl)-amino]-thiophene-2-carboxylic acid;

3-[(trans-4-Hydroxy-cyclohexyl)-(trans-4-methyl-cyclohexanecarbonyl)-amino]-5-(4-methyl-cyclohex-1-enyl)-thiophene-2-carboxylic acid;

5-Cyclohept-1-enyl-3-[(trans-4-hydroxy-cyclohexyl)-(trans-4-methyl -cyclohexanecarbonyl)-amino]-thiophene-2-carboxylic acid;

5-Cycloheptyl-3-[(trans-4-hydroxy-cyclohexyl)-(trans-4-methyl-cyclohexanecarbonyl) -amino]-thiophene-2-carboxylic acid;

5-Cyclohex-1-enyl-3-[isopropyl-(trans-4-methyl-cyclohexanecarbonyl)-amino]-thiophene-2-carboxylic acid;

5-Cyclohex-1-enyl-3-[(trans-4-methyl-cyclohexanecarbonyl)-(4-oxo-cyclohexyl)-amino]-thiophene-2-carboxylic acid;

5-Cyclohex-1-enyl-3-[(cis-4-hydroxy-cyclohexyl)-(trans-4-methyl-cylohexanecarbonyl) -amino]-thiophene-2-carboxylic acid;

5-Cyclohex-1-enyl-3-[(trans-4-methyl-cyclohexanecarbonyl)-phenyl-amino]-thiophene-2-carboxylic acid;

5-Cyclohex-1-enyl-3-[cyclohexyl-(4-methyl-cyclohexanecarbonyl)-amino]-thiophene-2-carboxylic acid;

5-Cyclohex-1-enyl-3-[(trans-4-methoxy-cyclohexyl)-(4-methyl-cylohexanecarbonyl) -amino]-thiophene-2-carboxylic acid;

5-(4-Tert-butyl-cyclohex-1-enyl)-3-[(4-hydroxy-cyclohexyl)-(4-methyl -cyclohexanecarbonyl)-amino]-thiophene-2-carboxylic acid;

5-(1,4,Dioxa-spiro[4.5.]dec-7-en-8-yl)-3-[(4-hydroxy-cyclohexyl)-(4-methyl -cyclohexanecarbonyl)-amino]-thiophene-2-carboxylic acid;

5-Cyclopent-1-enyl-3-[(2,4-dichloro-benzoyl)-isopropyl-amino]-thiophene-2-carboxylic acid;

5-Cyclopent-1-enyl-3-[(4-hydroxy-cyclohexyl)-(4-methyl-cyclohexanecarbonyl)-amino]-thiophene-2-carboxylic acid;

5-(4,4-dimethyl-cyclohexyl)-3-[(cis-4-methoxy-cyclohexyl)-(trans-4-methyl -cyclohexanecarbonyl)-amino]-thiophene-2-carboxylic acid;

Morpholine-4-carboxylic acid, 4-[(2-carboxy-5-cyclohex-1-enyl-thiophene-yl)-(4-methyl -cyclohexanecarbonyl)-amino]-cyclohexyl ester;

5-Cyclohex-1-enyl-3-[[4-(1-methoxy2-methyl-propylcarbamoyloxy)-cyclohexyl]-(4-methyl-cyclohexanecarbonyl)-amino]-thiophene-2-carboxylic acid;

5-(4,4-Dimethyl-cyclohex-1-enyl)-3-[(4-methoxy-cyclohexyl)-(4-methyl -cyclohexanecarbonyl)-amino]-thiophene-2-carboxylic acid;

5-(4,4-Dimethyl-cyclohexyl)-3-[(4-methoxy-cyclohexyl)-(4-methyl -cyclohexanecarbonyl)-amino]-thiophene-2-carboxylic acid;

5-Cyclohex-1-enyl-3-[(4-ethoxy-cyclohexyl)-(4-methyl-cyclohexanecarbonyl)-amino]-thiophene-2-carboxylic acid;

5-Cyclohex-1-enyl-3-[(cis-4-methoxy-cyclohexyl)-(4-methyl-cylohexanecarbonyl) -amino]-thiophene-2-carboxylic acid;

5-Cyclohex-1-enyl-3-[(4-methoxymethoxy-cyclohexyl)-(4-methyl-cylohexanecarbonyl) -amino]-thiophene-2-carboxylic acid;

3-[(4-trans-hydroxy-cyclohexyl)-(4-trans-methyl-cyclohexanecarbonyl)-amino]-5-(4-oxo -cyclohex-1-enyl)-thiophene-2-carboxylic acid;

5-{4-benzyloxyimino-cyclohex-1-enyl}-3-[(4-trans-hydroxy-cyclohexyl)-(4-trans-methyl -cyclohexanecarbonyl)-amino]-thiophene-2-carboxylic acid;

5-{4-ethoxyimino-cyclohex-1-enyl}-3-[(4-trans-hydroxy-cyclohexyl)-(4-trans-methyl -cyclohexanecarbonyl)-amino]-thiophene-2-carboxylic acid;

5-bicyclo[2.2.1]hept-2-en-2-yl-3-[(4-trans-hydroxy-cyclohexyl)-(4-trans-methyl -cyclohexanecarbonyl)-amino]-thiophene-2-carboxylic acid;

5-cyclohex-1-enyl-3-[(trans-4-methyl-cyclohexanecarbonyl)-(tetrahydro-pyran-4-yl) -amino]-thiophene-2-carboxylic acid;

5-cyclohex-1-enyl-3-[[1,3]dioxan-5-yl-(trans-4-methyl cyclohexanecarbonyl)-amino]-thiophene-2-carboxylic acid;

5-cyclohex-1-enyl-3-[(2,4-dichloro-benzoyl)-isopropyl-amino]-thiophene-2-carboxylic acid;

5-cyclohex-1-enyl-3-[(1,3-dimethyl-2,4-dioxo-1,3-diaza-spiro [4.5]dec-8-yl)-(trans-4-methyl-cyclohexanecarbonyl)-amino]-thiophene-2-carboxylic acid;

3-[(trans-4-hydroxy-cyclohexyl)-(trans-4-methyl-cyclohexanecarbonyl)-amino]-5-(4-phenoxy-cyclohex-1-enyl)-thiophene-2-carboxylic acid;

RS-5-(4-hydroxy-cyclohex-1-enyl)-3-[(4-trans-hydroxy-cyclohexyl)-(4-trans-methyl -cyclohexanecarbonyl)-amino]-thiophene-2-carboxylic acid;

5-(4,4-dimethyl-cyclohex-1-enyl)-3-[(trans-4-hydroxy-cyclohexyl)-(trans-4-methyl -cyclohexanecarbonyl)-amino]-thiophen e-2-carboxylic acid;

5-cyclohex-1-enyl-3-[(trans-4-methyl-cyclohexanecarbonyl)-(2-methyl-[1,3]dioxan-5-yl) -amino]-thiophene-2-carboxylic acid;

5-cyclohex-1-enyl-3-[methyl-(trans-4-methyl-cyclohexanecarbonyl)-amino]-thiophene-2-carboxylic acid;

5-cyclohex-1-enyl-3-[(4,4-dimethyl-cyclohexyl)-(trans-4-methyl-cylohexanecarbonyl) -amino]-thiophene-2-carboxylic acid;

5-cyclohex-1-enyl-3-[(trans-4-methyl-cyclohexanecarbonyl)-(3-methyl-cyclohexyl) -amino]-thiophene-2-carboxylic acid;

3-[bicyclo[3.2.1]oct-3-yl-(trans-4-methylcyclohexanecarbonyl)-amino]-5-cyclohex-1-enyl-thiophene-2-carboxylic acid;

5-cyclohex-1-enyl-3-[(trans-4-methyl-cyclohexanecarbonyl)-(cis4-[1,2,4]triazol-1-yl -cyclohexyl)-amino]-thiophene-2-carboxylic acid;

5-cyclohex-1-enyl-3-[(trans-4-methyl-cyclohexanecarbonyl)-(tetrahydrothiopyran-4-yl) -amino]-thiophene-2-carboxylic acid;

3-[isopropyl-(trans-4-methyl-cyclohexanecarbonyl)-amino]-5-(4-methyl-cyclohex-1-enyl)-thiophene-2-carboxylic acid;

3-[(4-trans-tert-butyl-cyclohexyl)-(4-trans-methyl-cyclohexanecarbonyl)-amino]-5-cyclohex-1-enyl-thiophene-2-carboxylic acid;

3-[(4-cis-tert-butyl-cyclohexyl)-(4-trans-methyl-cyclohexanecarbonyl)-amino]-5-cyclohex-1-enyl-thiophene-2-carboxylic acid;

5-cyclohept-1-enyl-3-[cyclohexyl-(4-trans-methyl-cyclohexanecarbonyl)-amino]-thiophene-2-carboxylic acid;

RS-3-[cyclohexyl-(4-trans-methyl-cyclohexanecarbonyl)-amino]-5-(4-methyl-cyclohex-1-enyl)-thiophene-2-carboxylic acid;

5-cyclohex-1-enyl-3-[(trans-4-methylcyclohexanecarbonyl)-(trans-4-[1,2,4]triazol-1-yl -cyclohexyl)-amino]-thiophene-2-carboxylic acid;

3-[(cis-4-cyanocyclohexyl)-(trans-4-methylcyclohexanecarbonyl)-amino]-5-cyclohex-1-enyl-thiophene-2-carboxylic acid;

3-[(trans-4-cyanocyclohexyl)-(trans-4-methyl-cyclohexanecarbonyl)-amino]-5-cyclohex -1-enyl-thiophene-2-carboxylic acid;

5-cyclohex-1-enyl-3-[cyclopropyl-(trans-4-methyl-cyclohexanecarbonyl)-amino]-thiophene-2-carboxylic acid;

5-cyclohex-1-enyl-3-[(trans-4-methyl-cyclohexanecarbonyl)-(trans-4-methyl-cyclohexyl)-amino]-thiophene-2-carboxylic acid;

5-cyclohex-1-enyl-3-[(trans-4-methyl-cyclohexanecarbonyl)-(cis-4-methyl-cyclohexyl)-amino]-thiophene-2-carboxylic acid;

5-cyclohex-1-enyl-3-[(4-ethoxyimino-cyclohexyl)-(trans-4-methyl-cylohexanecarbonyl)-amino]-thiophene-2-carboxylic acid;

5-(3-hydroxy-cyclohex-1-enyl)-3-{(trans-4-methyl-cyclohexanecarbonyl)-[trans-4-(tetrahydro-pyran-2-yloxy)-cyclohexyl]-amino}-thiophene-2-carboxylic acid;

4-[(2-carboxy-5-cyclohex-1-enyl-thiophen-3-yl)-(trans-4-methyl-cylohexanecarbonyl)-amino]-1-methyl-piperidinium 5-cyclohex-1-enyl-3-[(cis-4-fluoro-cyclohexyl)-(trans-4-methyl-cylohexanecarbonyl)-amino]-thiophene-2-carboxylic acid;

RS-3-[(4-trans-methyl-cyclohexanecarbonyl)-(4-oxo-cyclohexyl)-amino]-5-(2-methyl -cyclohex-2-enyl)-thiophene-2-carboxylic acid;

RS-3-[(4-trans-methyl-cyclohexanecarbonyl)-(4-oxo-cyclohexyl)-amino]-5-(6-methyl -cyclohex-1-enyl)-thiophene-2-carboxylic acid;

RS-3-[(4-trans-hydroxy-cyclohexyl)-(4-trans-methyl-cyclohexanecarbonyl)-amino]-5-(6-methyl-cyclohex-1-enyl)-thiophene-2-carboxylic acid;

RS-3-[(4-trans-hydroxy-cyclohexyl)-(4-trans-methyl-cyclohexanecarbonyl)-amino]-5-(5-methyl-cyclohex-1-enyl)-thiophene-2-carboxylic acid;

5-cyclohex-1-enyl-3-{(trans-4-methyl-cyclohexanecarbonyl)-[trans-4-(1-tetrazol-5-yl) -cyclohexyl]-amino}-thiophene-2-carboxylic acid;

5-cyclohex-1-enyl-3-[(trans-4-methyl-cyclohexanecarbonyl)-(1-oxo-hexahydro-1-thiopyran-4-yl)-amino]-thiophene-2-carboxylic acid;

5-(4,4-dimethyl-cyclohexyl)-3-[(trans-4-hydroxy-cyclohexyl)-(trans-4-methyl -cyclohexanecarbonyl)-amino]-thiophene-2-carboxylic acid;

5-cyclohex-1-enyl-3-[(cis/trans-decahydro-naphthalen-2-yl)-(4trans-methyl -cyclohexanecarbonyl)-amino]-thiophene-2-carboxylic acid;

RS-5-cyclohex-1-enyl-3-[(4-trans-methyl-cyclohexanecarbonyl)-(1,2,3,4-tetrahydro -naphthalen-2-yl)-amino]-thiophene-2-carboxylic acid;

RS-5-cyclohex-1-enyl-3-[(7-methoxy-1,2,3,4-tetrahydro-naphthalen-2-yl)-(4-trans -methyl-cyclohexanecarbonyl)-amino]-thiophene-2-carboxylic acid;

3-[(3-trans-carboxy-4-trans-methylcarbamoyl-cyclohexyl)-(4-trans-methyl -cyclohexanecarbonyl)-amino]-5-cyclohex-1-enyl-thiophene-2-carboxylic acid;

5-cyclohex-1-enyl-3-[(trans-4-methyl-cyclohexanecarbonyl)-(1-oxo-hexahydro-1-thiopyran-4-yl)-amino]-thiophene-2-carboxylic acid;

5-cyclohex-1-enyl-3-[(trans-4-fluoro-cyclohexyl)-(trans-4-methyl-cylohexanecarbonyl) -amino]-thiophene-2-carboxylic acid;

4-[(5-cyclohex-1-enyl-2-methoxycarbonyl-thiophen-3-yl)-(trans-4-methyl -cyclohexanecarbonyl)-amino]-1-methyl-piperidinium; chloride;

RS-5-cyclohex-1-enyl-3-[(4-trans-methyl-cyclohexanecarbonyl)-(2-methyl-1,3-dioxo -octahydro-isoindol-5-yl)-amino]-thiophene-2-carboxylic acid;

5-cyclohex-1-enyl-3-[cis-(1,3-dimethyl-2-oxo-1,3-diazaspiro [4.5]dec-8-yl)-(trans-4-methyl-cyclohexanecarbonyl)-amino]-thiophene-2-carboxylic acid;

5-cyclohex-1-enyl-3-[trans-(1,3-dimethyl-2-oxo-1,3-diaza-spiro[4.5]dec-8-yl)-(trans-4-methyl-cyclohexanecarbonyl)-amino]-thiophene-2-carboxylic acid;

5-(4,4-dimethyl-cyclohex-1-enyl)-3-[(1,3-dimethyl-2,4-dioxo-1,3-diaza-spiro [4.5]dec-8-yl)-(trans-4-methyl-cyclohexanecarbonyl)-amino]-thiophene-2-carboxylic acid;

5-Cyclohex-1-enyl-3-(2,4-dimethyl-benzenesulfonylamino)-thiophene-2-carboxylic acid 3-[(trans-4-hydroxy-cyclohexyl)-(trans-4-methyl-cyclohexanecarbonyl)-amino]-5-(trans -4-methyl-cyclohexyl)-thiophene-2-carboxylic acid;

3-[(trans-4-hydroxy-cyclohexyl)-(trans-4-methyl-cyclohexanecarbonyl)-amino]-5-(cis-4-methyl-cyclohexyl)-thiophene-2-carboxylic acid;

5-(4,4-dimethyl-cyclohexyl)-3-[(1,3-dimethyl-2,4-dioxo-1,3-diaza-spiro [4.5]dec-8-yl) -(trans-4-methyl-cyclohexanecarbonyl)-amino]-thiophene-2-carboxylic acid;

5-cyclohex-1-enyl-3-[(trans-4-methyl-cylohexanecarbonyl)-cis-(3-oxo-2-aza -spiro [4.5]dec-8-yl)-amino]-thiophene-2-carboxylic acid;

5-cyclohex-1-enyl-3-[(trans-4-methyl-cyclohexanecarbonyl)-trans-(3-oxo-2-aza -spiro [4.5]dec-8-yl)-amino]-thiophene-2-carboxylic acid;

5-(3-hydroxy-cyclohex-1-enyl)-3-[(trans-4-hydroxy-cyclohexyl)-(trans-4-methyl -cyclohexanecarbonyl)-amino]-thiophene-2-carboxylic acid;

5-(4,4-dimethyl-cyclohexyl)-3-[(trans-4-fluoro-cyclohexyl)-(trans-4-methyl -cyclohexanecarbonyl)-amino]-thiophene-2-carboxylic acid;

5-cyclohex-1-enyl-3-[(trans-4-methyl-cylohexanecarbonyl)-cis-(2-methyl-3-oxo-2-aza -spiro [4.5]dec-8-yl)-amino]-thiophene-2-carboxylic acid;

5-(4-cis/trans-hydroxy-cyclohexyl)-3-[(4-trans-hydroxy-cyclohexyl)-(4-trans-methyl -cyclohexanecarbonyl)-amino]-thiophene-2-carboxylic acid;

3-[(4-trans-hydroxy-cyclohexyl)-(4-trans-methyl-cyclohexanecarbonyl)-amino]-5-(4-oxo -cyclohexyl)-thiophene-2-carboxylic acid;

RS-5-cyclohex-1-enyl-3-[(4-trans-methyl-cyclohexanecarbonyl)-(3-oxo-octahydro -indolizin-7-yl)-amino]-thiophene-2-carboxylic acid;

4-[(2-carboxy-5-cyclohex-1-enyl-thiophen-3-yl)-(trans-4-methyl-cylohexanecarbonyl) -amino]-1,1-dimethyl-piperidinium;

4-[[5-cyclohex-1-enyl-2-(2,2-dimethyl-propionyloxymethoxycarbonyl)-thiophen-3-yl]-(trans-4-methyl-cyclohexanecarbonyl)-amino]-1-methyl-piperidinium chloride;

4-[(5-cyclohex-1-enyl-2-isopropoxycarbonyl oxymethoxycarbonyl-thiophen-3-yl)-(trans -4-methyl-cyclohexanecarbonyl)-amino]-1-methyl-piperidinium chloride;

5-cyclohex-1-enyl-3-[(4,4-difluoro-cyclohexyl)-(trans-4-methyl-cylohexanecarbonyl) -amino]-thiophene-2-carboxylic acid;

5-cyclohex-1-enyl-3-[[1-(2,2-difluoro-ethyl)-piperidin-4-yl]-(trans-4-methyl -cyclohexanecarbonyl)-amino]-thiophene-2-carboxylic acid;

5-(4,4-dimethyl-cyclohexyl)-3-[(trans-4-methyl-cyclohexanecarbonyl)-(1-methyl -piperidin-4-yl)-amino]-thiophene-2-carboxylic acid;

5-(4,4-dimethyl-cyclohex-1-enyl)-3-[(trans-4-methyl-cyclohexanecarbonyl)-cis-4-[1,2,4]triazol-1-yl-cyclohexyl)-amino]-thiophene-2-carboxylic acid;

5-(4,4-dimethyl-cyclohex-1-enyl)-3-[(trans-4-methyl-cyclohexanecarbonyl)-(trans-4-[1,2,4]triazol-1-yl-cyclohexyl)-amino]-thiophene-2-carboxylic acid;

5-cyclohex-1-enyl-3-[(trans, 4-methyl-cyclohexanecarbonyl)-(1-pyrimidin-5-yl -piperidin-4-yl)-amino]-thiophene-2-carboxylic acid;

5-(4,4-dimethyl-cyclohexyl)-3-[[1,3]dioxan-5-yl-(trans-4-methyl-cylohexanecarbonyl) -amino]-thiophene-2-carboxylic acid;

5-cyclohex-1-enyl-3-[(1-formyl-piperidin-4-yl)-(trans-4-methyl-cylohexanecarbonyl) -amino]-thiophene-2-carboxylic acid;

3-[(cis-4-cyano-4-methyl-cyclohexyl)-(trans-4-methyl-cyclohexanecarbonyl)-amino]-5-cyclohex-1-enyl-thiophene-2-carboxylic acid;

5-(4,4-dimethyl-cyclohexyl)-3-[(trans-4-methoxy-cyclohexyl)-(trans-4-methyl -cyclohexanecarbonyl)-amino]-thiophene-2-carboxylate(s)-5-amino-1-carboxy-pentyl -ammonium;

5-cyclohex-1-enyl-3-[(1-methanesulfonyl-piperidin-4-yl)-(trans-4-methyl -cyclohexanecarbonyl)-amino]-thiophene-2-carboxylic acid;

3-[(1-cyano-piperidin-4-yl)-(trans, 4-methyl-cyclohexanecarbonyl)-amino]-5-cyclohex-1-enyl-thiophene-2-carboxylic acid;

5-cyclohex-1-enyl-3-[(trans, 4-methyl-cyclohexanecarbonyl)-(1-pyrimidin-2-yl-piperidin -4-yl)-amino]-thiophene-2-carboxylic acid;

5-cyclohex-1-enyl-3-[(trans-4-methyl-cyclohexanecarbonyl)-(cis-4-[1,2,3]triazol-1-yl -cyclohexyl)-amino]-thiophene-2-carboxylic acid;

5-cyclohex-1-enyl-3-[(trans-4-methyl-cyclohexanecarbonyl)-(trans-4-[1,2,3]triazol-1-yl -cyclohexyl)-amino]-thiophene-2-carboxylic acid;

3-[(trans-4-cyano-4-methyl-cyclohexyl)-(trans-4-methyl-cyclohexanecarbonyl)-amino]-5-cyclohex-1-enyl-thiophene-2-carboxylic acid;

5-cyclohex-1-enyl-3-[(trans, 4-methyl-cyclohexanecarbonyl)-piperidin-4-yl-amino]-thiophene-2-carboxylic acid;

3-[(trans-4-methoxy-cyclohexyl)-(trans-4-methyl-cyclohexanecarbonyl)-amino]-5-(4-trifluoromethyl-cyclohexyl)-thiophene-2-carboxylic acid;

5-(4,4-dimethyl-cyclohexyl)-3-[(trans-4-methoxy-cyclohexyl)-(trans-4-methyl -cyclohexanecarbonyl)-amino]-thiophene-2-carboxylatemethyl-((2s,3r,4r,5r)-2,3,4,5,6-pentahydroxy-hexyl)-ammonium;

5-(4,4-dimethyl-cyclohexyl)-3-[(trans-4-methoxy-cyclohexyl)-(trans-4-methyl -cyclohexanecarbonyl)-amino]-thiophene-2-carboxylate(2-hydroxy-ethyl)-trimethyl-ammonium;

5-cyclohex-1-enyl-3-[(2-methoxy-1-methoxymethyl-ethyl)-(trans-4-methyl -cyclohexanecarbonyl)-amino]-thiophene-2-carboxylic acid;

5-cyclohexyl-3-[(4-trans-methoxy-cyclohexyl)-(4-trans-methyl-cylohexanecarbonyl) -amino]-thiophene-2-carboxylic acid;

3-[(4-trans-methoxy-cyclohexyl)-(4-trans-methyl-cyclohexanecarbonyl)-amino]-5-(4-oxo -cyclohexyl)-thiophene-2-carboxylic acid;

5-(4,4-dimethyl-cyclohex-1-enyl)-3-[(4-trans-methoxymethoxy-cyclohexyl)-(4-trans -methyl-cyclohexanecarbonyl)-amino]-thiophene-2-carboxylic acid;

RS-5-cyclohex-1-enyl-3-[cyclohex-3-enyl-(4-trans-methyl-cyclohexanecarbonyl)-amino]-thiophene-2-carboxylic acid;

5-(4,4-dimethyl-cyclohexyl)-3-[(4-trans-methoxymethoxy-cyclohexyl)-(4-trans-methyl -cyclohexanecarbonyl)-amino]-thiophene-2-carboxylic acid;

5-(4,4-dimethyl-cyclohexyl)-3-[(trans-4-methyl-cyclohexanecarbonyl)-(cis-4-[1,2,4]triazol-1-yl-cyclohexyl)-amino]-thiophene-2-carboxylic acid;

5-(4,4-dimethyl-cyclohexyl)-3-[(trans-4-methyl-cyclohexanecarbonyl)-(trans-4-[1,2,4]triazol-1-yl-cyclohexyl)-amino]-thiophene-2-carboxylic acid;

5-(2,6-difluoro-cyclohex-1-enyl)-3-[(trans-4-methoxy-cyclohexyl)-(trans-4-methyl -cyclohexanecarbonyl)-amino]-thiophene-2-carboxylic acid;

5-(2,3-difluoro-cyclohex-1-enyl)-3-[(trans-4-methoxy-cyclohexyl)-(trans-4-methyl -cyclohexanecarbonyl)-amino]-thiophene-2-carboxylic acid;

ammonium 5-cyclohex-1-enyl-3-[(4-methyl-cyclohexanecarbonyl)-(1-pyridin-3-ylmethyl -piperidin-4-yl)-amino]-thiophene-2-carboxylate;

5-(4,4-difluoro-cyclohexyl)-3-[(4-trans-methoxy-cyclohexyl)-(4-trans-methyl -cyclohexanecarbonyl)-amino]-thiophene-2-carboxylic acid;

RS-5-(4-fluoro-cyclohex-3-enyl)-3-[(4-trans-methoxy-cyclohexyl)-(4-trans-methyl -cyclohexanecarbonyl)-amino]-thiophene-2-carboxylic acid;

3-[(trans-4-methoxy-cyclohexyl)-(trans-4-methyl-cyclohexanecarbonyl)-amino]-5-(4-trifluoromethyl-cyclohex-1-enyl)-thiophene-2-carboxylic acid;

5-cyclohex-1-enyl-3-[(trans-4-ethoxymethoxy-cyclohexyl)-(trans-4-methyl -cyclohexanecarbonyl)-amino]-thiophene-2-carboxylic acid;

5-cyclohex-1-enyl-3-[(4-cis/trans-methoxymethyl-cyclohexyl)-(4-trans-methyl -cyclohexanecarbonyl)-amino]-thiophene-2-carboxylic acid;

5-cyclohex-1-enyl-3-[(trans, 4-methyl-cyclohexanecarbonyl)-(1-phenyl-piperidin-4-yl) -amino]-thiophene-2-carboxylic acid;

5-cyclohex-1-enyl-3-[(trans-4-methyl-cyclohexanecarbonyl)-trans(2-methyl-3-oxo-2-aza -spiro [4.5]dec-8-yl)-amino]-thiophene-2-carboxylic acid;

5-cyclohex-1-enyl-3-[trans(2-ethyl-3-oxo-2-aza-spiro [4.5]dec-8-yl)-(trans-4-methylcyclohexanecarbonyl)-amino]-thiophene-2-carboxylic acid;

5-cyclohex-1-enyl-3-[cis(2-ethyl-3-oxo-2-aza-spiro[4.5]dec-8-yl)-(trans-4-methylcyclohexanecarbonyl)-amino]-thiophene-2-carboxylic acid;

5-cyclohex-1-enyl-3-[(4-cis-methoxymethyl-cyclohexyl)-(4-trans-methyl -cyclohexanecarbonyl)-amino]-thiophene-2-carboxylic acid;

5-cyclohex-1-enyl-3-[(4-trans-methoxymethyl-cyclohexyl)-(4-trans-methyl -cyclohexanecarbonyl)-amino]-thiophene-2-carboxylic acid;

5-cyclohex-1-enyl-3-[(cis-4-isobutyrylamino-cyclohexyl)-(trans-4-methyl -cyclohexanecarbonyl)-amino]-thiophene-2-carboxylic acid;

5-cyclohex-1-enyl-3-[(trans-4-isobutyrylamino-cyclohexyl)-(trans-4-methyl -cyclohexanecarbonyl)-amino]-thiophene-2-carboxylic acid;

5-(4,4-dimethyl-cyclohexyl)-3-[(trans-4-methyl-cyclohexanecarbonyl)-(trans-4-[1,2,3]triazol-1-yl-cyclohexyl)-amino]-thiophene-2-carboxylic acid;

3-[benzo [1,3]dioxol-5-yl-(trans-4-methyl-cyclohexanecarbonyl)-amino]-5-cyclohex-1-enyl-thiophene-2-carboxylic acid;

5-(4-cis/trans-fluoro-cyclohexyl)-3-[(4-trans-methoxy-cyclohexyl)-(4-trans-methyl -cyclohexanecarbonyl)-amino]-thiophene-2-carboxylic acid;

5-(5,5-dimethyl-cyclohex-1-enyl)-3-[(4-trans-methoxy-cyclohexyl)-(4-trans-methyl -cyclohexanecarbonyl)-amino]-thiophene-2-carboxylic acid;

5-cyclohex-1-enyl-3-[[1-(2-fluoro-ethyl)-piperidin-4-yl]-(trans-4-methyl -cyclohexanecarbonyl)-amino]-thiophene-2-carboxylic acid;

5-cyclohex-1-enyl-3-{(trans-4-methyl-cyclohexanecarbonyl)-[4-(methyl-propionyl -amino)-cyclohexyl]-amino}-thiophene-2-carboxylic acid;

5-cyclohex-1-enyl-3-[(1-isobutyryl-piperidin-4-yl)-(trans-4-methyl -cyclohexanecarbonyl)-amino]-thiophene-2-carboxylic acid;

5-cyclohex-1-enyl-3-[(trans-4-methyl-cyclohexanecarbonyl)-(trans-4-methylsulfanylmethoxy-cyclohexyl)-amino]-thiophene-2-carboxylic acid;

3-[(4-trans-hydroxy-cyclohexyl)-(4-trans-methyl-cyclohexanecarbonyl)-amino]-thiophene-2-carboxylic acid;

5-bromo-3-[(trans-4-hydroxy-cyclohexyl)-(trans-4-methyl-cyclohexanecarbonyl)-amino]-thiophene-2-carboxylic acid;

3-[(trans-4-methoxy-cyclohexyl)-(trans-4-methyl-cyclohexanecarbonyl)-amino]-thiophene-2-carboxylic acid;

5-Cyclohex-2-enyl-3-[(trans-4-hydroxy-cyclohexyl)-(trans-4-methyl -cyclohexanecarbonyl)-amino]-thiophene-2-carboxylic acid;

5-Cyclohex-3-enyl-3-[(trans-4-hydroxy-cyclohexyl)-(trans-4-methyl -cyclohexanecarbonyl)-amino]-thiophene-2-carboxylic acid;

3-[(trans-4-Hydroxy-cyclohexyl)-(trans-4-methyl-cyclohexanecarbonyl)-amino]-5-(4-methyl-cyclohexyl)-thiophene-2-carboxylic acid;

3-[(trans-4-Hydroxy-cyclohexyl)-(trans-4-methyl-cyclohexanecarbonyl)-amino]-5-(4-methyl-cyclohex-2-enyl)-thiophene-2-carboxylic acid;

3-[(trans-4-Hydroxy-cyclohexyl)-(trans-4-methyl-cyclohexanecarbonyl)-amino]-5-(4-methyl-cyclohex-3-enyl)-thiophene-2-carboxylic acid;

3-[(trans-4-Hydroxy-cyclohexyl)-(trans-4-methyl-cyclohexanecarbonyl)-amino]-5-(4-phenyl-cyclohex-1-enyl)-thiophene-2-carboxylic acid;

3-[(trans-4-Hydroxy-cyclohexyl)-(trans-4-methyl-cyclohexanecarbonyl)-amino]-5-(4-phenoxy-cyclohex-1-enyl)-thiophene-2-carboxylic acid;

3-[(trans-4-Hydroxy-cyclohexyl)-(trans-4-methyl-cyclohexanecarbonyl)-amino]-5-(4-phenoxy-cyclohexyl)-thiophene-2-carboxylic acid;

3-[(trans-4-Hydroxy-cyclohexyl)-(trans-4-methyl-cyclohexanecarbonyl)-amino]-5-(3,4,4a, 5,6,7,8, 8a-octahydro-naphthalen-2-yl)-thiophene-2-carboxylic acid;

5-Bicyclo[2.2.1 ]hept-2-yl-3-[(trans-4-hydroxy-cyclohexyl)-(trans-4-methyl -cyclohexanecarbonyl)-amino]-thiophene-2-carboxylic acid;

5-Cyclohex-1-enyl-3-[(trans-4-methylcyclohexanecarbonyl)-(1-methyl-piperidin-4-yl) -amino]-thiophene-2-carboxylic acid;

5-Cyclohex-1-enyl-3-[isopropyl-(4-methyl-benzoyl)-amino]-thiophene-2-carboxylic acid; or a pharmaceutically acceptable salt thereof, a pharmaceutically acceptable solvate thereof, or a solvate of pharmaceutically acceptable salt thereof.

19. A compound according to claim 1, wherein said compound is:

5-Cyclohex-1-enyl-3-[(trans-4-hydroxy-cyclohexyl)-(trans-4-methyl-cylohexanecarbonyl) -amino]-thiophene-2-carboxylic acid;

5-Cyclohexyl-3-[(trans-4-hydroxy-cyclohexyl)-(trans-4-methyl-cylohexanecarbonyl) -amino]-thiophene-2-carboxylic acid;

5-Cyclopent-1-enyl-3-[(trans-4-hydroxy-cyclohexyl)-(trans-4-methyl-cyclohexanecarbonyl) -amino]-thiophene-2-carboxylic acid;

3-[(trans-4-Hydroxy-cyclohexyl)-(trans-4-methyl-cyclohexanecarbonyl)-amino]-5-(4-methyl -cyclohex-1-enyl)-thiophene-2-carboxylic acid;

5-Cyclohept-1-enyl-3-[(trans-4-hydroxy-cyclohexyl)-(trans-4-methyl-cylohexanecarbonyl) -amino]-thiophene-2-carboxylic acid;

5-Cycloheptyl-3-[(trans-4-hydroxy-cyclohexyl)-(trans-4-methyl-cylohexanecarbonyl) -amino]-thiophene-2-carboxylic acid;

5-Cyclohex-1-enyl-3-[isopropyl-(trans-4-methyl-cyclohexanecarbonyl)-amino]-thiophene-2-carboxylic acid;

5-Cyclohex-1-enyl-3-[(trans-4-methyl-cyclohexanecarbonyl)-(4-oxo-cyclohexyl)-amino]-thiophene-2-carboxylic acid;

5-Cyclohex-1-enyl-3-[(cis-4-hydroxy-cyclohexyl)-(trans-4-methyl-cylohexanecarbonyl) -amino]-thiophene-2-carboxylic acid;

5-Cyclohex-1-enyl-3-[(trans-4-methyl-cyclohexanecarbonyl)-phenyl-amino]-thiophene-2-carboxylic acid;

5-Cyclohex-1-enyl-3-[cyclohexyl-(4-methyl-cyclohexanecarbonyl)-amino]-thiophene-2-carboxylic acid;

5-Cyclohex-1-enyl-3-[(trans-4-methoxy-cyclohexyl)-(4-methyl-cylohexanecarbonyl) -amino]-thiophene-2-carboxylic acid;

5-(4-Tert-butyl-cyclohex-1-enyl)-3-[(4-hydroxy-cyclohexyl)-(4-methyl -cyclohexanecarbonyl)-amino]-thiophene-2-carboxylic acid;

5-(1,4,Dioxa-spiro[4.5.]dec-7-en-8-yl)-3-[(4-hydroxy-cyclohexyl)-(4-methyl -cyclohexanecarbonyl)-amino]-thiophene-2-carboxylic acid;

5-Cyclopent-1-enyl-3-[(2,4-dichloro-benzoyl)-isopropyl-amino]-thiophene-2-carboxylic acid;

5-Cyclopent-1-enyl-3-[(4-hydroxy-cyclohexyl)-(4-methyl-cyclohexanecarbonyl)-amino]-thiophene-2-carboxylic acid;

5-Cyclohex-2-enyl-3-[(trans-4-hydroxy-cyclohexyl)-(trans-4-methyl-cylohexanecarbonyl) -amino]-thiophene-2-carboxylic acid;

5-Cyclohex-3-enyl-3-[(trans-4-hydroxy-cyclohexyl)-(trans-4-methyl-cylohexanecarbonyl) -amino]-thiophene-2-carboxylic acid;

3-[(trans-4-Hydroxy-cyclohexyl)-(trans-4-methyl-cyclohexanecarbonyl)-amino]-5-(4-methyl -cyclohexyl)-thiophene-2-carboxylic acid;

3-[(trans-4-Hydroxy-cyclohexyl)-(trans-4-methyl-cyclohexanecarbonyl)-amino]-5-(4-methyl -cyclohex-2-enyl)-thiophene-2-carboxylic acid;

3-[(trans-4-Hydroxy-cyclohexyl)-(trans-4-methyl-cyclohexanecarbonyl)-amino]-5-(4-methyl -cyclohex-3-enyl)-thiophene-2-carboxylic acid;

3-[(trans-4-Hydroxy-cyclohexyl)-(trans-4-methyl-cyclohexanecarbonyl)-amino]-5-(4-oxo -cyclohex-1-enyl)-thiophene-2-carboxylic acid;

5-{4-[(Z)-Ethoxyimino]-cyclohex-1-enyl}-3-[(trans-4-hydroxycyclohexyl)(trans-4-methyl -cyclohexanecarbonyl)-amino]-thiophene-2-carboxylic acid;

3-[(trans-4-Hydroxy-cyclohexyl)-(trans-4-methyl-cyclohexanecarbonyl)-amino]-5-(4-phenyl-cyclohex-1-enyl)-thiophene-2-carboxylic acid;

3-[(trans-4-Hydroxy-cyclohexyl)-(trans-4-methyl-cyclohexanecarbonyl)-amino]-5-(4-phenoxy-cyclohex-1-enyl)-thiophene-2-carboxylic acid;

3-[(trans-4-Hydroxy-cyclohexyl)-(trans-4-methyl-cyclohexanecarbonyl)-amino]-5-(4-phenoxy-cyclohexyl)-thiophene-2-carboxylic acid;

3-[(trans-4-Hydroxy-cyclohexyl)-(trans-4-methyl-cyclohexanecarbonyl)-amino]-5-(3,4,4a, 5,6,7,8,8a-octahydro-naphthalen-2-yl)-thiophene-2-carboxylic acid;

5-Bicyclo[2.2.1]hept-2-en-2-yl-3-[(trans-4-hydroxy-cyclohexyl)-(trans-4-methyl-cyclohexanecarbonyl)-amino]-thiophene-2-carboxylic acid;

5-Bicyclo[2.2.1]hept-2-yl-3-[(trans-4-hydroxy-cyclohexyl)-(trans-4-methyl-cyclohexanecarbonyl)-amino]-thiophene-2-carboxylic acid;

5-Cyclohex-1-enyl-3-[[1,3]dioxan-5-yl-(trans-4-methyl-cyclohexanecarbonyl)-amino]-thiophene-2-carboxylic acid;

5-Cyclohex-1-enyl-3-[(trans-4-methylcyclohexanecarbonyl)-(1-methyl-piperidin-4-yl)-amino]-thiophene-2-carboxylic acid;

5-Cyclohex-1-enyl-3-[(1,3-dimethyl-2,4-dioxo-1,3-diaza-spiro[4.5]dec-8-yl)-(trans-4-methyl-cyclohexanecarbonyl)-amino]-thiophene-2-carboxylic acid Morpholine-4-carboxylic acid 4-[(2-carboxy-5-cyclohex-1-enyl-thiophen-3-yl)-(trans-4-methyl-cyclohexanecarbonyl)-amino]-cyclohexyl ester;

5-Cyclohex-1-enyl-3-[(2,4-dichloro-benzoyl)-isopropyl-amino]-thiophene-2-carboxylic acid;

5-Cyclohex-1-enyl-3-[isopropyl-(4-methyl-benzoyl)-amino]-thiophene-2-carboxylic acid;

5-Cyclohex-1-enyl-3-(2,4-dimethyl-benzenesulfonylamino)-thiophene-2-carboxylic acid; or a pharmaceutically acceptable salt thereof, a pharmaceutically acceptable solvate thereof, or a solvate of pharmaceutically acceptable salt thereof.

20. A pharmaceutical composition comprising at least one compound according to claim 1 and at least one pharmaceutically acceptable carrier or excipient.

21. A pharmaceutical combination comprising at least one compound according to claim 1 and at least one additional agent.

22. A pharmaceutical combination according to claim 21, wherein said at least one additional agent is selected from viral seine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

23. A pharmaceutical combination according to claim 22, wherein said at least one other antiviral agent is interferon α, ribavirin, silybum marianum, interleukine-12, amantadine, ribozyme, thymosin, N-acetyl cysteine or cyclosporin.

24. A method for treating a Flaviviridae viral infection in a host comprising administering to the host a therapeutically effective amount of at least one compound according to claim 1.

25. A method according to claim 24, wherein said viral infection is Hepatitis C viruS(HCV), bovine viral diarrhea viruS(BVDV), hog cholera virus, dengue fever virus, Japanese encephalitis virus or yellow fever virus.

26. A method according to claim 24, wherein said viral infection is Hepatitis C viral infection.

27. A method according to claim 24, further comprising administering at least one additional agent.

28. A method according to claim 27, wherein said at least one additional agent is selected from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

29. A method according to claim 28, wherein said at least one other antiviral agent is interferon α, ribavirin, silybum marianum, interleukine-12, amantadine, ribozyme, thymosin, N-acetyl cysteine or cyclosporin.

30. A method according to claim 1 wherein said compound and said at least one other antiviral agent are administered sequentially.

31. A method according to claim 27 wherein said compound and said at least one other antiviral agent are administered simultaneously.

32. A method for inhibiting or reducing the activity of viral polymerase in a host comprising administering to said host a therapeutically effective amount of a compound according to claim 1.

33. A method according to claim 32, further comprising administering one or more viral polymerase inhibitor.

34. A method according to claim 32, wherein said viral polymerase is a Flaviviridae viral polymerase.

35. A method according to claim 32, wherein said viral polymerase is a RNA-dependant RNA-polymerase.

36. A method according to claim 32, wherein said viral polymerase is HCV polymerase.

37. A method for inhibiting or reducing the activity of viral helicase in a host comprising administering to said host a therapeutically effective amount of a compound according to claim 1.

38. A compound according to claim 18, wherein said compound is:

5-Cyclohex-1-enyl-3-[cyclohexyl-(trans-4-methyl-cyclohexanecarbonyl)-amino]-thiophene-2-carboxylic acid;

5-Cyclohex-1-enyl-3-[(trans-4-methoxy-cyclohexyl)-(trans-4-methyl-cyclohexanecarbonyl)-amino]-thiophene-2-carboxylic acid;

5-(4-Tert-butyl-cyclohex-1-enyl)-3-[(trans-4-hydroxy-cyclohexyl)-(trans-4-methyl-cyclohexanecarbonyl)-amino]-thiophene-2-carboxylic acid;

5-(1,4,Dioxa-spiro[4.5.]dec-7-en-8-yl)-3-[(trans-4-hydroxy-cyclohexyl)-(trans-4-methyl-cyclohexanecarbonyl)-amino]-thiophene-2-carboxylic acid;

5-Cyclopent-1-enyl-3-[(trans-4-hydroxy-cyclohexyl)-(trans-4-methyl-cyclohexanecarbonyl)-amino]-thiophene-2-carboxylic acid;

5-Cyclohex-1-enyl-3-[[trans-4-morpholinocarbamoyloxy)-cyclohexyl]-(trans-4-methyl-cyclohexanecarbonyl)-amino]-thiophene-2-carboxylic acid;

5-Cyclohex-1-enyl-3-[[trans-4-(1-methoxycarbonyl-2-methyl-propylcarbamoyloxy)-cyclohexyl]-(trans-4-methyl-cyclohexanecarbonyl)-amino]-thiophene-2-carboxylic acid;

5-(4,4-Dimethyl-cyclohex-1-enyl)-3-[(trans-4-methoxy-cyclohexyl)-(trans-4-methyl-cyclohexanecarbonyl)-amino]-thiophene-2-carboxylic acid;

5-(4,4-Dimethyl-cyclohexyl)-3-[(trans-4-methoxy-cyclohexyl)-(trans-4-methyl-cyclohexanecarbonyl)-amino]-thiophene-2-carboxylic acid;

5-Cyclohex-1-enyl-3-[(trans-4-ethoxy-cyclohexyl)-(trans-4-methyl-cyclohexanecarbonyl)-amino]-thiophene-2-carboxylic acid;

5-Cyclohex-1-enyl-3-[(cis-4-methoxy-cyclohexyl)-(4-trans-methyl-cylohexanecarbonyl) -amino]-thiophene-2-carboxylic acid;

5-Cyclohex-1-enyl-3-[(trans-4-methoxymethoxy-cyclohexyl)-(trans-4-methyl -cyclohexanecarbonyl)-amino]-thiophene-2-carboxylic acid; or a pharmaceutically acceptable salt thereof, a pharmaceutically acceptable solvate thereof, or a solvate of pharmaceutically acceptable salt thereof.

39. A compound according to claim 19, wherein said compound is:

5-Cyclohex-1-enyl-3-[cyclohexyl-(trans-4-methyl-cyclohexanecarbonyl)-amino]-thiophene-2-carboxylic acid)

5-Cyclohex-1-enyl-3-[(trans-4-methoxy-cyclohexyl)-(trans-4-methyl-cylohexanecarbonyl) -amino]-thiophene-2-carboxylic acid;)

5-(4-Tert-butyl-cyclohex-1-enyl)-3-[(trans-4-hydroxy-cyclohexyl)-(trans-4-methyl -cyclohexanecarbonyl)-amino]-thiophene-2-carboxylic acid;) -

5-(1,4,Dioxa-spiro[4.5.]dec-7-en-8-yl)-3-[(trans-4-hydroxy-cyclohexyl)-(trans-4-methyl -cyclohexanecarbonyl)-amino]-thiophene-2-carboxylic acid);

5-Cyclopent-1-enyl-3-[(trans-4-hydroxy-cyclohexyl)-(trans-4-methyl-cylohexanecarbonyl) -amino]-thiophene-2-carboxylic acid) or a pharmaceutically acceptable salt thereof, a pharmaceutically acceptable solvate thereof, or a solvate of pharmaceutically acceptable salt thereof.

40. A compound according to claim 7, wherein $R_1$ is $C_{3-12}$ cycloalkyl unsubstituted or substituted one or more times by $R_{17}$, $C_{4-12}$ cycloalkenyl unsubstituted or substituted one or more times by $R_{17}$, —C(O)—$C_{3-12}$ cycloalkyl unsubstituted or substituted one or more times by $R_{17}$, —C(O)—$C_{4-12}$ cycloalkenyl unsubstituted or substituted one or more times by $R_{17}$, 5 to 12 member spiroheterocycloalkyl unsubstituted or substituted one or more times by $R_{17}$, or 8 to 12 member spiroheterocycloalkenyl unsubstituted or substituted one or more times by $R_{17}$;

$R_2$ is H, $C_{1-12}$ alkyl unsubstituted or substituted one or more times by $R_{17}$, $C_{2-12}$ alkenyl unsubstituted or substituted one or more times by $R_{17}$, $C_{2-12}$ alkynyl unsubstituted or substituted one or more times by $R_{17}$, $C_{6-14}$ aryl which is unsubstituted or substituted one or more times by $R_{18}$, $C_{7-16}$ unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{19}$, or 4-18 member heterocycle-alkyl unsubstituted or substituted one or more times by $R_{19}$;

$R_9$, $R_{10}$ and $R_{11}$ are each independently H, $C_{1-12}$ alkyl unsubstituted or substituted one or more times by $R_{17}$, $C_{2-12}$ alkenyl unsubstituted or substituted one or more times by $R_{17}$, $C_{2-12}$ alkynyl unsubstituted or substituted one or more times by $R_{17}$, $C_{6-14}$ aryl which is unsubstituted or substituted one or more times by $R_{18}$, $C_{7-16}$ aralkyl unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{19}$, or 4-18 member heterocycle-alkyl unsubstituted or substituted one or more times by $R_{19}$, alternatively, $R_{10}$ and $R_{11}$ are taken together with the nitrogen atom to form a 3 to 10 member heterocycle unsubstituted or substituted one or more times by $R_{19}$ or 5-12 member heteroaryl unsubstituted or substituted one or more times by $R_{19}$;

$R_a$ and $R_b$ are each independently H, $C_{1-12}$ alkyl unsubstituted or substituted one or more times by $R_{17}$, $C_{2-12}$ alkenyl unsubstituted or substituted one or more times by $R_{17}$, $C_{2-12}$ alkynyl unsubstituted or substituted one or more times by $R_{17}$, $C_{6-14}$ aryl which is unsubstituted or substituted one or more times by $R_{18}$, $C_{7-16}$ aralkyl unsubstituted or substituted one or more times by $R_{18}$, 5-12 member heteroaryl unsubstituted or substituted one or more times by $R_{19}$, 6-18 member heteroaralkyl unsubstituted or substituted one or more times by $R_{19}$, 3-12 member heterocycle unsubstituted or substituted one or more times by $R_{19}$, or 4-18 member heterocycle-alkyl unsubstituted or substituted one or more times by $R_{19}$;

or $R_a$ and $R_b$ are taken together with the oxygen atom to form a 5 to 10 member heterocycle unsubstituted or substituted one or more times by $R_{19}$ or a 5-12 member heteroaryl unsubstituted or substituted one or more times by $R_{19}$.

41. A compound according to claim 40, wherein $R_1$ is $C_{3-12}$ cycloalkyl unsubstituted or substituted one or more times by $R_{17}$, or $C_{4-12}$ cycloalkenyl unsubstituted or substituted one or more times by $R_{17}$.

42. A compound according to claim 40, wherein $R_2$ is $C_{3-12}$ cycloalkyl unsubstituted or substituted one or more times by $R_{17}$, or $C_{6-14}$ aryl which is unsubstituted or substituted one or more times by $R_{18}$.

43. A compound according to claim 40, wherein $R_3$ is $C_{3-12}$ cycloalkyl unsubstituted or substituted one or more times by $R_{17}$, or $C_{6-14}$ aryl which is unsubstituted or substituted one or more times by $R_{18}$.

44. A compound according to claim 40, wherein $R_1$ is $C_{3-12}$ cycloalkyl unsubstituted or substituted one or more times by $R_{17}$, or $C_{4-12}$ cycloalkenyl unsubstituted or substituted one or more times by $R_{17}$;

$R_2$ is $C_{3-12}$ cycloalkyl unsubstituted or substituted one or more times by $R_{17}$, or $C_{6-14}$ aryl which is unsubstituted or substituted one or more times by $R_{18}$; and $R_3$ is $C_{3-12}$ cycloalkyl unsubstituted or substituted one or more times by $R_{17}$, or $C_{6-14}$ aryl which is unsubstituted or substituted one or more times by $R_{18}$.

45. A compound according to claim 40, wherein Y is $COOR_9$ and $R_9$ is H or $C_{1-6}$alkyl.

46. A compound according to claim 44, wherein Y is $COOR_9$ and $R_9$ is H or $C_{1-6}$alkyl.

47. A compound according to claim 1, wherein said compound is in the form of a pharmaceutically acceptable salt selected from hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic, benzenesulphonic, L-arginine, L-Lysine, calcium, sodium, lithium, potassium, magnesium, choline, tromethamine, and $NR_4$ salts, wherein R is $C_{1-4}$ alkyl.

48. A compound according to claim 47, wherein said compound is a sodium, lithium, or potassium salt.

49. A compound according to claim 40, wherein Y is COOH.

50. A compound according to claim 47, wherein Y is COOH.

51. A compound according to claim 1, wherein $R_3$ is from H, methyl, ethyl, i-propyl, cyclopropyl, cyclohexyl, piperidinyl, -N($C_{1-6}$ alkyl)-piperidinyl, piperazinyl, pyrrolidinyl, azetidinyl, aziridinyl, piperidinylmethyl, dioxanyl, hexahydrothiopyrany, methylazepanyl, -N($C_{1-6}$ alkyl)-piperidinylmethyl dioxolanyl, tetrahydrothiopyranyl, dioxolanylmethyl, dioxanylmethyl, and azepanyl; any of which can be optionally substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, optionally substituted 5-12 member heteroaryl, optionally substituted 6-18 member heteroaralkyl, optionally substituted 3-12 member heterocycle, optionally substituted 4-18 member heterocycle-alkyl, hydroxyl, oxo, oxime, $NR_{13}R_{14}$, $C(O)OR_{12}$, cyano, azido, amidino and guanido;

wherein $R_{12}$, $R_c$, $R_d$, $R_{13}$ and $R_{14}$ are each independently chosen from H, $C_{1-12}$ alkyl, $C_{2-12}$ 12 alkenyl, $C_{2-12}$ alkynyl, $C_{6-14}$ aryl, 3-12 member heterocycle, 6-18 member heteroaralkyl, and $C_{7-18}$ aralkyl, or $R_c$ and $R_d$ are taken together with the oxygens to form an optionally substituted 3 to 10 member heterocycle or an optionally substituted 5-12 member heteroaryl, or $R_{13}$ and $R_{14}$ are taken together with the nitrogen to form an optionally substituted 3 to 10 member heterocycle or an optionally substituted 5-12 member heteroaryl.

52. A compound according to claim 1, wherein $R_2$ is cyclohexyl substituted by $C_{1-6}$ alkyl.

53. A compound according to claim 1, wherein $R_2$ is 4-methylcyclohexyl.

54. A compound according to claim 1, wherein $R_2$ is dichlorophenyl.

55. A pharmaceutical composition comprising at least one compound according to claim 18 and at least one pharmaceutically acceptable carrier or excipient.

56. A pharmaceutical combination comprising at least one compound according to claim 18 and at least one additional agent.

57. A pharmaceutical combination according to claim 56, wherein said at least one additional agent is selected from viral seine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

58. A pharmaceutical combination according to claim 57, wherein said at least one other antiviral agent is interferon α, ribavirin, silybum marianum, interleukine-12, amantadine, ribozyme, thymosin, N-acetyl cysteine or cyclosporin.

59. A method for treating a Flaviviridae viral infection in a host comprising administering to the host a therapeutically effective amount of at least one compound according to claim 18.

60. A method according to claim 59, wherein said viral infection is Hepatitis C viruS(HCV), bovine viral diarrhea viruS(BVDV), hog cholera virus, dengue fever virus, Japanese encephalitis virus or yellow fever virus.

61. A method according to claim 59, wherein said viral infection is Hepatitis C viral infection.

62. A method according to claim 59, further comprising administering at least one additional agent.

63. A method according to claim 62, wherein said at least one additional agent is selected from viral seine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

64. A method according to claim 63, wherein said at least one other antiviral agent is interferon α, ribavirin, silybum marianum, interleukine-12, amantadine, ribozyme, thymosin, N-acetyl cysteine or cyclosporin.

65. A method according to claim 62, wherein said compound and said at least one other antiviral agent are administered sequentially.

66. A method according to claim 62, wherein said compound and said at least one other antiviral agent are administered simultaneously.

67. A method for inhibiting or reducing the activity of viral polymerase in a host comprising administering to said host a therapeutically effective amount of a compound according to claim 18.

68. A method according to claim 67, further comprising administering one or more viral polymerase inhibitor.

69. A method according to claim 67, wherein said viral polymerase is a Flaviviridae viral polymerase.

70. A method according to claim 67, wherein said viral polymerase is a RNA-dependant RNA-polymerase.

71. A method according to claim 67, wherein said viral polymerase is HCV polymerase.

72. A compound according to claim 44, wherein $R_2$ is cyclohexyl substituted by $C_{1-6}$ alkyl.

73. A compound according to claim 44, wherein $R_2$ is dichlorophenyl.

74. A pharmaceutical composition comprising at least one compound according to claim 40 and at least one pharmaceutically acceptable carrier or excipient.

75. A pharmaceutical combination comprising at least one compound according to claim 40 and at least one additional agent.

76. A pharmaceutical combination according to claim 40, wherein said at least one additional agent is selected from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

77. A method for treating a Flaviviridae viral infection in a host comprising administering to the host a therapeutically effective amount of at least one compound according to claim 40.

78. A pharmaceutical combination according to claim 77, wherein said at least one other antiviral agent is interferon α, ribavirin, silybum marianum, interleukine-12, amantadine, ribozyme, thymosin, N-acetyl cysteine or cyclosporin.

79. A method according to claim 77, wherein said viral infection is Hepatitis C viruS(HCV), bovine viral diarrhea virus(BVDV), hog cholera virus, dengue fever virus, Japanese encephalitis virus or yellow fever virus.

80. A method according to claim 79, wherein said viral infection is Hepatitis C viral infection.

81. A method according to claim 79, further comprising administering at least one additional agent.

82. A method according to claim 81, wherein said at least one additional agent is selected from viral seine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

83. A method according to claim 82, wherein said at least one other antiviral agent is interferon c's, ribavirin, silybum marianum, interleukine-12, amantadine, ribozyme, thymosin, N-acetyl cysteine or cyclosporin.

84. A method according to claim 81, wherein said compound and said at least one other antiviral agent are administered sequentially.

85. A method according to claim 81, wherein said compound and said at least one other antiviral agent are administered simultaneously.

86. A method for inhibiting or reducing the activity of viral polymerase in a host comprising administering to said host a therapeutically effective amount of a compound according to claim 40.

87. A method according to claim 86, further comprising administering one or more viral polymerase inhibitor.

88. A method according to claim 86, wherein said viral polymerase is a Flaviviridae viral polymerase.

89. A method according to claim 86, wherein said viral polymerase is a RNA-dependant RNA-polymerase.

90. A method according to claim 86, wherein said viral polymerase is HCV polymerase.

* * * * *

UNITED STATES PATENT AND TRADEMARK OFFICE
CERTIFICATE OF CORRECTION

PATENT NO. : 7,569,600 B2  Page 1 of 1
APPLICATION NO. : 11/433749
DATED : August 4, 2009
INVENTOR(S) : Carl Poisson It is certified that error appears in the above-identified patent and that said Letters Patent is hereby corrected as shown below:

Column 16, line 30, reads "bicycloolanyl" should read -- bicyclooctanyl --

Column 223, line 39, reads "bicyclootanyl" should -- bicyclooctanyl --

Column 224, line 10, reads "$R_{18}$" should read -- $R_{17}$ --

Column 233, line 48, reads "seine" should read -- serine --

Column 233, line 63, reads "viruS(HCV)" should read -- virus (HCV) --

Column 233, line 64, reads "viruS(BVDV)" should read -- virus (BVDV) --

Column 237, line 45, reads "seine" should read -- serine --

Column 237, line 60, reads "viruS(HCV)" should read -- virus (HCV) --

Column 237, line 61, reads "viruS(BVDV)" should read -- virus (BVDV) --

Column 238, line 2, reads "seine" should read -- serine --

Column 238, line 57, reads "viruS(HCV)" should read -- virus (HCV) --

Column 238, line 58, reads "viruS(BVDV)" should read -- virus (BVDV) --

Column 238, line 65, reads "seine" should read -- serine --

Column 239, line 5, reads "interferon c's" should read -- interferon α --

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,569,600 B2 | Page 1 of 1 |
| APPLICATION NO. | : 11/433749 | |
| DATED | : August 4, 2009 | |
| INVENTOR(S) | : Denis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 292 days.

Signed and Sealed this

Twenty-eighth Day of December, 2010

David J. Kappos
*Director of the United States Patent and Trademark Office*